US008946188B2

(12) United States Patent
Tan et al.

(10) Patent No.: US 8,946,188 B2
(45) Date of Patent: Feb. 3, 2015

(54) ANTI-MICROBIAL AGENTS AND USES THEREOF

(71) Applicants: Sloan-Kettering Institute for Cancer Research, New York, NY (US); Cornell Research Foundation, Inc., Ithaca, NY (US)

(72) Inventors: Derek Shieh Tan, New York, NY (US); Luis E. N. Quadri, New York, NY (US); Jae-Sang Ryu, Seodaemun-gu (KR); Justin Scott Cisar, New York, NY (US); Julian Alberto Ferreras, Roosevelt Island, NY (US); Xuequan Lu, Flushing, NY (US)

(73) Assignees: Sloan-Kettering Institute for Cancer Research, New York, NY (US); Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 13/897,807

(22) Filed: May 20, 2013

(65) Prior Publication Data

US 2014/0024611 A1    Jan. 23, 2014

Related U.S. Application Data

(62) Division of application No. 11/911,525, filed as application No. PCT/US2006/014394 on Apr. 16, 2006, now Pat. No. 8,461,128.

(60) Provisional application No. 60/671,994, filed on Apr. 15, 2005.

(51) Int. Cl.
| | | |
|---|---|---|
| A01N 43/04 | (2006.01) |
| A61K 31/70 | (2006.01) |
| C07H 19/24 | (2006.01) |
| C07H 19/00 | (2006.01) |
| C07H 19/22 | (2006.01) |

(52) U.S. Cl.
CPC ............... *C07H 19/24* (2013.01); *C07H 19/00* (2013.01); *C07H 19/22* (2013.01)
USPC .................... 514/45; 514/43; 514/46; 514/47

(58) Field of Classification Search
None
See application file for complete search history.

(56) References Cited

U.S. PATENT DOCUMENTS

| | | | |
|---|---|---|---|
| 3,622,561 A | 11/1971 | Robins et al. |
| 4,029,884 A | 6/1977 | Stein et al. |
| 5,824,657 A | 10/1998 | Hill et al. |
| 7,989,430 B2 | 8/2011 | Aldrich et al. |

FOREIGN PATENT DOCUMENTS

| | | |
|---|---|---|
| GB | 2 284 811 A | 6/1995 |
| GB | 2 287 464 A | 9/1995 |

OTHER PUBLICATIONS

Chatgilialoglu et al. JACS (2003), vol. 125, pp. 3839-3848.*
International Search Report and Written Opinion for PCT/US2006/014394, mailed Nov. 9, 2006.
International Preliminary Report on Patentability for PCT/US2006/014394, mailed Oct. 25, 2007.
International Search Report and Written Opinion for PCT/US2006/46433, mailed May 24, 2007.
Abramovitch et al., Solution and flash vacuum pyrolyses of β-(3,5-disubstituted-phenyl) ethanesulfonyl azides. Sultam, pyrindine, and azepine formation. J Org Chem. 1984;49:5124-31.
Ambroise et al., Stereocontrolled synthesis of anti-α-hydroxy-β-amino and anti-α,β-diamino acid derivatives by epoxidation of 1-arylthio-1-nitroalkenes. Synthesis. 2002:2296-2308.
Barclay et al., Mycobactins and exochelins of *Mycobacterium tuberculosis, M. bovis, M. africanum* and other related species. J Gen Microbiol. Mar. 1988;134(3):771-6.
Bearden et al., Genetic organization of the yersiniabactin biosynthetic region and construction of avirulent mutants in *Yersinia pestis*. Infect Immun. May 1997;65(5):1659-68.
Bellaire et al., Genetic organization and iron-responsive regulation of the *Brucella abortus* 2,3- dihydroxybenzoic acid biosynthesis operon, a cluster of genes required for wild-type virulence in pregnant cattle. Infect Immun. Apr. 2003;71(4):1794-803.
Berge et al., Pharmaceutical salts. J Pharm Sci. Jan. 1977;66(1):1-19.
Bhardwaj et al., Oligonucleosides with a nucleobase-including backbone, Part 7, syn and anti conformations of a (5',8)-ethynediyl-linked adenosine dimer. Helv Chim Acta. 2002;85:699-711.
Bloch et al., Inhibition of protein synthesis by 5'-sulfamoyladenosine. Biochemistry. Nov. 23, 1971;10(24):4394-8.
Bloom et al., Tuberculosis: commentary on a reemergent killer. Science. Aug. 21, 1992;257(5073):1055-64.
Blumberg et al., American Thoracic Society/Centers for Disease Control and Prevention/Infectious Diseases Society of America: treatment of tuberculosis. Am J Respir Crit Care Med. Feb. 15, 2003;167(4):603-62.

(Continued)

*Primary Examiner* — Patrick Lewis
(74) *Attorney, Agent, or Firm* — Wolf, Greenfield & Sacks, P.C.; C. Hunter Baker

(57) ABSTRACT

Many pathogens, including *Mycobacterium tuberculosis* and *Yersinia pestis*, rely on an iron acquisition system based on siderophores, secreted iron-chelating compounds with extremely high Fe(III) affinity. The compounds of the invention are inhibitors of domain salicylation enzymes, which catalyze the salicylation of an aroyl carrier protein (ArCP) domain to form a salicyl-ArCP domain thioester intermediate via a two-step reaction. The compounds include the intermediate mimic 5'-O—[N-(salicyl)sulfamoyl]-adenosine (salicyl-AMS) and analogs thereof. These compounds are inhibitors of the salicylate activity of MbtA, YbtE, PchD, and other domain salicylation enzymes involved in the biosynthesis of siderophores. Therefore, these compounds may be used in the treatment of infection caused by microorganisms which rely on siderphore-based iron acquisition systems. Pharmaceutical composition and methods of using these compounds to treat or prevent infection are also provided as well as methods of preparing the inventive compounds.

28 Claims, 23 Drawing Sheets

(56) References Cited

OTHER PUBLICATIONS

Borges-Walmsley et al., Structure and function of efflux pumps that confer resistance to drugs. Biochem J. Dec. 1, 2003;376(Pt 2):313-38.
Boschiroli et al., Brucellosis: a worldwide zoonosis. Curr Opin Microbiol. Feb. 2001;4(1):58-64.
Boshoff et al., The transcriptional responses of *Mycobacterium tuberculosis* to inhibitors of metabolism: novel insights into drug mechanisms of action. J Biol Chem. Sep. 17, 2004;279(38):40174-84. Epub Jul. 9, 2004.
Bottone, *Yersinia enterocolitica*: the charisma continues. Clin Microbiol Rev. Apr. 1997;10(2):257-76.
Braun et al., Active transport of iron and siderophore antibiotics. Curr Opin Microbiol. Apr. 2002;5(2):194-201.
Braun, Iron uptake mechanisms and their regulation in pathogenic bacteria. Int J Med Microbiol. May 2001;291(2):67-79.
Brennan et al., The envelope of mycobacteria. Annu Rev Biochem. 1995;64:29-63.
Brown et al., Effects of phosphorylation of threonine 160 on cyclin-dependent kinase 2 structure and activity. J Biol Chem. Mar. 26, 1999;274(13):8746-56.
Brubaker, Factors promoting acute and chronic diseases caused by yersiniae. Clin Microbiol Rev. Jul. 1991;4(3):309-24.
Burdine et al., Target identification in chemical genetics: the (often) missing link. Chem Biol. May 2004;11(5):593-7.
Burns et al., Selective reduction of disulfides by tris(2-carboxyethyl)phosphine. J Org Chem. Oct. 1991;56(8):2648-50.
Cama et al., Design of amino acid sulfonamides as transition-state analogue inhibitors of arginase. J Am Chem Soc. Oct. 29, 2003;125(43): 13052-7.
Capilla et al., Characterization of the molecular mechanisms of quinolone resistance in *Yersinia enterocolitica* O:3 clinical isolates. J Antimicrob Chemother. Jun. 2004;53(6):1068-71. Epub Apr. 29, 2004.
Capilla et al., Epidemiological study of resistance to nalidixic acid and other antibiotics in clinical *Yersinia enterocolitica* O:3 isolates. J Clin Microbiol. Oct. 2003;41(10):4876-8.
Castro-Pichel et al., A facile synthesis of ascamycin and related analogs. Tetrahedron. 1987;43:383-9.
Cendrowski et al., *Bacillus anthracis* requires siderophore biosynthesis for growth in macrophages and mouse virulence. Mol Microbiol. Jan. 2004;51(2):407-17.
Chandra et al., Total synthesis of (−)- and (+)-lentiginosine. J Org Chem. Jun. 28, 2002;67(13):4630-3.
Chang et al., Benzyloxybenzaldehyde analogues as novel adenylyl cyclase activators. Bioorg Med Chem Lett. Aug. 6, 2001;11(15):1971-4.
Chemler et al., The B-Alkyl Suzuki-Miyaura Cross-Coupling Reaction: Development, Mechanistic Study, and Applications in Natural Product Synthesis A list of abbreviations can be found at the end of the article. Angew Chem Int Ed Engl. Dec. 17, 2001;40(24):4544-4568.
Choudhuri et al., Isoniazid accumulation in *Mycobacterium smegmatis* is modulated by proton motive force-driven and ATP-dependent extrusion systems. Biochem Biophys Res Commun. Mar. 24, 1999;256(3):682-4.
Cisar et al., Exploiting ligand conformation in selective inhibition of non-ribosomal peptide synthetase amino acid adenylation with designed macrocyclic small molecules. J Am Chem Soc. Jun. 27, 2007;129(25):7752-3. Epub Jun. 2, 2007.
Conti et al., Structural basis for the activation of phenylalanine in the non-ribosomal biosynthesis of gramicidin S. EMBO J. Jul. 16, 1997;16(14):4174-83.
Copeland, Tight binding inhibitors. In: Enzymes: A practical introduction to structure, mechanism, and data analysis. Wiley-VCH, Inc. Publications. New York. 2000:305-17.
Couch et al., Characterization of CmaA, an adenylation-thiolation didomain enzyme involved in the biosynthesis of coronatine. J Bacteriol. Jan. 2004;186(1):35-42.
Cover et al., *Yersinia enterocolitica*. N. Engl J Med. Jul. 6, 1989;321(1):16-24.
Crofton, Drug Treatment of Tuberculosis. Brit Med J. Jul. 30, 1960:370-3.
Crosa et al., Genetics and assembly line enzymology of siderophore biosynthesis in bacteria. Microbiol Mol Biol Rev. Jun. 2002;66(2):223-49.
Dai et al., First synthesis of a highly strained cyclodeca-1,5-diyne skeleton via intramolecular Sonogashira cross-coupling. Tetrahedron Lett. 2001;42:81-83.
De Almeida et al., Chromosomal irp2 gene in *Yersinia*: distribution, expression, deletion and impact on virulence. Microb Pathog. Jan. 1993;14(1):9-21.
De Voss et al., The salicylate-derived mycobactin siderophores of *Mycobacterium tuberculosis* are essential for growth in macrophages. Proc Natl Acad Sci U S A. Feb. 1, 2000;97(3):1252-7.
Domenech et al., Contribution of the *Mycobacterium tuberculosis* MmpL protein family to virulence and drug resistance. Infect Immun. Jun. 2005;73(6):3492-501.
Dovlatyan et al., Synthesis of 2,2-dioxo-4-chloro-1,2,3-oxathiazole-Δ3 and its 5,5-dimethyl derivative and some of their transformations. Armyan KMm Z. 1975;28:311-6.
Dye et al., Consensus statement. Global burden of tuberculosis: estimated incidence, prevalence, and mortality by country. WHO Global Surveillance and Monitoring Project. JAMA. Aug. 18, 1999;282(7):677-86.
Dye et al., Worldwide incidence of multidrug-resistant tuberculosis. J Infect Dis. Apr. 15, 2002;185(8):1197-202. Epub Apr. 1, 2002.
Eigner et al., Kinetic techniques for the investigation of amino acid: tRNA ligases (aminoacyl-tRNA synthetases, amino acid activating enzymes). Methods Enzymol. 1974;29(0):601-19.
Ertl et al., Fast calculation of molecular polar surface area as a sum of fragment-based contributions and its application to the prediction of drug transport properties. J Med Chem. Oct. 5, 2000;43(20):3714-7.
Fernandez et al., Identification of specific in vivo-induced (ivi) genes in *Yersinia ruckeri* and analysis of ruckerbactin, a catecholate siderophore iron acquisition system. Appl Environ Microbiol. Sep. 2004;70(9):5199-207.
Ferreras et al, Small-molecule inhibition of siderophore biosynthesis in *Mycobacterium tuberculosis* and *Yersinia pestis*. Nat Chem Biol. Jun. 2005;1(1):29-32. Epub May 24, 2005.
Fetherston et al., Analysis of the pesticin receptor from *Yersinia pestis*: role in iron-deficient growth and possible regulation by its siderophore. J Bacteriol. Apr. 1995;177(7):1824-33.
Finking et al., Aminoacyl adenylate substrate analogues for the inhibition of adenylation domains of nonribosomal peptide synthetases. Chembiochem. Sep. 5, 2003;4(9):903-6.
Florini et al., Inhibition of protein synthesis in vitro and in vivo by nucleocidin, an antitrypanosomal antibiotic. J Biol Chem. Mar. 10, 1966;241(5):1091-8.
Forrest et al., Aminoalkyl adenylate and aminoacyl sulfamate intermediate analogues differing greatly in affinity for their cognate *Staphylococcus aureus* aminoacyl tRNA synthetases. Bioorg Med Chem Lett. Aug. 21, 2000;10(16):1871-4.
Frieden et al., Tuberculosis. Lancet. Sep. 13, 2003;362(9387):887-99.
Furstner et al., Asymmetric synthesis of the fully functional macrolide core of salicylihalamide: remote control of olefin geometry during RCM. Org Lett. Nov. 16, 2000;2(23):3731-4.
Furstner et al., Total synthesis of (−)-salicylihalamide Chemistry. Dec. 17, 2001;7(24):5286-98.
Galimand et al., Multidrug resistance in *Yersinia pestis* mediated by a transferable plasmid. N. Engl J Med. Sep. 4, 1997;337(10):677-80.
Gehring et al., Iron acquisition in plague: modular logic in enzymatic biogenesis of yersiniabactin by *Yersinia pestis*. Chem Biol. Oct. 1998;5(10):573-86.
Gehring et al., The nonribosomal peptide synthetase HMWP2 forms a thiazoline ring during biogenesis of yersiniabactin, an iron-chelating virulence factor of *Yersinia pestis*. Biochemistry. Aug. 18, 1998;37(33):11637-50.
Geng et al., Synthesis of novel C2—C3'N-linked macrocyclic taxoids by means of highly regioselective Heck macrocyclization. Org Lett. Oct. 2, 2003;5(20):3733-6.

(56) References Cited

OTHER PUBLICATIONS

Gilligan, Therapeutic challenges posed by bacterial bioterrorism threats. Curr Opin Microbiol. Oct. 2002;5(5):489-95.

Giraud et al., Evidence for active efflux as the primary mechanism of resistance to ciprofloxacin in *Salmonella enterica* serovar typhimurium. Antimicrob Agents Chemother. May 2000;44(5):1223-8.

Gobin et al., Iron acquisition by *Mycobacterium tuberculosis*: isolation and characterization of a family of iron-binding exochelins. Proc Natl Acad Sci U S A. May 23, 1995;92(11):5189-93.

Gong et al., Characterization of the *Yersinia pestis* Yfu ABC inorganic iron transport system. Infect Immun. May 2001;69(5):2829-37.

Graves et al., Discovery of novel targets of quinoline drugs in the human purine binding proteome. Mol Pharmacol. Dec. 2002;62(6):1364-72.

Guiyoule et al., Transferable plasmid-mediated resistance to streptomycin in a clinical isolate of *Yersinia pestis*. Emerg Infect Dis. Jan.-Feb. 2001;7(1):43-8.

Gunji et al., Oligonucleosides with a nucleobase-including backbone part 3. Synthesis of acetylene-linked adenosine dimers. Helv Chim Acta. 2000;83:2975-92.

Gunji et al., Oligonucleosides with a nucleobase-including backbone part 2. Synthesis and structure determination of adenosine-derived monomers. Helv Chim Acta. 2000;83:1331-45.

Gupta et al., Crystal structure of Rv2118c: an AdoMet-dependent methyltransferase from *Mycobacterium tuberculosis* H37Rv. J Mol Biol. Sep. 14, 2001;312(2):381-91.

Hammer-Jespersen, Nucleoside catabolism. In: Metabolism of nucleotides, nucleosides, and nucleobases in microorganisms. Munch-Petersen, ed. Academic Press. London. 1983:203-58.

Hancock, The bacterial outer membrane as a drug barrier. Trends Microbiol. Jan. 1997;5(1):37-42.

Harris et al., Coordination chemistry of microbial iron transport compounds. 19. Stability constants and electrochemical behavior of ferric enterobactin and model complexes. J Am Chem Soc. 1979;101:6097-104.

He et al., Probing met repressor-operator recognition in solution. Nature. Oct. 1, 1992;359(6394):431-3.

Heacock et al., Synthesis and Aminoacyl-tRNA Synthetase Inhibitory Activity of Prolyl Adenylate Analogs. Bioorg Chem. 1996;24:273-89.

Heesemann, Chromosomal encoded siderophores are required for mouse virulence of enteropathogenic *Yersinia* species. FEMS Microbiol Lett. 1987;48:229-33.

Hogan et al., Why are bacteria refractory to antimicrobials? Curr Opin Microbiol. Oct. 2002;5(5):472-7.

Hotoda et al., Synthesis of cytidyl(3'-5')adenosine bearing 2'(3')-0-leucyl ester via a phosphorothioate trimester intermediate. Tetrahedron. 1990;46:1181-90.

Hughes, Exploiting genomics, genetics and chemistry to combat antibiotic resistance. Nat Rev Genet. Jun. 2003;4(6):432-41.

Jain et al., A facile synthesis of [N1,NH(2-)(15)N(2)], [N3,NH(2-)(15)N(2)] and [N2, N3,NH(2-)(15)N(3)]-labeled adenine. J Org Chem. Sep. 21, 2001;66(19):6472-5.

Jurado, Iron, infections, and anemia of inflammation. Clin Infect Dis. Oct. 1997;25(4):888-95.

Kansy et al., Physicochemical high throughput screening: parallel artificial membrane permeation assay in the description of passive absorption processes. J Med Chem. Mar. 26, 1998;41(7):1007-10.

Kappler et al., Approaches to isozyme-specific inhibitors. 17. Attachment of a selectivity-inducing substituent to a multisubstrate adduct. Implications for facilitated design of potent, isozyme-selective inhibitors. J Med Chem. Sep. 1990;33(9):2545-51.

Kappler et al., Isozyme-specific enzyme inhibitors. 14. 5'(R)-C-[(L-homocystein-S-yl)methyl]adenosine 5'-(beta,gamma-imidotriphosphate), a potent inhibitor of rat methionine adenosyltransferases. J Med Chem. Sep. 1987;30(9):1599-603.

Karsch et al., Synthesis of sultones by ring closing metathesis. Synlett. 2002:2019-22.

Keating et al., Reconstitution and characterization of the *Vibrio cholerae* vibriobactin synthetase from VibB, VibE, VibF, and VibH. Biochemistry. Dec. 19, 2000;39(50):15522-30.

Keese et al., The structural basis of the geminal-dimethyl effect. Tetrahedron. 1993;49:2055-64.

Khan et al., Lowering the entropic barrier for binding conformationally flexible inhibitors to enzymes. Biochemistry. Dec. 1, 1998;37(48):16839-45.

Kim et al., Aminoacyl-tRNA synthetases and their inhibitors as a novel family of antibiotics. Appl Microbiol Biotechnol. May 2003;61(4):278-88. Epub Mar. 1, 2003.

King et al., Alkanesulfonyl chlorides from alcohols via[2]betylates (alky 2-ammonioethanesulfonates). Synthesis. 1980:285-7.

Koppisch et al., Petrobactin is the primary siderophore synthesized by *Bacillus anthracis* str. Sterne under conditions of iron starvation. Biometals. Dec. 2005;18(6):577-85.

Kotch et al., Water-mediated association provides an ion pair receptor. J Am Chem Soc. Dec. 10, 2003;125(49):15140-50.

Kristinsson et al., In Synthesis and Chemistry of Agrochemicals IV. ACS Symposium Series. 1995:206-19.

Krohn et al., Synthesis and cytotoxic activity of C-glycosidic nicotinamide riboside analogues. J Med Chem. Feb. 7, 1992;35(3):511-7.

Landeka et al., Characterization of yeast seryl-tRNA synthetase active site mutants with improved discrimination against substrate analogues. Biochim Biophys Acta. Jul. 14, 2000;1480(12):160-70.

Lane et al., Novel extracellular mycobactins, the carboxymycobactins from *Mycobacterium avium*. Tetrahedron Lett. 1995;36:4129-32.

Lee et al., Targeting virulence for antimicrobial chemotherapy. Curr Opin Pharmacol. Oct. 2003;3(5):513-9.

Lerner et al., Bisubstrate inhibitors for the enzyme catechol-O-methyltransferase (COMT): influence of inhibitor preorganisation and linker length between the two substrate moieties on binding affinity. Org Biomol Chem. Jan. 7, 2003;1(1):42-9.

Lerner et al., X-ray Crystal Structure of a Bisubstrate Inhibitor Bound to the Enzyme Catechol-O-methyltransferase: A Dramatic Effect of Inhibitor Preorganization on Binding Affinity. Angew Chem Int Ed Engl. Nov. 5, 2001;40(21):4040-4042.

Li et al., Role of efflux pump(s) in intrinsic resistance of *Pseudomonas aeruginosa*: resistance to tetracycline, chloramphenicol, and norfloxacin. Antimicrob Agents Chemother. Aug. 1994;38(8):1732-41.

Lin et al., The efficacy of a *Salmonella* typhi Vi conjugate vaccine in two-to-five-year-old children. N. Engl J Med. Apr. 26, 2001;344(17):1263-9.

Lindberg, Vaccination against enteric pathogens: from science to vaccine trials. Curr Opin Microbiol. Feb. 1998;1(1):116-24.

Linne et al., Reactions catalyzed by mature and recombinant nonribosomal peptide synthetases. Methods Enzymol. 2004;388:293-315.

Lipinski et al., Experimental and computational approaches to estimate solubility and permeability in drug discovery and development setting. Adv Drug Delivery Rev. 1997;23:3-25.

Litwin et al., Role of catechol siderophore synthesis in *Vibrio vulnificus* virulence. Infect Immun. Jul. 1996;64(7):2834-8.

Liu et al., Synthesis of 5'-functionalized adenosine: Suppression of cyclonucleoside formation. Tetrahedron Lett. 2001;42:3153-4.

Liu et al., A general synthesis of 5'-azido-5'-deoxy-2',3'-O-isopropylidene nucleosides. J Org Chem. Dec. 14, 2001;66(25):8643-5.

Lounis et al., Iron and *Mycobacterium tuberculosis* infection. J Clin Virol. Feb. 2001;20(3):123-6.

Lutz et al., Highly enantioselective addition of mixed diorganozincs to aldehydes. J Org Chem. 1997;62:7895-8.

Markaverich et al., Purification and characterization of nuclear type II [$^3$H] Estradiol binding sites from the rat uterus: Covalent labeling with [$^3$H] luteolin. Steroids. Sep. 2001;66(9):707-19.

Marra, Can virulence factors be viable antibacterial targets? Expert Rev Anti Infect Ther. Feb. 2004;2(1):61-72.

Matsuda et al., Nucleosides and nucleotides. LXVI. Synthesis of 8,6'-cyclo-6'-deoxyhexofuranosyladenines: Adenosines fixed in an Anti-conformation. Chem Pharm Bull. 1986;34:1573-8.

(56) References Cited

OTHER PUBLICATIONS

Masjost et al., Structure-based design, synthesis, and in vitro evaluation of bisubstrate inhibitors for catechol O-methyltransferase (COMT). Chemistry. Mar. 17, 2000;6(6):971-82.
Matulic-Adamic et al., Synthesis and Structure of 1-Deoxy-1-phenyl-beta-D-ribofuranose and Its Incorporation into Oligonucleotides. J Org Chem. May 31, 1996;61(11):3909-3911.
May et al., Crystal structure DhbE, an archetype for aryl acid activating domains of modular nonribosomal peptide synthetases. Proc Natl Sci. 2002;99:12120-5.
McLoughlin et al., Kinetic and regiospecific interrogation of covalent intermediates in the nonribosomal peptide synthesis of yersiniabactin. J Am Chem Soc. Oct. 20, 2004;126(41):13265-75.
Meier et al., Improved conversion of adenosine to 3'-deoxyadenosine. Synlett. 1991:227-8.
Melendez et al., Synthesis and reactivity of cyclic sulfamidites and sulfamidates. Tetrahedron. 2003;59:2581-2616.
Midelfort et al., Applications of kinetic methods to aminoacyl-tRNA synthetases. Methods Enzymol. 1974;29(0):627-42.
Miethke et al., Inhibition of aryl acid adenylation domains involved in bacterial siderophore synthesis. FEBS J. Jan. 2006;273(2):409-19.
Miller et al., Yersiniabactin synthetase: a four-protein assembly line producing the nonribosomal peptide/polyketide hybrid siderophore of *Yersinia pestis*. Chem Biol. Mar. 2002;9(3):333-44.
Min et al., Crystal structure of a SIR2 homolog-NAD complex. Cell. Apr. 20, 2001;105(2):269-79.
Moriarty et al., Palladium catalyzed C-8 allylation and vinylation of adenosine, 2',3'-dideoxyadenosine nucleosides. Tetrahedron Lett. 1990;31:5877-80.
Mossessova et al., Ulp1-SUMO crystal structure and genetic analysis reveal conserved interactions and a regulatory element essential for cell growth in yeast. Mol Cell. May 2000;5(5):865-76.
Mueller et al., Enatioselective catalytic aziridinations and asymmetric nitrene insertions into CH bonds. Chem Rev. 2003;103:2905-19.
Munch-Petersen et al., Transport of nucleic acid precursors. In: Metabolism of nucleotides, nucleosides, and nucleobases in microorganisms. Munch-Petersen, ed. Academic Press. London. 1983:259-305.
Murray et al., Mortality by cause for eight regions of the world: Global Burden of Disease Study. Lancet. May 3, 1997;349(9061):1269-76.
Naka et al., The stereoselective synthesis of 4'-β-thioribonucleosides via the pummerer reaction. J Am Chem Soc. 2000;122:7233-43.
Nelson et al., Synthesis of hypoxanthine, guanine, and 6-thiopurine nucleosides of 6-deoxy-D-allofuranose. J Med Chem. Jul. 1983;26(7):1071-4.
Nesterenko et al., The use of pH to influence regio- and chemoselectivity in the asymmetric aminohydroxylation of styrenes. Org Lett. Feb. 6, 2003;5(3):281-4.
Nikaido, Prevention of drug access to bacterial targets: permeability barriers and active efflux. Science. Apr. 15, 1994;264(5157):382-8.
Norman et al., A convenient preparation of 3'-deoxyadenosine. Synthesis. 1983:304-6.
Okada et al., Efficient general method for sulfamoylation of a hydroxyl group. Tetrahedron Lett. 2000;41:7047-51.
Olakanmi et al., Gallium disrupts iron metabolism of mycobacteria residing within human macrophages. Infect Immun. Oct. 2000;68(10):5619-27.
Onwueme et al., Mycobacterial polyketide-associated proteins are acyltransferases: proof of principle with *Mycobacterium tuberculosis* PapA5. Proc Natl Acad Sci U S A. Mar. 30, 2004;101(13):4608-13. Epub Mar. 18, 2004.
Oravcova et al., Drug-protein binding sites. New trends in analytical and experimental methodology. J Chromatogr B Biomed Appl. Feb. 23, 1996;677(1):1-28.
Osada et al., Mechanism of action and selective toxicity of ascamycin, a nucleoside antibiotic. Antimicrob Agents Chemother. Feb. 1985;27(2):230-3.
Pangborn et al., Safe and convenient procedure for solvent purification. Organometallics. 1996;15:1518-20.

Parrish et al., Mechanisms of latency in *Mycobacterium tuberculosis*. Trends Microbiol. Mar. 1998;6(3):107-12.
Pattenden et al., The intramolecular Stille reaction in some target natural product syntheses. J Organomet Chem 2002. 653:261-8.
Paulsen, Multidrug efflux pumps and resistance: regulation and evolution. Curr Opin Microbiol. Oct. 2003;6(5):446-51.
Pelludat et al., The yersiniabactin biosynthetic gene cluster of *Yersinia enterocolitica*: organization and siderophore-dependent regulation. J Bacteriol. Feb. 1998;180(3):538-46.
Perry et al., *Yersinia pestis*—etiologic agent of plague. Clin Microbiol Rev. Jan. 1997;10(1):35-66.
Perry et al., Yersiniabactin from *Yersinia pestis*: biochemical characterization of the siderophore and its role in iron transport and regulation. Microbiology. May 1999;145 ( Pt 5):1181-90.
Peterson et al., Synthesis and biological evaluation of 5'-sulfamoylated purinyl carbocyclic nucleosides. J Med Chem. Oct. 30, 1992;35(22):3991-4000.
Piddock et al., Accumulation of rifampicin by *Mycobacterium aurum*, *Mycobacterium smegmatis* and *Mycobacterium tuberculosis*. J Antimicrob Chemother. Feb. 2000;45(2):159-65.
Pope et al., Characterization of isoleucyl-tRNA synthetase from *Staphylococcus aureus*. II. Mechanism of inhibition by reaction intermediate and pseudomonic acid analogues studied using transient and steady-state kinetics. J Biol Chem. Nov. 27, 1998;273(48):31691-701.
Posakony et al., New routes to N-alkylated cyclic sulfamidates. J Org Chem. Jul. 26, 2002;67(15):5164-9.
Preobrazhenskaya et al., Glycosylindoles. VII. Synthesis of 1-(D-beta-ribofuranosyl)indole. Tetrahedron. Dec. 1967;23(12):4653-60.
Quadri et al., Iron Metabolism in the Tubercle Bacillus and Other Mycobacteria. In: Tuberculosis and Tubercle Bacillus. Cole et al., eds. ASM Press. Washington, D.C. 2004:341-57.
Quadri et al., Assembly of the *Pseudomonas aeruginosa* nonribosomal peptide siderophore pyochelin: In vitro reconstitution of aryl-4, 2-bisthiazoline synthetase activity from PchD, PchE, and PchF. Biochemistry. Nov. 9, 1999;38(45):14941-54.
Quadri et al., Characterization of Sfp, a *Bacillus subtilis* phosphopantetheinyl transferase for peptidyl carrier protein domains in peptide synthetases. Biochemistry. Feb. 10, 1998;37(6):1585-95.
Quadri et al., Identification of a *Mycobacterium tuberculosis* gene cluster encoding the biosynthetic enzymes for assembly of the virulence-conferring siderophore mycobactin. Chem Biol. Nov. 1998;5(11):631-45.
Quadri, Assembly of aryl-capped siderophores by modular peptide synthetases and polyketide synthases. Mol Microbiol. Jul. 2000;37(1):1-12.
Quant et al., Chemical Synthesis of $^{13}$C-labelled Monomers for the Solid-Phase and Template Controlled Enzymatic Synthesis of DNA and RNA Oligomers. Tetrahedron Lett. 1994;35:6649-52.
Queron et al., Synthetic studies on bafilomycin A1: First formulation of the 16-membered macrolide via an Intramolecular Stille reaction. Tetrahedron Lett. 2004;45:4539-43.
Rachakonda et al., Challenges in antimicrobial drug discovery and the potential of nucleoside antibiotics. Curr Med Chem. Mar. 2004;11(6):775-93.
Rakin et al., The pesticin receptor of *Yersinia enterocolitica*: a novel virulence factor with dual function. Mol Microbiol. Jul. 1994;13(2):253-63.
Ratledge et al., Iron metabolism in pathogenic bacteria. Annu Rev Microbiol. 2000;54:881-941.
Register et al., Reduced virulence of a *Bordetella bronchiseptica* siderophore mutant in neonatal swine. Infect Immun. Apr. 2001;69(4):2137-43.
Reist et al., Pyrrolidine sugars. Synthesis of 4'-acetamidoadenosine and other derivatives of 4-amino-4-deoxy-D-ribose. J Org Chem. 1966;31:4025-30.
Rengaraju et al., 5'-(9-Sulfamoyladenosine (defluoronucleocidin) from a Streptomyces. Meiji Seika Kenkyu Nenpo. 1986:49-55.
Reshetnikova et al., Crystal structures of phenylalanyl-tRNA synthetase complexed with phenylalanine and a phenylalanyl-adenylate analogue. J Mol Biol. Apr. 2, 1999;287(3):555-68.

(56) References Cited

OTHER PUBLICATIONS

Robins et al., Biomimetic simulation of free radical-initiated cascade reactions postulated to occur at the active site of ribonucleotide reductases. J Am Chem Soc. 1999;121:1425-33.

Robins et al., Nucleic acid-related compounds. 88. Efficient conversion of ribonucleosides into their 2',3'-anhydro, 2'(and 3')-deoxy, 2',3'-didehydro-2',3¹-dideoxy, and 2'3'-dideoxynucleoside analogs. J Org Chem. 1995;60:7902-8.

Rusnak et al., Subcloning, expression, and purification of the enterobactin biosynthetic enzyme 2,3-dihydroxybenzoate-AMP ligase: demonstration of enzyme-bound (2,3-dihydroxybenzoyl)adenylate product. Biochemistry. Aug. 22, 1989;28(17):6827-35.

Russo et al., Crystal structure of the p27Kip1 cyclin-dependent-kinase inhibitor bound to the cyclin A-Cdk2 complex. Nature. Jul. 25, 1996;382(6589):325-31.

Saito et al., Chemical Synthesis of $^{13}C$-labeled anit-HIV nucleosides as mass-internal standards. Tetrahedron. 2002;58:9593-9603.

Sáchez-Céspedes et al., Clonal dissemination of *Yersinia enterocolitica* strains with various susceptibilities to nalidixic acid. J Clin Microbiol. Apr. 2003;41(4):1769-71.

Santi et al., Kinetics of aminoacyl-tRNA synthetases catalyzed ATP-PPi exchange. Methods Enzymol. 1974;29(0):620-7.

Sassetti et al., Genes required for mycobacterial growth defined by high density mutagenesis. Mol Microbiol. Apr. 2003;48(1):77-84.

Sassetti et al., Genetic requirements for mycobacterial survival during infection. Proc Natl Acad Sci U S A. Oct. 28, 2003;100(22):12989-94. Epub Oct. 20, 2003.

Sayyed et al., Asymmetric synthesis of L-DOPA and (*R*)-selegiline via, $OsO_4$ catalyzed asymmetric dihydroxylation. Tetrahedron: Asym. 2004;75:3111-6.

Schimmel et al., Aminoacyl tRNA synthetases as targets for new anti-infectives. FASEB J. Dec. 1998;12(15):1599-609.

Shuman et al., The synthesis of adenine 5'-O-sulfamoyl nucleosides related to nucleocidin. J Am Chem Soc. Jun. 4, 1969;91(12):3391-2.

Schnur et al., Improved glucose tolerance in rats treated with oxazolidinediones. J Med Chem. May 1986;29(5):770-8.

Searle et al., The cost of conformational order: Entropy changes in molecular associations. J Am Chem Soc. 1992;114:10690-7.

Shuman et al., The synthesis of adenine 5'-O-sulfamoyl nucleosides related to nucleocidin. J. Am. Chem Soc. Jun. 4, 1969;91(12):3391-2.

Sikkema et al., Resistance to pesticin, storage of iron, and invasion of HeLa cells by Yersiniae. Infect Immun. Mar. 1987;55(3):572-8.

Smith, *Mycobacterium tuberculosis* pathogenesis and molecular determinants of virulence. Clin Microbiol Rev. Jul. 2003;16(3):463-96.

Snider et al., Total synthesis of (−)-salicylihalamide A. Org Lett. Jun. 14, 2001;3(12):1817-20.

Snow et al., Chemical and biological properties of mycobactins isolated from various mycobacteria. Biochem J. Dec. 1969;115(5):1031-45.

Sokol et al., Role of ornibactin biosynthesis in the virulence of *Burkholderia cepacia*: characterization of pvdA, the gene encoding L-ornithine N(5)-oxygenase. Infect Immun. Sep. 1999;67(9):4443-55.

Somu et al., Rationally designed nucleoside antibiotics that inhibit siderophore biosynthesis of *Mycobacterium tuberculosis*. J Med Chem. Jan. 12, 2006;49(1):31-4.

Stachelhaus et al., Modular structure of peptide synthetases revealed by dissection of the multifunctional enzyme GrsA. J Biol Chem. Mar. 17, 1995;270(11):6163-9.

Stocks et al., Macrocyclic ring closures employing the intramolecular Heck reaction. Tetrahedron Lett. 1995;36:6555-8.

Suo et al., Tandem heterocyclization activity of the multidomain 230 kDa HMWP2 subunit of *Yersinia pestis* yersiniabactin synthetase: interaction of the 1-1382 and 1383-2035 fragments. Biochemistry. Oct. 19, 1999;38(42):14023-35.

Tavio et al., Mechanisms involved in the development of resistance to fluoroquinolones in *Escherichia coli* isolates. J Antimicrob Chemother. Dec. 1999;44(6):735-42.

Tibshirani et al., Diagnosis of multiple cancer types by shrunken centroids of gene expression. Proc Natl Acad Sci U S A. May 14, 2002;99(10):6567-72.

Tsunoda et al., Mitsunobu-type alkylation of p-toluenesulfonamide. A convenient new route to primary and secondary amines. Tetrahedron Lett. 1996;37:2457-8.

Vannada et al., Design, synthesis, and biological evaluation of beta-ketosulfonamide adenylation inhibitors as potential antitubercular agents. Org Lett. Oct. 12, 2006;8(21):4707-10.

Veber et al., Molecular properties that influence the oral bioavailability of drug candidates. J Med Chem. Jun. 6, 2002;45(12):2615-23.

Vergne et al., Iron chelators from mycobacteria (1954-1999) and potential therapeutic applications. Nat Prod Rep. Feb. 2000;17(1):99-116.

Vickers et al., Nucleoside transporter protein: Emerging targets for drug discovery. Emerg Therapeut Targets. 2000;4:515-39.

Visser et al., Importance of the ornibactin and pyochelin siderophore transport systems in *Burkholderia cenocepacia* lung infections. Infect Immun. May 2004;72(5):2850-7.

Vrudhula et al., Approaches to isozyme-specific inhibitors. 16. A novel methyl-C5' covalent adduct of L-ethionine and beta,gamma-imido-ATP as a potent multisubstrate inhibitor of rat methionine adenosyltransferases. J Med Chem. Apr. 1989;32(4):885-90.

Walsh, Titanium-catalyzed enantioselective additions of alkyl groups to aldehydes: mechanistic studies and new concepts in asymmetric catalysis. Acc Chem Res. Oct. 2003;36(10):739-49.

Walton et al., Indole and 4-aminoindole nucleosides. J Org Chem. Jan. 1968;33(1):192-7.

Wang et al., Chiral synthesis of carbocyclic analogues of L-ribofuranosides. J Org Chem. 1999;64:4173-8.

Wanger et al., Testing of *Mycobacterium tuberculosis* susceptibility to ethambutol, isoniazid, rifampin, and streptomycin by using Etest. J Clin Microbiol. Jul. 1996;34(7):1672-6.

Wayne et al., Nonreplicating persistence of *Mycobacterium tuberculosis*. Annu Rev Microbiol. 2001;55:139-63.

Ward et al., Using small molecules to study big questions in cellular microbiology. Cell Microbiol. Aug. 2002;4(8):471-82.

Weinberg, The development of awareness of iron-withholding defense. Perspect Biol Med. 1993 Winter;36(2):215-21.

Weinreb et al., Stoichiometry and specificity of in vitro phosphopantetheinylation and aminoacylation of the valine-activating module of surfactin synthetase. Biochemistry. Feb. 10, 1998;37(6):1575-84.

Wissing et al., Chemical proteomic analysis reveals alternative modes of action for pyrido[2,3-d]pyrimidine kinase inhibitors. Mol Cell Proteomics. Dec. 2004;3(12):1181-93. Epub Oct. 8, 2004.

Wnuk et al., Nucleic acid related compounds. 63. Synthesis of 5'deoxy-5'-methyleneadenosine and related Wittig-extended nucleosides. Can J Chem. 1991;69:334-8.

Wong et al., Susceptibilities of *Yersinia pestis* strains to 12 antimicrobial agents. Antimicrob Agents Chemother. Jul. 2000;44(7):1995-6.

Wooldridge et al., Iron uptake mechanisms of pathogenic bacteria. FEMS Microbiol Rev. Nov. 1993;12(4):325-48.

Xu et al., Three-dimensional structure of the tyrosine kinase c-Src. Nature. Feb. 13, 1997;385(6617):595-602.

Yang et al., Preparation of carbocyclic S-adenosylazamethionine accompanied by a practical synthesis of (−)-aristeromycin. J Org Chem. May 28, 2004;69(11):3993-6.

Zhang et al., Role of acid pH and deficient efflux of pyrazinoic acid in unique susceptibility of *Mycobacterium tuberculosis* to pyrazinamide. J Bacteriol. Apr. 1999;181(7):2044-9.

Zhu et al., Facile and highly selective 5'-desilylation of multisilylated nucleosides. J Chem Soc, Perkin Trans 1. 2000:2305-6.

\* cited by examiner

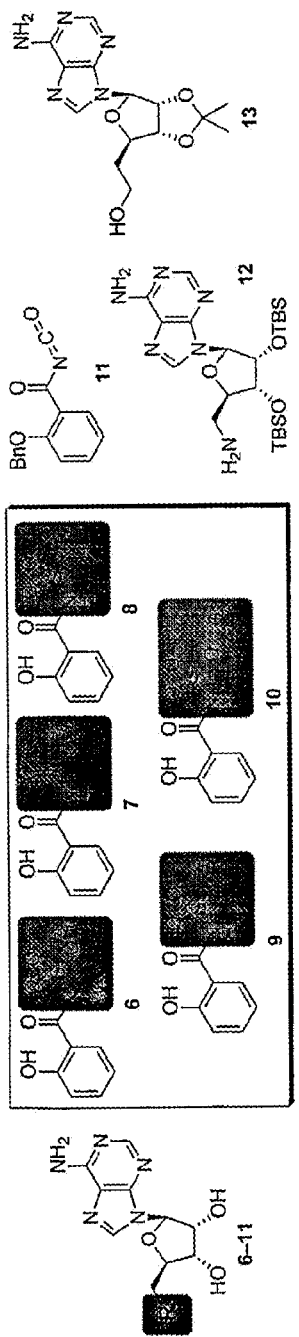
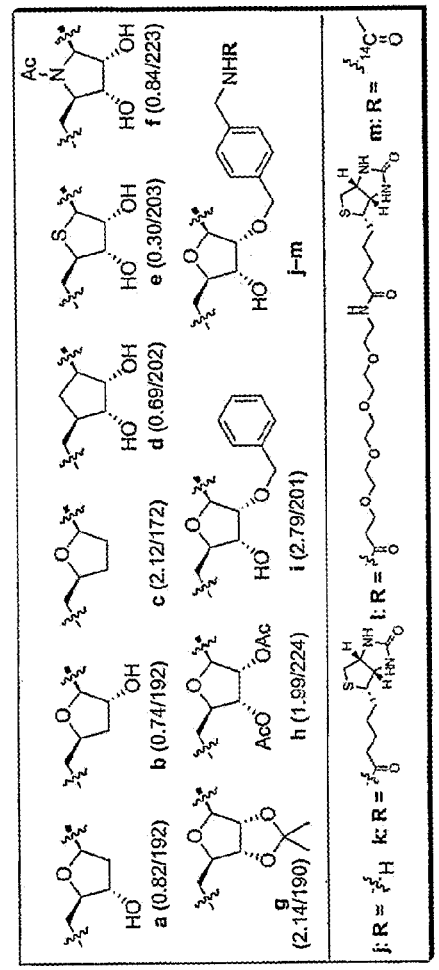
Figure 8
Figure 9
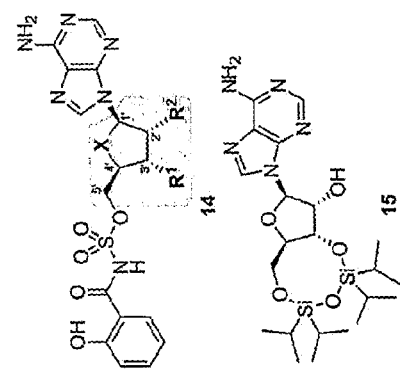

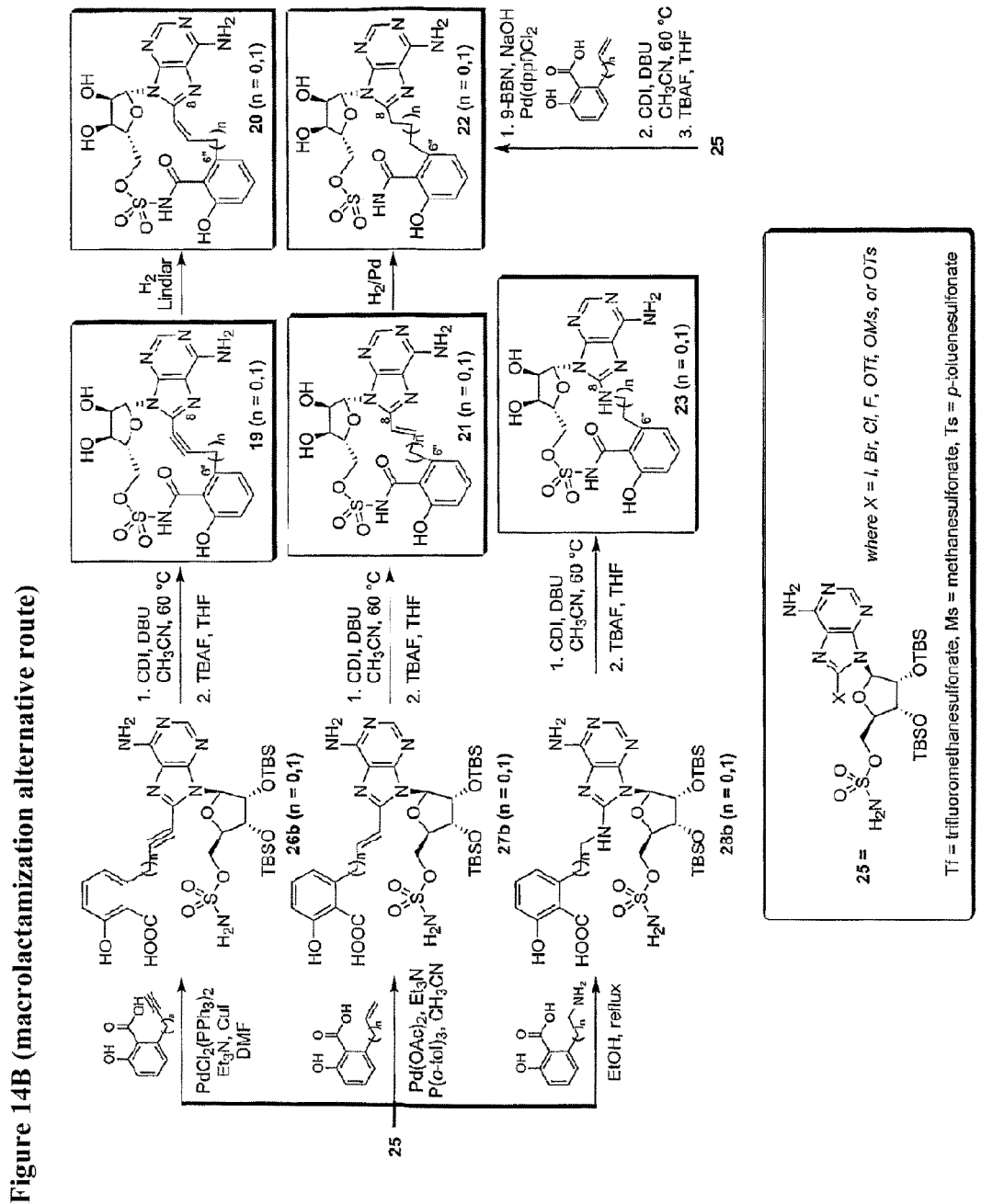
Figure 14B (macrolactamization alternative route)

Synthesis of Hexynyl Sulfonamide Adenosine

A, B, C

D, E, F

ANTI-MICROBIAL AGENTS AND USES THEREOF

RELATED APPLICATIONS

This application is a divisional of and claims priority under 35 USC. §120 to U.S. patent application, U.S. Ser. No. 11/911,525, filed Nov. 17, 2008, which claims priority to and is a national stage filing under 35 USC. §371 of international PCT application, PCT/US2006/014394, filed Apr. 14, 2006, which claims priority under 35 USC. §119(e) to U.S. provisional patent application, U.S. Ser. No. 60/671,994, filed Apr. 15, 2005, each of which is incorporated herein by reference.

GOVERNMENT SUPPORT

The work described herein was supported, in part, by a grant from the National Institutes of Health (P01AI056293, R21 AI063384-01, R21 AI063384-01). The United States government may have certain rights in the invention.

BACKGROUND OF THE INVENTION

Aryl-capped iron-chelating siderophores assist various pathogens in acquiring iron inside their mammalian host, where iron is tightly chelated. The siderophores are essential for infection. In particular, siderophores are essential for infection by *Mycobacterium tuberculosis*, the causative agent for tuberculosis (de Voss et al. *Proc. Natl., Acad. Sci. USA* 97:1252-57, 2000; incorporated herein by reference), and *Yersinia pestis*, the etiological agent of the plague (de Almeid et al. *Microb. Pathog.* 14:9-21, 1993; Bearden et al. *Infect. Immun.* 65:1659-1668, 1997; each of which is incorporated herein by reference). Other pathogens which depend on siderophore-based iron acquisition systems include *Yersinia enterolitica, Pseudomonas aeruginosa, Bacillus anthracis, Vibrio vulnificus, Yersinia ruckeri, Brucella abortus, Burkholderia cepacia, Burkholderia cenocepacia, Bordetella bronchiseptica, Acinebacter calcoaceticus, Escherichia coli, Salmonella enterica, Shigella* spp., and *Vibrio cholerae* (Litwin et al., *Infect. Immun.* 64:2834-38, 1996; Bellaire et al., *Infect. Immun.* 71:1794-803, 2003; Boschiroli et al., *Curr. Opin. Microbiol.* 4:58-64, 2001; Sokol et al., *Infect. Immun.* 67:4443-55, 1999; Register et al., *Infect. Immun.* 69:2137-43, 2001; each of which is incorporated herein by reference). Inside their hosts, iron is relatively abundant but is tightly bound to intracellular and extracellular components (Weinberg, *Perspect. Biol. Med.* 36:215-221, 1993; incorporated herein by reference). The pathogenic bacteria synthesize siderophores to acquire Fe(III) from their hosts (Wooldridge and Williams, *FEMS Microbiol. Rev.* 12:325-348, 1993; incorporated herein by reference). Siderophore biosynthesis is, therefore, an attractive target for the development of new antibiotics to treat tuberculosis, plague, and other infection caused by microorganisms that depend on siderophore (e.g. *Pseudomonas aeruginosa*).

The two siderophore families produced by *M. tuberculosis*, the cell-associated and soluble mycobactins (MBTs) (Quadri et al. in *Tuberculosis and Tubercle Bacillus* (eds. Cole et al.) 341-57 (ASM Press, Washington, D.C., 2004); incorporated herein by reference), and the *Y. pestis* siderophore, yersiniabactin (YBT) (Perry et al. *Microbiology* 145:1181-90, 1999; incorporated herein by reference), have salicyl-capped non-ribosomal peptide-polyketide hybrid scaffold (FIG. 1A). *Yersinia enterocolitica, Pseudomonas aeruginosa, Acinebacter calcoaceticus*, and *A. baumannii* also produce phenolic siderophores (also known as "salicyl-capped siderophores"). Other pathogens such as *E. coli, Salmonella enterica, Shigella* spp., and *Vibrio cholerae* produce closely related catechol-containing siderophores such as vibriobactin, anguibactin, and enterobactin (FIG. 1A). Siderophore biosynthetic pathways have undergone extensive investigations (Quadri, *Mol. Microbiol.* 37:1-12, 2000; Crosa et al. *Microbiol. Mol. Biol. Rev.* 66:223-49, 2002; each of which is incorporated herein by reference). During the biosyntheses of MBTs, YBT, and other phenolic siderophores, domain salicylation enzymes, such as MbtA and YbtE respectively, catalyze the salicylation of an aroyl carrier protein (ArCP) domain to form a salicyl-ArCP domain thioester intermediate via a two-step reaction (FIG. 1B) (Quadri et al. *Chem. Biol.* 5:631-45, 1998; Gehring et al. *Biochemistry* 37:11637-11650, 1998; each of which is incorporated herein by reference). The first step is ATP-dependent adenylation of salicylate to generate a salicyl-AMP intermediate (FIG. 1C), which remains non-covalently bound to the active site. The second step is the transesterification of the salicyl moiety onto the thiol of the phosphopantetheinyl prosthetic group of the ArCP domain (Quadri et al. *Chem. Biol.* 5:631-45, 1998; Gehring et al. *Biochemistry* 37:11637-11650, 1998; each of which is incorporated herein by reference). Since MbtA and YbtE have no homologs in humans, they are particularly attractive targets for the development of novel antibiotics that inhibit siderophore biosynthesis. Related 2,3-dihydroxybenzoate adenylation enzymes are involved in the biosynthesis of catechol-containing siderophores (also known as "2,3-dihydroxybenzoate-capped siderophores"). Other mechanistically related adenylate-forming enzymes have been shown to bind their cognate acyl-AMP intermediates 2-3 orders of magnitude more tightly than their carboxylic acid and ATP substrates (Kim et al. *Appl. Microbiol. Biotechnol.* 61:278-88, 2003; incorporated herein by reference). Among these are the acyl sulfamoyl adenosines (acyl-AMS) (Kim et al. *Appl. Microbiol. Biotechnol.* 61:278-88, 2003; Finking et al. *ChemBioChem* 4:903-906, 2003; each of which is incorporated herein by reference), inspired by the natural products, nucleodin (4), ascamycin (5), and AT-265 (6) (FIG. 1C).

Mechanism-based inhibitors of salicylation enzymes could be used to treat infection such as tuberculosis and the plague by inhibiting the salicylate adenylation activity of YbtE and MbtA. These compounds may also be useful in treating other infections caused by organisms which rely of siderophore-based iron acquisition systems. Therefore, inhibitors of salicylate adenylation enzymes would provide a new mechanism of action in combating infections, particularly ones caused by drug-resistant organisms.

SUMMARY OF THE INVENTION

The invention provides a system for treating infections. The compounds of the invention are inhibitors of the salicylate adenylation enzymes involved in the biosynthesis of salicyl-containing siderophores. Siderphores are natural products required for the growth of certain pathogenic bacteria in environments with low iron concentrations (e.g., in the human host). The compounds are generally of the formula:

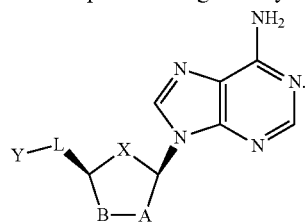

Other natural and non-natural bases besides adenine may be used in the inventive compounds. In addition, heterocyclic and carbocyclic ring systems may replace the adenine ring system. In certain embodiments, the five-membered ring is a ribose ring. In other embodiments, the five-membered ring is an arabinose, xylose, or lyxose ring. These compounds are related to the intermediate mimic 5'—O—[N-(salicyl)sulfamoyl]-adenosine (salicyl-AMS), which has the formula:

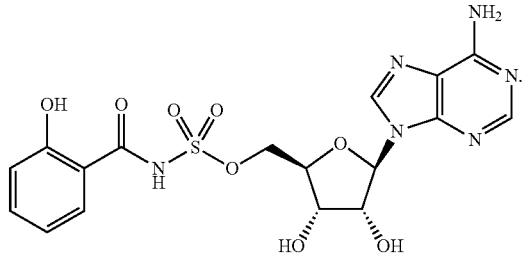 [SMILES: Nc1ncnc2c1ncn2[C@@H]1O[C@H](COS(=O)(=O)NC(=O)c2ccccc2O)[C@@H](O)[C@H]1O]

These compounds are preferably potent inhibitors of the salicylate adenylation activity of the domain salicylation enzymes such as MbtA (from *M. tuberculosis*), YbtE (from *Y. pestis*), and/or PchD (from *Pseudomonas aeruginosa*). In certain embodiments, the compounds are inhibitors of 2,3-dihydroxybenzoate adenylation enzymes such as DhbE. In other embodiments, the compounds are inhibitors of 3,4-dihydroxybenzoate adenylation enzymes (e.g., those found in *Bacillus anthracis* which produce anthrachelin, a catecholic siderophore) (Cendrowski et al., *Mol. Microbiol.* 51:407-17, 2004; Koppisch et al., *Biometals.* 18(6):577-85, 2005; each of which is incorporated herein by reference). In certain embodiments, the compounds are inhibitors of catechol siderophore synthesis in *Vibrio vulnificus, Yersinia ruckeri*, and *Brucella abortus* (Litwin et al. *Infect. Immun.* 64:2834-38, 1996; Fernandez et al. *Appl. Environ. Microbiol.* 70(9):5199-207, 2004; Bellaire et al., *Infect. Immun.* 71:1794-803, 2003; Boschiroli et al., *Curr. Opin. Microbiol.* 4:58-64, 2001; each of which is incorporated herein by reference).

In certain embodiments, the compounds are of the formula:

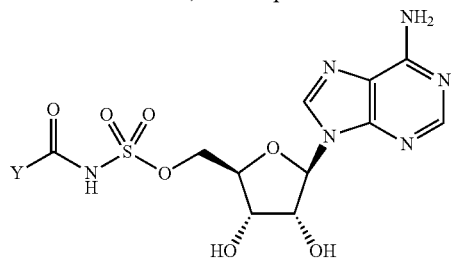

wherein the linker comprises a non-hydrolyzable acyl sulfamoyl group.

In certain other embodiments, the compounds are macrocylic compounds of the general formula:

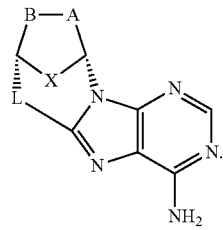

These compounds preferably adopt the conformation of the natural substrate bound to salicylate adenylation or 2,3-dihydroxybenzoate adenylation enzymes. In certain embodiments, this conformation is "cisoid" about the phospho-ribosyl backbone.

The invention also provides pharmaceutical compositions in which an inventive compound is mixed with a pharmaceutically acceptable excipient for administration to a subject. In certain embodiments, the pharmaceutical composition is used to treat a infection. The infection may be caused by any organism that possess salicylation enzymes The infection may also be caused by any organim that relies on a siderophore (e.g., a phenolic siderophore, a catecholic siderophore) for virulence. In certain embodiments, the causative microorganism is *M. tuberculosis, Y. pestis*, or *P. aeruginosa*. In other embodiments, the causative microorganism is *Bacillus anthracis, Vibrio vulnificus, Yersinia ruckeri*, or *Brucella abortus*. The compositions preferably contain a therapeutically effective amount of the compound necessary to inhibit the growth of the organism or kill the organism. The composition may provide the compound in amounts for multiple doses per day or a single dose per day for 5 days, 7 days, 10 days, 14 days, 28 days, 8 weeks, 6 months, 8 months, 1 year, or longer. For example, in the case of *M. tuberculosis* infection treatment may require treatment for 6-12 months or longer. The pharmaceutical composition may also be used for prophylaxing an individual who may become exposed to a pathogenic microorganism having salicylation enzymes. In certain embodiments, the pharmaceutical composition also includes another antibiotic to provide for combination therapy.

The invention in another aspect provides a method of treating an infection in a subject. The method comprises the steps of administering an inventive compound to a subject using any route; however, oral administration of the compound or a pharmaceutical composition thereof is preferable. A therapeutically acceptable amount of the compound is administered so that growth of the organism is inhibited or the organism is killed. Without wishing to be bound by any particular theory, the compound may inhibit the growth of the microorganism by inhibiting the biosynthesis of siderophores by the organism, thereby limiting the iron available to the organism.

The invention provides a method of preparing the inventive compounds. In one embodiment, the synthesis begins with the protection of the secondary hydroxyl groups of the nucleoside adenosine. The 5'-hydroxyl group of adenosine is then sulfamoylated to provide sulfamoyl adenosine. Activated salicylate or other acyl group is then coupled to the sulfamate amino group of sulfamoyl adenosine to yield the inventive compounds. The compound may be optionally purified. In certain embodiments, the compound is prepared as one enantiomer. In other embodiments, the compound is prepared as a racemate or mixture of diastereomers.

The invention also provides for a system for assaying the inventive compounds. The compounds of the invention may be assayed for activity by contacting the test compound with an enzyme with salicylate adenylation activity and then determining the inhibition or binding affinity. In certain embodiments the enzyme is YbtE, MbtA, or PchD. In certain embodiments, multiple salicylate adenylation enzymes are tested using the same test compound. These assays may be cell-based assays. The assay may also be an in vitro biochemical assay using purified or partially purified enzyme. The system includes the proteins, polynucleotides, substrates, buffers, cells, etc. necessary for practicing the inventive assay.

Definitions

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl) diphenylmethyl, 4,4',4"-tris(4,5-dichlorophthalimidophenyl) methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkoxy", or "thioalkyl" as used herein refers to an alkyl group, as previously defined, attached to the parent molecule through an oxygen atom or through a sulfur atom. In certain embodiments, the alkyl, alkenyl, and alkynyl groups contain 1-20 alipahtic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limted to, aziridinyl, pyrrolidinyl, piperidinyl, morpholinyl, pyrrolyl, imidazolyl, 1,3,4-trianolyl, and tetrazolyl.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CON(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

"Carbocycle": The term "carbocycle", as used herein, refers to an aromatic or non-aromatic ring in which each atom of the ring is a carbon atom.

"Independently selected": The term "independently selected" is used herein to indicate that the R groups can be identical or different.

"Labeled": As used herein, the term "labeled" is intended to mean that a compound has at least one element, isotope, or chemical compound attached to enable the detection of the compound. In general, labels typically fall into three classes: a) isotopic labels, which may be radioactive or heavy isotopes, including, but not limited to, $^2$H, $^3$H, $^{32}$P, $^{35}$S, $^{67}$Ga, $^{99m}$Tc (Tc-99m), $^{111}$In, $^{123}$I, $^{125}$I, $^{169}$Yb and $^{186}$Re; b) immune labels, which may be antibodies or antigens, which may be bound to enzymes (such as horseradish peroxidase) that produce detectable agents; and c) colored, luminescent, phosphorescent, or fluorescent dyes. It will be appreciated that the labels may be incorporated into the compound at any position that does not interfere with the biological activity or characteristic of the compound that is being detected. In certain embodiments, hydrogen atoms in the compound are replaced with deuterium atoms ($^2$H) to slow the degradation of compound in vivo. Due to isotope effects, enzymatic degradation of the deuterated tetracyclines may be slowed thereby increasing the half-life of the compound in vivo. In certain embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (See, Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

"Tautomers": As used herein, the term "tautomers" are particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridione-hydroxypyridine forms.

Definitions of non-chemical terms used throughout the specification include:

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

"Effective amount": In general, the "effective amount" of an active agent refers to the amount necessary to elicit the desired biological response. As will be appreciated by those of ordinary skill in this art, the effective amount of a compound may vary depending on such factors as the desired biological endpoint, the compounds to be delivered, the disease or condition being treated, etc. In certain embodiments, the effective amount of the compound is enough to achieve a bacteriocidal or bacteriostatic concentration of the compound at the site of the infection.

"Peptide" or "protein": According to the present invention, a "peptide" or "protein" comprises a string of at least three amino acids linked together by peptide bonds. The terms "protein" and "peptide" may be used interchangeably. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification (e.g., alpha amindation), etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. In certain embodiments, the modifications of the peptide lead to a more biologically active peptide.

BRIEF DESCRIPTION OF THE DRAWING

FIG. 8 shows the structures of salicyl-AMS analogs (8-10) to probe structure-activity relationships in the sulfamate region and key synthetic intermediates (11-13).

FIG. 9 shows the structures of salicyl-AMS analogs (14a-i) to probe SAR in the ribose region, affinity- and radiolabeled analogs (14k-m), and key synthetic intermediates (14j, 15). cLogP (ChemDraw/Biobyte) and calculated polar surface area (Ertl et al. *J. Med. Chem.* 43:3714-17, 2000; incorporated herein by reference) (MolInspiration) values are indicated in parentheses for comparison to salicyl-AMS (0.29/212).

FIG. 24 demonstrates the stability of salicyl-AMS in a variety of media. The stability of salicyl-AMS is shown in water (A), in *Y. pestis* culture media (PMH-D) (B), and in *M.* tuberculosis culture media (GAST-D) (C) for 3, 24, and 58 hours at 37° C. The stability of salicyl-AMS is also shown in *Y. pestis* lysates (grown to late log phase $OD_{620}$=0.93, lysed in spent broth via French press and sonication, centrifuged 3000 rpm×10 min.; total protein concentration=110 mg/mL) (D); in *Y. pestis* filter sterilized lysates (as above followed by filtration; total protein concentration=12.4 mg/mL) (E); and in mammalian cell sulture media (DMEM, 10% FCS) (F) for 1, 3, 8, and 24 hours at 37° C. In this stability study, salicyl-AMS-$d_4$ was added as an interal standard at the given time, proteins were precipitated with 1.5 volumes of $CH_3CN$, and samples of the supernatant were analyzed by LC-MS-MS. No degradation of salicyl-AMS was observed under any of the conditions tested.

Figure 25:
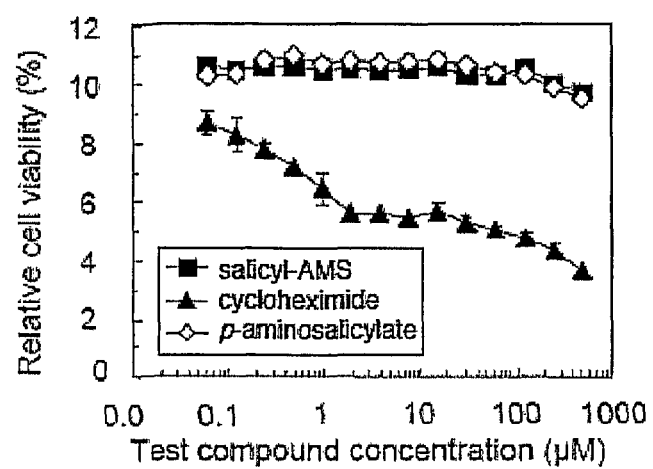

FIG. 25 demonstrates the acceptably low cytotoxicity of salicyl-AMS against mammalian cells as compared to the antituberculosis drug PAS (p-aminosalicylate) and the cytotoxic compound cycloheximide.

DETAILED DESCRIPTION OF CERTAIN PREFERRED EMBODIMENTS OF THE INVENTION

The invention provides compounds useful in the treatment of infections. These compounds act by inhibiting enzymes in the biosynthesis of salicyl-containing siderophores. Siderophores are typically used by certain bacteria to scavenge iron (Fe(III)) from the host. The enzymes inhibited are salicylate adenylation enzymes, which include MbtA (from *Mycobacterium tuberculosis*), YbtE (from *Yersinia pestis*), and PchD (from *Pseudomonas aeruginosa*). Certain of the compounds are particularly useful in treating *Mycobacterium tuberculosis* infection and *Yersinia pestis* infection (the plague). Certain compounds are also useful in treating other infectious diseases. Particularly useful compounds are those which are effective in killing or inhibiting the growth of antibiotic-resistant organisms (e.g., isoniazid-resistant *M. tuberculosis* or rifampin-resistant *M. tuberculosis*). The invention also provides pharmaceutical compositions and methods of treating a subject using the inventive compounds. Methods of preparing the compounds are also provided as well as methods of assaying the compounds for anti-microbial activity.

Compounds

The inventive compounds are analogs of adenosine monophosphate (AMP). In certain embodiments, the compounds are non-hydrolyzable acyl-AMP analogs which have been shown to be mechanism-based inhibitors of adenylate-forming enzymes. Compounds of the invention are of the general formula:

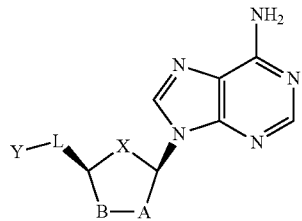

wherein X is O, S, —$CH_2$—, NH, or N-Ac;

A-B is —$(R_A)_2C$—$C(R_B)_2$— or —$R_AC$=$CR_B$—, wherein each occurrence of $R_A$ and $R_B$ is independently hydrogen, halogen, cyano, azido, hydroxyl, sulfhydryl, alkoxy, amino, alkylamino, dialkylamino; cyclic or acyclic, unsubstituted or substituted, branched or unbranched, aliphatic; cyclic or acyclic, unsubstituted or substituted, branched or unbranched heteroaliphatic; substituted or unsubstituted, branched or unbranched acyl; substituted or unsubstituted, branched or unbranched aryl; substituted or unsubstituted, branched or unbranched heteroaryl;

L is a substituted or unsubstituted, branched or unbranched, cyclic or acyclic aliphatic group; substituted or unsubstituted, branched or unbranched acyl; or substituted or unsubstituted, branched or unbranched, cyclic or acyclic heteroaliphatic group; and Y is absent or selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_Y$; —$C(=O)R_Y$; —$CO_2R_Y$; —CN; —SCN; —$SR_Y$; —$SOR_Y$; —$SO_2R_Y$; —$NO_2$; —$N_3$; —$N(R_Y)_2$; —$NHC(=O)R_Y$; —$NR_YC(=O)N(R_Y)_2$; —$OC(=O)OR_Y$; —$OC(=O)R_Y$; —$OC(=O)N(R_Y)_2$; —$NR_YC(=O)OR_Y$; or —$C(R_Y)_3$; wherein each occurrence of $R_Y$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety.

In certain preferred embodiments, X is oxygen. In other embodiments, X is sulfur. In yet other embodiments, X is —$CH_2$—. In still further embodiments, X is NH or NR, wherein R is acyl (e.g., acetyl) or $C_1$-$C_6$ alkyl.

In certain embodiments, A-B is —$(R_A)_2C$—$C(R_B)_2$— or —$R_AC$=$CR_B$—, wherein each occurrence of $R_A$ and $R_B$ is independently hydrogen, halogen, cyano, azido, hydroxyl, protected hydroxyl, sulfhydryl, alkoxy, amino, alkylamino, dialkylamino; cyclic or acyclic, unsubstituted or substituted, branched or unbranched aliphatic; or cyclic or acyclic, unsubstituted or substituted, branched or unbranched heteroaliphatic. In certain embodiments, A-B is —$(R_A)_2C$—$C(R_B)_2$— or —$R_AC$=$CR_B$—, wherein each occurrence of $R_A$ and $R_B$ is independently hydrogen, halogen, cyano, azido, hydroxyl, sulfhydryl, alkoxy, amino, alkylamino, dialkylamino; or $C_1$-$C_6$ alkyl group. In certain embodiments, at least one of $R_A$ and $R_B$ is —$NH_2$; —NHR'; —$N(R')_2$, or —$NR'_3^+$, wherein R' is selected from the group consisting of hydrogen; a nitrogen protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; and substituted or unsubstituted, branched or unbranched heteroaryl. In certain embodiments, at least one of $R_A$ and $R_B$ is —$NH_2$; —NHR'; —$N(R')_2$, or —$NR'_3^+$, wherein R' is selected from the group consisting of hydrogen; a nitrogen protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; and substituted or unsubstituted, branched or unbranched heteroaryl; and the other of $R_A$ and $R_B$ is hydrogen; alkoxy; —OP, wherein P is an oxygen-protecting group; or hydroxyl. In certain embodiments, at least one of $R_A$ and $R_B$ is —$NH_2$; —NHR'; —N(R')$_2$, or —NR'$_3^+$, wherein R' is hydrogen or $C_1$-$C_6$ alkyl. In certain embodiment, A-B is

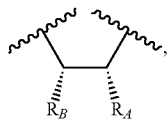

wherein each occurrence of $R_A$ and $R_B$ is independently hydrogen, halogen, cyano, azido, hydroxyl, protected hydroxyl, sulfhydryl, alkoxy, amino, alkylamino, dialkylamino; or $C_1$-$C_6$
alkyl group. In certain other embodiments, A-B is

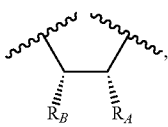

wherein $R_A$ and $R_B$ are each
independently H, —OH, or —OP, wherein each occurrence of P is independently a hydrogen or a protecting group (e.g., silicon-protecting group (e.g., TMS, TBS, TBDMS), acetyl (Ac), methyl (Me), ethyl (Et), propyl, butyl, benzyl (Bz), benzyl ester (Bn)). In certain embodiments, one of $R_A$ and $R_B$ is azido (—$N_3$). In certain embodiments, A-B is

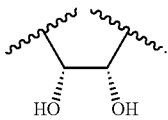

In certain embodiments, A-B is

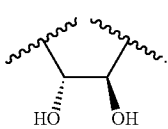

In other embodiments, A-B is

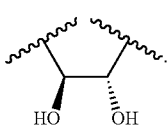

In certain embodiments, A-B is

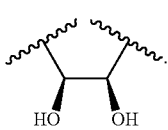

In other embodiments, A-B is

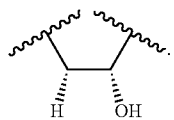

In yet other embodiments, A-B is

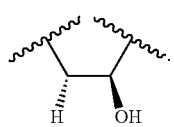

In yet other embodiments, A-B is

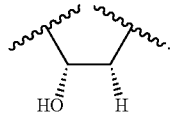

In yet other embodiments, A-B is

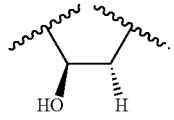

In still further embodiments, A-B is

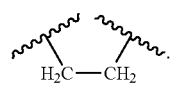

In certain embodiments, A-B is

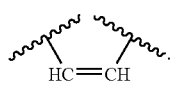

In certain embodiment, A-B is

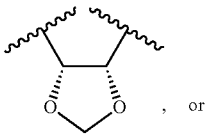

In certain other embodiments, A-B is

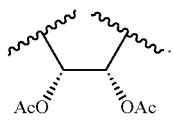

In other embodiments, A-B is

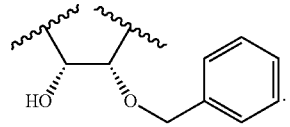 [SMILES: *[C@H](OCc1ccccc1)[C@@H](*)O]

In other embodiments, A-B is

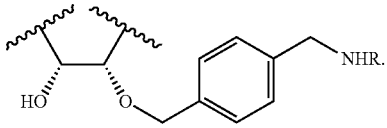

wherein R is hydrogen, acetyl, alkyl, labeled acetyl, $^{14}$C-labeled acetyl, biotin, a linker followed by biotin, or a linker attached to a solid support (for examples, see FIG. 9).

In certain embodiments, L is a substituted or unsubstituted, branched or unbranched, cyclic or acyclic aliphatic group. In other embodiments, L is a substituted or unsubstituted, branched or unbranched acyl group. In yet other embodiments, L is a substituted or unsubstituted, branched or unbranched, cyclic or acyclic heteroaliphatic group. In certain embodiments, L is acyclic. In certain particular embodiments, L is

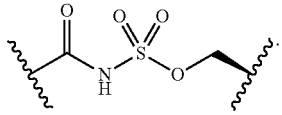

In other embodiments, L is

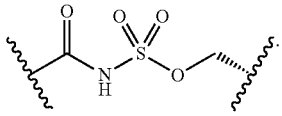

In certain other embodiments, L is

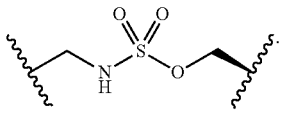

In other embodiments, L is selected from the group consisting of:

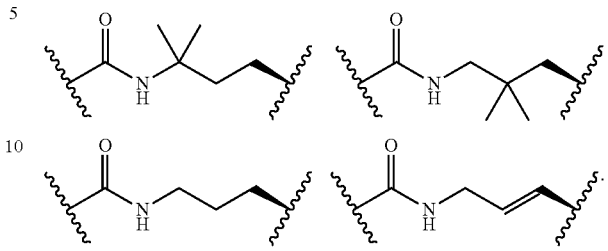

In certain other embodiments, L is selected from the group consisting of:

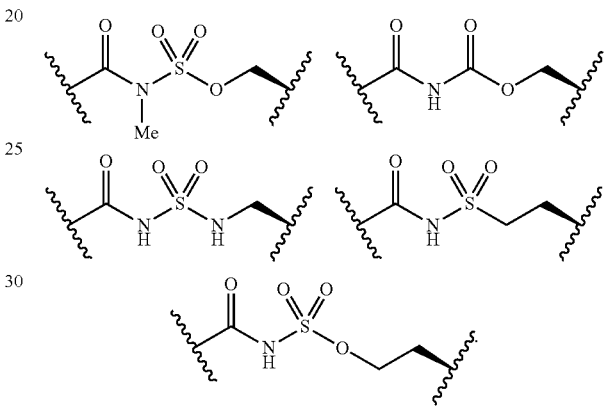

In certain other embodiments, L is selected from the group consisting of:

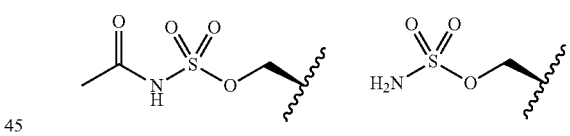

and Y is absent.

In certain embodiments, the linker L is designed to keep the molecule in a particular conformation. In certain embodiments, the linker L keeps the molecule in a "cisoid" conformation about the ribosylphosphate backbone. For example, L may include substituents on the C5' side chain such as a $C_1$-$C_6$ alkyl group; L may include a cis double bond; or L may include a carbocyclic or heterocyclic ring system such as a three-, four-, five-, or six-membered ring. In other embodiments, the linker L keeps the molecule in a "transoid" conformation about the ribosylphosphate backbone. In certain embodiments, L is selected from the group consisting:

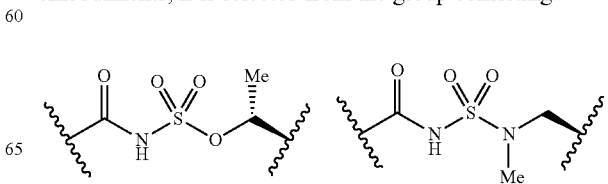

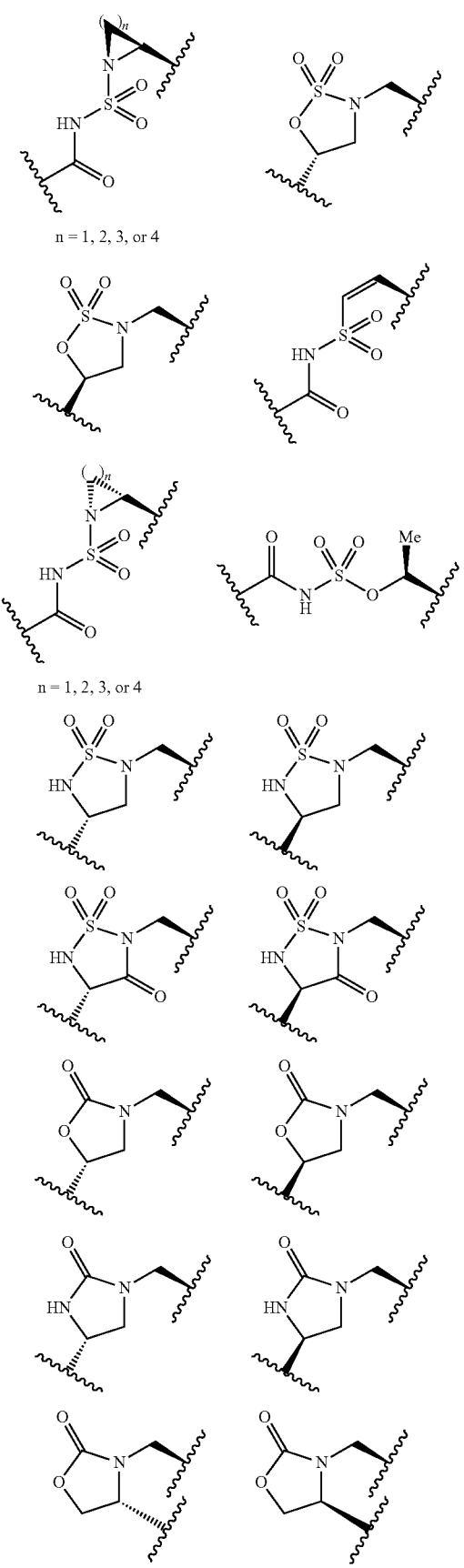

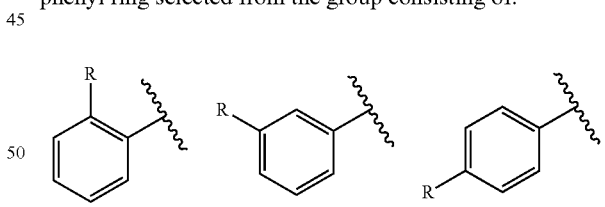

In certain embodiments, Y is a cyclic or acyclic, substituted or unsubstituted, branched or unbranched aliphatic group. In certain embodiments, Y is $C_1$-$C_6$ alkyl. In certain particular embodiments, Y is methyl. In other embodiments, Y is a cyclic or acyclic, substituted or unsubstituted, branched or unbranched heteroaliphatic group. In other embodiments, Y is a substituted or unsubstituted, branched or unbranched acyl group. In yet other embodiments, Y is a substituted or unsubstituted, branched or unbranched aryl group. In yet other embodiments, Y is a substituted or unsubstituted, branched or unbranched monocyclic aryl group. In yet other embodiments, Y is a substituted or unsubstituted, branched or unbranched bicyclic aryl group. In still further embodiments, Y is a substituted or unsubstituted, branched or unbranched heteroaryl group. In still further embodiments, Y is a substituted or unsubstituted, branched or unbranched monocylic heteroaryl group. In still further embodiments, Y is a substituted or unsubstituted, branched or unbranched bicyclic heteroaryl group. In certain embodiments, Y is a substituted or unsubstituted, aromatic or non-aromatic heterocyclic or carbocyclic monocyclic group, preferably a 5- or 6-membered ring. In certain embodiments, Y is a substituted or unsubstituted, aromatic or non-aromatic, heterocyclic or carbocyclic monocyclic group, preferably a 5- or 6-membered ring. In certain embodiments, Y is a substituted or unsubstituted, aromatic or non-aromatic heterocyclic or carbocyclic bicyclic group, preferably a 8-, 9-, 10-, 11-, or 12-membered ring system. In certain embodiments, Y is a substituted or unsubstituted, aromatic or non-aromatic, heterocyclic or carbocyclic monocylic group, preferably a 8-, 9-, 10-, 11-, or 12-membered ring system.

In certain embodiments, Y is a substituted or unsubstituted phenyl ring. In certain embodiments, Y is a mono-substituted phenyl ring selected from the group consisting of:

wherein R is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR'; —C(=O)R'; —CO$_2$R'; —CN; —N$_3$; —SCN; —SR'; —SOR'; —SO$_2$R'; —NO$_2$; —N(R')$_2$; —NHC(O)R'; or —C(R')$_3$; wherein each occurrence of R' is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, R is hydroxyl, amino, azido, protected hydroxyl, protected amino, thiol, alkoxy, lower alkyl, lower alkenyl, lower alkynyl, or halogen. In certain embodiments, R is hydroxyl, amino, thiol, methyl, trifluoromethyl, fluoro, chloro, —CH$_2$OH, —OAc, —NHAc, —NHCN, —NHSO$_2$Me, —NHCONH$_2$, —N$_3$, or —CH(CN)$_2$. In certain embodiments, R is —OH. In certain embodiments, R is —N$_3$. One or more R groups may together form a cyclic group, which may be carbocyclic or heterocyclic, or aromatic or non-aromatic. In certain embodiments, the R groups on adjacent carbons form an epoxide, aziridine, or cyclopropyl ring. In certain embodiments, Y is

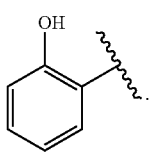 [SMILES: *c1ccccc1O]

Exemplary compounds of this class include:

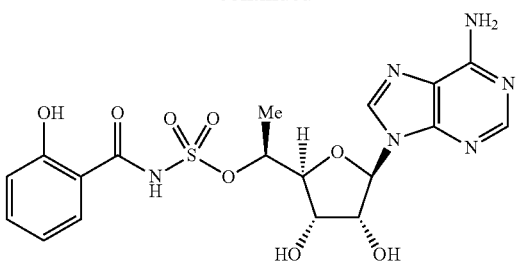

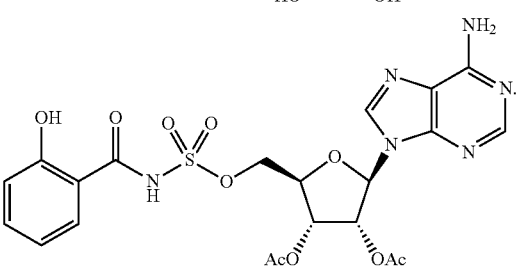

In certain embodiments, Y is a disubstituted phenyl ring selected from the group consisting of:

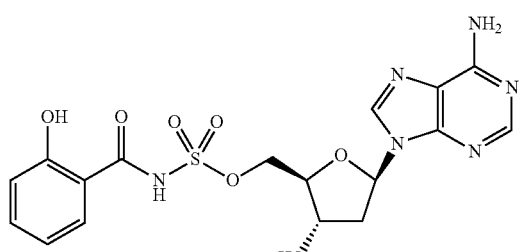

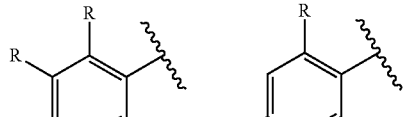

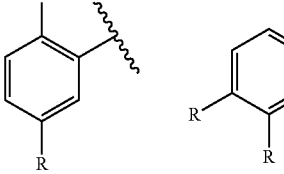
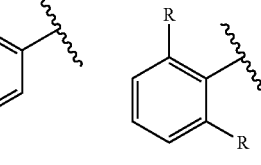

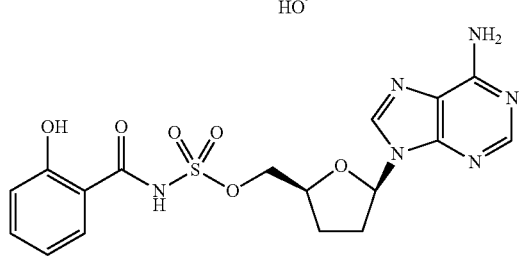

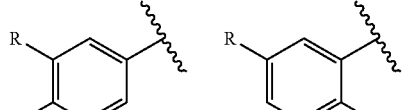

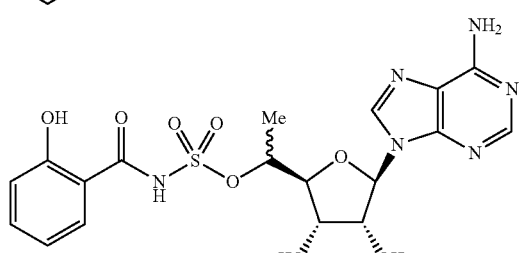

wherein R is as defined above. In certain embodiments, Y is

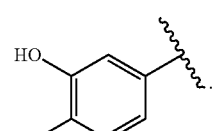

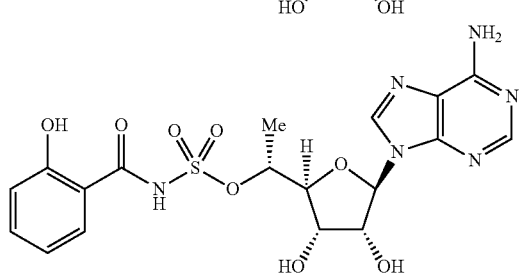

In certain embodiments, Y is selected from the group consisting of:

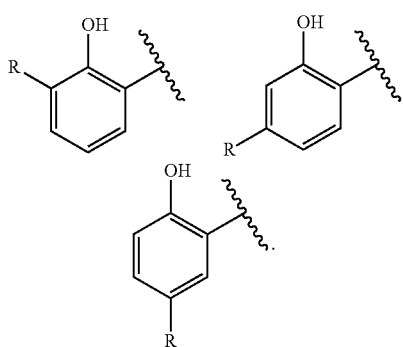

In certain embodiments, Y is

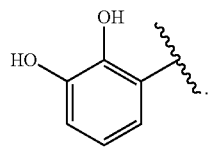

In other embodiments, Y is a trisubstituted phenyl ring selected from the group consisting of:

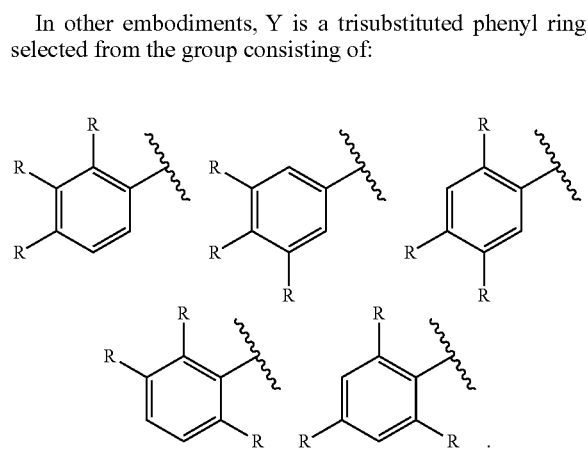

wherein R is as defined above.

In certain embodiments, Y is a substituted or unsubstituted heterocyclic group. Examples of possible heterocyclic groups include:

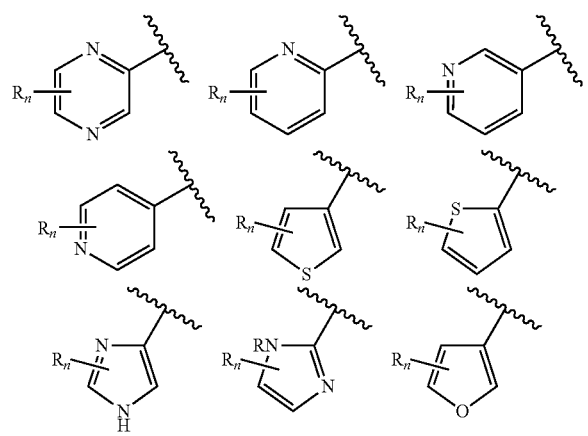

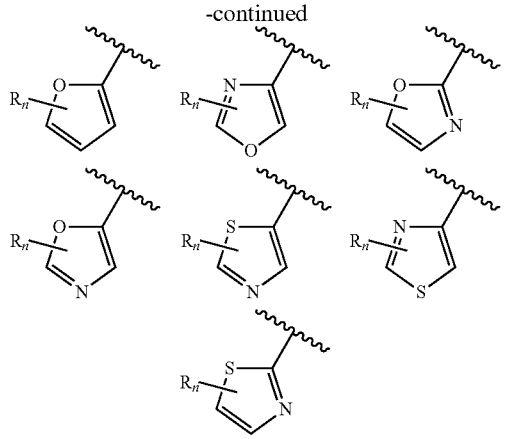

wherein R is as defined above, and n is an integer ranging from 0 to 4, inclusive.

In certain embodiments, Y is a substituted or unsubstituted bicyclic ring system:

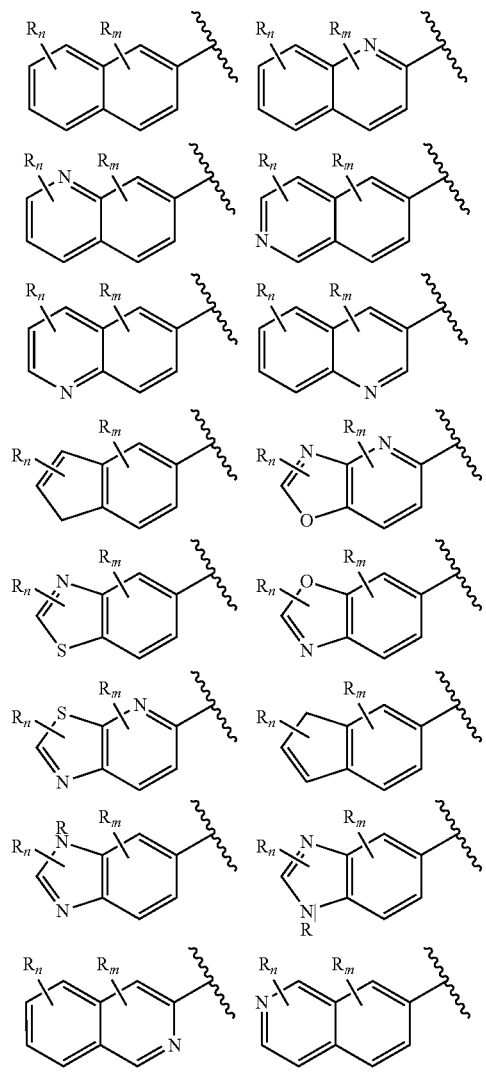

wherein R is as defined above; n is an integer ranging from 0 to 4, inclusive; and m is an integer ranging from 0 to 3, inclusive.

In certain embodiments, Y is a non-aromatic ring system. In certain embodiments, the ring system is fully saturated. In other embodiments, the ring system may contain 1, 2, 3, or 4 double bonds. The ring system may contain heteroatoms such as S, O, and N. Examples of non-aromatic ring systems include:

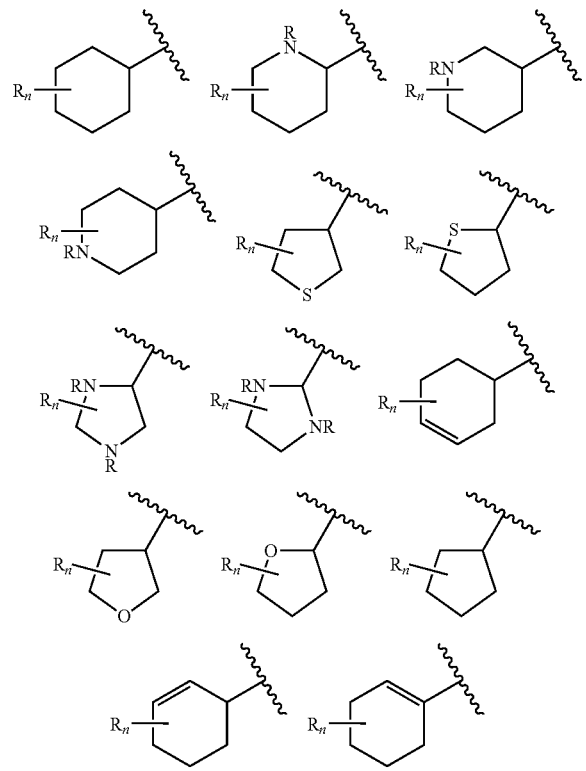

wherein R is as defined above; n is an integer ranging from 0 to 10, inclusive, preferably 1 to 5, inclusive.

In certain embodiments, Y is selected from the group consisting of:

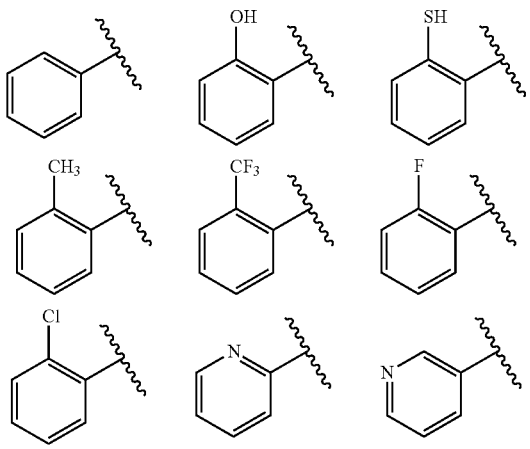

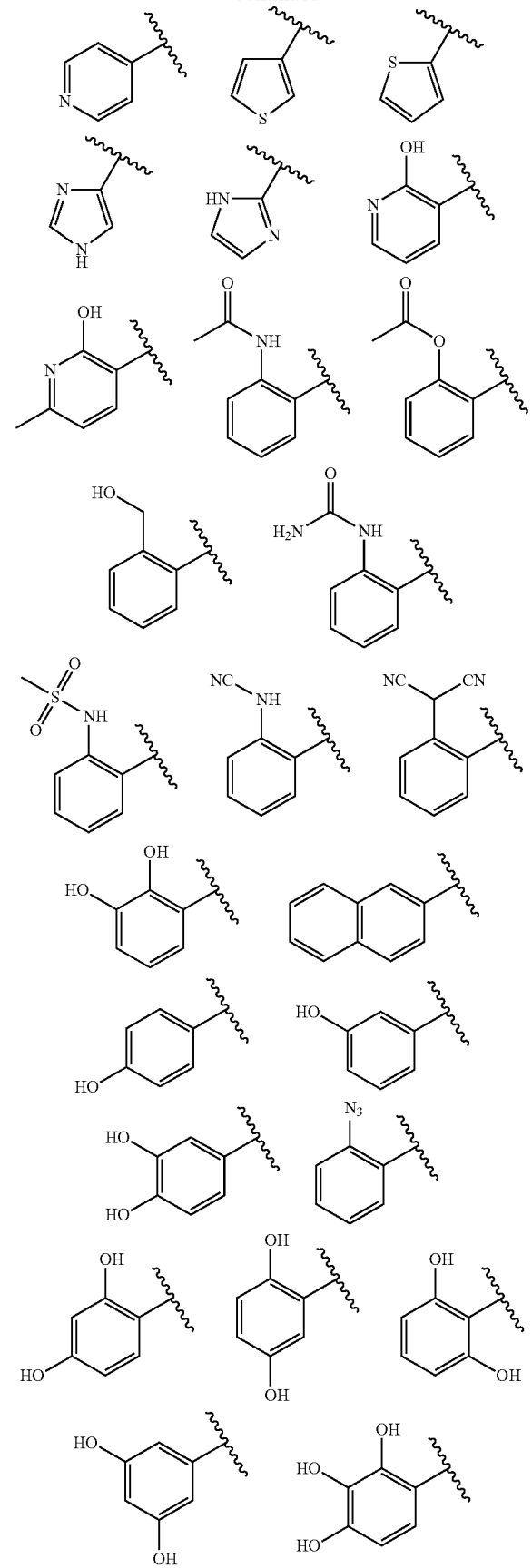

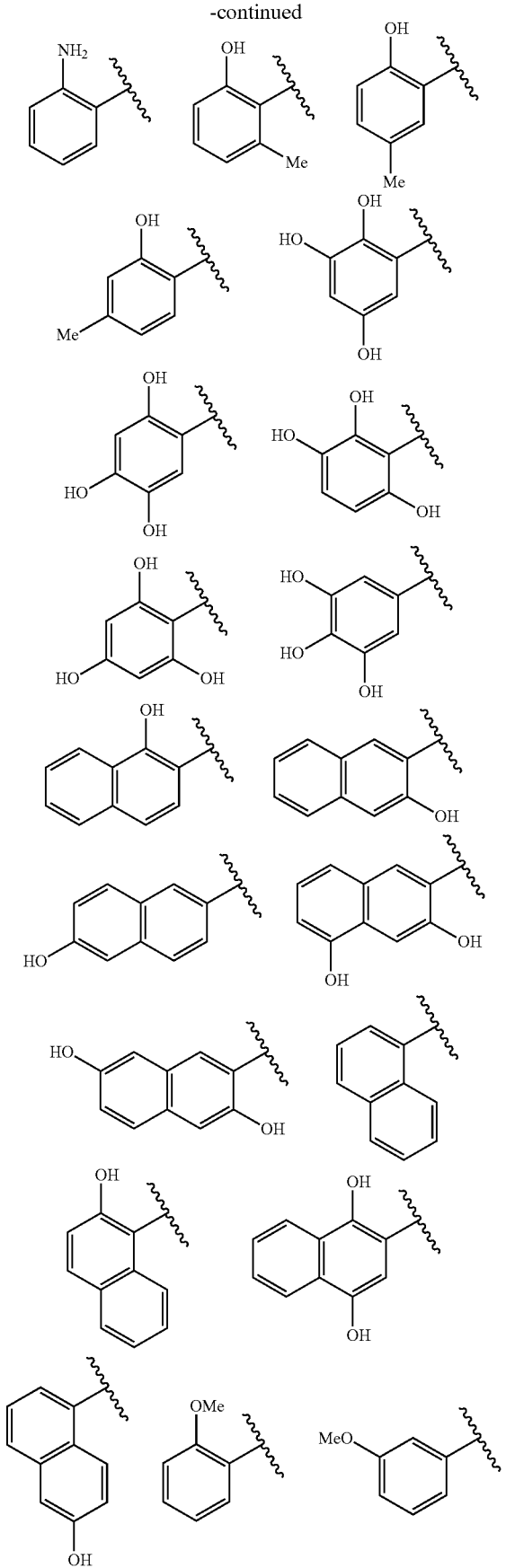
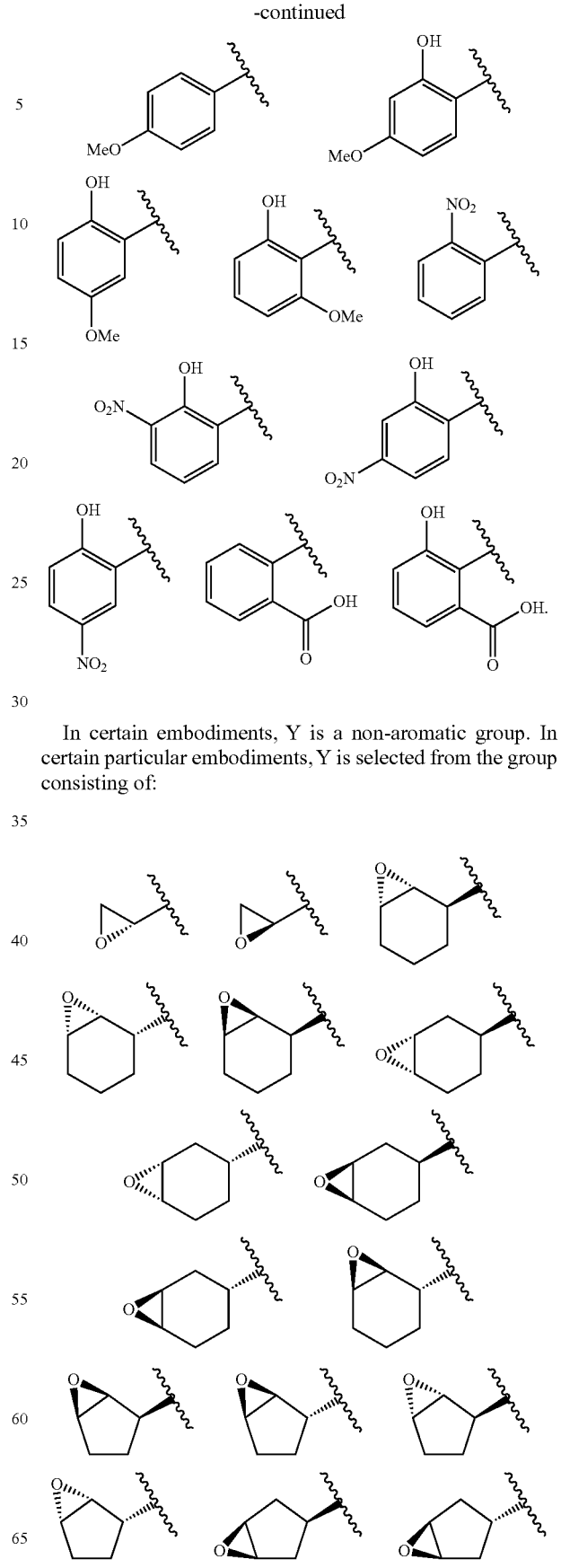
In certain embodiments, Y is a non-aromatic group. In certain particular embodiments, Y is selected from the group consisting of:
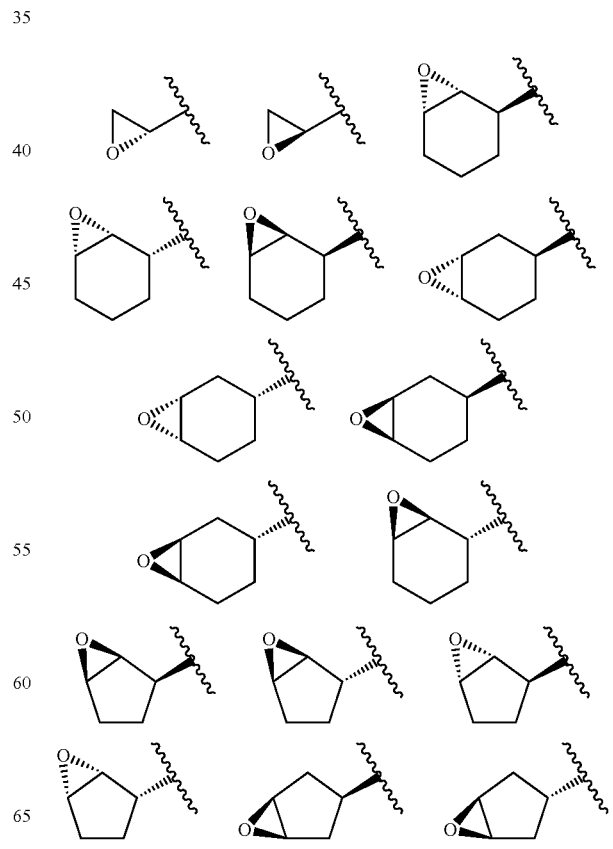

-continued

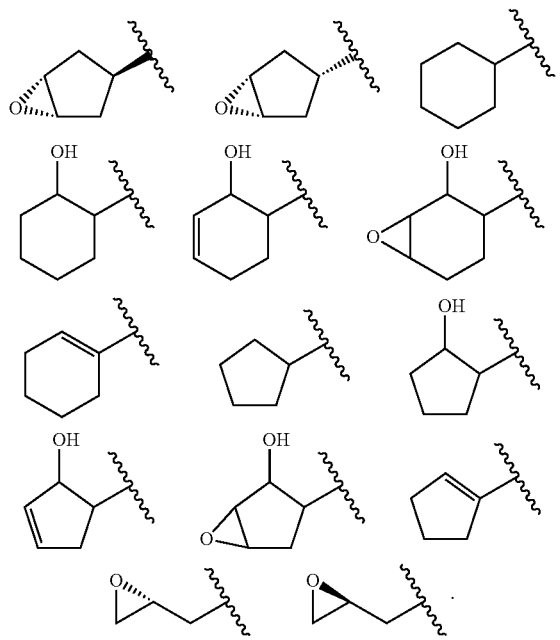

In certain embodiments, Y is hydrogen.

In certain embodiments, Y is substituted or unsubstituted, branched or unbranched aliphatic. In other embodiments, Y is substituted or unsubstituted, branched or unbranched heteroaliphatic. In certain embodiments, Y is

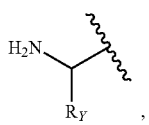

wherein $R_Y$ is as defined in the genera, classes, subclasses, and species described herein. In other embodiments, Y is

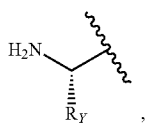

wherein $R_Y$ is as defined in the genera, classes, subclasses, and species described herein. In yet other embodiments, Y is

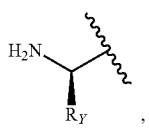

wherein $R_Y$ is as defined in the genera, classes, subclasses, and species described herein. In certain embodiments, $R_Y$ is a side chain of a natural amino acid. In other embodiments, $R_Y$ is a side chain of an unnatural amino acid. In certain embodiments, $R_Y$ is of the formula:

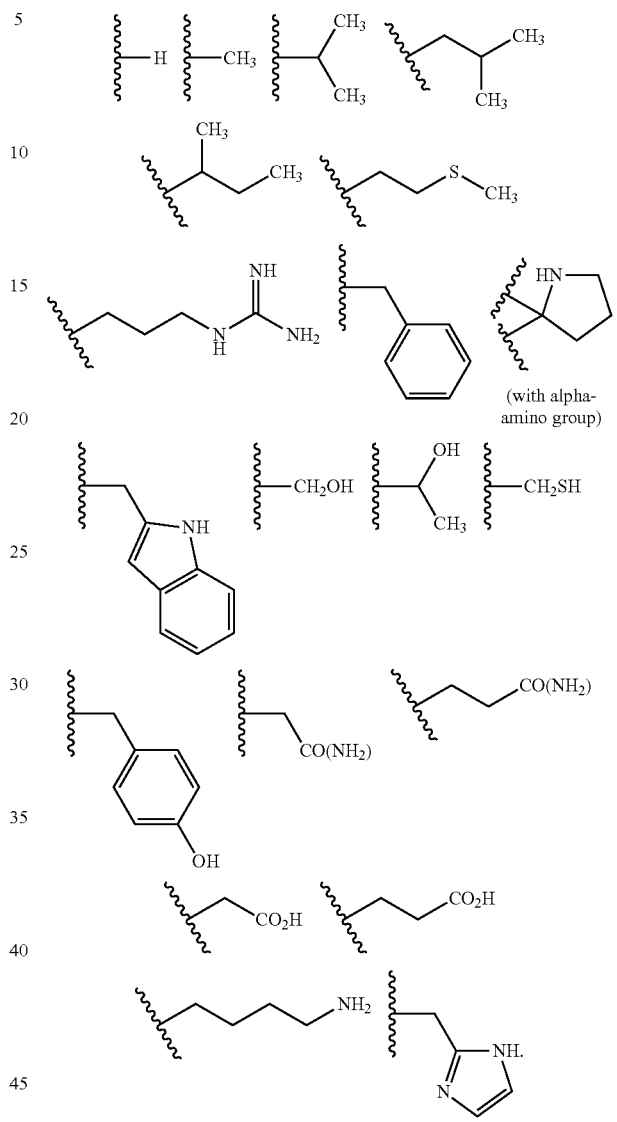

In certain embodiments, $R_Y$ is of the formula:

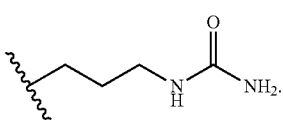 [SMILES: *CCCNC(N)=O]

In certain embodiments $R_Y$ is of the formula:

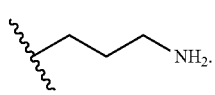 [SMILES: *CCCN]

Exemplary compounds include compounds of one of the formulae:

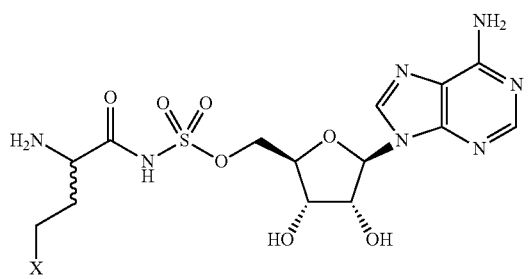

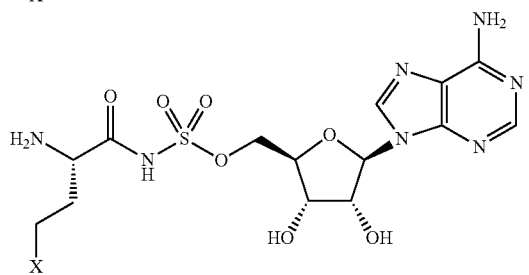

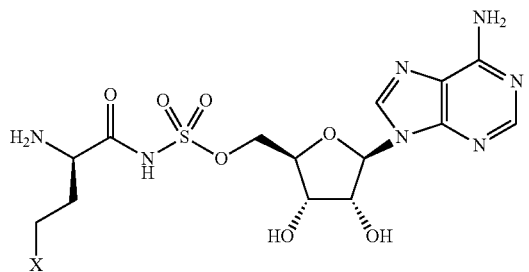

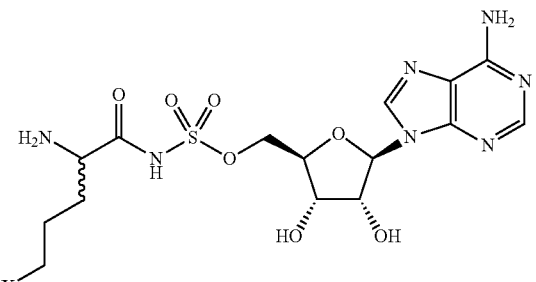

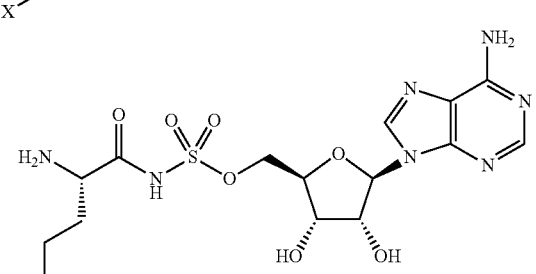

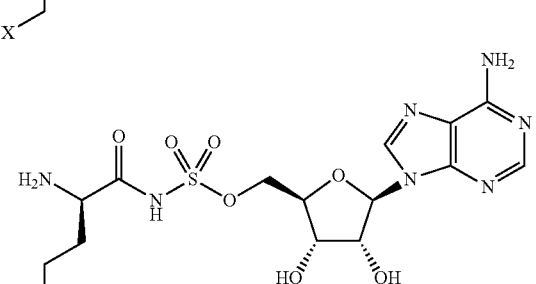

wherein X is —NH$_2$, —NHR$_Y$, —N(R$_Y$)$_2$, —N(R$_Y$)$_{3+}$, —NHOH, NR$_Y$IH, or

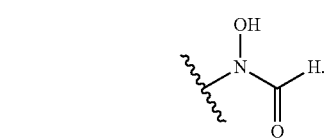

In certain embodiments, R$_Y$ is hydrogen. In other embodiments, R$_Y$ is halogen. In certain embodiments, R$_Y$ is aliphatic. In other embodiments, R$_Y$ is heteroaliphatic. In certain embodiments, R$_Y$ is aryl. In other embodiments, R$_Y$ is heteroaryl. In certain embodiments, R$_Y$ is alkyl. In other embodiments, R$_Y$ is C$_1$-C$_6$ alkyl. In still other embodiments, R$_Y$ is a nitrogen-protecting group.

In certain embodiments, Y is an alkyl group. In certain embodiments, Y is C$_1$-C$_{12}$ alkyl. In other embodiments, Y is C$_1$-C$_6$ alkyl. In certain embodiments, Y is propyl. In other embodiments, Y is ethyl. In still other embodiments, Y is methyl. The alkyl moiety may be optionally branched and/or substituted.

In certain embodiments, Y is an alkenyl group. Exemplary alkenyl groups include:

In certain embodiments, Y is acyl.

In certain embodiments, compounds are of the formula:

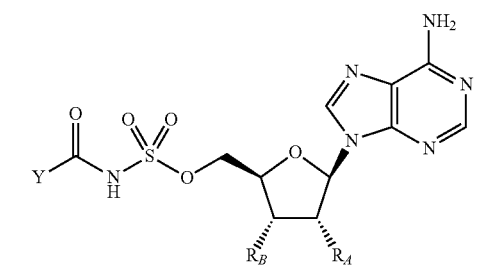

wherein R$_A$, R$_B$, and Y are as defined in the genera, classes, subclasses, and species described herein. In certain embodiments, the compound is of formula:

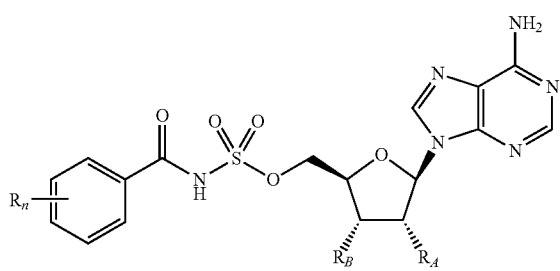

wherein $R_A$, $R_B$, and R are as defined in the genera, classes, subclasses, and species described herein; and n is an integer between 0 and 5, inclusive. In certain embodiments, n is 0. In certain embodiments, n is 1. In other embodiments, n is 2. In yet other embodiments, n is 3. In certain embodiments, at least one R is hydroxyl or protected hydroxyl. In other embodiments, at least one R is alkyoxy. In certain embodiments, the compound is of formula:

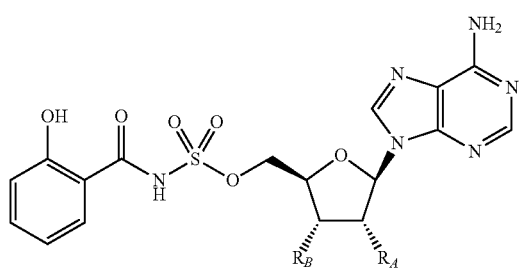

wherein $R_A$ and $R_B$ are as defined in the genera, classes, subclasses, and species described herein.

In certain embodiments, compounds are of the formula:

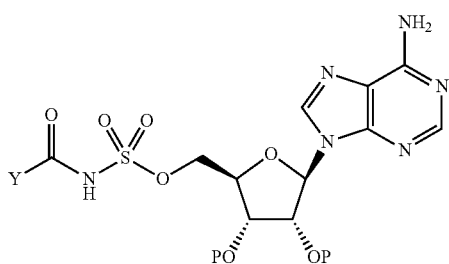

wherein

Y is as defined in the genera, classes, subclasses, and species described herein; and each occurrence of P is a hydrogen or an oxygen protecting group. In certain embodiments, both occurrence of P are hydrogen. In certain embodiments, at least one occurrence of P is hydrogen. In other embodiments, P is a silyl-protecting group. In yet other embodiments, P is $C_1$-$C_6$ alkyl. In still other embodiments, P is acyl. In certain particular embodiments, P is acetyl. In certain embodiments, compounds are of the formula:

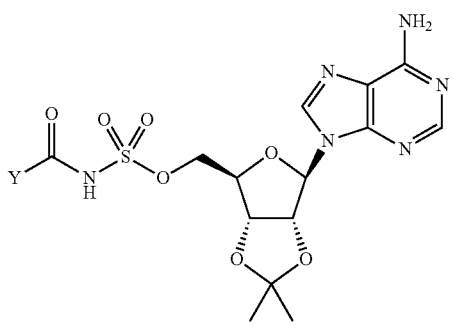

wherein Y is as defined in the genera, classes, subclasses, and species described herein.

In certain embodiments, compounds are of the formula:

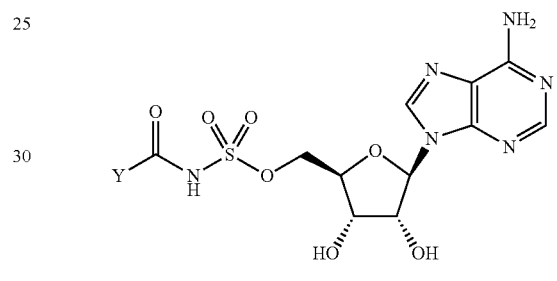

wherein Y is as defined above in the various genera, classes, and subclasses.

In certain embodiments, compounds are of the formula:

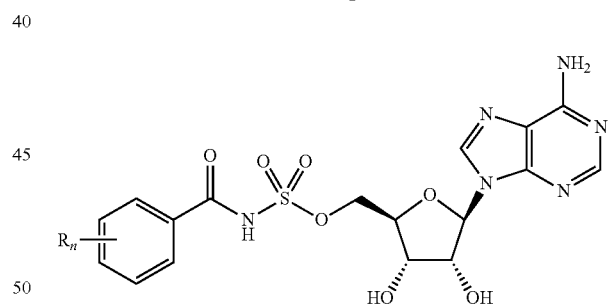

wherein R and n are as defined above.

In other embodiments, compounds are of the formula:

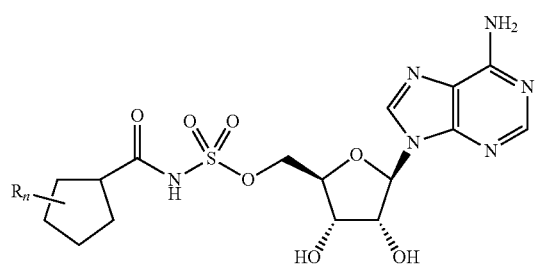

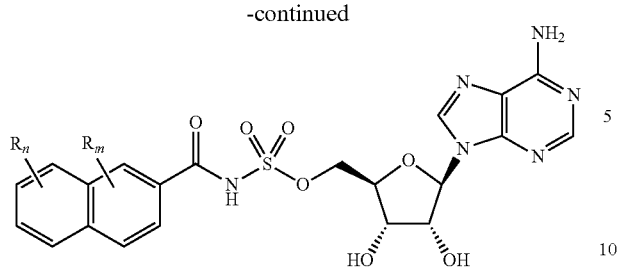

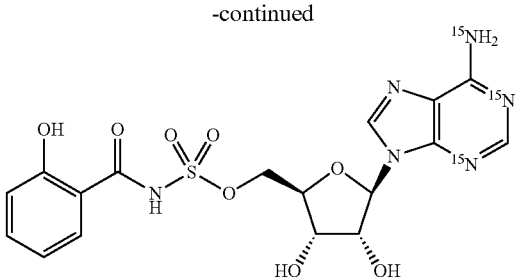

[adenine N1,N3,N6-15N3]-salicyl-AMS

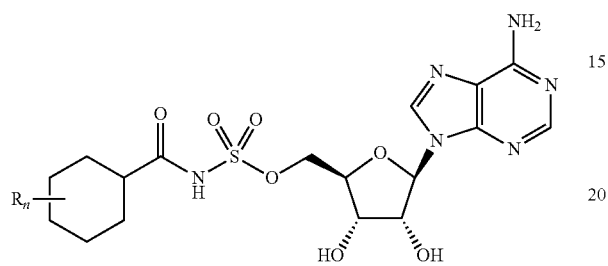

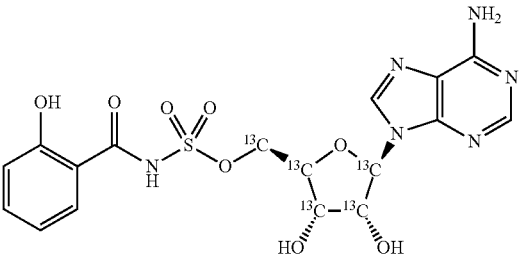

[ribose-13C5]-salicyl-AMS wherein R, n, and m are as defined above.

In certain embodiments, Y is absent.

In certain embodiments of the invention, a compound of the invention is labeled with an isotope. In certain embodiments, the isotope used is a radioactive isotope (e.g., $^{35}S$, $^{14}$, $^{3}H$, etc.). In other embodiments, the isotope is not radioactive (e.g., $^{2}H$, $^{13}C$, $^{15}N$, etc.). In certain embodiments, at least one position on the compound is deuterated. In other embodiments, multiple positions on the compound are deuterated. In other embodiments, the compound is labeled with $^{13}C$. In yet other embodiments, the compound is labeled with $^{15}N$. In certain embodiments, the compound may have more than one label. Exemplary stable isotope-labeled compound include compounds of formula:

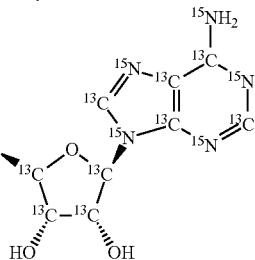

[adenine/ribose-13C10-adenine-15N5]-salicyl-AMS

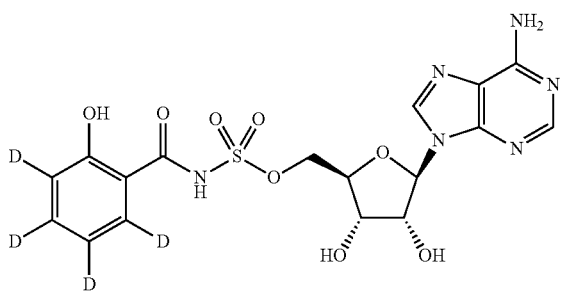

[salicyl ring-d4]-salicyl-AMS

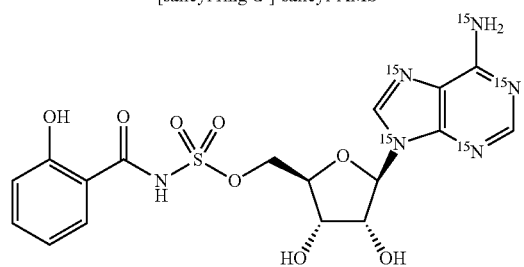

[adenine-15N5]-salicyl-AMS

Labeled compounds are particularly useful in studying the biological activity, stability, degradation, modification, pharmacokinetics, etc. of the inventive compounds. The labeled compounds are particularly useful in studying the adsorption, distribution, metabolism, and excretion of an inventive compound using techniques known in the art. For example, the non-labeled compound is administered and then recovered from various samples (e.g., blood, urine, tissue, etc.) taken from a subject (e.g., human, dog, rat, pig, mouse, etc.). After collection of the sample but before processing, the sample is spiked with a known amount of the analog labeled with a stable isoptope to serve as an internal standard. In certain embodiments, the processing involves the precipitation of proteins by the addition of an organic solvent and centrifugation. The sample is then analyzed by LC-MS-MS, and parent and fragment peaks are observed for the unlabeled and labeled compounds. The peaks from the stable-isotope labeled compound provide an internal standard which can be used to quantitate the amount of unlabeled compound in the sample. Compounds labeled with stable isotopes (e.g. $^{2}H$, $^{13}C$, $^{15}N$, etc.) are particularly useful in techniques involving mass spectral analysis.

Compounds labeled with radioactive isotopes are useful in autoradiography, scintillation counting, analysis by radioactive decay, imaging based on radioactive decay, imaging or counting based on beta or alpha particle emission, etc. Such labeled compounds may also be used in studying the biological activity, stability, degradation, modification, pharmacokinetics, etc. of the inventive compounds. Radiolabeled compounds are administered directly to a subject, and various samples obtained from the subject are counted (e.g., scintillation counting) to determine adsorption, distribution, metabolism, and excretion of the administered compound.

Exemplary compounds of the invention include:

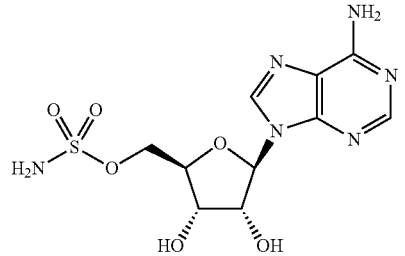

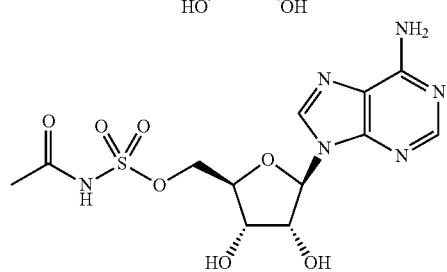

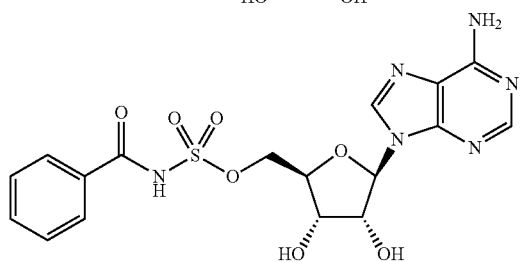

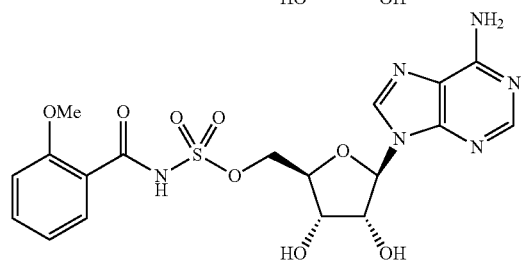

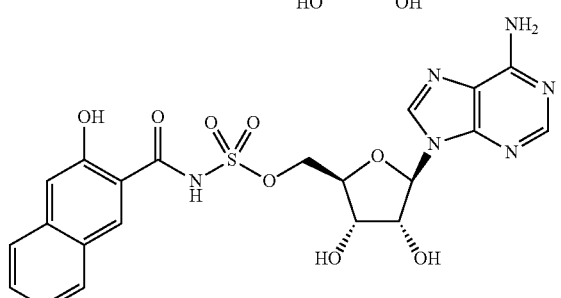

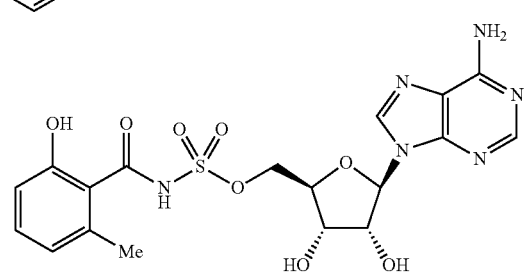

-continued

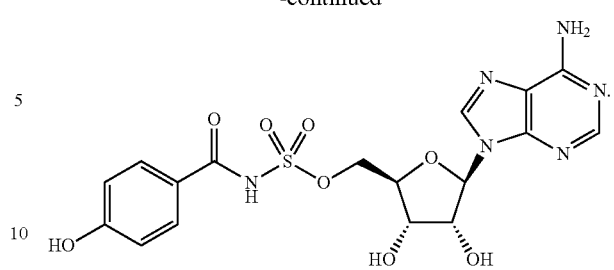

In another aspect, compounds of the invention are of the formula:

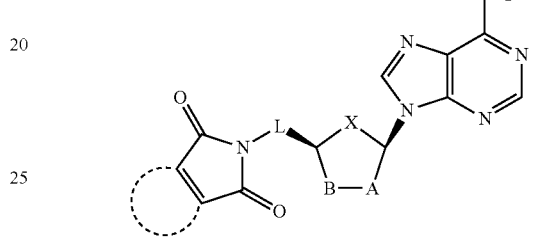

wherein A, B, X, and L are defined as above; and

is a non-existent, or a substituted or unsubstituted, aromatic or non-aromatic, carbocyclic or heterocyclic group. In certain embodiments,

is a substituted or unsubstituted phenyl ring. In certain embodiments,

is a substituted or unsubstituted heterocyclic ring. Preferably,

is a five- or six-membered ring. Exemplary compounds of this class include:

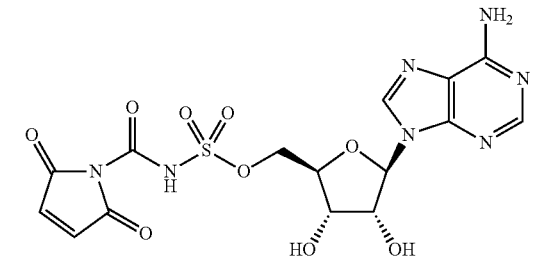

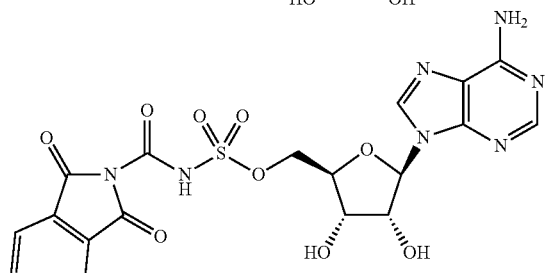

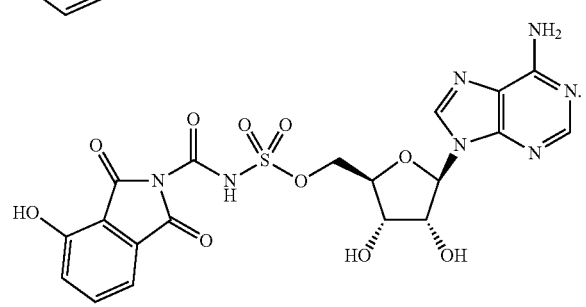

In another aspect, compound of the invention is of the formula:

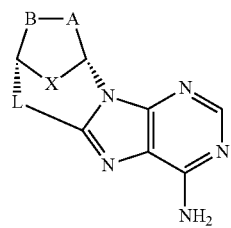

wherein A, B, X, and L are defined as above. In certain embodiments, the compound is of the formula:

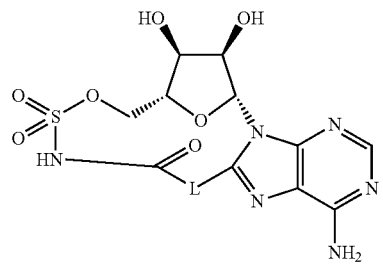

wherein L is defined as above. In certain embodiments, L is of the formula:

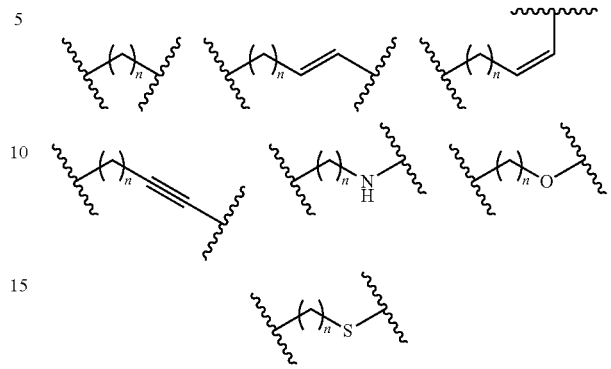

wherein n is 0, 1, 2, 3, 4, 5, or, 6; preferably 3, 4, 5, or 6.

In certain embodiments, the compound is of the formula:

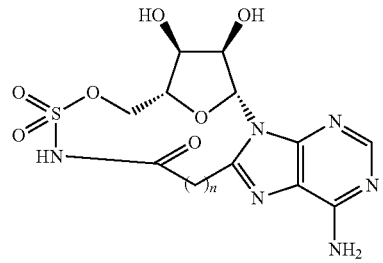

wherein n is 0, 1, 2, 3, 4, 5, or 6, preferably 1, 2, or 3.

In certain other embodiments, the compound is of the formula:

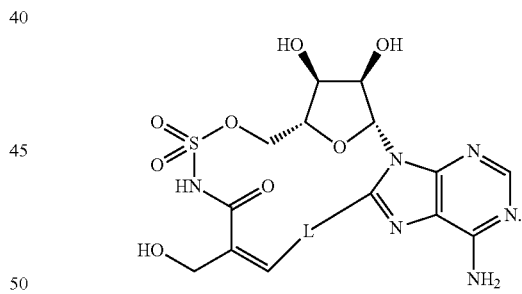

In certain embodiments, the compound is of the formula:

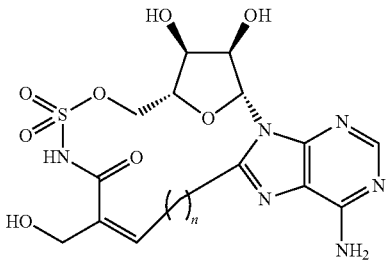

wherein n is 0, 1, 2, 3, or 4, preferably 0, 1, 2, or 3.

In certain other embodiments, the compound is of the formula:

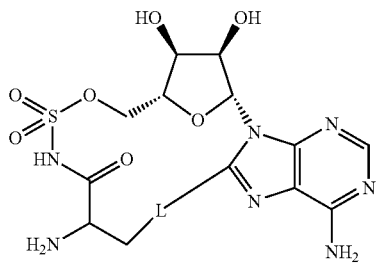

wherein L is as defined in the genera, classes, subclasses, and species described herein.

In certain embodiments, the compound is of formula:

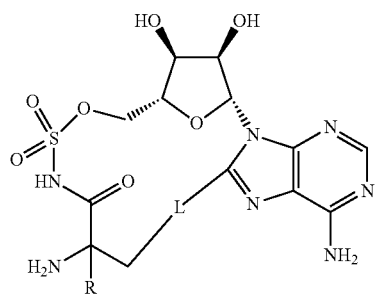

wherein

L is as defined in the genera, classes, subclasses, and species described herein; and R is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR'; —C(=O)R'; —CO$_2$R'; —CN; —N$_3$; —SCN; —SR'; —SOR'; —SO$_2$R'; —NO$_2$; —N(R')$_2$; —NHC(O)R'; or —C(R')$_3$; wherein each occurrence of R' is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, R is aliphatic. In certain embodiments, R is C$_1$—C$_6$ alkyl. In certain embodiments, R is a side chain of a natural or unnatural amino acid. In certain embodiments, R is of the formula:

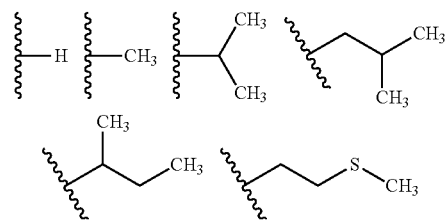

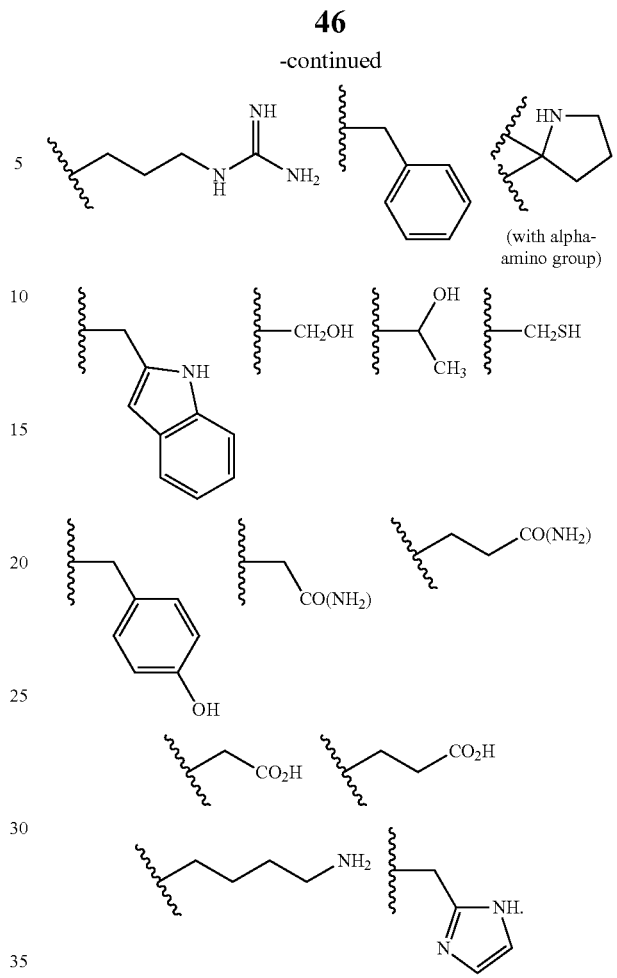

In certain embodiments, is a side chain of an unnatural amino acid. In certain embodiments, R is of the formula:

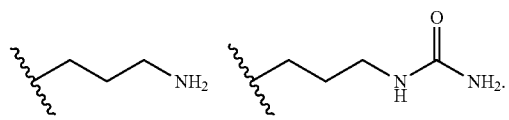 [SMILES: *CCCN ; *CCCNC(N)=O]

In certain embodiments, the compound is of the formula:

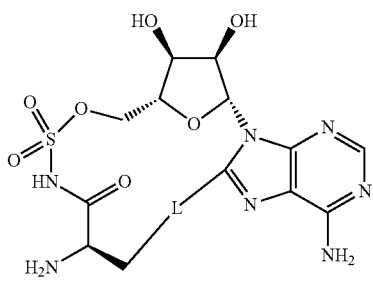

wherein L is as defined in the genera, classes, subclasses, and species described herein.

In certain embodiments, the compound is of the formula:

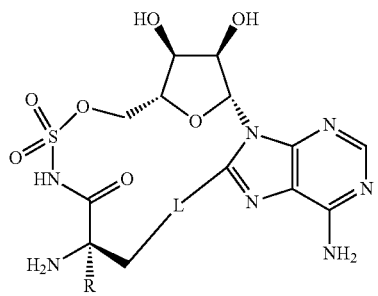

wherein R and L are as defined in the genera, classes, subclasses, and species described herein.

In certain embodiments, the compound is of the formula:

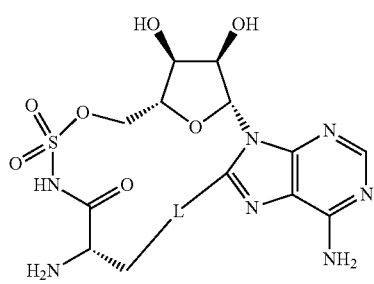

wherein L is as defined in the genera, classes, subclasses, and species described herein.

In certain embodiments, the compound is of the formula:

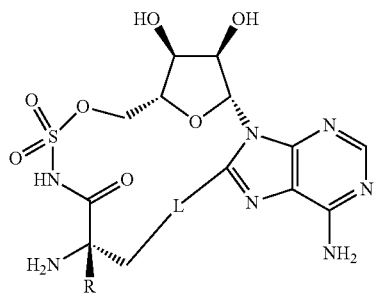

wherein L and R is as defined in the genera, classes, subclasses, and species described herein.

In certain embodiments, the compound is of the formula:

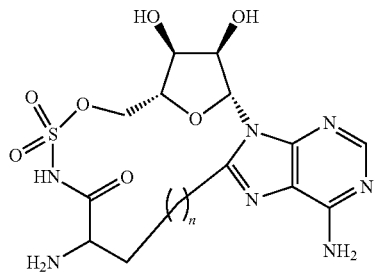

wherein n is 0, 1, 2, 3, or 4, preferably 0, 1, 2, or 3. In certain embodiments, n is 3.

In certain embodiments, the compound is of the formula:

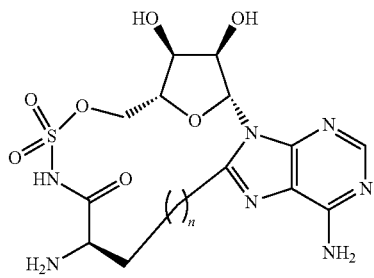

wherein n is 0, 1, 2, 3, or 4, preferably 0, 1, 2, or 3. In certain embodiments, n is 3.

In certain embodiments, the compound is of the formula:

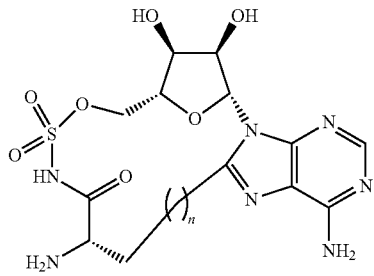

wherein n is 0, 1, 2, 3, or 4, preferably 0, 1, 2, or 3. In certain embodiments, n is 3. Exemplary compounds of this class include:

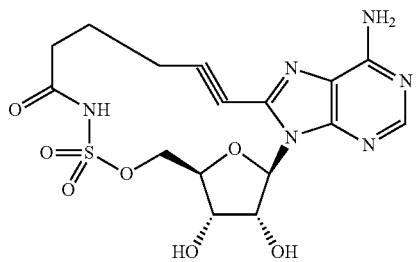

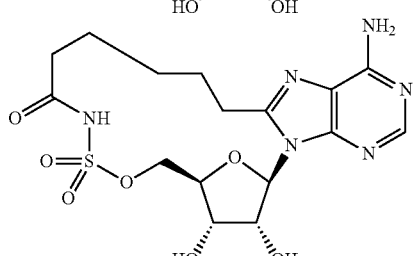

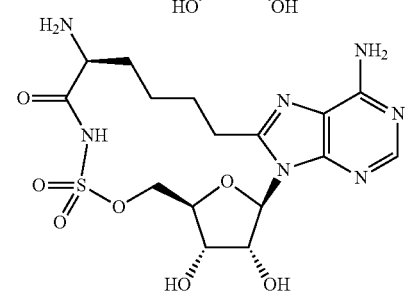

-continued

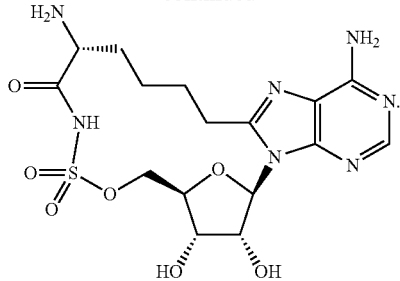

In certain embodiments, the compound is of one of the formulae:

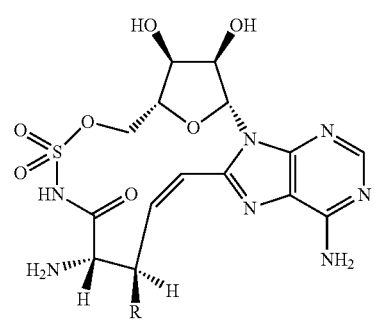

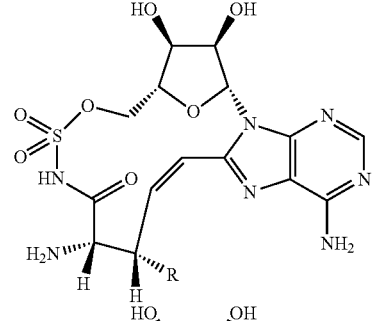

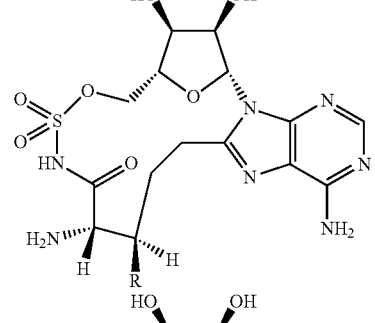

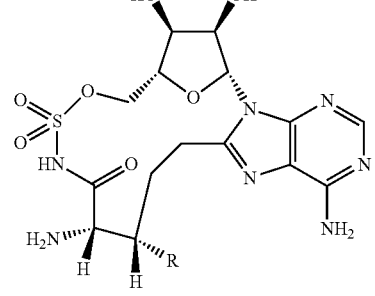

-continued

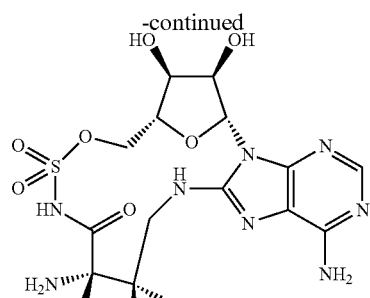

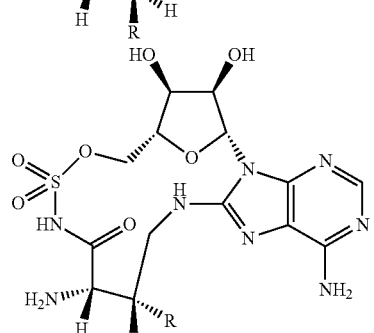

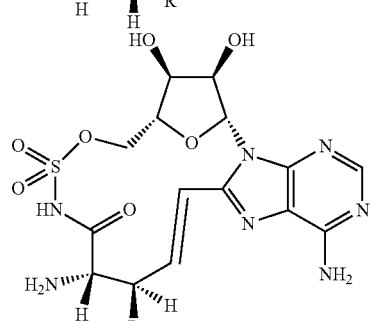

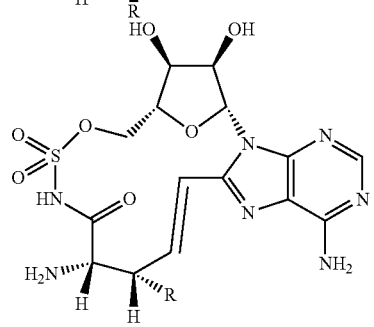

wherein R is as defined in the genera, classes, subclasses, and species thereof. In certain embodiments, R is hydrogen. In certain embodiments, R is aliphatic. In certain embodiments, R is hydroxyl. In other embodiments, R is thiol. In other embodiments, R is aryl. In certain embodiments, R is substituted phenyl. In other embodiments, R is unsubstituted phenyl. In yet other embodiments, R is heteroaryl. In certain embodiments, R is of the formula:

-continued

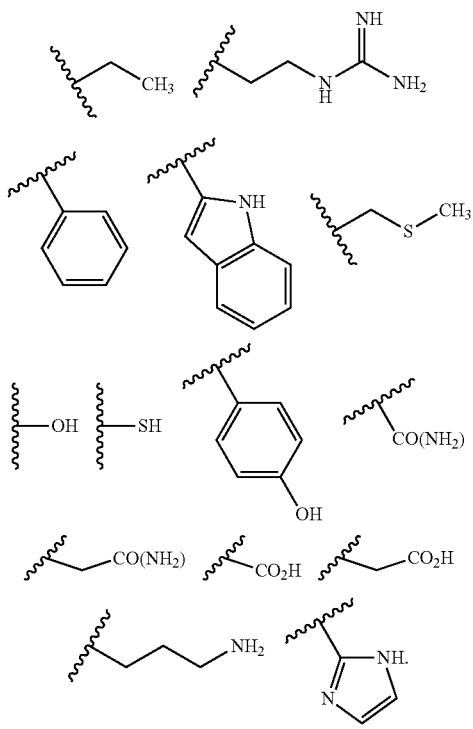

In other embodiments, R is of the formula:

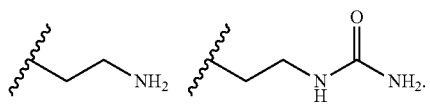

In certain particular embodiments, the compound is of the formula:

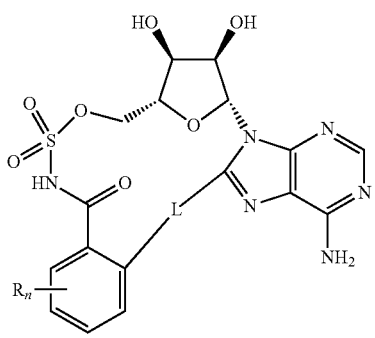

wherein R and n are defined as above, and L is a branched or unbranched, aliphatic or heteroaliphatic group. In certain embodiments, L is a 1-6 atom linker. In certain embodiments, L is a 1 atom liner. In certain embodiments, L is a 2 atom linker. In other embodiments, L is a 3 atom linker. In yet other embodiments, L is a 4 atom linker. In certain embodiments, the compound is of the formula:

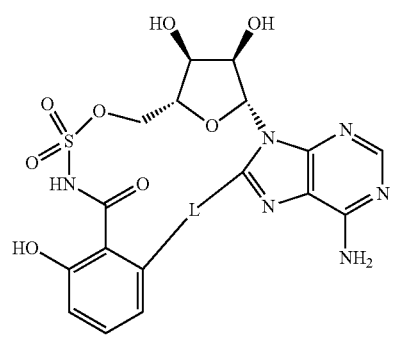

wherein L is defined as above. In other particular embodiments, the compound is selected from the group consisting of:

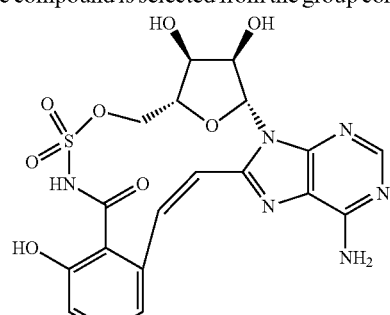

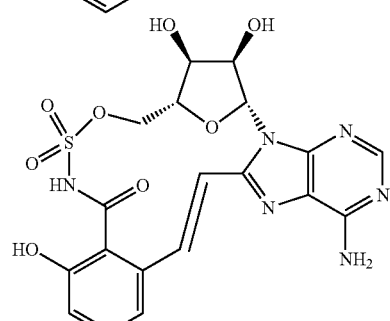

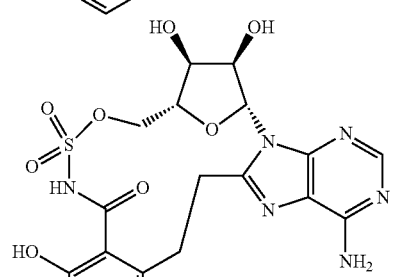

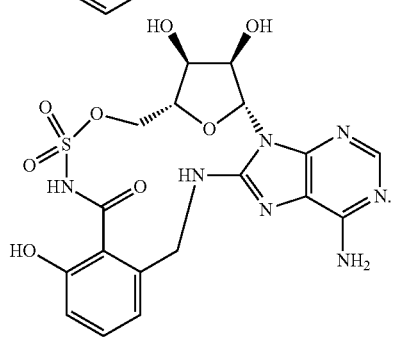

In certain embodiments, the compounds is of the formula:

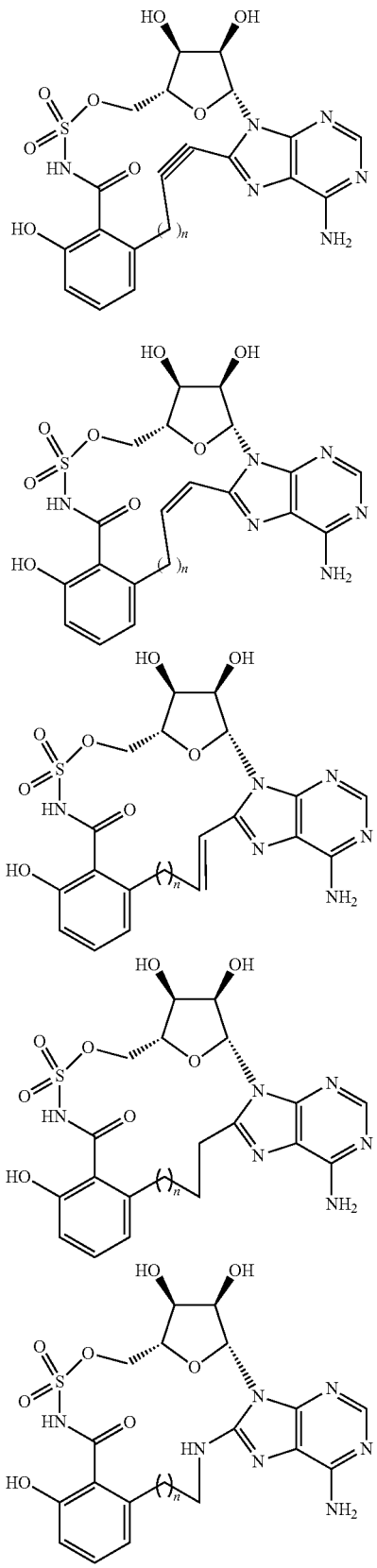

wherein n is 0 or 1.

The compounds of the invention as shown above include the base adenine attached to 1'-carbon of the ribose ring. As will be appreciated by those of skill in this art, other naturally occurring and non-naturally occurring bases can be included in the compound instead of adenine. Example include other purines such as guanine, inosine, or xanthine, or pyriminides such as cytosine, uracil, or thymine. Other aryl and heteroaryl groups may also be used instead of adenine. These groups may be monocyclic or polycyclic. These groups may be heterocyclic or carbocyclic. In certain embodiments, the group is monocyclic such as a phenyl ring, benzyl ring, thiazolyl ring, imidazolyl ring, pyrindinyl ring, etc. In certain other embodiments, adenine is replaced with a bicyclic ring system, preferably a five-membered ring fused to a six-membered ring or a six-membered ring fused to another six-membered ring. The ring system may include heteroatoms such as nitrogen, sulfur, and oxygen. In certain embodiments, the ring system includes at least one nitrogen atoms, preferably at least two nitrogen atoms, more preferably at least three nitrogen atoms. In other embodiments, the ring system does not include heteroatoms although heteroatoms may be found in the substituents. Examples of ring system which may be used in place of adenine include:

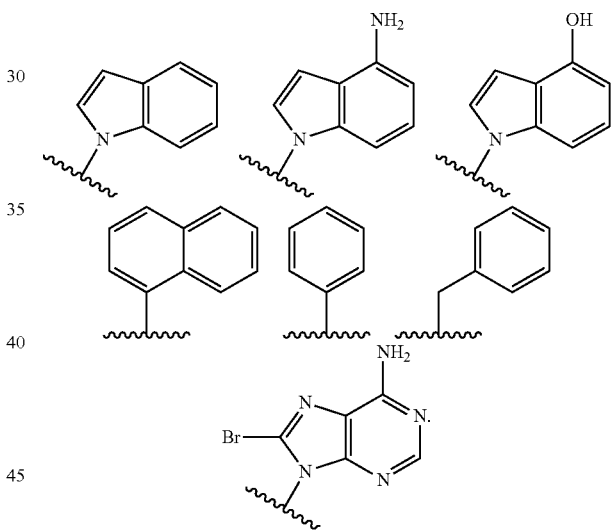

In certain embodiments, the compound is of the formula:

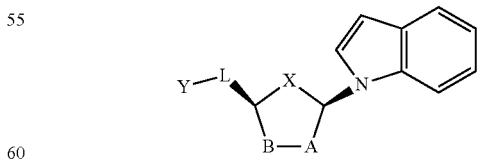

wherein A, B, X, L, and Y are as defined in the genera, classes, subclasses, and species defined herein. In certain embodiments, the compound is of the formula:

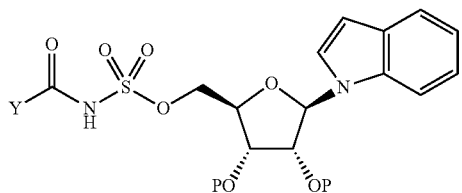

wherein Y is as defined in the genera, classes, subclasses, and species defined herein; and P is hydrogen or an oxygen-protecting group. In certain embodiments, P is hydrogen. In other embodiments, P is a silyl-protecting group. In yet other embodiments, P is acyl. In still other embodiments, P is acetyl. In certain embodiments, both P taken together form an acetonide protecting group. In certain embodiments, Y is substituted phenyl moiety. In certain embodiments, Y is a hydroxyl-substituted phenyl moiety.

Exemplary compounds of this class of adenine-modified compounds include compounds of formula:

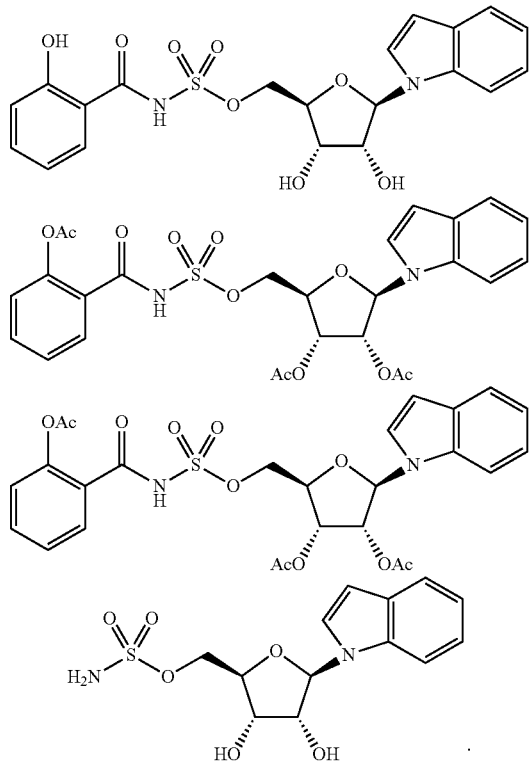

Without wishing to be bound by any particular theory, the compounds of the invention are preferably inhibitors of salicyl adenylation enzymes or dihydroxybenzoate adenylation enzymes. The compound may be a substrate or intermediate mimic. The compound may be mechanism-based inhibitor of the enzyme. The compound may also covalently modify the enzyme. In certain embodiments, the compound is a tight binding inhibitor. In other embodiments, the compound is a competitive inhibitor. In certain embodiments, the compound is a competitive inhibitor with respect to ATP and non-competitive with respect to salicylate or dihydroxybenzoate.

The compounds may prevent or inhibit the growth of microorganism relying on the synthesis of siderophores for the acquisition of iron. The compounds may be tested for inhibitory activity using various in vitro and in vivo tests. For example, the inhibitory activity of the compounds may be determined using in vitro assay with salicyl adenylation enzymes or dihydroxylbenzoate adenylation enzymes. The enzyme may be purified from a natural source or prepared recombinantly. Crude extracts of the enzyme may also be used. Details of various enzymatic assays are described below in the Examples. In certain embodiments, the $IC_{50}$ value of the compound determined by these assays is less than 50 nM, preferably less than 25 nM, more preferably less than 15 nM, even more preferably less than 10 nM, 5 nM, or 1 nM. For example, for salicyl-AMS, $IC_{50}$ values using the adenylation assay described in Example 1 range from around 10-15 nM.

The compounds of the invention may also inhibit the growth of or kill infectious organisms via another mechanism of action. In certain embodiments, the compounds may inhibit a biochemical pathway specific to the infectious organim and not found in the host. In certain embodiments, the compound may selectively inhibit a biochemical pathway found in the infectious organism. In other embodiments, the compound may target a virulence pathway in an infectious organism.

The compounds may also be tested for their ability to inhibit the growth of a microorganism in culture or in an animal including human clinical trials. Microorganisms include *M. tuberculosis, Y. pestis, Y. enterocolitica, P. aeruginosa, Acinebacter calcoaceticus, A. baumannii, E. coli, Salmonella enterica, Shigella* spp., *Bacillus anthracis, Vibrio vulnificus, Yersinia ruckeri, Brucella abortus*, and *Vibrio cholerae*. In certain embodiments, the bacterial growth assay is done under iron-limiting conditions. Examples of such tests are included in the Examples below. The $IC_{50}$ values for the compounds for inhibiting growth in deferrated culture media are preferably less than 100 μM, more preferably less than 50 μM, even more preferably less than 10 μM, and most preferably less than 1 μM or less than 0.1 μM. Salicyl-AMS has been shown to inhibit the growth of *Y. pestis* in deferrated culture media at an $IC_{50}$ of approximately 50 μM and *M. tuberculosis* at approximately 2 μM. The compound may also be tested in in vivo animal models of infection. The compound may be tested in human clinical trials. The compounds may also be tested in variety of other assays to determine various pharmacokinetic properties of the compound such as cell permeability, elimination, specificity, stability, etc.

Methods of Synthesis

The present invention also includes all steps and methodologies used in preparing the compounds of the invention as well as intermediates along the synthetic route. The present invention provides for the synthesis of salicyl-AMS and analogs thereof, including conformationally constrained analogs.

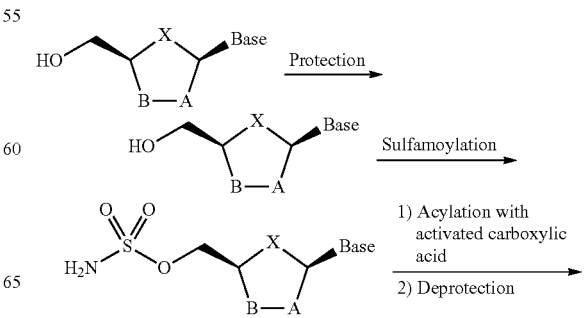

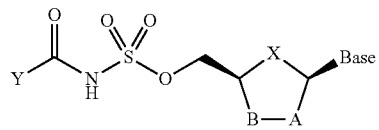

The synthesis of the compounds of the invention generally start with a nucleoside or nucleoside analogs. In certain embodiments, the nucleoside adenosine is used. As will be appreciated by those of skill in this art, other naturally occurring and non-naturally occurring analogs can also be used. Examples of analogs include inosine, guanosine, thymidine, uridine, cytidine, etc. Non-naturally occurring nucleosides with modification around the ribose ring may also be used as a starting material in preparing the inventive compounds. For example, 2'-deoxyribose, 3'-deoxyribose, 2',3'-dideoxyribose, 2'-haloribose, 3'-haloribose, 4'-carba-4'deoxyribose, 4'-thia-4'-deoxyribose, 4'acetoamido-4'deoxyribose, protected from of ribose, etc. may be used in the synthesis. In certain preferred embodiments, the ribose ring may be used to attach a tag (e.g., fluorescent, chemiluminescent, biotin, etc.) or label (e.g., radiolabel) or to attach the compound to a solid support (e.g., polymeric beads, resin).

The secondary hydroxyl groups of the nucleoside starting material are then protected. In certain embodiments, the hydroxyl groups are selectively protected. In other embodiments, all the hydroxyl groups of the staring material are protected and the 5'-primary hydroxyl group is unprotected for further modification (see FIG. 5). Optionally, functional groups on the base (e.g., amino groups, hydroxyl groups) may be protected. In certain embodiments, silicon-based protecting groups (e.g., TBS) are used. In one embodiment, adenosine is silylated followed by selective deprotection of the 5'-O-TBS group, thereby providing 2',3'-bis-O-TBS-adenosine (Zhu et al. *J. Chem. Soc., Perkin Trans.* 1 1:2305-06, 2000; incorporated herein by reference). In certain embodiments, the 2'- and 3'-hydroxyl groups of the ribose ring are protected using a acetonide protecting group. Optionally, the protection step is not required when the synthesis begins with a protected form of the starting material to begin with. For example, in certain embodiments, the synthesis begins with adenosine acetonide.

The protected nucleoside analogs is then sulfamoylated at the 5'-position to yield the corresponding sulfamate. In one embodiment, the sulfamoylation reaction is carried out using bis(tributyltin) oxide and sulfamoyl chloride (Castro-Pichel et al. *Tetrahedron* 43:383-89, 1987; incorporated herein by reference). In other embodiments, a tin-free sulfamoylation reaction is used. This eliminates the need for using toxic tin reagents. For example, a tin-free sulfamoylation reaction using $H_2NSO_2Cl$ in a solvent such as N,N-dimethylacetamide (DMA) (Okada et al. *Tetrahedron Lett.* 41:7047-51, 2000; incorporated herein by reference) may be used. Other methods of accomplishing the sulfamoylation reaction known in the art may also be used. In certain embodiments, the intermediate is of the formula:

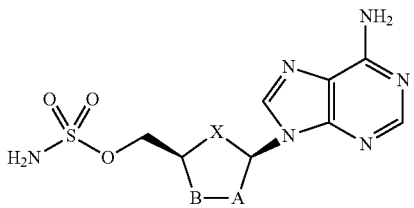

wherein A, B, and X are defined as above. In certain embodiments, the intermediate is of the formula:

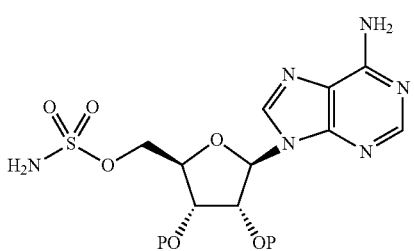

wherein P is hydrogen or an oxygen-protecting group (e.g., TBS). In certain embodiments, the hydroxyl-protecting groups are silyl-based protecting groups such as TBS. In certain embodiments, the intermediate is of the formula:

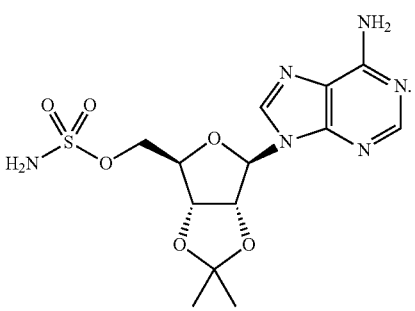 [SMILES: CC1(C)O[C@@H]2[C@H](O1)[C@@H](COS(N)(=O)=O)O[C@H]2n1cnc2c(N)ncnc21]

In certain embodiments, the synthesis is a solid phase synthesis (e.g., using a fluoride-labile silicon linker at the 2'- or 3'-carbon.

The sulfamate is then reacted with an activated carboxylic acid to yield the acyl-AMS analog. In certain embodiments, the carboxylic acid is a benzoate or a substituted benzoate. In certain embodiments, the carboxylic acid is salicylic acid. The carboxylic acid functional group may be activated with carbonyl imidazole (CDI). Any coupling reagent may be used in this reaction. Exemplary coupling reagents commonly used include EDC, DCC, HBTU, HATU, PyBOP, ByBrOP, PyAOP, and TFFH. The coupling reagents may optionally used in conjunction with the auxilliary reagents, HOBt and HOAt. As would be appreciated by one of skill in this art, the coupling may be accomplished using an acid chloride, acid bromide, acid fluoride, N-hydroxysuccinimide estes, N-hydroxybenzotriazole, activated amide, anhydrides, or other carboxylic acid derivative instead of an activating a carboxylic acid using a coupling reagent. The resulting compound is then optionally deprotected to yield the final product.

In another embodiment, the sulfamate is alkylated. In certain embodiments, the sulfamate is alkylated by Mitsunobu-type alkylation to prepare the alkyl-AMS analog. In other embodiments, the alkylation is performed by treament of the sulfamate with a base (e.g., DBU, Cs2CO3, etc.) and an alkyl halide or alkyl tosylate. In certain embodiments, cyanomethylenetributylphosphorane (CMBP) is used to selectively monoalkylate the primary sulfonamide (Tsunoda et al. *Tetrahedron Lett.* 37:2457-58, 1996; incorporated herein by reference) (see FIG. 7).

Labeled compounds of the invention may be prepared by using labeled reagents or starting materials in the synthesis above. For example, labeled adenosine or salicyclic acid may be obtained commercially and used in the above synthesis. In certain embodiments, 3,4,5,6-deuterosalicylic acid is used in the synthesis to obtain salicyl-AMS-$d_4$.

Other particular syntheses of compounds of the invention are given in the Figures and Examples herein.

Pharmaceutical Compositions

This invention also provides a pharmaceutical preparation comprising at least one of the compounds as described above and herein, or a pharmaceutically acceptable derivative thereof, which compounds inhibit the growth of or kill microorganisms, and, in certain embodiments of special interest inhibit the growth of or kill drug-resistant organisms. In certain embodiments, the organism is *Yersinia pestis, Yersinia enterocolitica, Mycobacterium tuberculosis, Pseudomonas aeruginosa, Acinetobacter calcoaceticus*, and *A. baumannii*. The compounds may also be used to treat infections with *Escherichia coli, Salmonella enterica, Shigella* spp., *Vibrio anguillarum, Bacillus anthracis, Vibrio vulnificus, Yersinia ruckeri, Brucella abortus*, and *Vibrio cholerae*. In treating an infection caused by an organism which produces an o-phenol-containing siderophore, the pharmaceutical composition may include a compound having an o-phenol moiety. In certain embodiments, the moiety may be isosteric and/or isoelectronic as compared to an o-phenol group. In treating an infection caused by an organism which produces a catechol-containing siderophore, the pharmaceutical composition may include a compound having a catechol moiety or an moiety which is isosteric and/or isoelectronic with a catechol group.

As discussed above, the present invention provides novel compounds having antimicrobial activity, and thus the inventive compounds are useful for the treatment of a variety of medical conditions including infectious diseases. Accordingly, in another aspect of the present invention, pharmaceutical compositions are provided, wherein these compositions comprise any one of the compounds as described herein, and optionally comprise a pharmaceutically acceptable carrier. In certain embodiments, the pharmaceutical composition comprises between 0.1 mg and 500 mg of the compound. In another embodiment, the pharmaceutical composition compreses between 1 mg and 100 mg of the compound, preferably between 1 mg and 50 mg of the compound or between 1 mg and 25 mg of the compound. In certain embodiments, the pharmaceutical composition includes 0.1, 1, 5, 10, 15, 20, 30, 40, 50, 60, 70, 80, 90, 100, 150, 200, 300, or 500 mg of the compound. In certain embodiments, these compositions optionally further comprise one or more additional therapeutic agents, e.g., another anti-microbial agent. In other embodiments, these compositions further comprise an anti-inflammatory agent such as aspirin, ibuprofen, acetaminophen, etc., pain reliever, or anti-pyretic.

It will also be appreciated that certain of the compounds of the present invention can exist in free form for treatment, or where appropriate, as a pharmaceutically acceptable derivative thereof. According to the present invention, a pharmaceutically acceptable derivative includes, but is not limited to, pharmaceutically acceptable salts, esters (e.g. acetate), salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1-19, 1977; incorporated herein by reference. The salts can be prepared in situ during the final isolation and purification of the compounds of the invention, or separately by reacting the free base functionality with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethane-sulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. In certain embodiments, the esters are cleaved by enzymes such as esterases.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T.

Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicles, dispersion or suspension aids, surface active agents, isotonic agents, thickening or emulsifying agents, preservatives, solid binders, lubricants and the like, as suited to the particular dosage form desired. *Remington's Pharmaceutical Sciences*, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; Cremophor; Solutol; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutical Compositions

The invention further provides a method of treating infections. In certain other embodiments, the inventive compounds are used in methods to treat proliferative diseases (e.g., cancer, benign tumors, angiogenesis, inflammatory disease, diabetic retinopathy, etc.). The method involves the administration of a therapeutically effective amount of the compound or a pharmaceutically acceptable derivative thereof to a subject (including, but not limited to a human or animal) in need of it.

The compounds and pharmaceutical compositions of the present invention may be used in treating or preventing any disease or conditions including infections (e.g., skin infections, GI infection, urinary tract infections, genito-urinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound of pharmaceutical compositions to the animal. In certain embodiments, the compound or pharmaceutical composition is administered orally. In other embodiments, the compound or pharmaceutical composition is administered parenterally.

In yet another aspect, according to the methods of treatment of the present invention, bacteria are killed, or their growth is inhibited by contacting the bacteria with an inventive compound or composition, as described herein. Thus, in still another aspect of the invention, a method for the treatment of infection is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of bacteria. The compounds and compositions, according to the method of the present invention, may be administered using any amount and any route of administration effective for killing or inhibiting the growth of bacteria. The exact amount required will vary from subject to subject, depending on the species, age, and general condition of the subject, the severity of the infection, the particular compound, its mode of administration, its mode of activity, and the like. The compounds of the invention are preferably formulated in dosage unit form for ease of administration and uniformity of dosage. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such an Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, USP. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

Assays for Biological Activity

In pursuit of inhibitors of salicylate adenylation enzymes and anti-microbial agents, the invention provides novel screening methods for identifying compounds with these desired biological properties. These assays include in vivo and in vitro assays. In one embodiment, the screening method is a high-throughput screening method that allows for the testing of anti-microbial activity against a variety of organisms in parallel.

In certain embodiments, the assay is an in vitro assay based on the inhibition of the activity of a salicylate adenylation enzyme. The enzyme may be purified, partially purified, or unpurified. The test compound is contacted with the enzyme, and the amount of inhibition of the enzymes activity is determined. The enzyme may be MbtA, YbtE, PchD, or another salicylated adenylation enzyme. In certain embodiments, the enzyme is a 2,3-dihydroxybenzoate adenylation enzyme (e.g., DhbE from *Bacillus subtilis*). In other embodiments, the enzyme is a 3,4-dihydroxybenzoate adenylation enzyme (e.g., from *Bacillus anthracis*). In other embodiments, the enzyme is a catechol adenylation enzyme from *Vibrio vulnificus, Yersinia ruckeri*, or *Brucella abortus*. The assay may be a radioactivity-based assay, a fluorescence-based assay, a colorimetric assay, etc. In certain embodiments, multiple assays under different conditions (e.g., pH, temperature, concentration of test compound, identity of test compound, salt concentration, enzyme concentration, substrate concentration, etc.) are performed in parallel in a high-throughput format.

A system for identifying a candidate compound that inhibits the growth of a microorganism comprises contacting at least one cell of a microorganism with a test compound and determining whether the cell divides or is killed. In certain embodiments, the microorganism is *M. tuberculosis*. In another embodiment, the microorganism is *Y. pestis*. In yet another embodiment, the microorganism is *P. aeruginosa*. In certain embodiments, the microorganism is *B. subtilis*. In certain embodiments, the microorganism is *Bacillus anthracis*. In other embodiments, the microorganism is *Vibrio vulnificus*. In yet other embodiments, the microorganims is *Yersinia ruckeri*. In still other embodiments, the microorganism is *Brucella abortus*. In still other embodiments, the microorganism is *Burkholderia cepacia* or *Burkholderia cenocepacia*. In other embodiments, the microorganism is *Bordetella bronchiseptica*. In certain embodiments, the microorganism depends on the production of a non-ribosomal peptide for growth, virulence, or survival. In certain embodiments, the microorganims depends on the production of an Fe(III) chelator for growth, virulence, or survival. In certain embodiments, the microorganims depends on the production of a siderophore for growth, virulence, or survival. In certain embodiments, the organism are resistant to one or more known antibiotics currently used in the clinic. The assay may be performed under iron-deficient and/or iron-rich media. In certain embodiments, the assay is a high-throughput assay allowing for the testing of various compounds, concentrations, microorganisms, growth conditions, etc. at once. In certain embodiments, the high-throughput assay is useful in analysing a collection of test compounds (e.g., a combinatorial library of test compounds, a historical collection of compounds). Any type of compounds including small molecules, peptides, proteins, polynucleotides, DNA, RNA, siRNA, biomolecules, etc. may be tested in the inventive assay systems. A kit useful in performing the inventive assay may include all or a subset of the following items: strains of the microorgansims for testing (e.g., slants), growth media, control compounds (both positive and negative controls), instructions, multi-well plates.

These and other aspects of the present invention will be further appreciated upon consideration of the following Examples, which are intended to illustrate certain particular embodiments of the invention but are not intended to limit its scope, as defined by the claims.

EXAMPLES

Example 1

Inhibitors of Siderophore Biosynthesis in *Mycobacterium tuberculosis* and *Yersinia pestis*

Figure 1A:
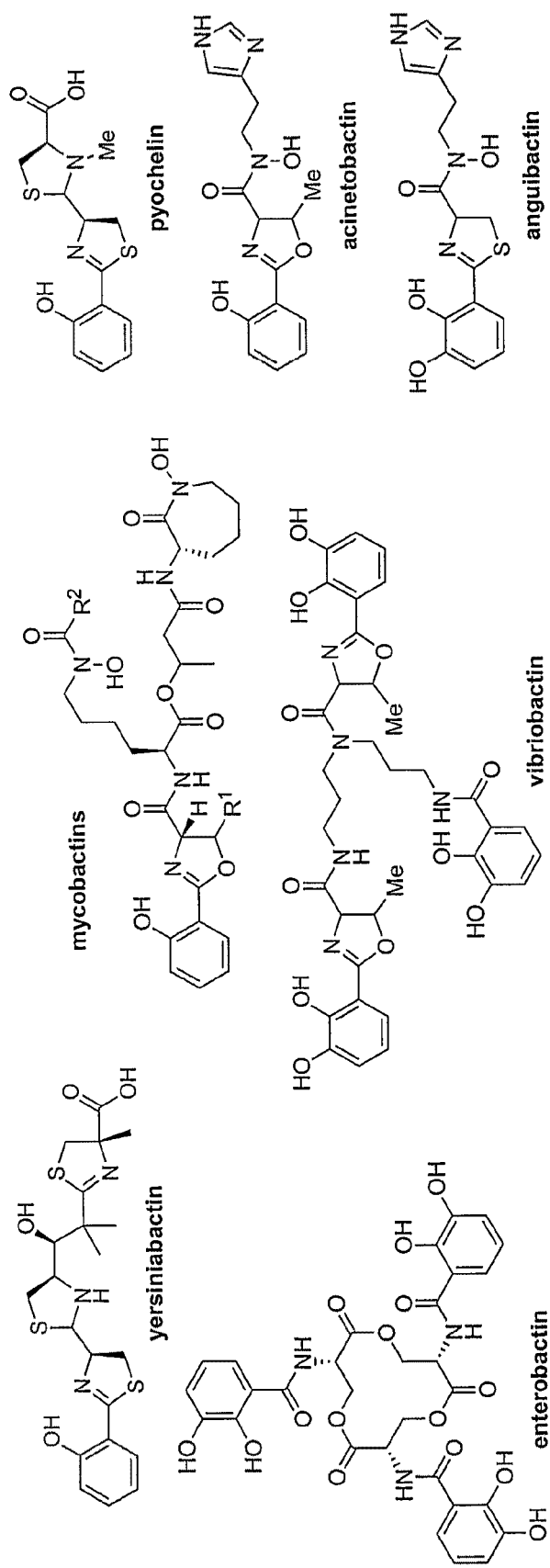
FIG. 1 shows the structures of salicyl-capped siderophores and 2,3-dihydroxybenzoyl-capped siderophores, aroyl-adenylate biosynthesis intermediates, and intermediate mimics. A. Yersiniabactin (*Yersinia* spp.), mycobactins (*M. tuberculosis*), pyochelin (*P. aeruginosa*), acinetobactin (*Acinetobacter* spp.), enterobactin (*E. coli, Salmonella* spp., *Shigella* spp.), vibriobactin (*V. cholera*), and anguibactin (*V. anguillarum*). Cell-associated mycobactins: R$^1$=H; R$^2$=(CH$_2$)$_{16-19}$CH$_3$, (CH$_2$)$_x$CH=CH(CH$_2$)$_y$CH$_3$, x+y=14-17. Soluble mycobactins: R$^1$=H, Me; R$^2$=(CH$_2$)$_{1-7}$COOCH$_3$, (CH$_2$)$_{1-7}$COOH, (CH$_2$)$_x$CH=CH(CH$_2$)$_y$COOCH$_3$, (CH$_2$)$_x$CH=CH(CH$_2$)$_y$COOH, x+y=1-5. Two-step ArCP domain salicylation reaction. C. Salicyl-AMS reaction intermediate, 1, its salicyl-AMS mimic, 2, the 2,3-dihydroxybenzoyl-AMP reaction intermediate, 3, and the related antibiotic nucleocidin, 4.

Other mechanistically related adenylate-forming enzymes have been shown to bind their cognate acyl-AMP intermediates 2-3 orders of magnitude more tightly than their carboxylic acid and ATP substrates (Kim et al. "Aminoacyl-tRNA synthetases and their inhibitors as a novel family of antibiotics" *Appl. Microbiol. Biotechnol.* 61, 278-288 (2003); incorporated herein by reference). Thus, various non-hydrolyzable acyl-AMP analogs have been used as mechanism-based inhibitors of adenylate-forming enzymes. Among these are the acyl sulfamoyl adenosines (acyl-AMS) (Kim et al. Aminoacyl-tRNA synthetases and their inhibitors as a novel family of antibiotics. *Appl. Microbiol. Biotechnol.* 61, 278-288 (2003); Finking et al. Aminoacyl adenylate substrate analogues for the inhibition of adenylation domains of nonribosomal peptide synthetases. *ChemBioChem* 4, 903-906 (2003); each of which is incorporated herein by reference), inspired by the natural product nucleocidin (Florini et al. Inhibition of protein synthesis in vitro and in vivo by nucleocidin, an antitrypanosomal antibiotic. *Journal of Biological Chemistry* 241, 1091-1098 (1966); incorporated herein by reference), 4 (FIG. 1C). Based on these considerations, we postulated that the reaction intermediate mimic 5'-O-[N-(salicyl)sulfamoyl]-adeno sine (salicyl-AMS), 2 (FIG. 1C), would be a potent inhibitor of the salicylate adenylation activity of YbtE, MbtA, and closely related enzymes such as PchD, the domain salicylation enzyme that is involved in the biosynthesis of the siderophore pyochelin in *Pseudomonas aeruginosa* (Quadri et al. "Assembly of the *Pseudomonas aeruginosa* nonribosomal peptide siderophore pyochelin: In vitro reconstitution of aryl-4,2-bisthiazoline synthetase activity from PchD, PchE, and PchF" *Biochemistry* 38, 14941-14954. (1999); incorporated herein by reference) (FIG. 1A).

Figure 4:
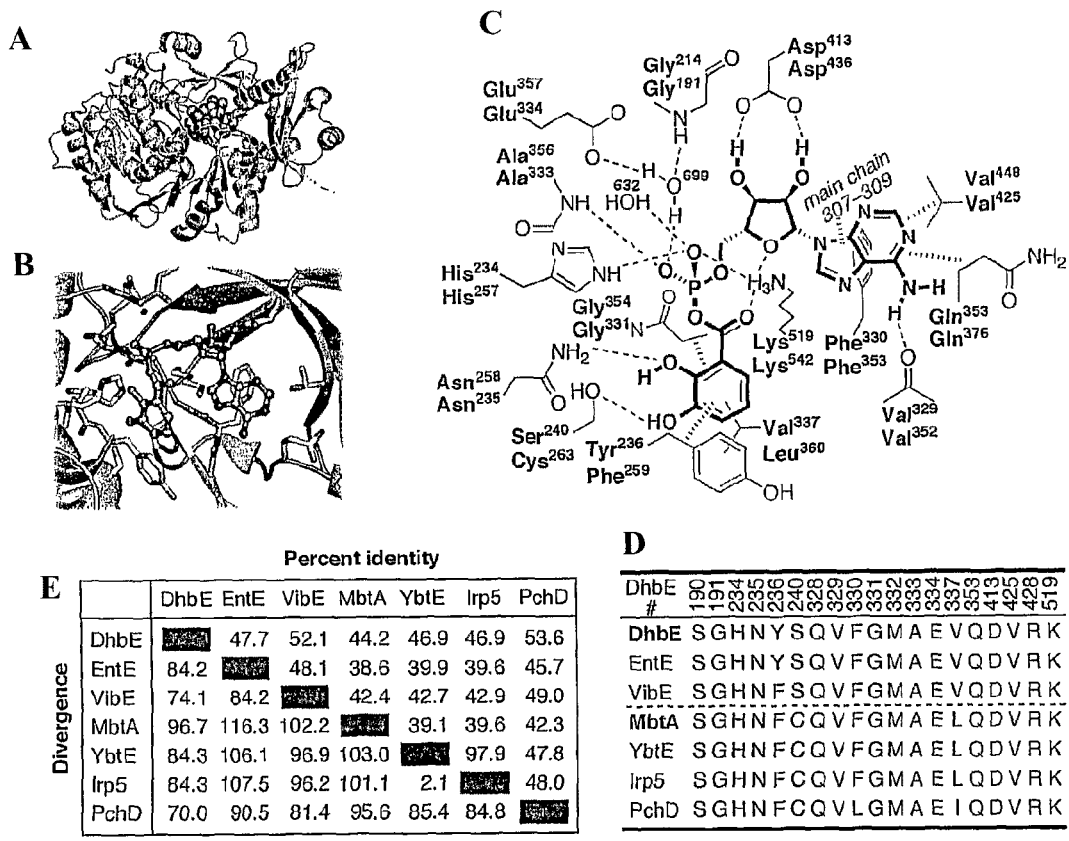
FIG. 4 shows the structural analysis of aroyl adenylate binding to adenylate-forming enzymes. A. Overview of dihydroxybenzoyl-AMP bound to DhbE. B. Close-up view of dihydroxybenzoyl-AMP in the DhbE active site. Residues within 4.0 Å of the ligand are displayed. C. Putative hydrogen bonding ( - - - ) and hydrophobic (ıııııııı) interactions of dihydroxybenzoyl-AMP with DhbE and corresponding conserved and analogous residues in YbtE. D. Alignment of putative binding residues in 2,3-dihydroxybenzoate adenylation enzymes (DhbE, EntE, VibE), salicylate adenylation enzymes (YbtE, Irp5, MbtA, PchD), and a phenylalanine adenylation enzyme (PheA). (Structural analysis: 1 MDB in MacPyMOL 0.95. Full amino acid alignments: NP_391078, NP_415126, AAC45927, NP_405468, T30345, NP_216900, NP_252918, with ClustalW in DNASTAR MegAlign 5.5.) E. Percent identity between DhbE, EntE, VibE, MbtA, YbtE, Irp5, and PchD.

To evaluate this idea further, we examined the reported cocrystal structure of a related adenylate-forming enzyme, DhbE, in complex with its cognate 2,3-dihydroxybenzoyl-AMP intermediate (May et al. Crystal structure of DhbE, an archetype for aryl acid activating domains of modular nonribosomal peptide synthetases. *Proc. Natl. Acad. Sci. USA.* 99, 12120-12125. (2002); incorporated herein by reference), 3 (FIG. 1C). The intermediate is bound by a significant number of interactions, and we identified the probable key binding residues, which are depicted in FIG. 4. We then performed full length amino acid sequence alignments of DhbE, YbtE, MbtA, PchD, and three other related aroyl adenylate-forming enzymes. Overall sequence identities were 40-50%, however, except for minor differences at the base of the binding pocket, which likely contribute to specificity for salicylate versus 2,3-dihydroxybenzoate (May et al. Crystal structure of DhbE, an archetype for aryl acid activating domains of modular nonribosomal peptide synthetases. *Proc. Natl. Acad. Sci. USA.* 99, 12120-12125. (2002); incorporated herein by reference), the putative aroyl-AMP binding residues were completely conserved across all of the enzymes (FIG. 4). This suggested that salicyl-AMP likely binds to YbtE, MbtA, and PchD in a similar fashion and, since binding of the phosphate group of 2,3-dihydroxybenzoyl-AMP appears to involve primarily hydrogen-bonding interactions rather than electrostatic interactions, we postulated that the uncharged sulfamate group in salicyl-AMS would be a viable surrogate for the phosphate group in salicyl-AMP.

Salicyl-AMS (FIG. 5) was synthesized and used an adenylation assay (see Methods) to determine dose-response curves for inhibition of the adenylation activity of YbtE, MbtA, and PchD at fixed, saturating substrate concentrations. The $IC_{50}$ values determined in these experiments using the Morrison equation (Copeland, R. A. in *Enzymes: A practical introduction to structure, mechanism, and data analysis* 305-317 (Wiley-VCH, Inc. Publications, New York, 2000); incorporated herein by reference) were 14.7±2.0 nM for YbtE (FIG. 2A), 10.7±2.0 nM for MbtA (FIG. 2B), and 12.5±2.2 nM for PchD (FIG. 2C). In contrast to salicyl-AMS, the parental compound 5'-O-(sulfamoyl)-adenosine (AMS), 8 (FIG. 5), did not inhibit adenylation when tested at up to 400 nM under the same conditions (not shown). The $IC_{50}$ values were ~½ [E] and consistent with the expected 1:1 stoichiometry for the enzyme-inhibitor complexes. We noted that $IC_{50}$ values similar to the enzyme concentration (i.e., within a factor of 10) are characteristic of tight binding inhibitors (TBIs) (Copeland, R. A. in *Enzymes: A practical introduction to structure, mechanism, and data analysis* 305-317 (Wiley-VCH, Inc. Publications, New York, 2000); incorporated herein by reference). Thus, based upon the large number of binding interactions in the aroyl-AMP binding model discussed above and the $IC_{50}$ values calculated from the dose-response curves, we hypothesized that salicyl-AMS behaves as a TBI. Importantly, the steady state approximations that permit application of the Henri-Michaelis-Menten equation to characterize inhibitor-enzyme interactions are not applicable to TBIs because of their high binding affinity (Copeland, R. A. in *Enzymes: A practical introduction to structure, mechanism, and data analysis* 305-317 (Wiley-VCH, Inc. Publications, New York, 2000); incorporated herein by reference). Instead, methodologies that consider an alternative steady state approach are more appropriate for analysis of TBIs (Copeland, R. A. in *Enzymes: A practical introduction to structure, mechanism, and data analysis* 305-317 (Wiley-VCH, Inc. Publications, New York, 2000)).

Thus, we further analyzed inhibition of YbtE by salicyl-AMS using methodologies for TBI (Copeland, R. A. in *Enzymes: A practical introduction to structure, mechanism, and data analysis* 305-317 (Wiley-VCH, Inc. Publications, New York, 2000)). We determined $IC_{50}$ values from dose-response curves for adenylation activity at saturating substrate concentrations across a range of YbtE concentrations (FIG. 2D). We observed a linear relationship between the $IC_{50}$ values and YbtE concentrations, with a slope of 0.43 ($R^2$=0.9594), corrected to 0.52 ($R^2$=0.9999) when the YbtE concentrations derived from the dose-response curve fits were used to adjust for errors in enzyme concentration and the inactive protein fraction. Since a slope of 0.5 is diagnostic of a TBI modality (Copeland, R. A. in *Enzymes: A practical introduction to structure, mechanism, and data analysis* 305-317 (Wiley-VCH, Inc. Publications, New York, 2000)), the results support our hypothesis that salicyl-AMS acts as a TBI.

We next determined $K_i^{app}$ values from dose-response curves using variable ATP or salicylate concentrations. The $K_i^{app}$ values increased linearly with increasing ATP concentration over a range of 0.2-60×$K_m^{ATP}$ [172 µM as determined in this study (not shown) and 350 µM as reported elsewhere (Gehring et al "The nonribosomal peptide synthetase HMWP2 forms a thiazoline ring during biogenesis of yersiniabactin, an iron-chelating virulence factor of *Yersinia pestis*" *Biochemistry* 37, 11637-11650. (1998); incorporated herein by reference)] and excess salicylate [~190×$K_m^{Sal}$; $K_m^{Sal}$=5.4 µM as determined in this study (not shown) and 4.6 µM as reported elsewhere (Gehring et al. "The nonribosomal peptide synthetase HMWP2 forms a thiazoline ring during biogenesis of yersiniabactin, an iron-chelating virulence factor of *Yersinia pestis*" *Biochemistry* 37, 11637-11650. (1998); incorporated herein by reference)] (FIG. 2E), a result indicative of competitive inhibition with respect to ATP (Copeland, R. A. in *Enzymes: A practical introduction to structure, mechanism, and data analysis* 305-317 (Wiley-VCH, Inc. Publications, New York, 2000)). For competitive TBIs, $$K_i^{app} = K_i\left(1 + \frac{[S]}{K_m}\right),$$

thus $K_i^{app}$=$K_i$ when [S]=0, and a $K_i$ value of 0.35±0.27 nM was calculated as the y-intercept of the line fitted to the data in FIG. 2E. In contrast, increasing salicylate concentration from 0.2-50× $K_m^{Sal}$ in the presence of excess ATP (~60×$K_m^{ATP}$) had no significant effect on $K_i^{app}$ (FIG. 2F). The independence of $K_i^{app}$ from salicylate concentration is diagnostic of non-competitive inhibition with respect to this substrate (Copeland, in *Enzymes: A practical introduction to structure, mechanism, and data analysis* 305-317 (Wiley-VCH, Inc. Publications, New York, 2000)), in which case $K_i^{app}$=$Ki^{20}$, and a Ki of 1.08±0.98 nM was calculated by averaging the $K_i^{app}$ values in FIG. 2F. Overall, our data confirm that salicyl-AMS behaves as a potent inhibitor of YbtE with a tight-binding modality.

Figure 1B:
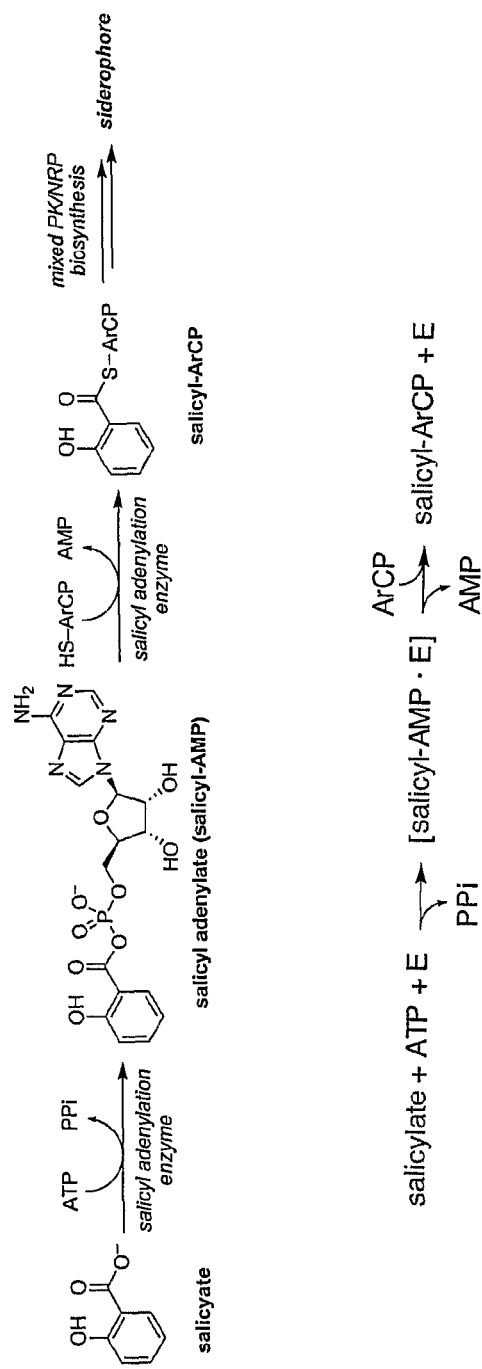
Figure 1C:
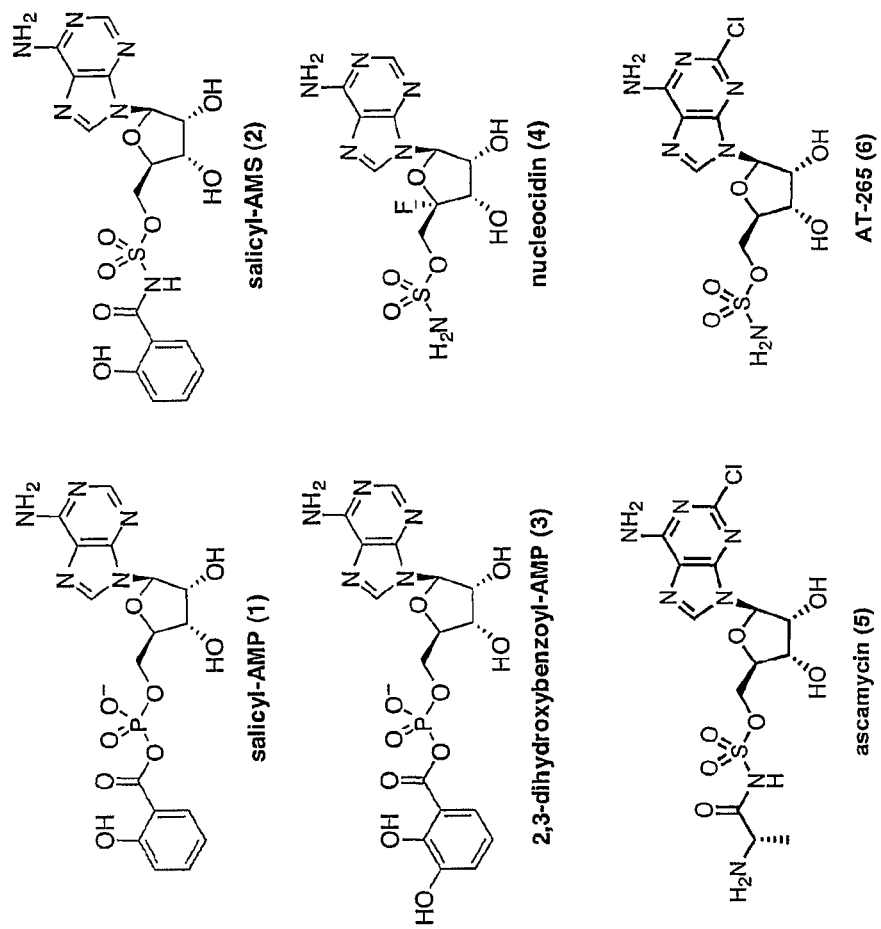

The results presented above demonstrate that salicyl-AMS inhibits the first step of the ArCP domain salicylation reaction catalyzed by YbtE, MbtA, and PchD (FIG. 1B). Thus, the inhibitor should also block formation of the salicyl-ArCP domain intermediate. To investigate this hypothesis, we developed a domain salicylation assay using YbtE, a phosphopantetheinylated $His_6$-tagged ArCP domain fragment (ypArCP-H6, 108 residues) from the *Y. pestis* HMWP2 synthetase, and 96-well flash plates (see Methods). The flash plate wells have a $Ni^{2+}$ coat for ypArCP-H6 binding and a scintillant coat that provides a scintillation proximity effect for detection of the YbtE-catalyzed incorporation of [$^3$H]- salicylate into well-bound ypArCP-H6. In this assay, salicyl-AMS potently inhibited [$^3$H]-salicyl-ypArCP-H6 formation, with an IC$_{50}$~½[E] (FIG. 2G). In contrast, AMS did not inhibit salicylation when tested at up to 400 μM under the same conditions (not shown). Thus, the results of this domain salicylation assay are in agreement with those obtained using the salicylate adenylation assay above.

Figure 3:
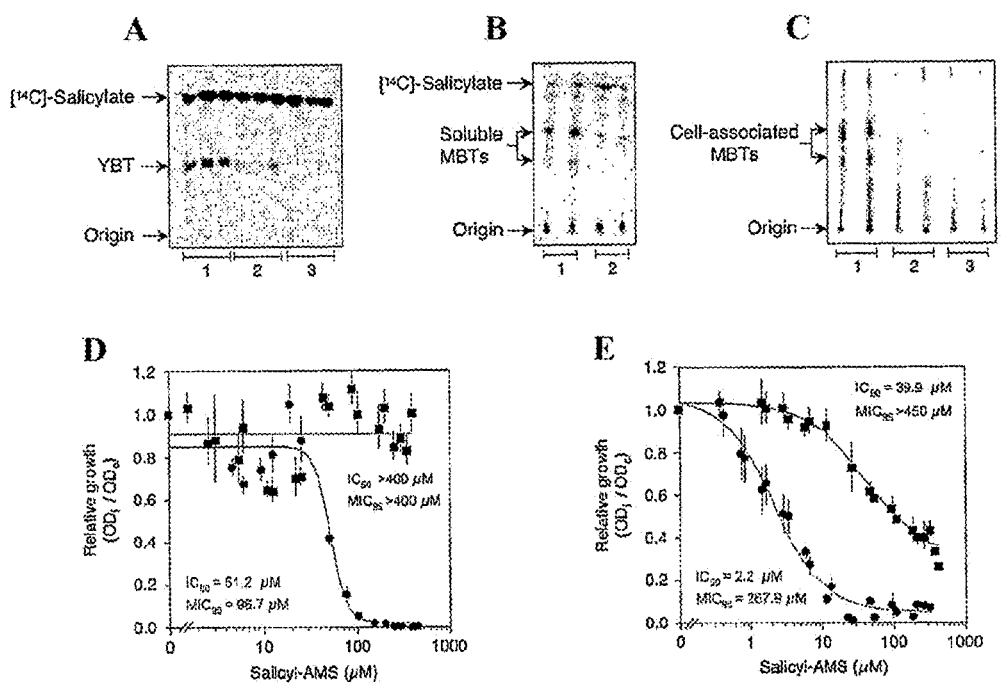
FIG. 3 shows the inhibition of siderophore production and bacterial growth by salicycl-AMS. A-C. Radiometric-TLC analyses of yersiniabactin (YBT, A), soluble mycobactins (MBTs, B), and cell-associated mycobactins (C). Duplicates and triplicates lanes are marked. Lanes 1, siderophores extracted from DMSO-treated control cultures; lanes 2, siderophores extracted from inhibitor-treated cultures; and lanes 3, extracts from siderophore-deficient strain *Y. pestis* KIM6 2082.1 (in A) and siderophore-deficient strain *M. tuberculosis* mbtF⁻ (in C). D-E. Dose-response for bacterial growth inhibition plotted with fractional growth of *Y. pestis* (D) and *M. tuberculosis* (E) in iron-deficient (filled circles) or iron-rich (filled squares) media as a function of salicyl-AMS concentration. ODi and ODc, optical density of inhibitor-treated cultures and DMSO-treated controls, respectively. The plots show means of triplicates with standard errors.

Having demonstrated that salicyl-AMS inhibits YbtE and MbtA, we next examined the ability of this compound to block siderophore biosynthesis in *Y. pestis* and *M. tuberculosis*. Radiometric siderophore production assays (see Methods below) revealed that salicyl-AMS inhibits both YBT production in *Y. pestis* and MBT production in *M. tuberculosis* (FIG. 3A-C). Under the conditions tested, YBT production was inhibited by ~5-fold relative to DMSO-treated controls and MBT production was virtually undetectable.

Since siderophore biosynthesis is required for efficient bacterial growth under iron-limiting conditions, we assessed the effect of salicyl-AMS upon *Y. pestis* and *M. tuberculosis* growth in iron-deficient culture media. Indeed, salicyl-AMS inhibited the growth of both organisms under these conditions (*Y. pestis*: $10_{50}$=51.2±4.7 μM, MIC$_{95}$=96.7 μM; *M. tuberculosis*: IC$_{50}$=2.2±0.3 μM, MIC$_{95}$=267.9 μM) (FIGS. 3D, E). Furthermore, salicyl-AMS (tested at up to 8×IC$_{50}$, 4×MIC$_{95}$) was not active against *Y. pestis* in iron-supplemented media (FIG. 3D), in which siderophore production is not required for growth. Under these conditions, salicyl-AMS (tested at up to 180×IC$_{50}$, 1.5×MIC$_{95}$) did inhibit *M. tuberculosis* growth, albeit with an 18-fold increase of IC$_{50}$ (39.9±7.6 μM) (FIG. 3E). This suggests that, in addition to blocking siderophore biosynthesis, salicyl-AMS may also inhibit *M. tuberculosis* growth by other mechanisms.

Salicyl-AMS is the first biochemically-confirmed inhibitor of siderophore biosynthesis (Quadri & Ratledge in *Tuberculosis and the Tubercle Bacillus* (eds. Cole, S. et al.) pp. 341-357 (ASM Press, Washington, D.C. 2004); incorporated herein by reference). Consistent with this activity, salicyl-AMS inhibits *M. tuberculosis* and *Y. pestis* growth under iron-limiting conditions. Thus, salicyl-AMS is a promising initial lead compound for the development of new antibiotics that block siderophore biosynthesis to treat tuberculosis and plague.

Methods

Synthetic Materials and Methods

Reagents were obtained from Aldrich Chemical or Acros Organics and used without further purification. Optima grade solvents were obtained from Fisher Scientific, degassed with argon, and purified on a solvent drying system as described elsewhere (Pangborn et al. "Safe and convenient procedure for solvent purification" *Organometallics* 15, 1518-1520 (1996); incorporated herein by reference). Reactions were performed in flame-dried glassware under positive Ar pressure with magnetic stirring. Cold baths were generated as follows: 0° C., wet ice/water; −78° C., dry ice/acetone. TLC was performed on 0.25 mm E Merck silica gel 60 F254 plates and visualized under UV light (254 nm) or by staining with potassium permanganate (KMnO$_4$) or cerium ammonium molybdenate (CAM). Flash chromatography was performed on E. Merck 230-400 mesh silica gel 60. NMR spectra were recorded on Bruker DRX500 or AMX400 instruments at 24° C. Chemical shifts are expressed in ppm relative to TMS ($^1$H, 0 ppm), CDCl$_3$ ($^{13}$C, 77.0 ppm), or DMSO-d$_6$ ($^1$H, 2.50 ppm; $^{13}$C, 39.51 ppm); coupling constants are expressed in Hz. Mass spectra were obtained at the MSKCC Analytical Core Facility on a PE SCIEX API 100 mass spectrometer by electrospray (ESI) ionization.

Synthesis of Salicyl-AMS and AMS

Figure 5:
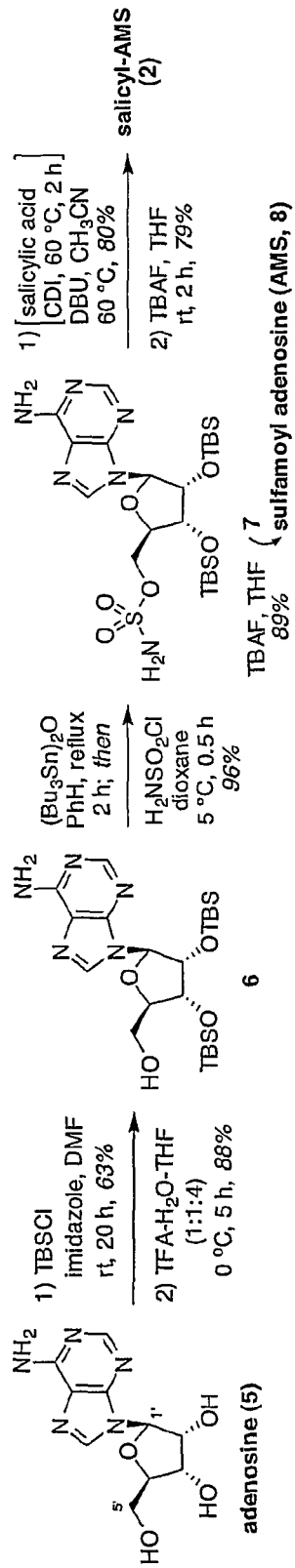
FIG. 5 depicts the synthesis of salicyl-AMS from adenosine. CDI=1,1'-carbonyldiimidazole; DBU=1,8-diazabicyclo [5.4.0]undec-7-ene; DMF=N,N-dimethylformamide; TBAF=tetrabutylammonium fluoride; TBS=t=butyldimethylsilyl; TFA=2,2,2-trifluoroacetic acid; THF=tetrahydrofuran.

Salicyl-AMS was synthesized as shown in FIG. 5. Silylation of adenosine, 5, followed by selective deprotection of 5'-O-TBS group provided 2',3'-bis-O-TBS-adenosine, 6 (Zhu et al. Facile and highly selective 5'-desilylation of multisilylated nucleosides. *J. Chem. Soc., Perkin Trans.* 1, 2305-2306 (2000); incorporated herein by reference). Silyl protecting groups at the 2'- and 3'-positions were used to set the stage for future syntheses of analogs to be carried out either in solution or on a solid support using a silyl ether linker Sulfamoylation of 6 at the 5'-position using bis(tributyltin) oxide and sulfamoyl chloride (Castro-Pichel et al. A facile synthesis of ascamycin and related analogs. *Tetrahedron* 43, 383-389 (1987); incorporated herein by reference) provided sulfamate, 7. Salicylate was preactivated with carbonyl diimidazole, then coupled to the sulfamate amino group of 7 (Forrest et al. Aminoalkyl adenylate and aminoacyl sulfamate intermediate analogues differing greatly in affinity for their cognate *Staphylococcus aureus* aminoacyl tRNA synthetases. *Bioorg. Med. Chem. Lett.* 10, 1871-1874 (2000); incorporated herein by reference). Subsequent deblocking of the TBS protecting groups with TBAF afforded salicyl-AMS, 2. The synthesis was accomplished in 5 steps and 31% overall yield. Analytical data for salicyl-AMS, 2, are as follows. TLC: R$_f$=0.33 (5:1 EtOAc/MeOH). $^1$H NMR (400 MHz, DMSO-d$_6$): δ 8.40 (s, 1H), 8.12 (s, 1H), 7.81 (dd, 1H, J=7.7, 1.4), 7.28-7.24 (m, 3H), 6.75 (d, 1H, J=7.7), 6.74 (t, 1H, J=7.7), 5.92 (d, 1H, J=6.4), 5.49 (d, 1H, J=6.1), 5.35 (d, 1H, J=4.8), 4.62 (dd, 1H, J=6.4, 5.8), 4.25-4.08 (m, 4H). $^{13}$C NMR (125 MHz, DMSO-d$_6$): δ 160.7, 156.0, 152.6, 149.6, 139.3, 132.6, 129.9, 119.9, 118.9, 117.5, 116.6, 86.9, 82.5, 73.5, 70.8, 68.1, 48.6. ESI-MS m/z: (pos) 467 [M+H]$^+$, 489 [M+Na]$^+$; (neg) 465 [M−H]$^-$.

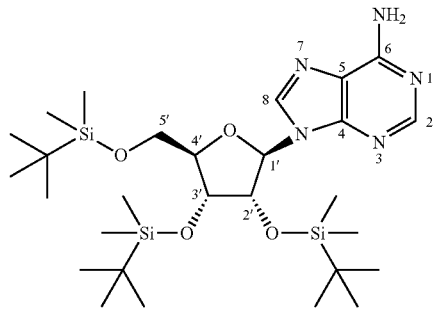 [SMILES: CC(C)(C)[Si](C)(C)OC[C@H]1O[C@@H](n2cnc3c(N)ncnc32)[C@H](O[Si](C)(C)C(C)(C)C)[C@@H]1O[Si](C)(C)C(C)(C)C]

2',3',4'-O,O,O,-Tris(t-butyldimethylsilyl)adenosine (1)

tert-Butyldimethylsilyl chloride (16.3 g, 105 mmol, 3.5 equiv) in anhyd DMF (20 mL) was added to a solution of (−)-adenosine (8.09 g, 30 mmol) and imidazole (18.4 g, 270 mmol, 9.0 equiv) in anhyd DMF (40 mL). The white slurry turned to a colorless solution in 10 min. The resulting clear solution was stirred overnight. The reaction mixture was then diluted with CH$_2$Cl$_2$, washed with 3× satd aq NaHCO$_3$, dried (MgSO$_4$), filtered, and concentrated. The residue was purified by column chromatography. (elution with 3:1 hexane/EtOAc) to yield 1 as white solid (11.5 g, 63%).

TLC: R$_f$ 0.29 (1:1 hexanes/EtOAc). $^1$H-NMR (400 MHz, CDCl$_3$): δ 8.33 (s, 1H), 8.15 (s, 1H), 6.02 (d, 1H, J=5.2), 4.69 (t, 1H, J=4.9), 4.32 (t, 1H, J=3.8), 4.12 (m, 1H), 4.03 (dd, 1H, J=11.4, 4.4), 3.79 (dd, 1H, J=11.4, 2.8), 0.95 (s, 9H), 0.93 (s, 9H), 0.79 (s, 9H), 0.13 (s, 3H), 0.12 (s, 3H), 0.10 (s, 3H), 0.09 (s, 3H), −0.04 (s, 3H), −0.23 (s, 3H). $^{13}$C-NMR (125 MHz, CDCl$_3$): δ 155.7, 153.1, 150.1, 139.8, 120.3, 88.5, 85.7, 75.9, 72.2, 62.7, 26.3, 26.0, 25.6, 18.7, 18.3, 18.1, −4.2, −4.5, −4.5, −4.9, −5.2, −5.2. ESI-MS m/z: (pos) 610.3 [M+H]$^+$, 632.3 [M+Na]$^+$; (neg) 608.4 [M−H]$^−$, 644.4 [M+Cl]$^−$.

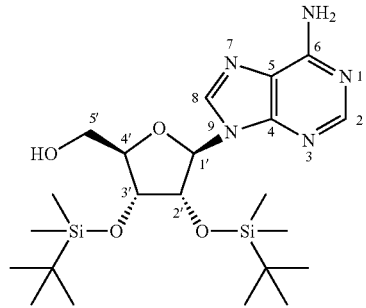 [SMILES: CC(C)(C)[Si](C)(C)O[C@@H]1[C@H](O[Si](C)(C)C(C)(C)C)[C@@H](CO)O[C@H]1n1cnc2c(N)ncnc21]

2′,3′-O,O-Bis(t-butyldimethylsilyl)adenosine (2)

A mixture of TFA (1.75 mL) and H$_2$O (1.75 mL) was added to a cooled (0° C.) solution of tris(TBS)adenosine 1 (350 mg, 574 mmol) in THF (7 mL). The reaction mixture was stirred at 0° C. After 5 h, aq NaHCO$_3$ was added at 0° C. The aqueous layer was extracted 3× with EtOAc, washed with H$_2$O and brine, dried (MgSO$_4$), filtered, and concentrated. The residue was purified by flash chromatography (elution with 1:1 hexane/EtOAc) to afford 2 as a white solid (251.6 mg, 88%).

TLC: R$_f$ 0.22 (EtOAc), 0.37 (9:1 CH$_2$Cl$_2$/MeOH). $^1$H-NMR (400 MHz, CDCl$_3$): δ 8.35 (s, 1H), 7.83 (s, 1H), 6.71 (dd, 1H, J=12.2, 1.8), 5.78 (d, 1H, J=7.9), 5.56 (br s, 2H), 5.05 (dd, 1H, J=7.9, 4.6), 4.33 (d, 1H, J=4.6), 4.16 (s, 1H), 3.94 (d, 1H, J=13.0), 3.70 (t, 1H, J=12.7), 0.95 (s, 9H), 0.75 (s, 9H), 0.13 (s, 3H), 0.12 (s, 3H), −0.14 (s, 3H), −0.62 (s, 3H). $^{13}$C-NMR (125 MHz, DMSO-d$_6$): δ 156.2, 152.3, 148.9, 140.2, 119.5, 87.6, 87.1, 74.1, 73.0, 61.4, 48.6, 25.7, 25.4, 17.8, 17.5, −4.7, −4.8, −4.9, −5.8. ESI-MS m/z: (pos) 496.3 [M+H]$^+$, 518.2 [M+Na]$^+$; (neg) 530.2 [M+Cl]$^−$.

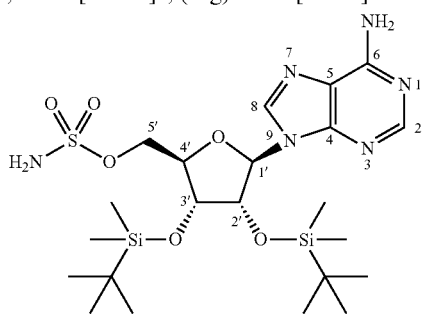

2′,3′-O,O-Bis(t-butyldimethylsilyl)-5′-O-sulfamoyladenosine (3)

Bis(tributyltin) oxide (7.43 mL, 14.0 mmol, 3.5 equiv) was added dropwise to a solution of bis(TBS)adenosine 2 (1.98 g, 4.0 mmol) in anhyd benzene (130 mL). The resulting white suspension was refluxed with stirring. After 2 h, the reaction mixture was cooled to 5° C. Sulfamoyl chloride (2.08 g, 18.0 mmol, 4.5 equiv) in dioxane (65 mL) was added dropwise to the reaction mixture, stirred for an additional 30 min at 5° C. The solvent was then removed in vacuo. The residue was rinsed 3× with hot (40° C.) hexane. The solid was washed with 1 N NH$_3$ solution in MeOH. The crude material was purified by column chromatography (elution with 15:1 CH$_2$Cl$_2$/MeOH) to yield 3 as white solid (2.2 g, 96%)

TLC: R$_f$ 0.2 (9:1 CH$_2$Cl$_2$/MeOH). $^1$H-NMR (400 MHz, DMSO-d$_6$): δ 8.36 (s, 1H), 8.16 (s, 1H), 7.66 (br s, 2H), 7.33 (br s, 2H), 5.95 (d, 1H, J=6.6), 4.97 (dd, 1H, J=6.6, 4.3), 4.38-4.41 (m, 2H), 4.31 (dd, 1H, J=10.8, 5.8), 4.18 (m, 1H), 0.93 (s, 9H), 0.71 (s, 9H), 0.15 (s, 3H), 0.12 (s, 3H), −0.09 (s, 3H), −0.38 (s, 3H). $^{13}$C-NMR (125 MHz, DMSO-d$_6$): δ 156.1, 152.7, 149.4, 139.8, 119.3, 87.0, 82.8, 73.7, 72.4, 68.0, 25.7, 25.4, 17.7, 17.5, −4.7, −4.8, −4.9, −5.6. ESI-MS m/z: (pos) 575.3 [M+H]$^+$; (neg) 573.2 [M−H]$^−$, 609.2 [M+Cl]$^−$.

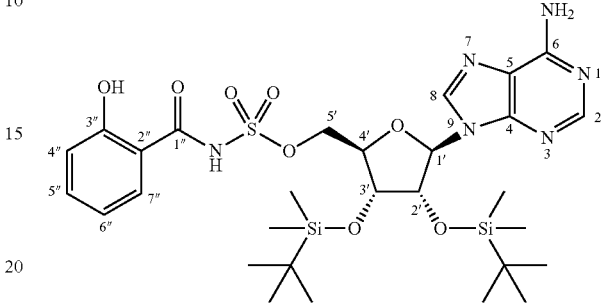

2′,3′-O,O-Bis(t-butyldimethylsilyl)-5′-O-(N-salicylsulfamoyl)adenosine (4)

A solution of salicylic acid (66 mg, 477 μmol, 3.0 equiv) and 1,1′-carbonyldiimidazole (93 mg, 575 mmol, 3.6 equiv) in anhyd acetonitrile (4 mL) was stirred at 60° C. for 2 h under argon atmosphere. The reaction mixture was cooled to rt. A mixture of bis(TBS)sulfamoyladenosine 3 (92 mg, 160 mmol) and DBU (36 μL, 241 mmol, 1.5 equiv) was then added dropwise to the reaction mixture. The resulting yellow solution was again stirred at 60° C. After an additional 30 min, the reaction mixture was diluted with H$_2$O. The aqueous layer was extracted 3× with EtOAc, washed with 1 N HCl, satd aq NaHCO$_3$, and brine, dried (MgSO$_4$), filtered, and concentrated. The residue was purified by flash column chromatography (elution with 9:1 CH$_2$Cl$_2$/MeOH 5:1 CH$_2$Cl$_2$/MeOH) to afford 4 as a white solid (89 mg, 80%). TLC: R$_f$ 0.21 (17:3 EtOAc/MeOH). $^1$H-NMR (400 MHz, DMSO-d$_6$): δ 8.45 (s, 1H), 8.09 (s, 1H), 7.84 (dd, 1H, J=7.8, 1.8), 7.28 (br s, 2H), 7.26 (m, 1H), 6.76-6.71 (m, 2H), 5.95 (d, 1H, J=7.3), 4.92 (dd, 1H, J=4.3, 7.3), 4.36 (d, 1H, J=4.3), 4.29 (dd, 1H, J=4.8, 11), 4.23-4.16 (m, 2H), 0.9 (s, 9H), 0.65 (s, 9H), 0.1 (s, 3H), 0.09 (s, 3H), −0.12 (s, 3H), −0.46 (s, 3H). $^{13}$C-NMR (125 MHz, DMSO-d$_6$): δ 171.1, 160.7, 156.0, 152.6, 149.7, 139.4, 132.6, 129.9, 119.8, 118.9, 117.4, 116.5, 86.2, 83.9, 74.5, 73.2, 67.4, 25.7, 25.4, 17.7, 17.4, −4.8, −4.9, −5.8, −5.9. ESI-MS m/z: (pos) 695.3 [M+H]$^+$, 717.2 [M+Na]$^+$; (neg) 693.2 [M−H]$^−$.

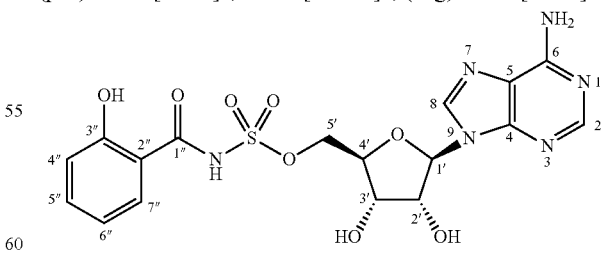

5′-O—(N-Salicylsulfamoyl)adenosine (Salicyl-AMS, 5)

TBAF (1.0 M in THF, 100 μL, 0.1 mmol, 2.5 equiv) was added dropwise to a solution of bis(TBS)salicylsulfamoyladenosine 4 (28 mg, 0.04 mmol) in anhyd THF (1.6 mL). The reaction mixture was stirred at rt for 30 min. The solvent was then evaporated. The residue was purified by flash column chromatography (elution with 5:1 EtOAc/MeOH) to afford 5 as a white solid (14.8 mg, 79%). TLC: $R_f$ 0.33 (5:1 EtOAc/MeOH). $^1$H-NMR (400 MHz, DMSO-$d_6$): δ 8.40 (s, 1H), 8.12 (s, 1H), 7.81 (dd, 1H, J=7.7, 1.4), 7.28-7.24 (m, 3H), 6.75 (d, 1H, J=7.7), 6.74 (t, 1H, J=7.7), 5.92 (d, 1H, J=6.4), 5.49 (d, 1H, J=6.1), 5.35 (d, 1H, J=4.8), 4.62 (dd, 1H, J=6.4, 5.8), 4.25-4.08 (m, 4H). $^{13}$C-NMR (125 MHz, DMSO-$d_6$): δ 171.1, 160.7, 156.0, 152.6, 149.6, 139.3, 132.6, 129.9, 119.9, 118.9, 117.5, 116.6, 86.9, 82.5, 73.5, 70.8, 68.1. ESI-MS m/z: (pos) 467 [M+H]$^+$, 489 [M+Na]$^+$; (neg) 465 [M−H]$^−$.

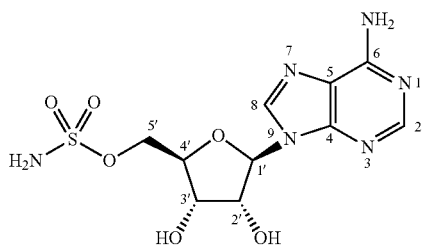 [SMILES: Nc1ncnc2c1ncn2[C@@H]1O[C@H](COS(N)(=O)=O)[C@@H](O)[C@H]1O]

5'-O-Sulfamoyladenosine (AMS, 6)

TBAF (1.0 M in THF, 250 μL, 0.25 mmol, 2.5 equiv) was added dropwise to a solution of bis(TBS)sulfamoyladenosine 3 (57.4 mg, 0.1 mmol) in anhyd THF (4.0 mL). The reaction mixture was stirred at rt for 30 min. The solvent was then evaporated. The residue was purified by column chromatography (elution with 5:1 EtOAc/MeOH) to afford 6 as a white solid (31 mg, 89%).

TLC: $R_f$ 0.18 (6:1 EtOAc/MeOH). $^1$H-NMR (500 MHz, DMSO-$d_6$): δ 8.30 (s, 1H), 8.15 (s, 1H), 7.60 (br s, 2H), 7.31 (br s, 2H), 5.93 (d, 1H, J=5.3), 5.62 (d, 1H, J=6.0), 5.44 (d, 1H, J=5.4), 4.63 (app q, 1H, J=5.4), 4.29 (dd, 1H, J=10.7, 3.8), 4.23 (app q, 1H, J=4.9), 4.19 (dd, 1H, J=10.6, J=6.0), 4.14 (m, 1H). $^{13}$C-NMR (125 MHz, DMSO-$d_6$): δ 156.1, 152.7, 149.4, 139.4, 119.1, 87.5, 81.5, 73.0, 70.3, 68.7. ESI-MS m/z: (pos) 347.1 [M+H]$^+$, 368.9 [M+Na]$^+$; (neg) 344.9 [M−H]$^−$, 380.9 [M+Cl]$^−$F.

Protein Production.

YbtE and MbtA were expressed in *E. coli* BL21(DE3) as IPTG-inducible N-terminally His$_6$Smt3-tagged proteins using plasmids pSmt3YbtE and pSmt3 MbtA, respectively. Plasmid pSmt3YbtE was constructed by cloning the YbtE coding region as a BamHI-HindIII fragment into pSMT3 (Mossessova et al. Ulp1-SUMO crystal structure and genetic analysis reveal conserved interactions and a regulatory element essential for cell growth in yeast. *Mol. Cell.* 5, 865-876. (2000); incorporated herein by reference). This fragment was PCR amplified with primers JfybteF (5'-aaaggggatccatgaat-tcttcctttgaatc-3') and JfybteR (5'-ggtttaagcttattgggcagaatggc-gataac-3') from genomic DNA. Plasmid pSmt3 MbtA was constructed by inserting the MbtA coding segment as a BamHI-HindIII fragment into pSMT3. The MbtA fragment was PCR amplified with primers JfmbtaF (5'-aaggaggatccat-gccaccgaaggcggcag-3') and JfmbtaR (5'-ttgacaagcttcaatg-gcagcgctgggtcg-3') from plasmid pMBTA (Quadri et al. Identification of a *MycobacteriuM. tuberculosis* gene cluster encoding the biosynthetic enzymes for assembly of the virulence-conferring siderophore mycobactin. *Chem. Biol.* 5, 631-645. (1998); incorporated herein by reference). Cloning was carried out using standard methods (Sambrook, J., Fritsch, E. F. & Maniatis, T. *Molecular cloning. A laboratory manual*. New York Cold Spring Harbor Laboratory (Cold Spring Harbor, N.Y., 1989); incorporated herein by reference). For protein production, the strains expressing the tagged proteins were cultivated in LB broth (Sambrook, J., Fritsch, E. F. & Maniatis, T. *Molecular cloning. A laboratory manual*. New York Cold Spring Harbor Laboratory (Cold Spring Harbor, N.Y., 1989)) (5 L) containing kanamycin (30 μg/ml) with orbital shaking (250 rpm) at 37° C. Cultures ($OD_{600}$=0.6) were induced with 0.5 mM IPTG for 4 h before the cells were harvested and resuspended in lysis buffer (75 ml, 50 mM Tris.HCl pH 8, 0.5 M NaCl, 20% sucrose, 1 mM BME, 1 mM PMSF, 10 mM imidazole, 0.1% IGEPAL). Resuspended cells were disrupted using a French pressure cell and cellular debris was removed from the lysates by ultracentrifugation. The tagged proteins were purified by nickel column chromatography using Ni-NTA Superflow resin according to the manufacturer's instructions (Qiagen). Purified proteins were dialyzed against a solution of 0.2 M NaCl, 25 mM Tris.HCl (pH 8.0), 2 mM DTT, and 5% glycerol. Tagged YbtE and MbtA were treated with SUMO protease (Invitrogen) to remove the tag as reported (Onwueme et al. Mycobacterial polyketide-associated proteins are acyl-transferases: proof of principle with MycobacteriuM. *tuberculosis* PapAS. *Proc. Natl. Acad. Sci. USA.* 101, 4608-13 (2004); incorporated herein by reference). Tag-free YbtE and MbtA were purified by gel filtration using Superdex 200 resin according to the manufacturer's instructions (Amersham Biosciences). Protein samples were concentrated (<10 mg/ml) and stored at −80° C. Recombinant C-terminally His$_6$-tagged Yp ArCP domain (ypArCP—H6), C-terminally His$_6$-tagged PchD (PchD-H6), and phosphopantetheinyl transferase Sfp were purified as reported (Gehring et al. The nonribosomal peptide synthetase HMWP2 forms a thiazoline ring during biogenesis of yersiniabactin, an iron-chelating virulence factor of *Yersinia pestis*. *Biochemistry* 37, 11637-11650. (1998); Quadri et al. Assembly of the *Pseudomonas aeruginosa* nonribosomal peptide siderophore pyochelin: In vitro reconstitution of aryl-4, 2-bisthiazoline synthetase activity from PchD, PchE, and PchF. *Biochemistry* 38, 14941-14954. (1999); Quadri et al. Characterization of Sfp, a *Bacillus subtilis* phosphopantetheinyl transferase for peptidyl carrier protein domains in peptide synthetases. *Biochemistry* 37, 1585-95. (1998); each of which is incorporated herein by reference).

Adenylation assay and data analysis. Adenylation was measured with an ATP-[$^{32}$P]-pyrophosphate (PPi) exchange assay as reported (Quadri et al. Identification of a *Mycobacterium. tuberculosis* gene cluster encoding the biosynthetic enzymes for assembly of the virulence-conferring siderophore mycobactin. *Chem. Biol.* 5, 631-645. (1998); Gehring et al. The nonribosomal peptide synthetase HMWP2 forms a thiazoline ring during biogenesis of yersiniabactin, an iron-chelating virulence factor of *Yersinia pestis*. Biochemistry 37, 11637-11650. (1998); Quadri et al. Assembly of the *Pseudomonas aeruginosa* nonribosomal peptide siderophore pyochelin: In vitro reconstitution of aryl-4,2-bisthiazoline synthetase activity from PchD, PchE, and PchF. Biochemistry 38, 14941-14954. (1999); each of which is incorporated herein by reference). Reactions (100 μl) were initiated by addition of the domain salicylation enzyme. Exchange reactions used to obtain the dose-response curves shown in FIGS. 2A-C each contained: 75 mM Tris.HCl (pH 8.8); 10 mM $MgCl_2$; 2 mM DTT; 5% glycerol; 1 mM sodium [$^{32}$P]-PPi (5 Ci/mol, PerkinElmer); 10 mM ATP ($−60 \times K_m^{ATP}$); 250, 500, and 140 μM salicylate ($−50 \times K_m^{Sal}$) in reactions with YbtE, MbtA, and PchD, respectively; 20 nM domain salicylation enzyme; and inhibitor added in DMSO (1% of reaction volume) at the concentrations indicated. Reactions were incubated at 37° C. for 15 min for YbtE and PchD, and for 30 min for MbtA. The dose-response data sets were fitted to the Morrison equation (Copeland, R. A. in *Enzymes: A practical introduction to structure, mechanism, and data analysis* 305-317 (Wiley-VCH, Inc. Publications, New York, 2000)), $$\frac{v_i}{v_c} = 1 - \frac{([E]+[I]+K_i^{app}) - \sqrt{([E]+[I]+K_i^{app})-4[E][I]}}{2[E]}, \quad \text{Eq. (1)}$$

where $v_i$; and $v_c$ are the activities measured in inhibitor-containing reactions and DMSO-containing (1%) controls, respectively. $IC_{50}$ values were calculated with the equation $$IC_{50} = \frac{1}{2}[E] + K_i^{app}, \quad \text{Eq. (2)}$$

(Copeland, R. A. in *Enzymes: A practical introduction to structure, mechanism, and data analysis* 305-317 (Wiley-VCH, Inc. Publications, New York, 2000)), and using the $K_i^{app}$ derived from the Eq. (1) curve fit. In experiments to determine $IC_{50}$ values at different YbtE concentrations (FIG. 2D), each reaction had the composition noted above except that ATP and salicylate were both at 1 mM, the inhibitor was included in a 0-200 nM range, and YbtE was added at the concentrations indicated. Reactions were incubated at 37° C. for 15 min. The dose-response data were fitted to Eq. (1) and the $IC_{50}$ values were calculated with Eq. (2). In the experiments to determine $K_i^{app}$ values (FIGS. 2E and 2F), dose-response curves were determined with the inhibitor in a 0-150 nM range, YbtE at 20 nM, and either ATP fixed at 10 mM and salicylate at 1.3, 2.6, 5.2, 10.4, 20.8, 50, and 250 μM, or salicylate fixed at 1 mM and ATP at 0.04, 0.08, 0.16, 0.32, 0.64, 1.5, and 10 mM. [YbtE $K_m^{ATP}$=172 μM as determined in this study (not shown) and 350 μM as reported elsewhere (Gehring et al. The nonribosomal peptide synthetase HMWP2 forms a thiazoline ring during biogenesis of yersiniabactin, an iron-chelating virulence factor of *Yersinia pestis*. *Biochemistry* 37, 11637-11650. (1998); incorporated herein by reference); YbtE $K_m^{Sal}$=5.4 μM as determined in this study (not shown) and 4.6 μM as reported elsewhere (Gehring et al. The nonribosomal peptide synthetase HMWP2 forms a thiazoline ring during biogenesis of yersiniabactin, an iron-chelating virulence factor of *Yersinia pestis*. Biochemistry 37, 11637-11650. (1998); incorporated herein by reference)]. Other components were included as indicated above. Dose-response data sets were fitted to Eq. (1) to obtain a $K_i^{app}$ for each dose-response curve. For competitive TBIs, $$K_i^{app} = K_i\left(1 + \frac{[S]}{K_m}\right),$$

thus $K_i^{app}=K_i$ when [S]=0, and the $K_i$ value was calculated as the y-intercept of the line fitted to the data (Smith. *Mycobacterium tuberculosis* pathogenesis and molecular determinants of virulence. *Clin. Microbiol. Rev.* 16, 463-496. (2003); incorporated herein by reference) (FIG. 2E). For non-competitive inhibition $K_i^{app}=K_i$, and the $K_i$ was calculated by averaging the $K_i^{app}$ values (Smith. *Mycobacterium tuberculosis* patho-genesis and molecular determinants of virulence. *Clin. Microbiol. Rev.* 16, 463-496. (2003); incorporated herein by reference) (FIG. 2F). All data sets were fitted using Kaleidagraph™ software.

Domain Salicylation Assay.

The assay was performed in 96-well Nickel Chelate Coated FlashPlate® PLUS plates (flash plates) (PerkinElmer). Plate wells have a scintillant coat and a $Ni^{2+}$ coat for $His_6$-tagged protein binding. YbtE-catalyzed incorporation of the [$^3$H]-salicyl group into well-bound phosphopantetheinylated ypArCP-H6 leads to [$^3$H]-salicyl-ypArCP-H6 formation, which is quantified with a plate counter. To obtain phosphopantetheinylated domain, ypArCP-H6 was co-expressed with Sfp (expressed from plasmid pSU20-Sfp (Couch et al. Characterization of CmaA, an adenylation-thiolation didomain enzyme involved in the biosynthesis of coronatine. *J. Bacteriol.* 186, 35-42. (2004); incorporated herein by reference)), and the purified ypArCP-H6 domain was further incubated with Sfp and coenzyme A for maximum modification as reported (Weinreb et al. Stoichiometry and specificity of in vitro phosphopantetheinylation and aminoacylation of the valine-activating module of surfactin synthetase. *Biochemistry* 37, 1575-1584. (1198); incorporated herein by reference). Domain binding to wells was done as recommended by the plate manufacturer. After binding, wells were loaded with reaction mixtures (30 μl) containing 75 mM MES (pH 6.5), 1 mM TCEP, 100 μM ATP, 150 nM [$^3$H]-salicylate (33 Ci/mmol, Vitrax Inc.), and inhibitor (added in DMSO as 1% of the reaction volume) at the concentrations indicated (FIG. 2G). Reactions were started by addition of YbtE (20 μl) at 70 nM. After incubation at 37° C. for 1.5 h, reactions were chased with 300 μl of PBS containing 1 mM salicylate, the wells were washed with chase solution (3×100 μl), and [$^3$H]-salicyl-ypArCP-H6 was quantified using a TopCount® Microplate counter (Packard BioScience). Dose-response data were fitted to Eq. (1) and the $IC_{50}$ was calculated with Eq. (2).

Siderophore Production Assays.

YBT was isolated from supernatants of *Y. pestis* cultures (avirulent strain KIM6-2082.1+(Gong et al. Characterization of the *Yersinia pestis* Yfu ABC inorganic iron transport system. *Infect. Immun.* 69, 2829-2837. (2001); incorporated herein by reference), 200 μl, initial $OD_{620}$=0.1) grown for 15 h with agitation (220 rpm) at 37° C. in chelex-100 deferrated PMH medium (Bearden et al. Genetic organization of the yersiniabactin biosynthetic region and construction of avirulent mutants in *Yersinia pestis*. Infect Immun 65, 1659-68. (1997); incorporated herein by reference) (PMH-D) containing [$^{14}$C]-salicylate (20 μM, 55 mCi/mmol) for siderophore labeling and inhibitor (200 μM) or DMSO (0.25%) as above. YBT-deficient *Y. pestis* strain KIM6 2082.1 (Gong et al. Characterization of the *Yersinia pestis* Yfu ABC inorganic iron transport system. *Infect. Immun.* 69, 2829-2837. (2001); incorporated herein by reference) treated with DMSO as above was used as an additional control. Culture supernatants were extracted twice with one volume of EtOAc, the organic solvent was evaporated, and the YBT was resuspended in MeOH for radiometric-TLC analysis (Al Sil G/UV plates (Whatman) and 90:10:5 $CHCl_3$/EtOH/AcOH). Plates were exposed to a phosphoimager screen for 24 h and analyzed with a Storm Phosphoimager (Molecular Dynamics). The identity of the YBT spot ($R_f$=0.39) was confirmed by atmospheric pressure chemical ionization mass spectrometry (YBT-iron complex ion (Perry et al. Yersiniabactin from *Yersinia pestis*: biochemical characterization of the siderophore and its role in iron transport and regulation. *Microbiology* 145, 1181-90. (1999); incorporated herein by reference):

$C_{21}H_{24}N_3O_4S_3HFe^+$, m/z=535.0) of samples purified by preparative TLC (not shown). For analysis of mycobacterial siderophores, *M. tuberculosis* H37Rv cultures (500 µl, initial $OD_{580}$=0.2) were grown for 3 days at 37° C. without shaking in chelex-100 deferrated GAST medium (De Voss et al. The salicylate-derived mycobactin siderophores of *Mycobacteriu M. tuberculosis* are essential for growth in macrophages. *Proc. Natl. Acad. Sci. USA*. 97, 1252-1257. (2000); incorporated herein by reference) (GAST-D) containing [$^{14}$C]-salicylate for siderophore labeling and inhibitor (200 µM) or DMSO (0.25%) in controls. The MBT-deficient *M. tuberculosis* strain mbtF (kindly provided by C. Nathan, Cornell Medical College) treated with DMSO as above was used as an additional control. Cell pellets of inhibitor- and DMSO-treated cultures were incubated for 12 h with 300 µl EtOH. After incubation, the debris were removed by centrifugation, one volume of water and $FeCl_3$ (to 2.2 mM) were added to the EtOH supernatant, and cell-associated MBTs were extracted from the mixture twice with one volume of $CHCl_3$. For isolation of soluble MBTs, $FeCl_3$ (to 0.6 mM) was added to culture supernatants before siderophore extraction as above. Extracts were dried and resuspended in $CHCl_3$ before radiometric-TLC analysis using Al Sil G/UV plates (Whatman) and 2:3:3 petroleum ether/n-BuOH/EtOAc as eluent. Plates were exposed to a phosphoimager screen for 72 h and analyzed with a Storm Phosphoimager (Molecular Dynamics). $R_f$ values of MBTs (0.45 and 0.6) were in agreement with those reported (Barclay et al. Mycobactins and exochelins of *Mycobacterium tuberculosis, M. bovis, M. africanum* and other related species. *J. Gen. Microbiol*. 134, 771-776. (1988); incorporated herein by reference). *M. tuberculosis* and *Y. pestis* were allowed to grow for ~2 generations before siderophore analysis. This growth takes place even in the presence of inhibitor due to the residual iron and/or siderophore present in the relatively large inoculum used. Samples analyzed were corrected for small optical density differences observed between the inhibitor- and DMSO-treated cultures.

Growth Inhibition Assays.

*Y. pestis* KIM6-2082.1+ was grown in PMH-D for iron-deficient conditions and in PMH-D supplemented with 200 µM $FeCl_3$ for iron-rich conditions. *M. tuberculosis* H37Rv was grown in GAST-D for iron-deficient conditions and in GAST-D supplemented with 200 µM $FeCl_3$ for iron-rich conditions. Salicyl-AMS was added (from a stock solution in DMSO) to the media at the concentrations indicated in FIGS. 3D and 3E. DMSO (0.5%) was added to the untreated controls. *Y. pestis* and *M. tuberculosis* cultures, inoculated at $OD_{620}$=0.005 and $OD_{580}$=0.01 respectively, were incubated in 96-well plates at 37° C. (200 µl/well; 22 h, 220 rpm for *Y. pestis*; 8 days, stationary condition for *M. tuberculosis*) and growth was measured as optical density after incubation. $IC_{50}$ and $MIC_{95}$ values were calculated by fitting the dose-response data of FIGS. 3D and 3E to the sigmoidal equation $$\frac{OD_i}{OD_c} = b + \frac{(a-b)}{1+([I]/IC_{50})^s}, \quad \text{Eq. (3),}$$

where $OD_i$ and $OD_c$ are optical densities of inhibitor-treated cultures and DMSO-treated controls respectively, a and b are the top and bottom of the curve respectively, and s is the slope (Hill coefficient). Data were fitted using Kaleidagraph software.

Example 2

Design, Synthesis, and Testing of Salicyl-AMS and Analogs Thereof

New antibiotics are urgently needed to combat infectious diseases, due to the increasing incidence of multidrug resistant bacteria (Hughes, D. "Microbial genetics: Exploiting genomics, genetics and chemistry to combat antibiotic resistance." *Nat. Rev. Genet*. 2003, 4, 432-441; Hogan, D.; Kolter, R. "Why are bacteria refractory to antimicrobials?" *Curr. Opin. Microbiol*. 2002, 5, 472-477; each of which is incorporated herein by reference) and their potential use as agents of bioterrorism (Gilligan, P. H. "Therapeutic challenges posed by bacterial bioterrorism threats." *Curr. Opin. Microbiol*. 2002, 5, 489-495; incorporated herein by reference). Siderophore biosynthesis is critical for bacterial uptake of $Fe^{3+}$ from the host, which is required for growth and virulence. These antibiotics would provide a vital new line of defense against pathogenic bacteria and could be used prophylactically or therapeutically, either as single agents or in combination with other therapeutic modalities. The salicylate adenylation enzymes that catalyze the required first step in the biosynthesis of aryl-capped siderophores in a variety of pathogenic bacteria are a potential target for the design of new antibiotics (Quadri, L. E. N. "Assembly of aryl-capped siderophores by modular peptide synthetases and polyketide synthases." *Mol. Microbiol*. 2000, 37, 1-12; incorporated herein by reference). Three of these pathogens have been designated as priorities for biodefense research by the NIAID: *Yersinia pestis*, the etiologic agent of the plague; *Yersinia enterocolitica*, a food- and waterborne gastroenteritic pathogen; and *Mycobacterium tuberculosis*, the causative agent of tuberculosis. Siderophore-deficient strains of these bacteria exhibit drastically reduced virulence in mouse models for infection, supporting siderophore biosynthesis as a promising new antibiotic target. Genetic knockouts alone are insufficient for this purpose, since they provide only a steady state approximation of inhibition. Small molecule inhibitors are needed to study this dynamic, tightly regulated process (Potuzak, J. S.; Moilanen, S. B.; Tan, D. S. "Discovery and applications of small molecule probes for studying biological processes." *Biotechnol. Genet. Eng. Rev*. 2004, 21, 11-77; Ward, G. E.; Carey, K. L.; Westwood, N.J. "Using small molecules to study big questions in cellular microbiology." *Cell. Microbiol*. 2002, 4, 471-482; each of which is incorporated herein by reference).

Small molecule inhibitors of salicylate adenylation enzymes have been designed and prepared to block siderophore biosynthesis and, hence, iron uptake and bacterial growth and virulence. These inhibitors will be crucial for validating this enzyme class, and siderophore biosynthesis in general, as a new antibiotic target. We have developed a mechanism- and structure-based lead compound, salicyl-AMS, which is a potent inhibitor of salicylate adenylation enzymes in biochemical assays ($K_d$≤1 nM) and a moderate inhibitor of bacterial growth in iron-limiting media ($IC_{50}$=25-52 µM).

Pathogenic Bacteria as Agents of Bioterrorism

Pathogenic bacteria, particularly MDR and/or weaponized forms, pose an ongoing threat as potential agents of bioterrorism or biological warfare.

*Yersinia pestis*

*Y. pestis* is the causative agent of both the bubonic and pneumonic plague (Perry, R. D.; Fetherston, J. D. "*Yersinia pestis*—Etiologic agent of plague." *Clin. Microbiol. Rev*. 1997, 10, 35-66; incorporated herein by reference). One of the most virulent bacteria known, ≤10 cells are capable of causing disease (Brubaker, R. R. "Factors promoting acute and chronic diseases caused by yersiniae." *Clin. Microbiol. Rev.* 1991, 4, 309-324; incorporated herein by reference). Pneumonic plague is especially dangerous since it can be transmitted readily between humans by inhalation of respiratory droplets from infected patients. Treatment with antibiotics is effective only if started quickly with the onset of symptoms. If treatment is delayed more than 24 hours, mortality rates remain high, even in countries with advanced health care. Although a killed vaccine was licensed for use in the US by high risk individuals to prevent bubonic plague, the vaccine is ineffective against pneumonic plague, has not been produced since 1999, and is no longer available. The potential use of *Y. pestis* as a biological weapon is based on methods that have been developed to produce and aerosolize large amounts of bacteria. Thus, *Y. pestis* has been designated as a Category A Priority Pathogen by the NIAID, and siderophore biosynthesis in particular has been highlighted as a promising therapeutic target ("NIAID Biodefense Research Agenda for CDC Category A Agents," National Institute of Allergy and Infectious Diseases, 2002).

*Y. pestis* also presents an ongoing public health issue. Although usually viewed as a disease of the $14^{th}$ century, cases of bubonic and pneumonic plague continue today. *Y. pestis* is readily found in infected rodents in both urban and rural settings and animal-to-human transmission occurs via infected fleas. Globally, an average of 2500 cases of plague are reported annually (1988-1997 data) with a 15% mortality rate in spite of adequate treatment (WHO "Human plague in 1998 and 1999." *Wkly. Epidemiol. Rec.* 2000, 75, 338-343; incorporated herein by reference). In the US, 112 cases were reported during 1998-2002. As recently as November 2002, two cases of bubonic plague were reported in New York City, involving a couple who contracted the disease from rodents near their home in Santa Fe, N. Mex. (CDC "Imported plague—New York City, 2002." *Morbid. Mortal. Wkly. Rpt.* 2003, 52, 725-728; incorporated herein by reference). Despite rapid diagnosis and treatment with gentimicin, doxycycline, ciprofloxacin, vancomycin, and activated protein C, the male patient's condition deteriorated rapidly. He only recovered after a 6-week stay in intensive care with hemodialysis, mechanical ventilation, and bilateral foot amputations due to ischemia. The female patient recovered after hospitalization and treatment with multiple antibiotics. This example highlights the extreme danger posed by *Y. pestis* even with rapid diagnosis and advanced treatments.

Even more worrisome, an MDR strain of *Y. pestis*, resistant to all first-line and several prophylactic antibiotics, was reported in an outbreak of bubonic plague in Madagascar in the late 1990's (Galimand et al. "Multidrug resistance in *Yersinia pestis* mediated by a transferable plasmid." *New Engl. J. Med.* 1997, 337, 677-680; incorporated herein by reference). Another stain was resistant to streptomycin, the current antibiotic of choice for treating plague (Guiyoule et al. "Transferable plasmid-mediated resistance to streptomycin in a clinical isolate of *Yersinia pestis*." *Emerg. Infect. Diseases* 2001, 7, 43-48; incorporated herein by reference). Both strains carried the resistance genes on plasmids that can be transferred between other *Enterobactericeae* genera or easily bioengineered (Gilligan, "Therapeutic challenges posed by bacterial bioterrorism threats." *Curr. Opin. Microbiol.* 2002, 5, 489-495; incorporated herein by reference). The emergence of these strains, thus, raises serious concerns about our ability to control outbreaks of MDR *Y. pestis* resulting from bioterrorism or biological warfare.

*Yersinia enterocolitica*

*Y. enterocolitica* is a food- and water-borne pathogen that causes yersiniosis, a gastroenteritic infectious disease (Cover, T. L.; Aber, R. C. "*Yersinia enterocolitica*." *New Engl. J. Med.* 1989, 321, 16-24; incorporated herein by reference). The primary effects are fever, abdominal pain, inflammatory diarrhea, nausea, and vomiting lasting 1-3 weeks, with children particularly at risk. Although most minor cases resolve naturally with supportive rehydration, yersiniosis can also lead to reactive arthritis, chronic infection, and septicemia, transfer of infection to the bloodstream, which carries a 34-50% mortality rate (Cover et al. "*Yersinia enterocolitica*." *New Engl. J. Med.* 1989, 321, 16-24; incorporated herein by reference). More severe or complicated cases, and those involving infants, usually require hospitalization and treatment with antibiotics such as aminoglycosides, doxycycline, trimethoprim-sulfamethoxazole, or fluoroquinolines. No vaccines are currently available, although live attenuated strains are being studied. Since deliberate contamination of centralized food and water supplies in the US could be exploited for bioterrorism, *Y. enterocolitica* has been designated as a Category B Priority Pathogen by the NIAID ("NIAID Biodefense Research Agenda for CDC Category B and C Priority Pathogens," National Institute of Allergy and Infectious Diseases, 2003; incorporated herein by reference). Further, intentional exposure may be difficult to detect in a timely fashion, since yersiniosis outbreaks occur sporadically in the US and can be easily misdiagnosed as appendicitis.

Yersiniosis is also a public health concern, with a 2003 incidence rate of 4 cases per million persons in the US (CDC "Preliminary FoodNet data on the incidence of infection with pathogens transmitted commonly through food—Selected sites, United States, 2003." *Morbid. Mortal. Wkly. Rpt.* 2004, 53, 338-343; incorporated herein by reference). Pigs are a major animal reservoir for *Y. enterocolitica*, although rodents, rabbits, sheep, cattle, horses, dogs, and cats may also carry the bacteria. Infection most often occurs by ingestion of contaminated food, especially milk and undercooked pork products such as chitterlings. Person-to-person and animal-to-person transmission can also occur as a result of poor hygiene in handling fecal matter, via direct contact or contamination of water supplies. The increasing emergence of antibiotic resistant strains (Capilla et al. "Characterization of the molecular mechanisms of quinolone resistance in *Yersinia enterocolitica* 0:3 clinical isolates." *J. Antimicrob. Chemother.* 2004, 53, 1068-1071; Capilla et al. "Epidemiological study of resistance to nalidixic acid and other antibiotics in clinical *Yersinia enterocolitica* 0:3 isolates." *J. Clin. Microbiol.* 2003, 41, 4876-4878; Sanchez-Cespedes et al. "Clonal dissemination of *Yersinia enterocolitica* strains with various susceptibilities to nalidixic acid." *J. Clin. Microbiol.* 2003, 41, 1769-1771; each of which is incorporated herein by reference) coupled with the potential for deliberate contamination of food and water supplies make *Y. enterocolitica* a serious concern.

*Mycobacterium tuberculosis*

*M. tuberculosis* is the causative agent of tuberculosis (TB). Primarily a disease of the lung, TB can also cause deadly systemic infections (Frieden et al. "Tuberculosis." *Lancet* 2003, 362, 887-899; Bloom, B. R. *Tuberculosis: Pathogenesis, protection, and control*; ASM Press.: Washington, D.C., 1994; incorporated herein by reference). Person-to-person transmission occurs via airborne droplets generated by patients with active disease. Statistically, 30% of exposed individuals become infected and inhalation of as few as 1-10 bacteria is sufficient to cause infection (Bloom et al. "Tuberculosis: Commentary on a reemergent killer" *Science* 1992, 257, 1055-1064; incorporated herein by reference). Infected persons may progress immediately to active disease, or carry asymptomatic latent infections for months to a lifetime, with 2-23% of these eventually progressing to active disease (Parrish et al. "Mechanisms of latency in *Mycobacterium tuberculosis.*" *Trends Microbiol.* 1998, 6, 107-112; incorporated herein by reference). TB is usually treated over the course of several months with an antibiotic cocktail of isoniazid, rifampicin, pyrazinamide, and ethambutol ("American Thoracic Society/Centers for Disease Control and Prevention/Infectioius Diseases Society of America: Treatment of tuberculosis." *Am. J. Respir. Crit. Care Med.* 2003, 167, 603-662; incorporated herein by reference). Patients with isoniazid and rifampicin-resistant TB are at high risk for treatment failure and must receive multiple additional i. v. and oral antibiotics. One TB vaccine is licensed in the US, but it is not recommended due to its highly variable efficacy. Globally, the average mortality rate for TB is 23% if treated, and 40-60% if left untreated. In particular, MDR strains pose a major threat, requiring long-term treatment with expensive second-line antibiotics at an estimated average cost of $180,000/patient ("NIAID Biodefense Research Agenda for CDC Category B and C Priority Pathogens," National Institute of Allergy and Infectious Diseases, 2003; incorporated herein by reference). As a result, epidemics of MDR-TB would likely result in casualty rates approaching those for untreated disease, and MDR *M. tuberculosis* has been designated as a Category C Priority Pathogen by the NIAID ("NIAID Biodefense Research Agenda for CDC Category B and C Priority Pathogens," National Institute of Allergy and Infectious Diseases, 2003).

In global public health terms, TB is among the top ten leading killers, with 8.7 million new cases and 2-3 million deaths annually (Murray et al. "Mortality by cause for eight regions of the world: Global Burden of Disease Study." *Lancet* 1997, 349, 1269-1276; incorporated herein by reference). It is estimated that $1/3^{rd}$ of the world's population is infected with *M. tuberculosis*, including 10-15 million in the US (Dye et al. "Consensus statement. Global burden of tuberculosis: Estimated incidence, prevalence, and mortality by country. WHO Global Surveillance and Monitoring Project." *J. Am. Med. Assoc.* 1999, 282, 677-686; CDC "The use of preventive therapy for tuberculous infection in the United States. Recommendations of the Advisory Committee for Elimination of Tuberculosis." *Morbid. Mortal. Wkly. Rpt.* 1990, 39, 9-12; each of which is incorporated herein by reference). Further, MDR-TB is a global pandemic, with an estimated 273,000 new cases reported in 2000 (Dye et al. "Worldwide incidence of multidrug-resistant tuberculosis." *J. Infect. Diseases* 2002, 185, 1197-1202; incorporated herein by reference). Of the 16,377 cases of tuberculosis reported in the US in 2000, 1% of these were resistant to at least isoniazid and rifampicin (CDC "Tuberculosis morbidity among US-born and foreign-born populations—United States, 2000." *Morbid. Mortal. Wkly. Rpt.* 2002, 51, 101-104; incorporated herein by reference). The 1988-1992 epidemic in New York City involved over 3,700 cases, of which at least 19% were MDR. Containment of this outbreak cost approximately $1 billion ("NIAID Biodefense Research Agenda for CDC Category B and C Priority Pathogens," National Institute of Allergy and Infectious Diseases, 2003). Thus, the potential use of MDR *M. tuberculosis* as an agent of bioterrorism poses a grave threat.

Other Pathogenic Bacteria

Salicylate adenylation enzymes are also present in *Pseudomonas aeruginosa, Acinetobacter calcoaceticus*, and *A. baumannii*, which are all associated with dangerous hospital-acquired infections (Quadri, L. E. N. "Assembly of aryl-capped siderophores by modular peptide synthetases and polyketide synthases." *Mol. Microbiol.* 2000, 37, 1-12; Crosa, J. H.; Walsh, C. T. "Genetics and assembly line enzymology of siderophore biosynthesis in bacteria." *Microbiol. Mol. Biol. Rev.* 2002, 66, 223-249; each of which is incorporated herein by reference). Closely related dihydroxybenzoate adenylation enzymes are present in *Escherichia coli, Salmonella enterica, Shigella* spp., and *Vibrio cholerae*, which are food- and water-borne bacteria that have also been designated as Category B Priority Pathogens by the NIAID ("NIAID Biodefense Research Agenda for CDC Category B and C Priority Pathogens," National Institute of Allergy and Infectious Diseases, 2003).

Bacterial Iron Uptake and Siderophore Biosynthesis

Iron is an essential trace nutrient for most bacteria. It plays a central role in vital metabolic functions (Coughlan, M. P. "The role of iron in microbial metabolism." *Sci. Prog.* 1971, 59, 1-23; incorporated herein by reference) and is also required for growth and virulence of pathogenic bacteria including *Y. pestis, Y. enterocolitica*, and *M. tuberculosis*. In mammalian hosts, most $Fe^{3+}$ is bound to intracellular and extracellular components such as heme, transferrin, and lactoferrin. This renders the free iron concentration ($10^{-15}$-$10^{-24}$ M) well below that required by these bacteria ($10^{-6}$-$10^{-7}$ M) (Jurado, R. L. "Iron, infections, and anemia of inflammation."*Clin. Infect. Diseases* 1997, 25, 888-895; Braun, V. "Iron uptake mechanisms and their regulation in pathogenic bacteria." *Intl. J. Med. Microbiol.* 2001, 291, 67-79; each of which is incorporated herein by reference). During infection, the free iron concentration is further reduced by a host iron sequestration mechanism that induces hypoferremia. In response, pathogenic (and free living) bacteria have developed iron acquisition systems to guarantee an adequate supply of iron. Among these are systems based on iron-chelating small molecules called siderophores (Braun et al. "Active transport of iron and siderophore antibiotics." *Curr. Opin. Microbiol.* 2002, 5, 194-201; incorporated herein by reference). These compounds, which have extremely high affinity for $Fe^{3+}$ (up to $K_d \approx 10^{-52}$ M!!), (Harris et al. "Coordination chemistry of microbial iron transport compounds. 19. Stability constants and electrochemical behavior of ferric enterobactin and model complexes." *J. Am. Chem. Soc.* 1979, 101, 6097-6104; Perry et al. "Yersiniabactin from *Yersinia pestis*: Biochemical characterization of the siderophore and its role in iron transport and regulation." Microbiology 1999, 145, 1181-1190; each of which is incorporated herein by reference) are biosynthesized by the bacteria, are secreted into the host medium, capture iron from host proteins, and are then transported back into the bacteria.

The siderophore produced by *Y. pestis* and *Y. enterocolitica* is called yersiniabactin (FIG. 1) (Perry et al. "Yersiniabactin from *Yersinia pestis*: Biochemical characterization of the siderophore and its role in iron transport and regulation." *Microbiology* 1999, 145, 1181-1190; incorporated herein by reference). Two closely related families of cell-associated (Snow et al. "Chemical and biological properties of mycobactins isolated from various *Mycobacteria.*" *Biochem. J.* 1969, 115, 1031-1045; incorporated herein by reference) and soluble (Gobin et al. "Iron acquisition by *Mycobacterium tuberculosis*: Isolation and characterization of a family of iron-binding exochelins." *Proc. Natl. Acad. Sci. USA.* 1995, 92, 5189-5193; Lane et al. "Novel extracellular mycobactins, the carboxymycobactins from *Mycobacterium avium.*" *Tetrahedron Lett.* 1995, 36, 4129-4132; each of which is incorporated herein by reference) siderophores are produced in *M. tuberculosis* and are referred to collectively herein as the mycobactins. These siderophores have in common an o-phenolic ring and are biosynthesized by hybrid non-ribosomal peptide/ polyketide synthetase clusters (Quadri, "Assembly of aryl-capped siderophores by modular peptide synthetases and polyketide synthases." *Mol. Microbiol.* 2000, 37, 1-12; Crosa et al. "Genetics and assembly line enzymology of siderophore biosynthesis in bacteria." *Microbiol. Mol. Biol. Rev.* 2002, 66, 223-249; each of which is incorporated herein by reference). Related o-phenol-containing siderophores include pyochelin in *P. aeruginosa* and acinetobactin in *Acinetobacter* spp (Quadri, "Assembly of aryl-capped siderophores by modular peptide synthetases and polyketide synthases." *Mol. Microbiol.* 2000, 37, 1-12; Crosa et al. "Genetics and assembly line enzymology of siderophore biosynthesis in bacteria." *Microbiol. Mol. Biol. Rev.* 2002, 66, 223-249; each of which is incorporated herein by reference). Other related siderophores, which contain a catechol moiety, include enterobactin in *E. coli*, *Salmonella* spp., and some *Shigella* spp; vibriobactin in *V. cholerae*; and anguibactin in *V. anguillarum*.

Extensive evidence indicates that the siderophore-based iron uptake system is a promising antibiotic target. Yersiniabactin is essential for *Y. pestis* growth in iron-limiting medium and is required for virulence in s.q. infected mice (Fetherston et al. "Analysis of the pesticin receptor from *Yersinia pestis*: Role in iron-deficient growth and possible regulation by its siderophore." *J. Bacteriol.* 1995, 177, 1824-1833; Bearden, S. W.; Fetherston, J. D.; Perry, R. D. "Genetic organization of the Yersiniabactin biosynthetic region and construction of avirulent mutants in *Yersinia pestis*." *Infect. Immun.* 1997, 65, 1659-1668; each of which is incorporated herein by reference). Yersiniabactin-deficient strains have a $10^5$-fold weaker $LD_{50}$ in these mice compared to wt strains. Since the yersiniabactin system is essential for iron acquisition during early stages of the plague, it has been specifically highlighted by the NIAID as an excellent potential target for early intervention and treatment ("NIAID Biodefense Research Agenda for CDC Category A Agents," National Institute of Allergy and Infectious Diseases, 2002). Yersiniabactin-deficient *Y. enterocolitica* is likewise avirulent in i.p. infected mice (Heesemann, "Chromosomal-encoded siderophores are required for mouse virulence of enteropathogenic *Yersinia* species." *FEMS Microbiol. Lett.* 1987, 48, 229-233; incorporated herein by reference) and drastically reduced in virulence in i.v. challenged mice (Rakin et al. "The pesticin receptor of *Yersinia enterocolitica*: A novel virulence factor with dual function." *Mol. Microbiol.* 1994, 13, 253-263; incorporated herein by reference). Conversely, iron overload is associated with an increased risk of yersiniosis and septicemia (Bottone, "*Yersinia enterocolitica*: The charisma continues." *Clin. Microbiol. Rev.* 1997, 10, 257-276; incorporated herein by reference). Mycobactin-deficient strains of *M. tuberculosis* are severely restricted for growth in iron-limiting medium (De Voss et al. "The salicylate-derived mycobactin siderophores of *Mycobacterium tuberculosis* are essential for growth in macrophages." *Proc. Natl. Acad. Sci. U.S.A.* 2000, 97, 1252-1257; incorporated herein by reference). In addition, mycobactin-deficient strains exhibit a growth defect that is exacerbated upon long-term culturing, even in iron-sufficient conditions (Sassetti et al. "Genes required for mycobacterial growth defined by high density mutagenesis." *Mol. Microbiol.* 2003, 48, 77-84; incorporated herein by reference). Unfortunately, this defect precluded inclusion of these mutants in a recent study that identified *M. tuberculosis* genes specifically required for mycobacterial growth in vivo (Sassetti et al. "Genetic requirements for mycobacterial survival during infection." *Proc. Natl. Acad. Sci. U.S.A.* 2003, 100, 12989-12994; incorporated herein by reference). Conversely, iron excess intensifies TB progression in humans and animal models (Lounis et al. "Iron and *Mycobacterium tuberculosis* infection." *J. Clin. Virol.* 2001, 20, 123-126; incorporated herein by reference).

The first step in the biosynthesis of o-phenol-capped siderophores is adenylation of salicylate (FIG. 1B). The salicyl adenylate intermediate (salicyl-AMP) then undergoes transthioesterification onto an aroyl carrier protein (ArCP). The biosynthesis then proceeds by condensation with downstream building blocks (amino acids and malonates), and post-coupling modification reactions (reduction, cyclodehydration, etc.). Closely related 2,3-dihydroxybenzoate (DHB) adenylation enzymes carry out analogous steps in the biosynthesis of catechol-capped siderophores. Key salicylate adenylation enzymes include YbtE in *Y. pestis* (Gehring et al. "The nonribosomal peptide synthetase HMWP2 forms a thiazoline ring during biogenesis of yersiniabactin, an iron-chelating virulence factor of *Yersinia pestis*." Biochemistry 1998, 37, 11637-11650; incorporated herein by reference), IrpS in *Y. enterocolitica* (Pelludat et al. "The yersiniabactin biosynthetic gene cluster of *Yersinia enterocolitica*: Organization and siderophore-dependent regulation." *J. Bacteriol.* 1998, 180, 538-546; incorporated herein by reference), and MbtA in *M. tuberculosis* (Quadri et al. "Identification of a *Mycobacterium tuberculosis* gene cluster encoding the biosynthetic enzymes for assembly of the virulence-conferring siderophore mycobactin" *Chem. Biol.* 1998, 5, 631-645; incorporated herein by reference). Since these enzymes catalyze the required first step in the biosynthesis of yersiniabactin and the mycobactins, they are attractive targets for the development of small molecule inhibitors that block siderophore biosynthesis, and hence, iron uptake and bacterial growth and virulence. Moreover, since there are no human enzymes with analogous functions, mechanism-based inhibitors of salicylate adenylation enzymes should have excellent selectivity for bacterial cells.

The siderophore system is an example of a promising new class of antibiotic targets called virulence factors (Marra, "Can virulence factors be viable antibacterial targets?" *Expert Rev. Anti-Infective Ther.* 2004, 2, 61-72; Ali et al. "Novel targets for antibiotic drug design." *Curr. Opin. Invest. Drugs* 2002, 3, 1712-1717; Lee et al. "Targeting virulence for antimicrobial chemotherapy." *Curr. Opin. Pharmacol.* 2003, 3, 513-519; each of which is incorporated herein by reference). Virulence factors can be defined as any product that aids an organism in establishing an infection and causing disease in the host. These targets have important differences from conventional antibiotic targets such as cell wall biosynthesis, protein synthesis, DNA replication, and RNA polymerase. Although inhibition of virulence factors will likely be insufficient for lethality, several lines of reasoning support the hypothesis that targeting virulence factors should provide a valuable new line of defense against pathogenic bacteria: (1) Inhibition of virulence factors should allow the natural innate and adaptive defense responses of the host to overcome the infection. (2) Virulence factor-targeted antibiotics could also be used in combination with other drugs and therapeutic modalities. (3) Such antibiotics should be less susceptible to the development of drug resistance, since the very fact that they would not be lethal reduces or removes the selection pressure for survival that leads to resistance. (4) Such antibiotics should be highly selective for bacteria over mammalian cells, since virulence factors are found only in bacteria; in contrast, most of the processes targeted by conventional antibiotics are essential to both bacteria and mammalian cells. (5) Such antibiotics could be used not only therapeutically, but also prophylactically to prevent infection. Indeed, vaccines have been developed based on several virulence factors, (Lindberg, "Vaccination against enteric pathogens: From science to vaccine trials." *Curr. Opin. Microbiol.* 1998, 1, 116-124; incorporated herein by reference) including Vi, the capsular polysaccharide of *Salmonella typhi*, which was recently shown to be safe, immunogenic, and >90% effective against typhoid fever in children 2-5 years old (Lin et al. "The efficacy of a *Salmonella typhi* Vi conjugate vaccine in two-to-five-year-old children." *New Engl. J. Med.* 2001, 344, 1263-1269; incorporated herein by reference).

Results

Siderophore biosynthesis pathways in *Y. pestis* and *M. tuberculosis* have been studied extensively (Quadri, "Assembly of aryl-capped siderophores by modular peptide synthetases and polyketide synthases." *Mol. Microbiol.* 2000, 37, 1-12; Crosa, J. H.; Walsh, C. T. "Genetics and assembly line enzymology of siderophore biosynthesis in bacteria." *Microbiol. Mol. Biol. Rev.* 2002, 66, 223-249; each of which is incorporated herein by reference). The resulting mechanistic understanding of these pathways provided us with the opportunity to design a small molecule inhibitor to block siderophore biosynthesis in pathogenic bacteria. We then evaluated the inhibitor in a series of biochemical and cellular assays.

Design and Synthesis of Salicyl-AMS as a Mechanism- and Structure-Based Inhibitor of Salicylate Adenylation Enzymes We noted at the outset that adenylate-forming enzymes that are mechanistically (but not structurally) related to salicylate adenylation enzymes have been shown to bind their cognate acyl-AMP intermediates significantly more tightly ($\approx$2-3 orders of magnitude) than their substrates (carboxylic acids and ATP) (Kim et al. "Aminoacyl-tRNA synthetases and their inhibitors as a novel family of antibiotics." *Appl. Microbiol. Biotechnol.* 2003, 61, 278-288; incorporated herein by reference). Thus, various non-hydrolyzable acyl-AMP analogs have been used as mechanism-based inhibitors of adenylate-forming enzymes. Among these are the acyl sulfamoyl adenosines (acyl-AMS), inspired by the natural product nucleocidin (Florini et al. "Inhibition of protein synthesis in vitro and in vivo by nucleocidin, an antitrypanosomal antibiotic." *J. Biol. Chem.* 1966, 241, 1091-1098) (FIG. 1C). Based on these considerations, we postulated that the reaction intermediate mimic 5'-O—[N-(salicyl)sulfamoyl]-adenosine (salicyl-AMS) would be a potent inhibitor of the salicyl adenylation activity of YbtE, MbtA, and PchD (from *P. aeruginosa* pyochelin synthetase (Quadri et al. "Assembly of the *Pseudomonas aeruginosa* nonribosomal peptide siderophore pyochelin: In vitro reconstitution of aryl-4,2-bisthiazoline synthetase activity from PchD, PchE, and PchF." *Biochemistry* 1999, 38, 14941-14954; incorporated herein by reference)).

To evaluate this idea further, we examined the structure of a related DHB adenylation enzyme, DhbE from *Bacillus subtilis* bacillibactin synthetase, in complex with its cognate DHB-AMP intermediate (May et al. "Crystal structure of DhbE, an archetype for aryl acid activating domains of modular nonribosomal peptide synthetases." *Proc. Natl. Acad. Sci. USA* 2002, 99, 12120-12125; incorporated herein by reference). We identified the putative key binding residues depicted in FIG. 4. We then performed full length amino acid sequence alignments of DhbE, YbtE, MbtA and PchD, along with Irp5, EntE (DHB adenylation enzyme from *E. coli* enterobactin synthase) (Rusnak et al. "Subcloning, expression, and purification of the enterobactin biosynthetic enzyme 2,3-dihydroxybenzoate-AMP ligase: Demonstration of enzyme-bound (2,3-dihydroxybenzoyl)adenylate product." *Biochemistry* 1989, 28, 6827-6835; incorporated herein by reference), VibE (DHB adenylation enzyme from *V. cholera* vibriobactin synthase) (Keating et al. "Reconstitution and characterization of the *Vibrio cholerae* vibriobactin synthetase from VibB, VibE, VibF, and VibH." *Biochemistry* 2000, 39, 15522-15530), and PheA (phenylalanine adenylation enzyme from *B. brevis* gramicidin S synthase) (Stachelhaus et al. "Modular structure of peptide synthetases revealed by dissection of the multifunctional enzyme GrsA." *J. Biol. Chem.* 1995, 270, 6163-6169; incorporated herein by reference) for comparison.

Overall sequence identities were $\approx$40-50%, except for YbtE/Irp5 (98.1%) and PheA (16-22%). However, as indicated in FIG. 4D, the putative binding residues are highly conserved across both the salicylate and DHB adenylation enzymes. The minor differences observed at the base of the aroyl binding pocket have been proposed to contribute to specificity for salicylate versus DHB (May et al. "Crystal structure of DhbE, an archetype for aryl acid activating domains of modular nonribosomal peptide synthetases." *Proc. Natl. Acad. Sci. USA* 2002, 99, 12120-12125; incorporated herein by reference). We noted in particular that binding of the phosphate group appears to involve primarily hydrogen-bonding interactions, rather than electrostatic interactions. This suggested that a sulfamate group in salicyl-AMS would be a suitable surrogate for the phosphate group in salicyl-AMP. Moreover, Marahiel has recently reported that phenylalanyl-AMS is a potent inhibitor of the phenylalanine adenylation domain, PheA, from gramicidin S synthetase (Finking et al. "Aminoacyl adenylate substrate analogues for the inhibition of adenylation domains of nonribosomal peptide synthetases." *ChemBioChem* 2003, 4, 903-906; incorporated herein by reference).

We thus synthesized salicyl-AMS by the route shown in FIG. 5. Silylation of adenosine, followed by selective deprotection of 5'-O-TBS group, provided 2',3'-bis-O-TBS-adenosine, 6 (Zhu et al. "Facile and highly selective 5'-desilylation of multi-silylated nucleosides." *J. Chem. Soc., Perkin Trans.* 1 2000, 2305-2306; incorporated herein by reference). We elected to use silyl protecting groups at the 2'- and 3'-positions to set the stage for future analog syntheses to be carried out either in solution or on solid support using a silyl ether linker Sulfamoylation of 6 at the 5'-position using bis(tributyltin) oxide and sulfamoyl chloride (Castro-Pichel et al. "A facile synthesis of ascamycin and related analogs." *Tetrahedron* 1987, 43, 383-389; incorporated herein by reference) provided sulfamate 7. Salicylate was preactivated with carbonyl diimidazole, then coupled to the sulfamate nitrogen of 7 (Forrest et al. "Aminoalkyl adenylate and aminoacyl sulfamate intermediate analogues differing greatly in affinity for their cognate *Staphylococcus aureus* aminoacyl tRNA synthetases." *Bioorg. Med. Chem. Lett.* 2000, 10, 1871-1874; incorporated herein by reference). Subsequent deblocking of the TBS protecting groups with TBAF afforded salicyl-AMS in a total of 5 steps and 31% overall yield. 5'-O-(Sulfamoyl)-adenosine (AMS) was also synthesized as a control compound by deprotection of 7 directly.

Biochemical Evaluation of Salicyl-AMS
ATP-PPi Exchange Assay

We first used an ATP-[$^{32}$P]-pyrophosphate (PPi) exchange assay (Gehring et al. "The nonribosomal peptide synthetase HMWP2 forms a thiazoline ring during biogenesis of yersiniabactin, an iron-chelating virulence factor of *Yersinia pestis.*" *Biochemistry* 1998, 37, 11637-11650; Quadri et al. "Identification of a *Mycobacterium tuberculosis* gene cluster encoding the biosynthetic enzymes for assembly of the virulence-conferring siderophore mycobactin." *Chem. Biol.* 1998, 5, 631-645; Quadri et al. "Assembly of the *Pseudomo-* nas aeruginosa nonribosomal peptide siderophore pyochelin: In vitro reconstitution of aryl-4,2-bisthiazoline synthetase activity from PchD, PchE, and PchF." *Biochemistry* 1999, 38, 14941-14954; each of which is incorporated herein by reference) to determine dose-response curves for inhibition of the adenylation activity of YbtE, MbtA, and PchD by salicyl-AMS at fixed, saturating substrate concentrations. YbtE and MbtA were expressed in *E. coli* BL21(DE3) as IPTG-inducible N-terminally $His_6Smt3$-tagged proteins, then purified and cleaved (Onwueme et al. "Mycobacterial polyketide-associated proteins are acyltransferases: Proof of principle with *Mycobacterium tuberculosis* PapAS." *Proc. Natl. Acad. Sci. U.S.A.* 2004, 101, 4608-4613; incorporated herein by reference). C-terminally $His_6$-tagged PchD was overproduced in *E. coli* and purified as reported (Gehring et al. "The nonribosomal peptide synthetase HMWP2 forms a thiazoline ring during biogenesis of yersiniabactin, an iron-chelating virulence factor of *Yersinia pestis*." *Biochemistry* 1998, 37, 11637-11650; Quadri et al. "Assembly of the *Pseudomonas aeruginosa* nonribosomal peptide siderophore pyochelin: In vitro reconstitution of aryl-4,2-bisthiazoline synthetase activity from PchD, PchE, and PchF." *Biochemistry* 1999, 38, 14941-14954; Quadri et al. "Characterization of Sfp, a *Bacillus subtilis* phosphopantetheinyl transferase for peptidyl carrier protein domains in peptide synthetases." *Biochemistry* 1998, 37, 1585-1595; each of which is incorporated herein by reference). Reactions (100 μL) were initiated by addition of 20 nM enzyme to 75 mM Tris-HCl (pH 8.8); 10 mM $MgCl_2$; 2 mM DTT; 5% glycerol; 1 mM sodium [$^{32}$P]-PPi (5 Ci/mol, Perkin Elmer); 10 mM ATP ($\approx 60 \times K_m$); 250, 500, and 140 μM salicylate ($\approx 50 \times K_m$) for YbtE, MbtA, and PchD; and inhibitor in DMSO (1% of reaction volume) at varying concentrations. Reactions were incubated at 37° C. for 15 min for YbtE and PchD, and for 30 min for MbtA.

The $IC_{50}$ values determined from these experiments were 14.7±2.0 nM for YbtE, 10.7±2.0 nM for MbtA, and 12.5±2.2 nM for PchD (FIG. 2A, B, C). In contrast, the parent AMS compound did not inhibit adenylation when tested at up to 400 nM under the same conditions (not shown). The $IC_{50}$ values were≈½×[E] and consistent with the expected 1:1 stoichiometry for the enzyme-inhibitor complexes. $IC_{50}$ values similar to enzyme concentration (i.e., within a factor of 10) are characteristic of tight binding inhibitors (TBIs) (Copeland, "Tight binding inhibitors." In *Enzymes: A practical introduction to structure, mechanism, and data analysis*; Second ed.; Wiley-VCH, Inc. Publications: New York, 2000, pp. 305-317; incorporated herein by reference). Thus, we hypothesized that salicyl-AMS behaves as a TBI. Importantly, the steady state approximations that permit application of the Henri-Michaelis-Menten equation to characterize enzyme-inhibitor interactions are not applicable to TBIs because of their high binding affinity. Therefore, we applied specialized methodologies for TBI analysis that consider an alternative steady state approach. These methodologies have been used to characterize various TBIs, including reaction intermediate-based inhibitors of the adenylation activity of aminoacyl-tRNA synthetases (Pope et al. "Characterization of isoleucyl-tRNA synthetase from *Staphylococcus aureus*. II. Mechanism of inhibition by reaction intermediate and pseudomonic acid analogs studied using transient and steady-state kinetics." *J. Biol. Chem.* 1998, 273, 31691-31701; incorporated herein by reference).

We selected YbtE for further analysis of salicyl-AMS using the TBI methodologies. Dose-response data sets were fitted to the Morrison equation, (Copeland, R. A. "Tight binding inhibitors." In *Enzymes: A practical introduction to structure, mechanism, and data analysis*; Second ed.; Wiley-VCH, Inc. Publications: New York, 2000, p 305-317) eq. (1), and $IC_{50}$ values were calculated with eq. (2) using $K_i^{app}$ derived from the curve fit. $IC_{50}$ values were determined at several different concentrations of YbtE over a salicyl-AMS range of 0-200 nM under the conditions described above, except that the ATP and salicylate concentrations were both 1 mM.

$$\frac{v_i}{v_0} = 1 - \frac{([E]+[I]+K_i^{app}) - \sqrt{([E]+[I]+K_i^{app})^2 - 4[E][I]}}{2[E]} \quad \text{eq. (1)}$$

$$IC_{50} = \frac{1}{2}[E] + K_i^{app} \quad \text{eq. (2)}$$

We found that the $IC_{50}$ value for salicyl-AMS increased linearly with increasing YbtE concentration (FIG. 2D) with a slope of 0.43 ($R^2$=0.9594), corrected to 0.52 ($R^2$=0.9999) if the YbtE concentration determined from the Morrison curve fit is used to adjust for errors in enzyme concentration and the inactive protein fraction. A slope of 0.5 is diagnostic of a TBI modality, (Copeland, "Tight binding inhibitors." In *Enzymes: A practical introduction to structure, mechanism, and data analysis*; Second ed.; Wiley-VCH, Inc. Publications: New York, 2000, pp. 305-317; incorporated herein by reference) supporting our hypothesis that salicyl-AMS is a TBI.

We next determined $K_i^{app}$ values for salicyl-AMS from dose-response curves using variable ATP or salicylate concentrations. Salicyl-AMS was assayed over a concentration range of 0-150 nM, with 20 nM YbtE and either (1) 10 mM ATP and 1.3-250 μM salicylate, or (2) 1 mM salicylate and 0.04-10 mM ATP. The dose-response data were fitted to eq. (1) to obtain a $K_i^{app}$ for each curve. We found that the KaPP values increased linearly with increasing ATP concentration, indicative of a competitive mode of inhibition with respect to ATP (FIG. 2E) (Copeland, "Tight binding inhibitors." In *Enzymes: A practical introduction to structure, mechanism, and data analysis*; Second ed.; Wiley-VCH, Inc. Publications: New York, 2000, p 305-317; incorporated herein by reference). The concentrations tested correspond to 0.2-60× $K_m$(ATP) and 190×$K_m$(salicylate). [$K_m$(ATP) was calculated at 172 μM in this study (not shown) and 350 μM elsewhere (Gehring et al. "The nonribosomal peptide synthetase HMWP2 forms a thiazoline ring during biogenesis of yersiniabactin, an iron-chelating virulence factor of *Yersinia pestis*." *Biochemistry* 1998, 37, 11637-11650; incorporated herein by reference); $K_m$(salicylate) was calculated at 5.4 μM in this study (not shown) and 4.6 μM elsewhere (Gehring et al. "The nonribosomal peptide synthetase HMWP2 forms a thiazoline ring during biogenesis of yersiniabactin, an iron-chelating virulence factor of *Yersinia pestis*." *Biochemistry* 1998, 37, 11637-11650; incorporated herein by reference)]. For competitive TBIs, K is related to $K_i^{app}$ as shown in eq. (3) (Copeland, "Tight binding inhibitors." In *Enzymes: A practical introduction to structure, mechanism, and data analysis*; Second ed.; Wiley-VCH, Inc. Publications: New York, 2000, p 305-317; incorporated herein by reference). Thus, $K_i$=$K_i^{app}$ when [S]=0, and we calculated a $K_i$(ATP) value of 0.35±0.27 nM as the y intercept of the line fitted to the data in FIG. 2E.

$$K_i^{app} = K_i\left(1 + \frac{[S]}{K_m}\right) \quad \text{eq. (3)}$$

In contrast to the case with ATP, increasing salicylate concentration from 0.2-50×$K_m$ (salicylate) in the presence of excess ATP (60×$K_m$) had no significant effect on $K_i^{app}$ (FIG.

2F), diagnostic of a non-competitive modality with respect to this substrate (Copeland, "Tight binding inhibitors." In *Enzymes: A practical introduction to structure, mechanism, and data analysis*; Second ed.; Wiley-VCH, Inc. Publications: New York, 2000, p 305-317; incorporated herein by reference). For such non-competitive TBIs, $K_i=K_i^{app}$. Thus, a $K_i$ (salicylate) value of 1.08±0.98 nM was calculated from the average of $K_i^{app}$ values in FIG. 2F. Overall, our data demonstrate that salicyl-AMS behaves as a potent inhibitor of YbtE with a tight-binding modality.

ArCP Salicylation Assay

The results described above demonstrated that salicyl-AMS inhibits the first of the two steps catalyzed by YbtE, MbtA, and PchD leading to ArCP salicylation (FIG. 1B). Thus, salicyl-AMS should also inhibit the overall ArCP salicylation process. To investigate this hypothesis, we developed an ArCP salicylation assay using a phosphopantetheinylated 100-amino acid ArCP domain fragment (ypArCP-H6) from *Y. pestis* HMWP2 synthetase. The phosphopantetheinylated ArCP domain was generated by coexpression of ypArCP-H6 with the phosphopantetheinyl transferase Sfp (expressed from plasmid pSU20-Sfp) (Couch et al. "Characterization of CmaA, an adenylation-thiolation didomain enzyme involved in the biosynthesis of coronatine." *J. Bacteriol.* 2004, 186, 35-42; incorporated herein by reference). The purified ArCP domain was then incubated with Sfp and coenzyme A to maximize modification stoichiometry (Weinreb et al. "Stoichiometry and specificity of in vitro phosphopantetheinylation and aminoacylation of the valine-activating module of surfactin synthetase." *Biochemistry* 1998, 37, 1575-1584; incorporated herein by reference). The ArCP domain fragment was then immobilized in 96-well FlashPlate PLUS plates (PerkinElmer). The plates have a $Ni^{2+}$ coat for ypArCP-H6 binding and a scintillant coat to provide a scintillation proximity effect for detection of YbtE-catalyzed incorporation of [$^3$H]-salicylate onto well-bound ypArCP-H6. After ypArCP-H6 binding, the wells were loaded with reaction mixtures (30 µl) containing 75 mM MES (pH 6.5), 1 mM TCEP, 100 µM ATP, 150 nM [$^3$H]-salicylate (33 Ci/mmol, Vitrax), and salicyl-AMS (in DMSO as 1% of total reaction volume) at various concentrations. The reactions were initiated by addition of 70 nM YbtE and incubated at 37° C. for 1.5 h. Reactions were then chased with 300 µL PBS containing cold 1 mM salicylate. The wells were washed with chase solution and [$^3$H]-salicyl-ypArCP-H6 was quantified using a TopCount Microplate counter (Packard). The dose-response data were fitted to eq. (1), and the $IC_{50}$ values were calculated with eq. (2).

In this assay, salicyl-AMS again inhibited [$^3$H]-salicyl-ypArCP-H6 formation with an $IC_{50} \approx \frac{1}{2} \times [E]$ (FIG. 2G). In contrast, the parent AMS compound did not inhibit salicylation when tested at up to 400 µM under the same conditions (not shown). Thus, our results for salicyl-AMS inhibition of ArCP domain salicylation are in agreement with those described above for the inhibition of the salicylate adenylation step.

Cellular Evaluation of Salicyl-AMS

Siderophore biosynthesis is known to be required for efficient growth of *Y. pestis* (Fetherston et al. "Analysis of the pesticin receptor from *Yersinia pestis*: Role in iron-deficient growth and possible regulation by its siderophore." *J. Bacteriol.* 1995, 177, 1824-1833; Bearden et al. "Genetic organization of the Yersiniabactin biosynthetic region and construction of avirulent mutants in *Yersinia pestis*." *Infect. Immun.* 1997, 65, 1659-1668; each of which is incorporated herein by reference) and *M. tuberculosis* (De Voss et al. "The salicylate-derived mycobactin siderophores of *Mycobacterium tuberculosis* are essential for growth in macrophages." *Proc. Natl. Acad. Sci. U.S.A.* 2000, 97, 1252-1257; incorporated herein by reference) in extremely deferrated culture medium, conditions that mimic those in a mammalian host during infection. Since salicyl-AMS inhibits the required first step in the biosynthesis of yersiniabactin and the mycobactins, we investigated the ability of this compound to inhibit *Y. pestis* and *M. tuberculosis* growth under these conditions. We used an avirulent *Y. pestis* strain KIM6-2082.1+ (Gong et al. "Characterization of the *Yersinia pestis* Yfu ABC inorganic iron transport system." *Infect. Immun.* 2001, 69, 2829-2837; incorporated herein by reference) and deferrated medium [PMH medium deferrated with Chelex-100 resin (PMH-D)] (Fetherston et al. "Analysis of the pesticin receptor from *Yersinia pestis*: Role in iron-deficient growth and possible regulation by its siderophore." *J. Bacteriol.* 1995, 177, 1824-1833; Bearden et al. "Genetic organization of the Yersiniabactin biosynthetic region and construction of avirulent mutants in *Yersinia pestis*." *Infect. Immun.* 1997, 65, 1659-1668; each of which is incorporated herein by reference). Yersiniabactin production is induced in PMH-D and allows *Y. pestis* KIM6-2082.1+ to grow in all PMH media. Conversely, loss of yersiniabactin production causes a very drastic growth reduction in extremely deferrated medium [PMH-D medium deferrated further by precipitation with $CaCl_2$ (PMH-DS)]. Thus, *Y. pestis* was adapted by growing in PMH-D, harvested, and resuspended ($OD_{600}$ 0.005) in PMH-DS. The suspension was loaded (100 µl/well) into 96-well plates containing PMH-DS (100 µl/well) supplemented with DMSO and salicyl-AMS at various concentrations. Similarly, *M. tuberculosis* H37Rv was grown in GAST low iron medium (De Voss et al. "The salicylate-derived mycobactin siderophores of *Mycobacterium tuberculosis* are essential for growth in macrophages." *Proc. Natl. Acad. Sci. U.S.A.* 2000, 97, 1252-1257; incorporated herein by reference) that was further deferrated with Chelex-100 (GAST-D). *M. tuberculosis* grows well in both media, while a mycobactin-deficient mutant displays a significant growth reduction in GAST and a very drastic growth reduction in GAST-D (De Voss et al. "The salicylate-derived mycobactin siderophores of *Mycobacterium tuberculosis* are essential for growth in macrophages." *Proc. Natl. Acad. Sci. U.S.A.* 2000, 97, 1252-1257; incorporated herein by reference). Exponentially growing cells of *M. tuberculosis* were harvested and resuspended ($OD_{600}$ 0.02) in GAST-D. The suspensions were loaded (100 µl/well) in wells containing media (100 µl/well) supplemented with salicyl-AMS in DMSO as described above.

$$\frac{OD_i}{OD_0} = b + \frac{(a-b)}{1+([I]/IC_{50})^c} \qquad \text{eq. (4)}$$

The $OD_{600}$ values of the cultures were measured before and after plate incubation (22 h, 37° C., 220 rpm for *Y. pestis*; 8 days, 37° C., stationary conditions for *M. tuberculosis*). $IC_{50}$ values were calculated by fitting the dose-response data to the standard four-parameter sigmoidal equation shown in eq. (4), where a and b are the top and bottom of the curve and c is the slope (Hill coefficient). Gratifyingly, salicyl-AMS inhibited both *Y. pestis* and *M. tuberculosis* growth under these iron-deficient conditions with $IC_{50}$ values of 52±5 µM and 25±3 µM, respectively (FIG. 3D, E). By way of comparison, streptomycin has an MIC of 2.6-6.9 M against 92 *Y. pestis* strains (Wong et al. "Susceptibilities of *Yersinia pestis* strains to 12 antimicrobial agents." *Antimicrob. Agents Chemother.* 2000, 44, 1995-1996; incorporated herein by reference) and 0.4-1.7

µM against the *M. tuberculosis* H37Rv reference strain (Wanger et al. "Testing of *Mycobacterium tuberculosis* susceptibility to ethambutol, isoniazid, rifampin, and streptomycin by using Etest." *J. Clin. Microbiol.* 1996, 34, 1672-1676; incorporated herein by reference). Notably, the parent AMS compound is not a suitable control since, as an analog of nucleocidin, it is known to inhibit growth by other mechanisms (Bloch, A.; Coutsogeorgopoulos, C. "Inhibition of protein synthesis by 5'-sulfamoyladenosine." *Biochemistry* 1971, 10, 4394-4398; Rengaraju, S.; Narayanan, S.; Ganju, P. L.; Amin, M. A.; Iyengar, M. R. S.; Sasaki, T.; Miyadoh, S.; Shomura, T.; Sezaki, M.; Kojima, M. "5'-β-Sulfamoyladenosine (defluoronucleocidin) from a *Streptomyces*." *Meiji Seika Kenkyu Nenpo* 1986, 49-55; each of which is incorporated herein by reference). Thus, we are currently assessing the influence of salicyl-AMS upon siderophore biosynthesis proper through [$^3$H]-salicylate labeling experiments. We are also conducting rescue experiments involving addition of exogenous siderophore and assaying for non-specific growth inhibition under iron-sufficient conditions where *Y. pestis* and *M. tuberculosis* growth is independent of siderophore production (Fetherston et al. "Analysis of the pesticin receptor from *Yersinia pestis*: Role in iron-deficient growth and possible regulation by its siderophore." *J. Bacteriol.* 1995, 177, 1824-1833; Bearden et al. "Genetic organization of the Yersiniabactin biosynthetic region and construction of avirulent mutants in *Yersinia pestis." Infect. Immun.* 1997, 65, 1659-1668; De Voss et al. "The salicylate-derived mycobactin siderophores of *Mycobacterium tuberculosis* are essential for growth in macrophages" *Proc. Natl. Acad. Sci. U.S.A.* 2000, 97, 1252-1257; each of which is incorporated herein by reference).

To our knowledge, salicyl-AMS is the first inhibitor of a siderophore biosynthesis enzyme. This compound has potent activity in two biochemical inhibition assays and also inhibits *Y. pestis* and *M. tuberculosis* growth under iron-deficient conditions, which mimic those in a mammalian host during infection. Although we have not tested *Y. enterocolitica* directly, we note that its yersiniabactin synthetase salicyl adenylation enzyme, Irp5, has 98.1% sequence identity with YbtE (FIG. 4E and data not shown), indicating that YbtE inhibitors are highly likely to have similar activity against Irp5 and *Y. enterocolitica*. Salicyl-AMS is a valuable lead compound that provides us with a starting point to develop novel antibiotics for biodefense.

Research Design and Methods

Our studies will build upon our salicyl-AMS lead compound, which is a low nM inhibitor of YbtE and MbtA, but exhibits only moderate activity against siderophore-dependent growth of *Y. pestis* and *M. tuberculosis* in iron-deficient media. We hypothesize that the cellular activity of salicyl-AMS is restricted by one or more pharmacological factors: (1) cell permeability, (2) inhibitor efflux, (3) inhibitor specificity, (4) inhibitor stability.

General Considerations

A variety of nucleoside analogs have been investigated as antibiotics, however, relatively little is known about the SAR of this class, especially as pertains to permeability, efflux, specificity, and stability (Rachakonda et al. "Challenges in antimicrobial drug discovery and the potential of nucleoside antibiotics." *Curr. Med. Chem.* 2004, 11, 775-793; incorporated herein by reference). Thus, an empirical approach to optimization of salicyl-AMS is desired. However, several general considerations will guide our efforts: (1) Poor cell permeability may be hindering salicyl-AMS from reaching its targets. Gram-negative bacteria such as *Y. pestis* and *Y. enterocolitica* have, in addition to the inner cytoplasmic membrane, a lipopolysaccharide-rich outer membrane that provides an additional permeability barrier and intrinsic resistance to hydrophilic antibiotics (Hancock, "The bacterial outer membrane as a drug barrier." *Trends Microbiol.* 1997, 5, 37-42; Nikaido, "Prevention of drug access to bacterial targets: permeability barriers and active efflux." *Science* 1994, 264, 382-388; each of which is incorporated herein by reference). The mycolic acid-rich mycobacterial cell wall of *M. tuberculosis* serves a similar function (Brennan et al "The envelope of mycobacteria." *Ann. Rev. Biochem.* 1995, 64, 29-63; incorporated herein by reference). However, hydrophobic compounds are able to pass through these membranes via passive diffusion (Plesiat et al. "Outer membranes of Gram-negative bacteria are permeable to steroid probes." *Mol. Microbiol.* 1992, 6, 1323-1333; incorporated herein by reference). Indeed, among the fluoroquinolone antibiotics, increased hydrophobicity translates to increased activity against *M. tuberculosis* (Brennan et al. "The envelope of mycobacteria." *Ann. Rev. Biochem.* 1995, 64, 29-63). Hydrophobicity is often estimated using cLogP, the calculated log of the n-octanol/water partition coefficient. Also, polar surface area and the number of rotatable bonds have been inversely correlated to oral bioavailability, (Veber et al. "Molecular properties that influence the oral bioavailability of drug candidates." *J. Med. Chem.* 2002, 45, 2615-2623; incorporated herein by reference) in which membrane permeability plays a major role. Thus, adjusting these properties of salicyl-AMS may increase its cellular activity. (2) Drug efflux pumps may also prevent intracellular accumulation of salicyl-AMS. Five families of non-specific bacterial efflux pumps have been identified (Nikaido, "Prevention of drug access to bacterial targets: permeability barriers and active efflux." *Science* 1994, 264, 382-388; Borges-Walmsley et al. "Structure and function of efflux pumps that confer resistance to drugs." *Biochem. J.* 2003, 376, 313-338; Paulsen, "Multidrug efflux pumps and resistance: Regulation and evolution." *Curr. Opin. Microbiol.* 2003, 6, 446-451; each of which is incorporated herein by reference). Recently available crystal structures indicate that these proteins have large hydrophobic binding pockets, but provide few insights on how to prevent drug binding. One intriguing strategy is the use of salicyl-AMS analogs that are covalent inhibitors and, thus, not susceptible to efflux. (3) Poor specificity of salicyl-AMS may allow binding by other bacterial proteins that use adenosine cofactors. Since these are likely to be in much greater total abundance than the salicyl adenylation enzymes, this would titrate out the activity. Thus, structure-guided efforts to design salicyl-AMS analogs with greater specificity may also provide enhanced cellular activity. (4) Poor stability of salicyl-AMS, due to degradation or modification, either spontaneous or enzymatic, would also reduce its activity. This could involve nucleoside catabolism, (Hammer-Jespersen, "Nucleoside catabolism." In *Metabolism of nucleotides, nucleosides, and nucleobases in microorganisms*; Munch-Petersen, A., Ed.; Academic Press: London, 1983, pp. 203-258; incorporated herein by reference) hydrolysis of salicylimide or sulfamate, or nucleophilic displacement of the sulfamate. Modifying salicyl-AMS accordingly to increase its stability may also increase its cellular activity.

Identification of salicylate adenylation enzyme inhibitors with potent cellular activity requires a balance of both binding affinity and favorable pharmacological properties. To achieve an appropriate balance, SAR must be determined so that structural changes can be made, for example, to increase cell permeability without significantly compromising binding affinity. We will synthesize a series of salicyl-AMS analogs, designed in conjunction with a structural model we have developed, to delineate SAR for these multiple factors.

Structural Model for Salicyl-AMS Binding to Salicylate Adenylation Enzymes

Figure 6:
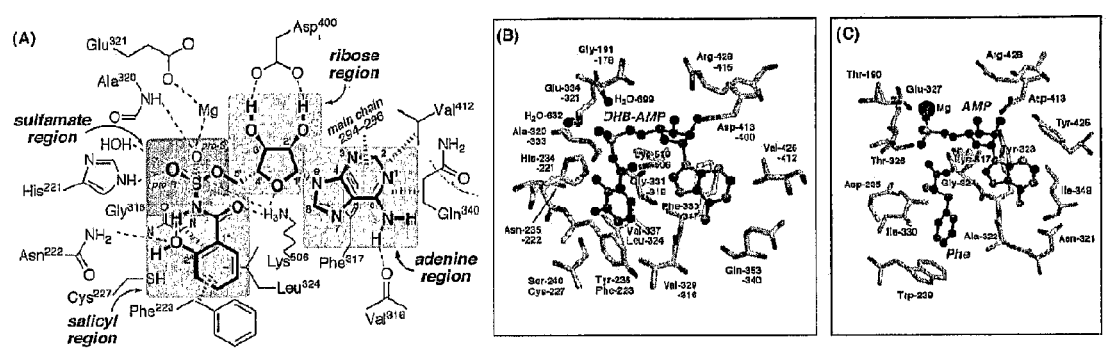
FIG. 6 shows a structural model for salicyl-AMS binding to salicylate adenylation enzymes. A. Putative binding interactions between salicyl-AMS and YbtE and four regions that will be modified to determine SAR. B. Binding residues of the dihydroxybenzoate adenylation enzyme DhbE and its cognate intermediate DHB-AMP. Salicyl-AMS is proposed to bind similarly to salicylate adenylation enzymes and corresponding residue numbers in YbtE are shown. C. Binding residues of the phenylalanine adenylation enzyme PheA with AMP and phenylalanine. (Structural analysis: 1MDB, 1AMU in RasMol 2.5; residues within 4.0 Å of ligands are displayed.)

As described in the above, we have examined the cocrystal structure of DhbE with its cognate reaction intermediate DHB-AMP to identify putative binding interactions (FIG. 4) (May et al. "Crystal structure of DhbE, an archetype for aryl acid activating domains of modular nonribosomal peptide synthetases." *Proc. Natl. Acad. Sci. USA* 2002, 99, 12120-12125; incorporated herein by reference). Alignment of the amino acid sequences of various DHB and salicyl adenylation enzymes indicates that these binding residues are highly conserved. Thus, we have developed a structural model in which salicyl-AMS binds to YbtE and MbtA via interactions analogous to those observed for DHB-AMP binding to DhbE (FIG. 6). We have also examined the crystal structure of PheA, a phenylalanine adenylation enzyme from *Bacillus brevis* gramicidin S synthase, in complex with phenylalanine and AMP (Conti et al. "Structural basis for the activation of phenylalanine in the non-ribosomal biosynthesis of gramicidin S." *EMBO J.* 1997, 16, 4174-4183; incorporated herein by reference). Overall, these ligands are bound in an orientation that is similar to that of DHB-AMP binding to DhbE, providing additional support for our structural model.

Our model provides a starting point for structure-guided design of analogs to probe the SAR of salicylate adenylation enzyme inhibitors. We will explore the SAR in four regions of the inhibitor. Of particular interest will be (1) analogs having an electrophilic group in the salicyl region to bind covalently to Cys-227 (YbtE), (2) analogs substituted at the 2'- or 3'-OH groups in the ribose region to increase permeability and specificity and to provide biotin- and radiolabeled probes, (3) analogs in which the adenine region is replaced with a hydrophobic ring to increase cell permeability while maintaining hydrophobic interactions with the enzyme. We expect to begin by synthesizing subsets of the analogs described herein.

Salicyl Region Modifications

Our structural model (FIG. 6) indicates that the salicyl region of salicyl-AMS is involved in the following binding interactions (YbtE numbering): (1) hydrogen bonding between the carbonyl oxygen and the Lys-506 ε-amino group, (2) hydrogen bonding between the phenolic 2'-hydroxyl group and the Asn-222 γ-amino group, (3) hydrophobic interactions between the aromatic ring and the Gly-318 main chain, the Leu-324 sidechain, and the Phe-223 β-carbon, (4) a possible intramolecular hydrogen bond between the phenolic 2"-OH and the NH of the sulfamate region. Notably, Ser-240 in DhbE is replaced by Cys-227 in YbtE and Cys-263 in MbtA. Thus, we may be able to use an electrophilic group on the inhibitor to bind covalently to this thiol. While covalent interactions are usually viewed as increasing binding affinity, as well as the potential for non-specific binding, they can, in fact, increase specificity, since other proteins that may bind the inhibitor will likely lack an appropriately-oriented nucleophile for covalent binding. Indeed, irreversible covalent inhibitors may have additional pharmacokinetic advantages since they would not be subject to efflux pumps and even brief exposure of the salicylate adenylation enzymes to the inhibitor would result in prolonged suppression of siderophore biosynthesis that could be overcome only by expression of new protein. Our structural analysis also suggests that the carbonyl and o-phenolic groups are both important for binding, but that additional substitutions on the aromatic ring may be tolerated.

Figure 7:
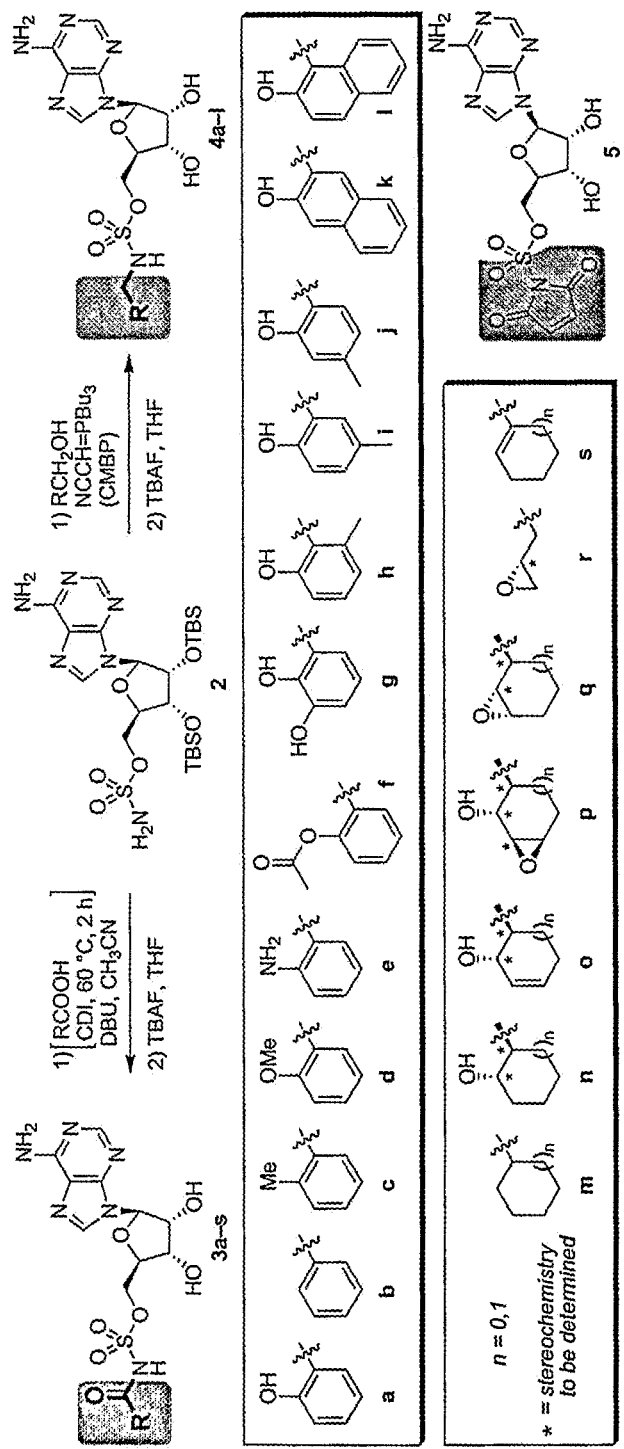
FIG. 7 is a scheme for the synthesis of acyl-AMS (3a-s, 5) and alkyl-AMS analogs (4a-l) of salicyl-AMS to determine salicyl region SAR.

We will probe the SAR in the salicyl region with the salicyl-AMS analogs shown in FIG. 7. These modifications may affect binding affinity and specificity in particular. It will be interesting to compare our results to a recent investigation of YbtE substrate specificity with respect to various substituted benzoate precursors (McLoughlin et al. "Kinetic and regiospecific interrogation of covalent intermediates in the nonribosomal peptide synthesis of yersiniabactin." *J. Am. Chem. Soc.* 2004, 126, 13265-13275; incorporated herein by reference). Acyl-AMS analogs 3a-s and 5 will be derived from the 2',3'-silylated intermediate 2, or its known acetonide variant (Peterson, E. M.; Brownell, J.; Vince, R. "Synthesis and biological evaluation of 5'-sulfamoylated purinyl carbocyclic nucleosides." *J. Med. Chem.* 1992, 35, 3991-4000; incorporated herein by reference). Acetylated analog 3f may not bind directly, but may be active as a prodrug, wherein the acetate group would improve cell permeability, then be hydrolyzed by non-specific esterases or lipases once inside the cell. We expect that compound 3h will bind comparably to salicyl-AMS, since the methyl group is directed into an empty pocket between the aromatic ring and the C8 position of the adenine ring. This will have important implications for developing macrocyclic analogs via direct tethering of this methyl group to the C8 position.

Since the aromatic ring in salicyl-AMS appears to be bound by general hydrophobic interactions and not by specific π-interactions, we expect that the reduced analogs 3m-o should also bind. If these compounds are effective inhibitors, this will set the stage for incorporation of electrophilic epoxides in 3p and 3q that can form selective covalent bonds with Cys-227 in YbtE and Cys-263 in MbtA. We will also investigate the linear variant 3r, and Michael acceptors 3s and 5. The results with 3m-o will also be relevant to developing macrocyclic analogs that have an appropriate overall conformation to mimic salicyl-AMS.

We will also synthesize the alkyl-AMS analog 4a by Mitsunobu-type alkylation of 2 using cyanomethylenetributylphosphorane (CMBP), which is selective for monoalkylation of primary sulfonamides (Tsunoda et al. "Mitsunobu-type alkylation of p-toluenesulfonamide. A convenient new route to primary and secondary amines" *Tetrahedron Lett.* 1996, 37, 2457-2458; incorporated herein by reference). If the alkyl-AMS analog 4a does bind, this would warrant investigation of additional analogs 4b-l as an avenue to compounds with increased stability and permeability.

Sulfamate Region Modifications

Our structural model (FIG. 6) indicates that the sulfamate region of salicyl-AMS is involved in the following binding interactions (YbtE numbering): (1) hydrogen bonding between the pro-R oxygen and the His-221 imidazole τ-nitrogen, the Lys-506 ε-amino group, and/or an ordered $H_2O$ (632 in DhbE), (2) coordination between the pro-S oxygen and a Mg ion (observed in the PheA structure and replaced by $H_2O$-669 in the DhbE structure), (3) a hydrogen bond between the pro-S oxygen and the Ala-320 main chain amide NH, (4) a possible intramolecular hydrogen bond between the sulfamate NH group and the o-phenolic hydroxyl in the salicyl region. This suggests that the 5'-oxygen of the ribose ring might be replaced without adversely affecting binding; substitution at this position is pertinent to the synthesis of conformationally constrained analogs as discussed below. Our analysis also suggests that replacement of the sulfamate with a carbamate or sulfamide might be accommodated.

We will probe the SAR in the sulfamate region with the salicyl-AMS analogs shown in FIG. 8. These modifications may affect binding affinity and chemical stability in particular. The N-methylated analog 6 will be synthesized from 2 by Mitsunobu-type alkylation with methanol as above (FIG. 7), (Tsunoda et al. "Mitsunobu-type alkylation of p-toluenesulfonamide. A convenient new route to primary and secondary amines" *Tetrahedron Lett.* 1996, 37, 2457-2458; incorporated herein by reference) followed by salicylation and deprotection as usual. Since our structural model suggests that the sulfamate NH in salicyl-AMS participates in an intramolecular hydrogen bond with the o-phenolic hydroxyl of the salicyl moiety, we expect that this N-substitution may cause a significant change in conformation and binding affinity. We will synthesize carbamate analog 7 by direct acylation of 2 with O-benzyl-N-salicylisocyanate 11 (derived from treatment of O-benzylsalicylamide (Chang, C. Y.; Kuo, S. C.; Lin, Y. L.; Wang, J. P.; Huang, L. J. "Benzyloxybenzaldehyde analogues as novel adenylyl cyclase activators." *Bioorg. Med. Chem. Lett.* 2001, 11, 1971-1974; incorporated herein by reference) with oxalyl chloride (Speziale, A. J.; Smith, L. R. "New and convenient synthesis of acyl isocyanates." *J. Org. Chem.* 1962, 27, 3742-3743; incorporated)), followed by deprotection. This analog will probe the effect of replacing the sulfamate moiety in salicyl-AMS with a carbamate, effectively deleting one of the sulfone oxygens. We will synthesize the sulfamide analog 8 from the known 5'-amino-5'-deoxy-2',3'-O-bis-TBS-adenosine 12 (Kotch, F. W.; Sidorov, V.; Lam, Y.-F.; Kayser, K. J.; Li, H.; Kaucher, M. S.; Davis, J. T. "Water-mediated association provides an ion pair receptor." *J. Am. Chem. Soc.* 2003, 125, 15140-15150; incorporated herein by reference) or the corresponding acetonide (Liu, F.; Austin, D. J. "Synthesis of 5'-functionalized adenosine: Suppression of cyclonucleoside formation." *Tetrahedron Lett.* 2001, 42, 3153-3154; incorporated herein by reference). We will synthesize the desoxy analog 9 from the known acetonide-protected homoadenosine 13 (Robins, M. J.; Guo, Z.; Samano, M. C.; Wnuk, S. F. "Biomimetic simulation of free radical-initiated cascade reactions postulated to occur at the active site of ribonucleotide reductases." *J. Am. Chem. Soc.* 1999, 121, 1425-1433; incorporated herein by reference). We will convert the terminal hydroxyl to a sulfonamide according to ample literature precedents, (King, J. F.; Aslam, M. "Alkanesulfonyl chlorides from alcohols via [2]betylates (alkyl 2-ammonioethanesulfonates)." *Synthesis* 1980, 285-287; Abramovitch, R. A.; Holcomb, W. D.; Thompson, W. M.; Wake, S. "Solution and flash vacuum pyrolyses of (3-(3,5-disubstituted-phenyl)ethanesulfonyl azides. Sultam, pyrindine, and azepine formation." *J. Org. Chem.* 1984, 49, 5124-5131; Cama, E.; Shin, H.; Christianson, D. W. "Design of amino acid sulfonamides as transition-state analogue inhibitors of arginase." *J. Am. Chem. Soc.* 2003, 125, 13052-13057; each of which is incorporated herein by reference) then salicylate and deprotect as usual to provide 9. Since the ribose 5'-oxygen does not appear to be involved in any hydrogen bonds, these two modifications should be tolerated and, if so, installation of additional substituents at this position will be explored both here and to generate conformationally constrained analogs. Finally, we will also synthesize the homologated analog 10 from homoadenosine 13 by analogy to our established route. The ability to add substituents to this additional carbon would have implications for the design of other analogs and conformationally constrained analogs.

Ribose Region Modifications

Our structural model (FIG. 6) indicates that the ribose region of salicyl-AMS is involved in the following binding interactions (YbtE numbering): (1) hydrogen bonding of either the 2'-OH or 3'-OH to the Asp-400 β-carboxylate, (2) hydrogen bonding of the ring 4'-oxygen to the Lys-506 ε-amino group. Notably, the binding orientation of salicyl-AMS is such that the 2'- and 3'-OH groups are directed out of the active site, suggesting that substitution of one of the oxygens can be accommodated while the other maintains a hydrogen bond with Asp-400. This could be exploited to generate prodrugs and affinity- or radiolabeled probes. Along these lines, Marahiel has reported that 2'-O-substitution of phenylalanyl-AMS with a biotin tag has essentially no effect upon inhibition of PheA in an ATP-PPi exchange assay (Finking et al. "Aminoacyl adenylate substrate analogues for the inhibition of adenylation domains of nonribosomal peptide synthetases." *ChemBioChem* 2003, 4, 903-906; incorporated herein by reference). Our analysis also suggests that replacement of the ring 4'-oxygen with carbon or nitrogen would have a detrimental effect upon binding.

We will probe the SAR in the ribose region with the salicyl-AMS analogs shown in FIG. 9. In particular, we expect that these analogs may have better permeability, since they should be more hydrophobic than salicyl-AMS (as estimated by increased cLogP and decreased polar surface area) (Veber, D. F.; Johnson, S. R.; Cheng, H.-Y.; Smith, B. R.; Ward, K. W.; Kopple, K. D. "Molecular properties that influence the oral bioavailability of drug candidates." *J. Med. Chem.* 2002, 45, 2615-2623; Ertl, P.; Rohde, B.; Selzer, P. "Fast calculation of molecular polar surface area as a sum of fragment-based contributions and Its application to the prediction of drug transport properties." *J. Med. Chem.* 2000, 43, 3714-3717; each of which is incorporated herein by reference). We will synthesize deoxygenated analogs 14a-c and ring-modified analogs 14d-f using our established route (FIG. 5) from the corresponding known adenosine analogs: 2'-deoxyadenosine (Aldrich), 3'-deoxyadenosine (Norman, D. G.; Reese, C. B. "A convenient preparation of 3'-deoxyadenosine." *Synthesis* 1983, 304-306; Meier, C.; Huynh Dinh, T. "Improved conversion of adenosine to 3'-deoxyadenosine." *Synlett* 1991, 227-228; each of which is incorporated herein by reference), 2',3'-dideoxyadenosine, (Robins, M. J.; Wilson, J. S.; Madej, D.; Low, N. H.; Hansske, F.; Wnuk, S. F. "Nucleic acid-related compounds. 88. Efficient conversions of ribonucleosides into their 2',3'-anhydro, 2'(and 3')-deoxy, 2',3'-didehydro-2',3'-dideoxy, and 2',3'-dideoxynucleoside analogs." *J. Org. Chem.* 1995, 60, 7902-7908), 4'-carba-4'-deoxyadenosine (Wang, P.; Agrofoglio, L. A.; Newton, M. G.; Chu, C. K. "Chiral synthesis of carbocyclic analogues of L-ribofuranosides." *J. Org. Chem.* 1999, 64, 4173-4178; Yang, M.; Ye, W.; Schneller, S. W. "Preparation of carbocyclic S-adenosylazamethionine accompanied by a practical synthesis of (−)-aristeromycin." *J. Org. Chem.* 2004, 69, 3993-3996; incorporated herein by reference), 4'-thia-4'-deoxyadenosine (Naka, T.; Minakawa, N.; Abe, H.; Kaga, D.; Matsuda, A. "The stereoselective synthesis of 4'-β-thioribonucleosides via the pummerer reaction." *J. Am. Chem. Soc.* 2000, 122, 7233-7243; incorporated herein by reference), and 4'-acetamido-4'-deoxyadenosine (Reist, E. J.; Gueffroy, D. E.; Blackford, R. W.; Goodman, L. "Pyrrolidine sugars. Synthesis of 4'-acetamidoadenosine and other derivatives of 4-amino-4-deoxy-D-ribose." *J. Org. Chem.* 1966, 31, 4025-4030; incorporated herein by reference). These modifications may improve inhibitor stability to nucleoside catabolic enzymes.

The 2'- and 3'-OH groups also provide convenient handles to introduce additional substituents. In our structural model, these hydroxyl groups are directed out of the binding site, indicating that these substitutions should be tolerated and may increase specificity for salicylate adenylation enzymes. Doubly-substituted analogs 14g and 14h will be synthesized from the corresponding adenosine 2',3'-acetonide (Peterson et al. "Synthesis and biological evaluation of 5'-sulfamoylated purinyl carbocyclic nucleosides." *J. Med. Chem.* 1992, 35, 3991-4000; incorporated herein by reference) and 2',3'- diacetate (Aldrich) (Hotoda et al. "Synthesis of cytidyl(3'-5') adenosine bearing 2'(3')-O-leucyl ester via a phosphorothioate triester intermediate." *Tetrahedron* 1990, 46, 1181-1190; incorporated herein by reference). 14h may be a valuable prodrug, in which the acetates improve cell permeability, then are cleaved intracellularly by non-specific esterases or lipases to generate the parent salicyl-AMS inhibitor.

We will also synthesize the 2'-O-benzylated analog 14i by benzylation of the 3',5'-disiloxane 15 (Aldrich), followed by conversion to the 5'-O-(N-salicyl)sulfamate using our established route. This analog should still allow for hydrogen bonding from the 3'-OH to the Asp-40013-carboxylate, while increasing permeability and specificity. We will also synthesize biotinylated analogs 14k and 14l by acylation of the benzylamine 14j with EZ-link NHS-LC-Biotin (Pierce 21336) or EZ-link NHS-PEO$_4$-Biotin (Pierce 21330). We will then use these affinity labeled compounds to identify other proteins that may bind to salicyl-AMS, providing valuable information toward increasing the specificity of our inhibitors. The amino group in 14j will also provide a convenient handle to generate the [$^{14}$C]-radiolabeled analog 14m, which, along with [$^{3}$H]-salicylate-labeled salicyl-AMS, will be useful for analysis of drug accumulation, specificity and stability.

Adenine Region Modifications

Our structural model (FIG. 6) indicates that the adenine region of salicyl-AMS is involved in the following binding interactions (YbtE numbering): (1) hydrophobic interaction, perhaps in the form of a face-to-edge π-π interaction, between the back face of the adenine ring and the Phe-317 aromatic sidechain, (2) hydrophobic interaction between the N1-C2 region and the Val-412 sidechain, (3) hydrophobic interaction between the N1-C6 region and the Gln-340 β- and γ-carbons, (4) hydrophobic interaction between the front face of the adenine ring and the Gly-294/Ala-295/Arg-296 main chain, (5) hydrogen bonding between the 6-NH$_2$ group and the Val-316 main chain carbonyl oxygen. This appears to be the only hydrogen bonding interaction involving the adenine ring. In contrast, the adenine ring is generally bound by multiple hydrogen bonds in other proteins that bind adenosine cofactors. This suggests that replacement of adenine with other hydrophobic aromatic substituents should not adversely affect binding affinity and may well increase specificity. Moreover, these hydrophobic substitutions should increase permeability. We note that it is unlikely that salicyl-AMS or its analogs will be substrates for bacterial nucleoside nutrient importers due to the large 5'-O-(N-salicyl)sulfamate substituent (Munch-Petersen, A.; Mygind, B. "Transport of nucleic acid precursors." In *Metabolism of nucleotides, nucleosides, and nucleobases in microorganisms*; Munch-Petersen, A., Ed.; Academic Press: London, 1983, p 259-305; Vickers, M. F.; Young, J. D.; Baldwin, S. A.; Mackey, J. R.; Cass, C. E. "Nucleoside transporter proteins: Emerging targets for drug discovery." *Emerg. Therapeut. Targets* 2000, 4, 515-539; each of which is incorporated herein by reference). In contrast, nucleoside analogs used in cancer chemotherapy, which are substrates for related mammalian transporters, are unsubstituted at the 5'-OH (Kong, W.; Engel, K.; Wang, J. "Mammalian nucleoside transporters." *Curr. Drug Metab.* 2004, 5, 63-84).

Figure 10:
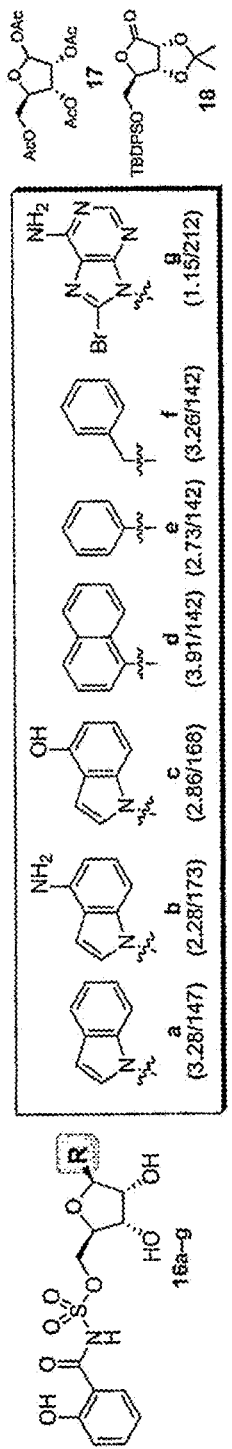
FIG. 10 shows the structures of salicyl-AMS analogs (16a-g) to probe structure-activity relationships in the adenine region and key synthetic intermediates (17, 18). cLogP (ChemDraw/Biobyte) and calculated polar surface area (Ertl et al. *J. Med. Chem.* 43:3714-17, 2000; incorporated herein by reference) (MolInspiration) values are indicated in parentheses for comparison to salicyl-AMS (0.29/212).

We will investigate salicyl-AMS analogs with modifications in the adenine region to probe the SAR in this area (FIG. 10). In particular, we expect these analogs to be more hydrophobic, and hence more permeable, than salicyl-AMS itself, as suggested by their higher cLogP values and lower calculated polar surface areas (Veber et al. "Molecular properties that influence the oral bioavailability of drug candidates." *J. Med. Chem.* 2002, 45, 2615-2623; Ertl et al. "Fast calculation of molecular polar surface area as a sum of fragment-based contributions and Its application to the prediction of drug transport properties." *J. Med. Chem.* 2000, 43, 3714-3717; each of which is incorporated herein by reference). We will synthesize the ribofuranosylindole analogs 16a-c by precedented addition of the corresponding indoline precursors to tetra-O-acetylribose (17), (Preobrazhenskaya, M. N.; Vigdorchik, M. M.; Suvorov, N. N. "Glycosulindoles. VII. Synthesis of 1-(β-D-ribofuranosyl)indole." *Tetrahedron* 1967, 23, 4653-4660; Walton, E.; Holly, F. W.; Jenkins, S. R. "Indole and 4-aminoindole nucleosides." *J. Org. Chem.* 1968, 33, 192-197; each of which is incorporated herein by reference) followed by DDQ oxidation to the indole, appropriate protecting group manipulations, and 5'-O—(N-salicyl)sulfamoylation using our established procedures. These analogs should maintain the hydrophobic interactions of the adenine ring in salicyl-AMS and the latter two, 16b and 16c, should also participate in a hydrogen bond with Val-316.

We will also investigate the C-nucleoside analogs 16d-f, which we will synthesize by addition of the appropriate aryl lithium or Grignard reagent to ribonolactone 18 (Krohn, K.; Heins, H.; Wielckens, K. "Synthesis and cytotoxic activity of C-glycosidic nicotinamide riboside analogs." *J. Med. Chem.* 1992, 35, 511-517; Matulic-Adamic, J.; Beigelman, L.; Portmann, S.; Egli, M.; Usman, N. "Synthesis and structure of 1-deoxy-1-phenyl-(3-D-ribofuranose and Its incorporation into oligoribonucleotides." *J. Org. Chem.* 1996, 61, 3909-3911; each of which is incorporated herein by reference), followed by stereoselective reduction of the lactol with BF$_3$.OEt$_2$/Et$_3$SiH, (Krohn, K.; Heins, H.; Wielckens, K. "Synthesis and cytotoxic activity of C-glycosidic nicotinamide riboside analogs." *J. Med. Chem.* 1992, 35, 511-517; Matulic-Adamic, J.; Beigelman, L.; Portmann, S.; Egli, M.; Usman, N. "Synthesis and structure of 1-deoxy-1-phenyl-β-D-ribofuranose and Its incorporation into oligoribonucleotides." *J. Org. Chem.* 1996, 61, 3909-3911; each of which is incorporated herein by reference) appropriate protecting group manipulations, and 5'-O-(N-salicyl)sulfamoylation as usual. In addition to increased cell permeability and specificity, these C-nucleoside analogs should be more stable than salicyl-AMS. Notably, C-alkyl nucleoside analogs of 11e-AMP have been advanced as cell permeable inhibitors of bacterial Ile-tRNA synthetase with promising activity against *Streptococcus pyogenes* in a mouse model (Schimmel et al. "Aminoacyl tRNA synthetases as targets for new anti-infectives." *FASEB J.* 1998, 12, 1599-1609; incorporated herein by reference).

Finally, we will synthesize salicyl-8-bromo-AMS (16g) from 8-bromoadenosine (Aldrich). Similar to the case with salicyl region analog 3h above, we expect that this analog will bind comparably to salicyl-AMS, since the bromide group is directed into an empty pocket between the adenine ring and the 6"-position of the salicyl ring. This will set the stage for the synthesis of macrocyclic analogs as described below.

Synthesis of Macrocyclic and Conformationally Constrained Analogs of Salicyl-AMS to Increase Cellular Permeability and Specificity Our structural model for salicyl-AMS binding to salicylate adenylation enzymes (FIG. 6) suggests that the inhibitor is bound in a specific, unusual "cisoid" conformation. We propose herein to exploit this structural information by synthesizing novel macrocyclic and conformationally constrained analogs that should adopt a similar pharmacophoric conformation. We expect that these analogs should benefit from increased specificity, binding affinity, and permeability.

Unusual "Cisoid" Pharmacophoric Conformation in DHB-AMP

Figure 11:
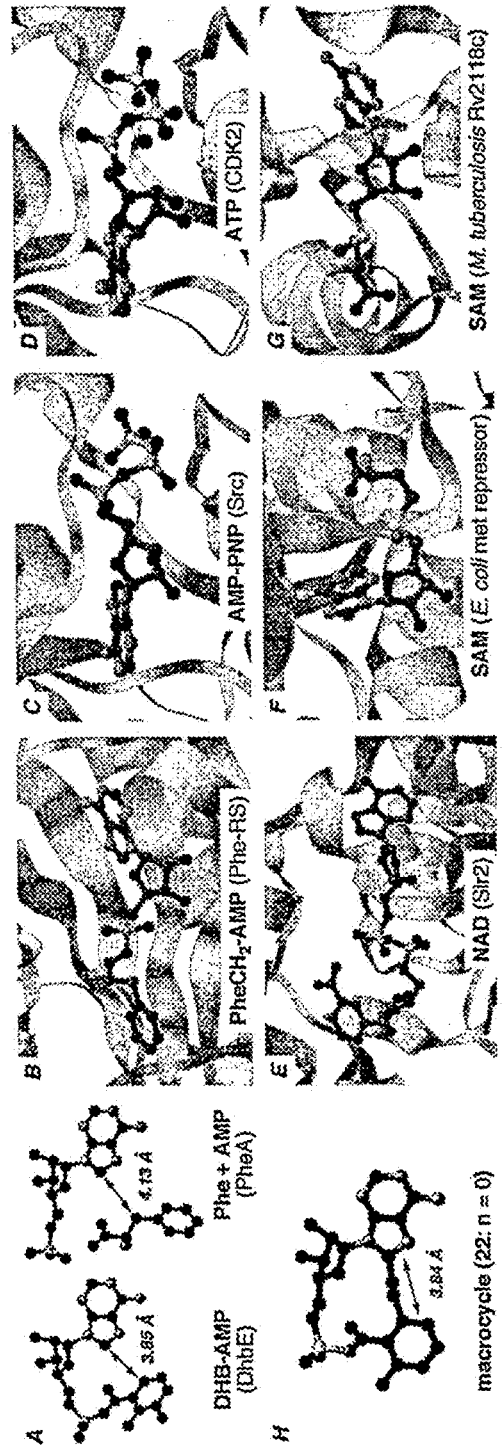
FIG. 11 shows: A. "Cisoid" pharmacophoric conformation of adenylation domain ligands DHB-AMP (DhbE) and Phe+AMP (PheA). Bound conformations of other adenosine-containing ligands viewed from outside the binding pocket: B. PheCH₂-AMP in phenylalanyl-tRNA synthetase (Phe-RS), C. AMP-PNP in Src tyrosine kinase, D. ATP in serine/threonine cyclin-dependent kinase 2 (CDK2), E. NAD in histone deacetylase Sir2, F. SAM (S-adenosyl-methionine) in *E. coli* met repressor, G. SAM in a putative *M. tuberculosis* methyl transferase. H. A macrocyclic analog of salicyl-AMS mimics the cisoid pharmacophoric conformation. (Structural analysis: 1MDB, 1B7Y, 2SRC, 1B38, 1ICI, 1CMA, 1I9G in RasMol 2.5; distance measurements and MM2 minimization in Chem3D 5.0.)

One of the most striking features of the DhbE crystal structure (May et al. "Crystal structure of DhbE, an archetype for aryl acid activating domains of modular nonribosomal peptide synthetases." *Proc. Natl. Acad. Sci. USA* 2002, 99, 12120-12125; incorporated herein by reference) is that the salicyl group and adenine ring of DHB-AMP are presented in a "cisoid" conformation about the ribosylphosphate backbone (FIGS. 6 and 11). Phenylalanine and the adenine ring of AMP are bound in a similar orientation in the structure of PheA (Conti et al. "Structural basis for the activation of phenylalanine in the non-ribosomal biosynthesis of gramicidin S." *EMBO J.* 1997, 16, 4174-4183; incorporated herein by reference). Our investigations revealed that this is a quite unusual conformation. In contrast, phenylalaninyl-AMP (PheCH$_2$-AMP) is bound in a "transoid" or extended conformation in the structure of *Thermus thermophilus* phenylalanyl-tRNA synthetase (Phe-tRS) (Reshetnikova, L.; Moor, N.; Lavrik, O.; Vassylyev, D. G. "Crystal structures of phenylalanyl-tRNA synthetase complexed with phenylalanine and a phenylalanyl-adenylate analogue." *J. Mol. Biol.* 1999, 287, 555-568; incorporated herein by reference). This enzyme catalyzes the same phenylalanine adenylation first step as PheA, but is structurally unrelated. Notably, the overall binding orientation is also distinct, with the 2'- and 3'-OH groups of the ribose ring directed down into the binding pocket. Indeed, inspection of each of the other 14 available ligand-bound aminoacyl-tRNA synthetase structures indicates that this general transoid binding conformation and orientation is maintained throughout both Class I and Class II tRNA synthetases (data not shown). Similar transoid conformations are also observed in the structures of other adenosine cofactor-dependent enzymes, including the tyrosine kinase Src (Xu, W.; Harrison, S. C.; Eck, M. J. "Three-dimensional structure of the tyrosine kinase c-Src." *Nature* 1997, 385, 595-602; incorporated herein by reference) and the serine/threonine kinase CDK2 (Brown et al. "Effects of phosphorylation of threonine 160 on cyclin-dependent kinase 2 structure and activity." *J. Biol. Chem.* 1999, 274, 8746-8756; Russo, A. A.; Jeffrey, P. D.; Patten, A. K.; Massague, J.; Pavletich, N. P. "Crystal structure of the p27Kip1 cyclin-dependent-kinase inhibitor bound to the cyclin A-Cdk2 complex." Nature 1996, 382, 325-331; each of which is incorporated herein by reference) (ATP), the NAD-dependent histone deacetylase Sir2 (Min, J.; Landry, J.; Sternglanz, R.; Xu, R.-M. "Crystal structure of a SIR2 homolog-NAD complex." *Cell* 2001, 105, 269-279; incorporated herein by reference), the *E. coli* met repressor (SAM, S-adenosyl-methionine) (He et al. "Probing met repressor-operator recognition in solution." *Nature* 1992, 359, 431-433; incorporated herein by reference) and the putative *M. tuberculosis* RNA methyltransferase Rv2118c (SAM) (Gupta et al. "Crystal structure of Rv2118c: An AdoMet-dependent methyltransferase from *Mycobacterium tuberculosis* H37Rv." *J. Mol. Biol.* 2001, 312, 381-391; incorporated herein by reference).

Thus, the cisoid pharmacophoric conformation observed in DhbE and PheA is unusual, if not unique. Our sequence alignments and structural model (FIG. 6) suggest that this conformation is also relevant to salicylate adenylation enzymes such as YbtE and MbtA. As such, salicyl-AMS analogs that favor the cisoid conformation should have high specificity for salicylate adenylation enzymes over other bacterial and human targets. This could be achieved either by macrocyclization, linking the C8 position of the adenine ring to the nearby C6"-position of the salicyl ring, or by introducing small rings or substituents along the C5'-to-salicylate chain that would make the cisoid conformation less unfavorable relative to the transoid conformation (cf. Thorpe-Ingold effect). Although these analogs may not match the pharmacophoric conformation precisely, any reduction in enthalpy of binding would be offset, to some extent, by the decreased entropic cost of binding (Searle, M. S.; Williams, D. H. "The cost of conformational order: Entropy changes in molecular associations." *J. Am. Chem. Soc.* 1992, 114, 10690-10697; Khan, A. R.; Parrish, J. C.; Fraser, M. E.; Smith, W. W.; Bartlett, P. A.; James, M. N. G. "Lowering the entropic barrier for binding conformationally flexible inhibitors to enzymes." *Biochemistry* 1998, 37, 16839-16845; each of which is incorporated herein by reference). Moreover, since the number of rotatable bonds in a molecule has been inversely correlated to oral bioavailablity (Veber, D. F.; Johnson, S. R.; Cheng, H.-Y.; Smith, B. R.; Ward, K. W.; Kopple, K. D. "Molecular properties that influence the oral bioavailability of drug candidates." *J. Med. Chem.* 2002, 45, 2615-2623; Li, J. J.; Holsworth, D. D.; Hu, L.-Y. "Molecular properties that influence the oral bioavailability of drug candidates." Chemtracts 2003, 16, 439-442; each of which is incorporated herein by reference), of which membrane permeability is a key component, these constrained analogs may also benefit from improved permeability compared to salicyl-AMS.

Macrocyclic Analogs of Salicyl-AMS

Figure 12:
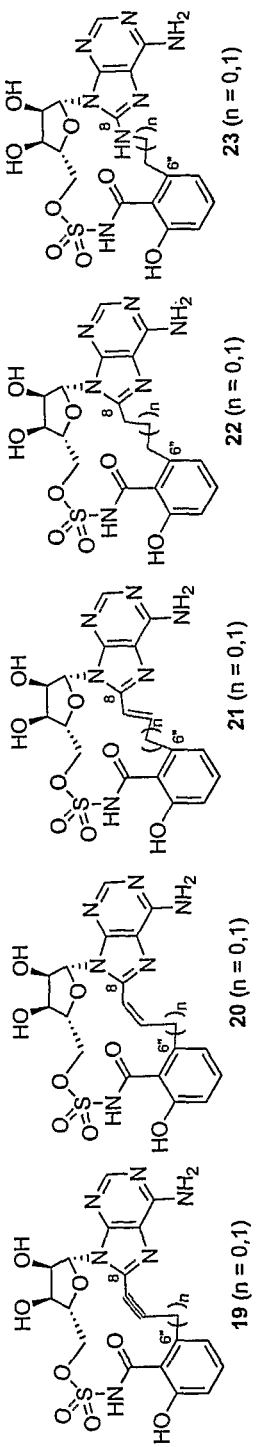
FIG. 12 shows the structures of macrocyclic analogs 19-23 designed to enforce a cisoid pharmacophoric conformation.

Our structural analysis of DhbE indicates a 3.85 Å distance between C8 of the adenine ring and the C6"-position of the acyl group. Molecular modeling suggests that a 2-3 atom linker between these positions in salicyl-AMS should enforce an appropriate overall cisoid conformation (FIG. 11H). We have designed macrocyclic analogs 19-23 with different linker geometries arising from alkyne, cis-alkene, trans-alkene, alkane, and aminoalkane functionalities (FIG. 12). Although these analogs may not match the pharmacophoric conformation precisely, this may be accommodated by plasticity in the binding pocket. Moreover, a one or two log decrease in binding affinity (from 1 nM) would be acceptable if these analogs have more favorable pharmacological properties that result in a net increase cellular activity.

Figure 13:
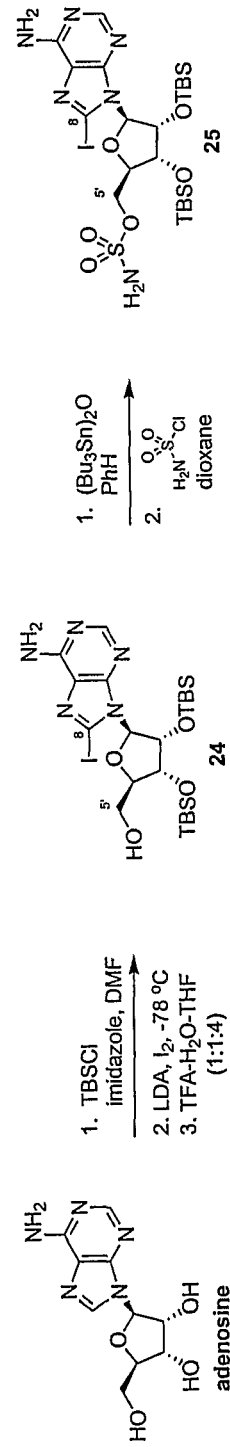
FIG. 13 is a scheme of the synthesis of the key protected 8-iodo-5'-O-sulfamoyladenosine intermediate 25.
Figure 14A:
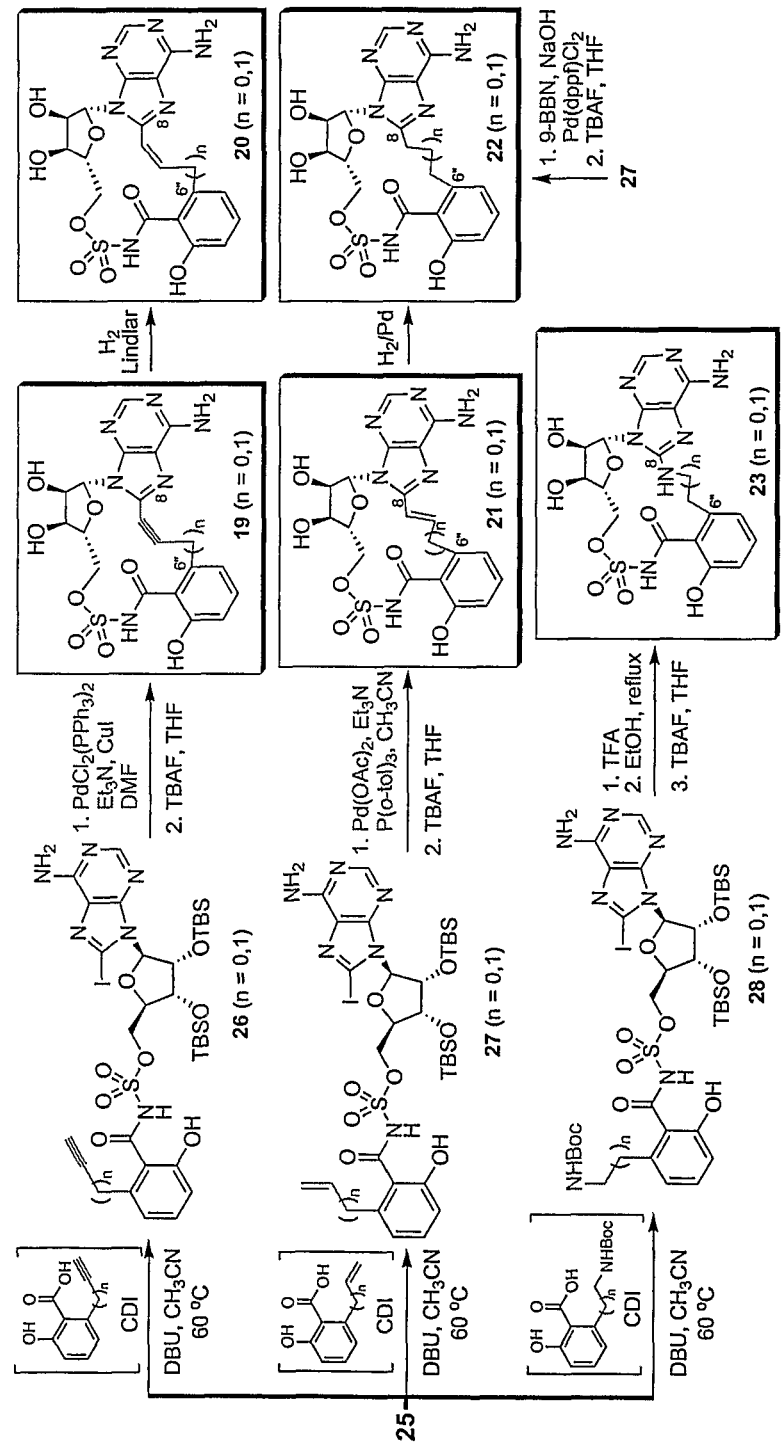
FIG. 14 shows: A. a unified synthetic route to macrocyclic analogs from key intermediate 25 using Sonogashira cross coupling (19), Heck cross coupling (21), and $S_NAr$ macrocyclization (23). Hydrogenations of 19 and 21 will provide 20 and 22. Alternatively, 22 can be made via B-alkyl Suzuki-Miyaura macrocyclization of 27. B. an alternative synthetic scheme to macrocyclic analogs with the palladium cross coupling first followed by the N-acylation step.

We will synthesize all of these macrocycles by a variation on our established synthetic route, using 8-iodoadenosine and substituted salicylates as the key building blocks (FIG. 14). Thus, adenosine will be converted to the protected 8-iodoadenosine 24, (Moriarty et al. "Palladium catalyzed C-8 allylation and vinylation of adenosine, 2'-deoxyadenosine and 2',3'-dideoxyadenosine nucleosides." *Tetrahedron Lett.* 1990, 31, 5877-5880; incorporated herein by reference) via a precedent iodination method, (Moriarty, R. M.; Epa, W. R.; Awasthi, A. K. "Palladium catalyzed C-8 allylation and vinylation of adenosine, 2'-deoxyadenosine and 2',3'-dideoxyadenosine nucleosides." Tetrahedron Lett. 1990, 31, 5877-5880; Bhardwaj, P. K.; Vasella, A. "Oligonucleosides with a nucleobase-including backbone, Part 7, syn and anti conformations of a (5',8)-ethynediyl-linked adenosine dimer." *Helv. Chim. Acta* 2002, 85, 699-711; Gunji, H.; Vasella, A. "Oligonucleosides with a nucleobase-including backbone part 3. Synthesis of acetyleno-linked adenosine dimers." *Helv. Chim. Acta* 2000, 83, 2975-2992; Gunji, H.; Vasella, A. "Oligonucleosides with a nucleobase-including backbone part 2. Synthesis and structure determination of adenosine-derived monomers." *Helv. Chim. Acta* 2000, 83, 1331-1345; each of which is incorporated herein by reference), followed by sulfamoylation as usual to form the key intermediate 25 (FIG. 13). Alkyne- and alkene-substituted salicylates will be made by Stille coupling of 6-OTf-salicylates (Furstner, A.; Dierkes, T.; Thiel, O. R.; Blanda, G. "Total synthesis of (−)-salicylihalamide." *Chem. Eur. J.* 2001, 7, 5286-5298; Snider, B. B.;

Song, F. "Total synthesis of (−)-salicylihalamide A." *Org. Lett.* 2001, 3, 1817-1820; Furstner, A.; Thiel, O. R.; Blanda, G. "Asymmetric synthesis of the fully functional macrolide core of salicylihalamide: Remote control of olefin geometry during RCM." *Org. Lett.* 2000, 2, 3731-3734; each of which is incorporated herein by reference), then coupled to 25. Macrocyclizations of the resulting alkynyl/alkenyl halides 26 and 27 will then be effected using cross-coupling reaction conditions such as Sonogashira (19) (Dai, W. M.; Wu, A. "First synthesis of a highly strained cyclodeca-1,5-diyne skeleton via intramolecular Sonogashira cross-coupling" *Tetrahedron Lett.* 2001, 42, 81-83; Dai, W.-M. "Natural product inspired design of enediyne prodrugs via rearrangement of an allylic double bond." *urr. Med. Chem.* 2003, 10, 2265-2283; each of which is incorporated herein by reference), Heck (21) (Stocks, M. J.; Harrison, R. P.; Teague, S. J. "Macrocyclic ring closures employing the intramolecular Heck reaction." *Tetrahedron Lett.* 1995, 36, 6555-6558; Geng, X.; Miller, M. L.; Lin, S.; Ojima, I. "Synthesis of novel C2-C3' N-linked macrocyclic Taxoids by means of highly regioselective Heck macrocyclization." *Org. Lett.* 2003, 5, 3733-3736; each of which is incorporated herein by reference); B-alkyl Suzuki-Miyaura (22) (Chemler, S. R.; Trauner, D.; Danishefsky, S. J. "The B-alkyl Suzuki-Miyaura cross-coupling reaction: Development, mechanistic study, and applications in natural product synthesis." *Angew. Chem. Intl. Ed.* 2001, 40, 4544-4568; incorporated herein by reference); and Stille (Queron, E.; Lett, R. "Synthetic studies on bafilomycin A1: First formation of the 16-membered macrolide via an intramolecular Stille reaction." *Tetrahedron Lett.* 2004, 45, 4539-45431; Pattenden, G.; Sinclair, D. J. "The intramolecular Stille reaction in some target natural product syntheses." *J. Organomet. Chem.* 2002, 653, 261-268; Duncton, M. A. J.; Pattenden, G. "The intramolecular Stille reaction." *J. Chem. Soc., Perkin Trans.* 1 1999, 1235-1246; each of which is incorporated herein by reference) (not shown) reactions. We will also synthesize the cis-alkene-linked analog 20 and the alkane-linked analog 22 by catalytic hydrogenation of the corresponding alkynyl analog 19 and alkenyl analog 21, respectively. The amine-linked analog 23 will be synthesized from the common intermediate 25 using $S_NAr$ macrocyclization of 28 (Zhu, "$S_NAr$-based macrocyclization via biaryl ether formation. Application in natural product synthesis." *Synlett* 1997, 133-144; incorporated herein by reference). We will also explore other disconnections, especially initial coupling of the substituted salicylates to the adenine ring of 25, followed by macrolactamization of the salicylic acid group onto the sulfamate nitrogen. We note further that, if analogs with saturated rings in the salicyl region are found to bind, this will open the door for similar replacements in these macrocyclic analogs, which would provide slightly different overall conformations for evaluation.

Conformationally Constrained Analogs of Salicyl-AMS

Figure 15:
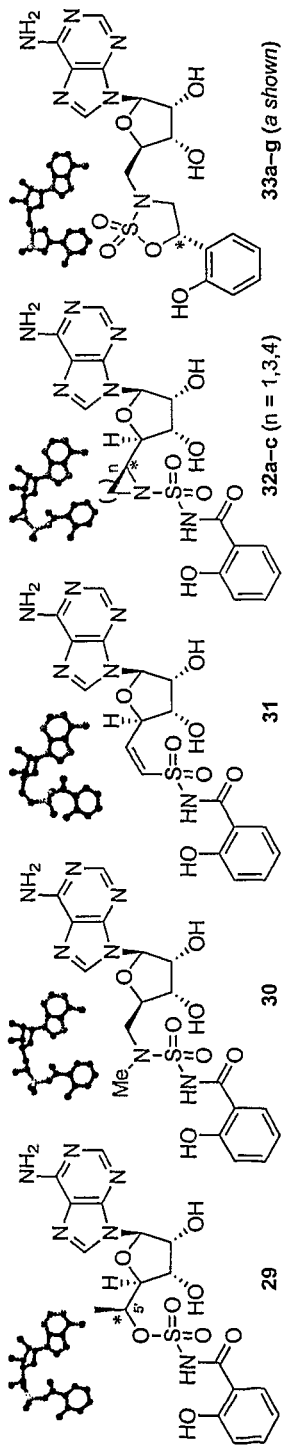
FIG. 15 depicts the structures of conformationally constrained analogs 29-33 designed to promote the cisoid conformation.

The cisoid conformation can also be promoted by introducing other conformational constraints along the C5'-to-salicylate carbonyl axis of salicyl-AMS. While these would not make the cisoid conformation favored per se, they will make it less unfavorable relative to the transoid conformation by raising the energy of the latter, in analogy to the Thorpe-Ingold effect (Keese, R.; Meyer, M. "The structural basis of the geminal-dimethyl effect." *Tetrahedron* 1993, 49, 2055-2064; incorporated herein by reference). Thus, we will synthesize a variety of analogs to exploit this effect (FIG. 15). We are particularly interested in (1) inhibitors with substituents on the C5' sidechain (29, 30), (2) inhibitors with a cis double bond (31), and (3) inhibitors with small ring constraints (32, 33).

We will synthesize both epimeric 5'-methyl-substituted analogs 29 from 5'-methyladenosine, of which both 5'-epimers are known (Kappler, F.; Vrudhula, V. M.; Hampton, A. "Isozyme-specific enzyme inhibitors. 14.5°(R)—C-[(L-homocystein-S-yl)methyl]adenosine 5'-(β,γ-imidotriphosphate), a potent inhibitor of rat methionine adenosyltransferases." *J. Med. Chem.* 1987, 30, 1599-1603; Kappler, F.; Hampton, A. "Approaches to isozyme-specific inhibitors. 17. Attachment of a selectivity-inducing substituent to a multisubstrate adduct. Implications for facilitated design of potent, isozyme-selective inhibitors." *J. Med. Chem.* 1990, 33, 2545-2551; Nelson, V.; El Khadem, H. S.; Whitten, B. K.; Sesselman, D. "Synthesis of hypoxanthine, guanine, and 6-thiopurine nucleosides of 6-deoxy-D-allofuranose." *J. Med. Chem.* 1983, 26, 1071-1074; each of which is incorporated herein by reference), by analogy to our established synthetic route for salicyl-AMS. We will also synthesize the N5'-methylsulfamide analog 30 by methylation of the known 5'-amino-5'-deoxy-2',3'-O-bis-TBS-adenosine 12 (Kotch et al. "Water-mediated association provides an ion pair receptor." *J. Am. Chem. Soc.* 2003, 125, 15140-15150; incorporated herein by reference) (FIG. 8) or the corresponding acetonide (Liu et al. "Synthesis of 5'-functionalized adenosine: Suppression of cyclonucleoside formation." *Tetrahedron Lett.* 2001, 42, 3153-3154; incorporated herein by reference), followed by sulfamoylation and salicylation as usual. Furthermore, if the homoadenosine-derived analog 10 is found to be active, we will explore additional single and double substitution patterns.

Figure 16:
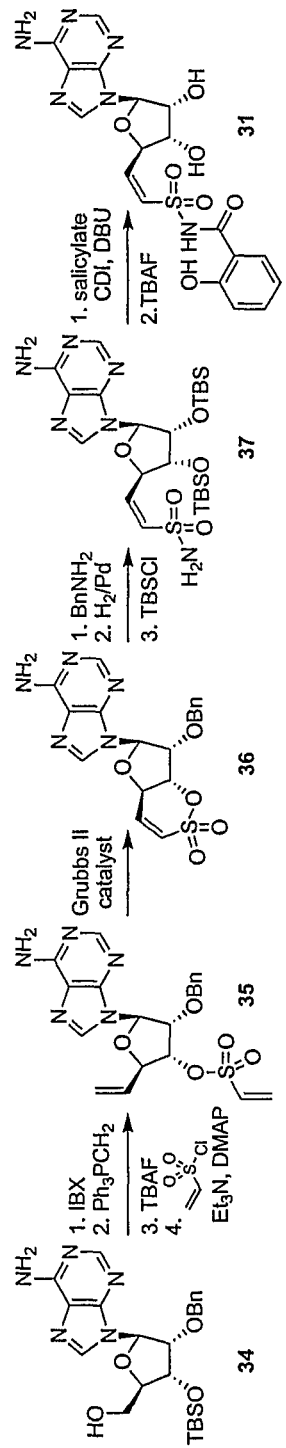
FIG. 16 shows the synthesis of cis alkene analog 31 via vinylsulfonate ring-closing metathesis.

We will synthesize the cis alkene analog 31 via precedented vinylsulfonate ring closing olefin metathesis (Karsch et al. "Synthesis of sultones by ring closing metathesis." *Synlett* 2002, 2019-2022; incorporated herein by reference) of 35 (FIG. 16). The commercially available 3',5'-disiloxane 15 (FIG. 9) will be converted to the orthogonally protected intermediate 34 by 2'-benzylation followed by selective silyl protecting group manipulations (Zhu et al. "Facile and highly selective 5'-desilylation of multi-silylated nucleosides." *J. Chem. Soc., Perkin Trans.* 1 2000, 2305-2306; incorporated herein by reference). Precedented oxidation and Wittig olefination (Lerner et al. "Bisubstrate inhibitors for the enzyme catechol-O-methyltransferase (COMT): Influence of inhibitor preorganization and linker length between the two substrate moieties on binding affinity." *Org. Biomol. Chem.* 2003, 1, 42-49; incorporated herein by reference) at the 5'-position will be followed by 3'-desilylation and sulfonylation to afford 35. After conversion to the cyclic sulfonate 36, aminolysis (Schetty, G. "Naphthalene derivatives. II. The action of acyl chlorides on naphthosultone according to Friedel-Crafts." *Helv. Chim. Acta* 1947, 30, 1650-1660; incorporated herein by reference), protecting group manipulations, salicylation, and deprotection as usual will provide 31. We recognize that the vinyl sulfonamide moiety is potentially reactive. However, if this functional group proves problematic, it can be replaced by introduction of bioisosteric cyclopropanes across the double bond.

Figure 17:
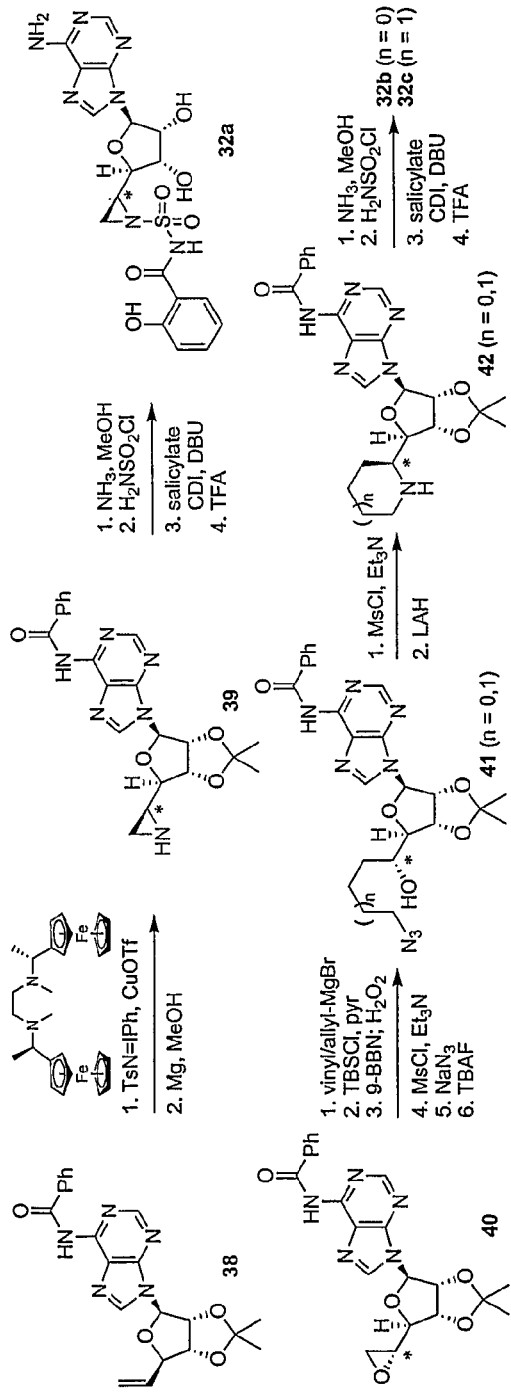
FIG. 17 shows syntheses of aziridine analog 32a, pyrrolidine analog 32b, and piperidine analog 32c.

We will synthesize both epimeric aziridine sulfamide analogs 32a from the known protected alkene 38 (Wnuk, S. F.; Robins, M. J. "Nucleic acid related compounds. 63. Synthesis of 5'-deoxy-5'-methyleneadenosine and related Wittig-extended nucleosides." *Can. J. Chem.* 1991, 69, 334-338; incorporated herein by reference) using catalytic stereoselective aziridination (FIG. 17) (Mueller, P.; Fruit, C. "Enantioselective catalytic aziridinations and asymmetric nitrene insertions into CH bonds." *Chem. Rev.* 2003, 103, 2905-2919; incorporated herein by reference). Subsequent sulfamoylation, salicylation, and deprotection steps will provide 32a. Alternatively, the aziridines 39 can be synthesized from the corresponding hydroxyazide (cf. 41) via mesylation and azide reduction with in situ cyclization (Sayyed, I. A.; Sudalai, A. "Asymmetric synthesis of L-DOPA and (R)-selegiline via, OsO$_4$-catalyzed asymmetric dihydroxylation." *Tetrahedron: Asym.* 2004, 15, 3111-3116; incorporated herein by reference) (not shown). The pyrrolidine and piperidine analogs 32b and 32c will be synthesized from the known epoxide 40 (Matsuda, A.; Ueda, T. "Nucleosides and nucleotides. LXVI. Synthesis of 8,6'-cyclo-6'-deoxyhexofuranosyladenines: Adeno sines fixed in an anti-conformation." *Chem. Pharm. Bull.* 1986, 34, 1573-1578; incorporated herein by reference) by conversion to hydroxyazides 41, mesylation, and azide reduction with in situ S$_N$2 cyclization (Chandra, K. L.; Chandrasekhar, M.; Singh, V. K. "Total synthesis of (−)- and (+)-lentiginosine." *J. Org. Chem.* 2002, 67, 4630-4633; incorporated herein by reference). Alternatively, the hydroxyazide 41 can be synthesized from the corresponding aldehyde (Vrudhula et al. "Approaches to isozyme-specific inhibitors. 16. A novel methyl-05' covalent adduct of L-ethionine and β,γ-imido-ATP as a potent multisubstrate inhibitor of rat methionine adenosyltransferases." *J. Med. Chem.* 1989, 32, 885-890; incorporated herein by reference) via stereoselective alkylzinc additions (Walsh, P. J. "Titanium-catalyzed enantioselective additions of alkyl groups to aldehydes: Mechanistic studies and new concepts in asymmetric catalysis." *Accts. Chem. Res.* 2003, 36, 739-749; Lutz, C.; Knochel, P. "Highly enantioselective addition of mixed diorganozincs to aldehydes." *J. Org. Chem.* 1997, 62, 7895-7898; each of which is incorporated herein by reference). The cyclic amines 42 will be converted to 32b and 32c via the same process used for 32a.

Figure 18:
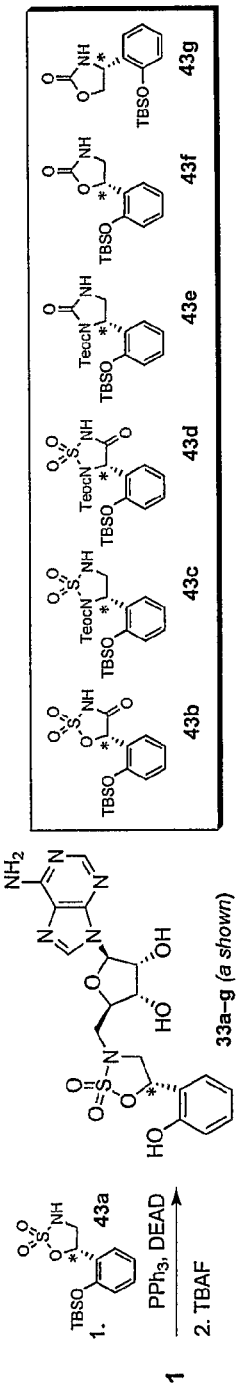
FIG. 18 shows syntheses of cyclic sulfamidate and related analogs 33a-g by Mitsunobu substitution of the 5'-OH.
Figure 19:
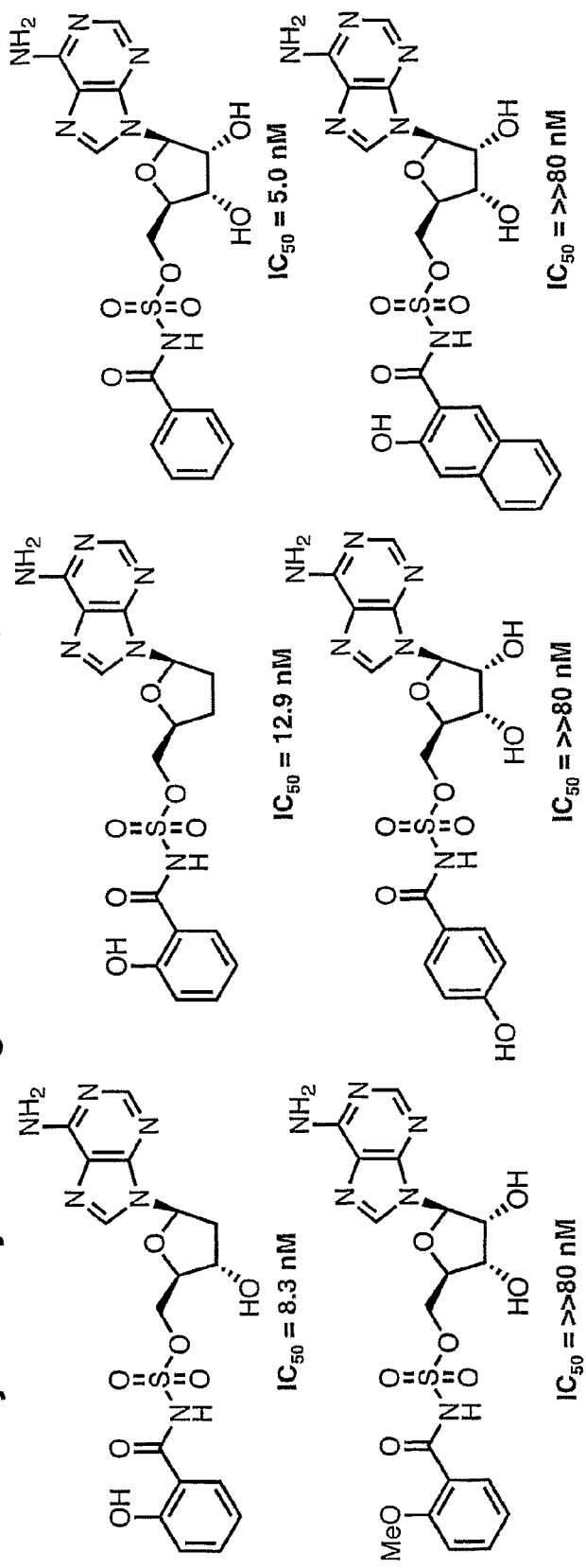
FIG. 19 lists the inhibitory activity of second generation salicyl-AMS inhibitors in the flash plate assay.
Figure 20:
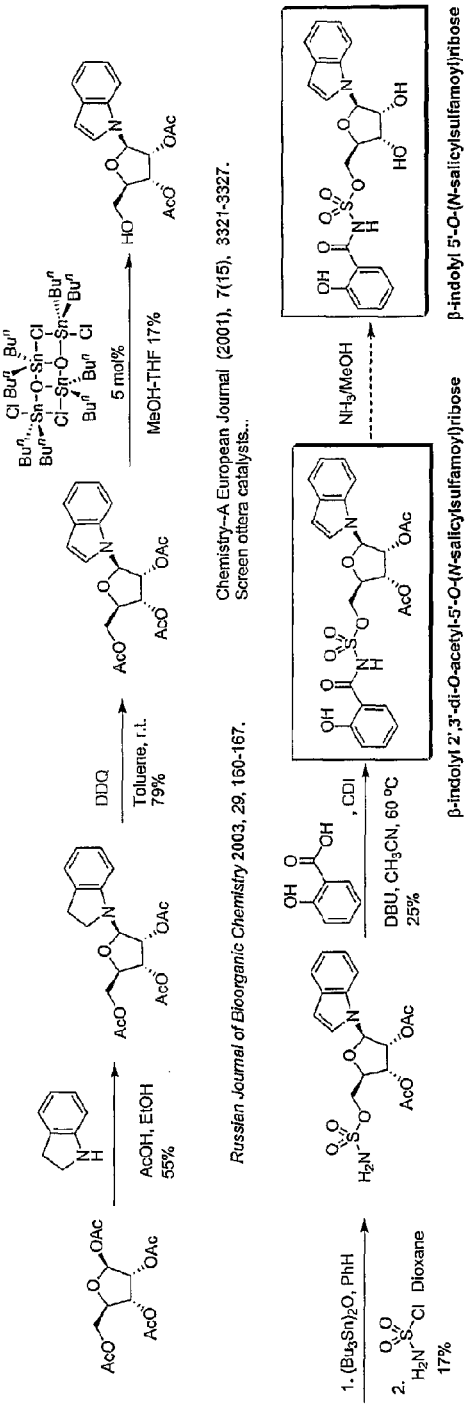
FIG. 20 shows two synthetic routes to an adenine-replaced analog, β-indolyl 5'-O—(N-salicylsulfamoyl)ribose (salicycl-IRMS).
Figure 20:
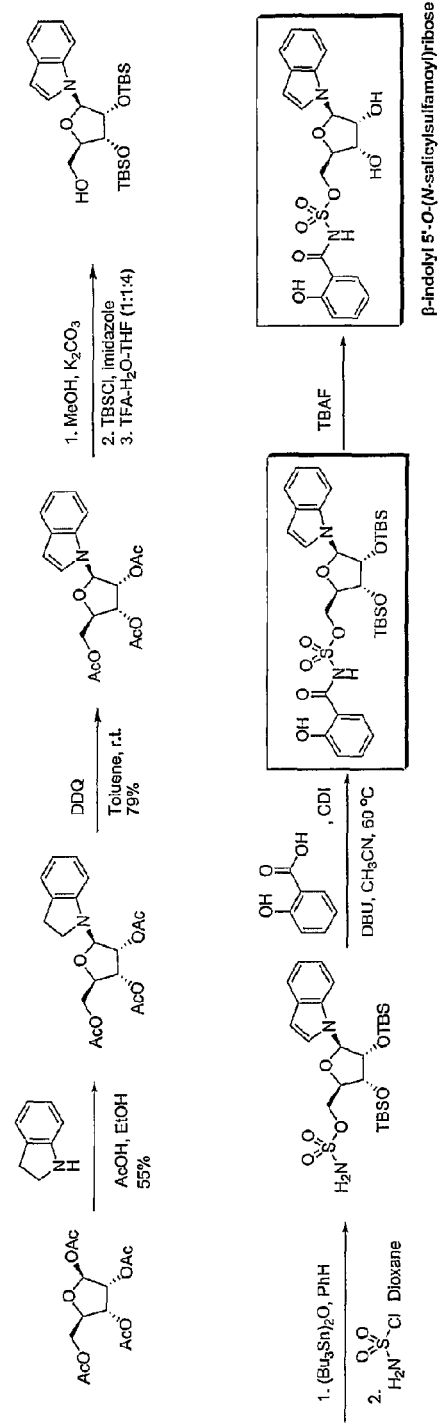
Figure 21:
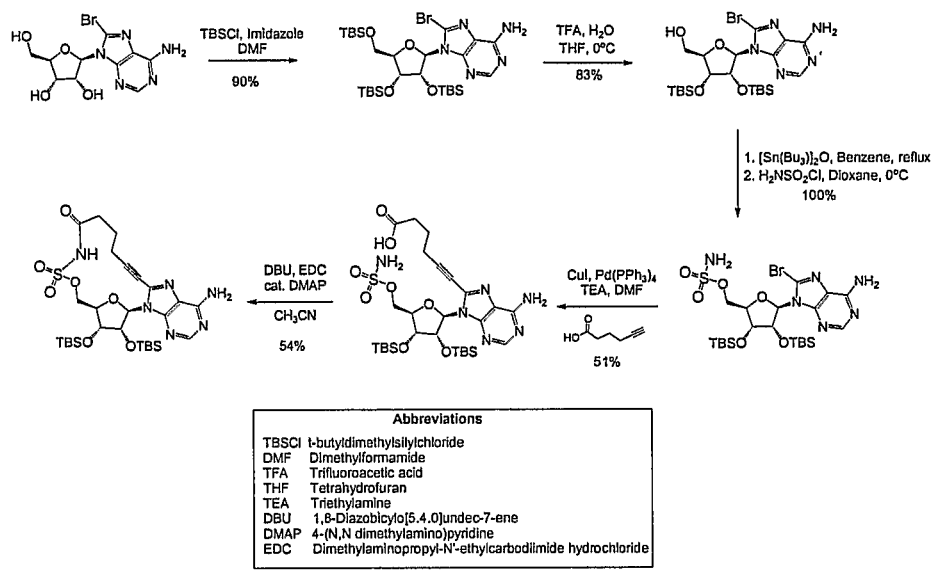
FIG. 21 depicts the synthesis of hexynyl sulfonamide adenosine.
Figure 22:
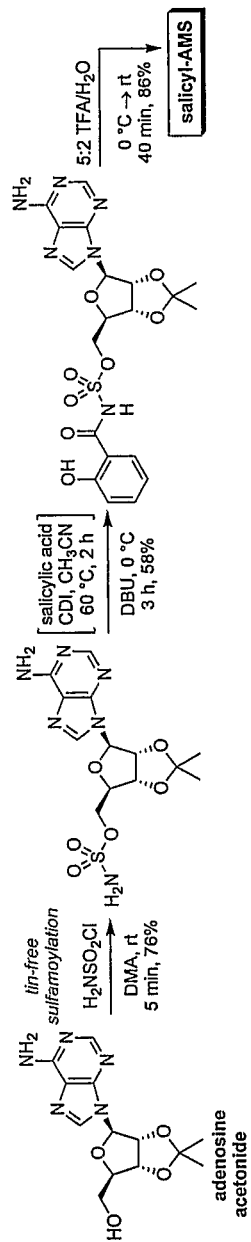
FIG. 22 is a scheme depicting an exemplary three-step synthesis of salicyl-AMS from a commercially available starting material, adenosine acetonide. This synthetic route does not require the use of toxic tin reagents.
Figure 23:
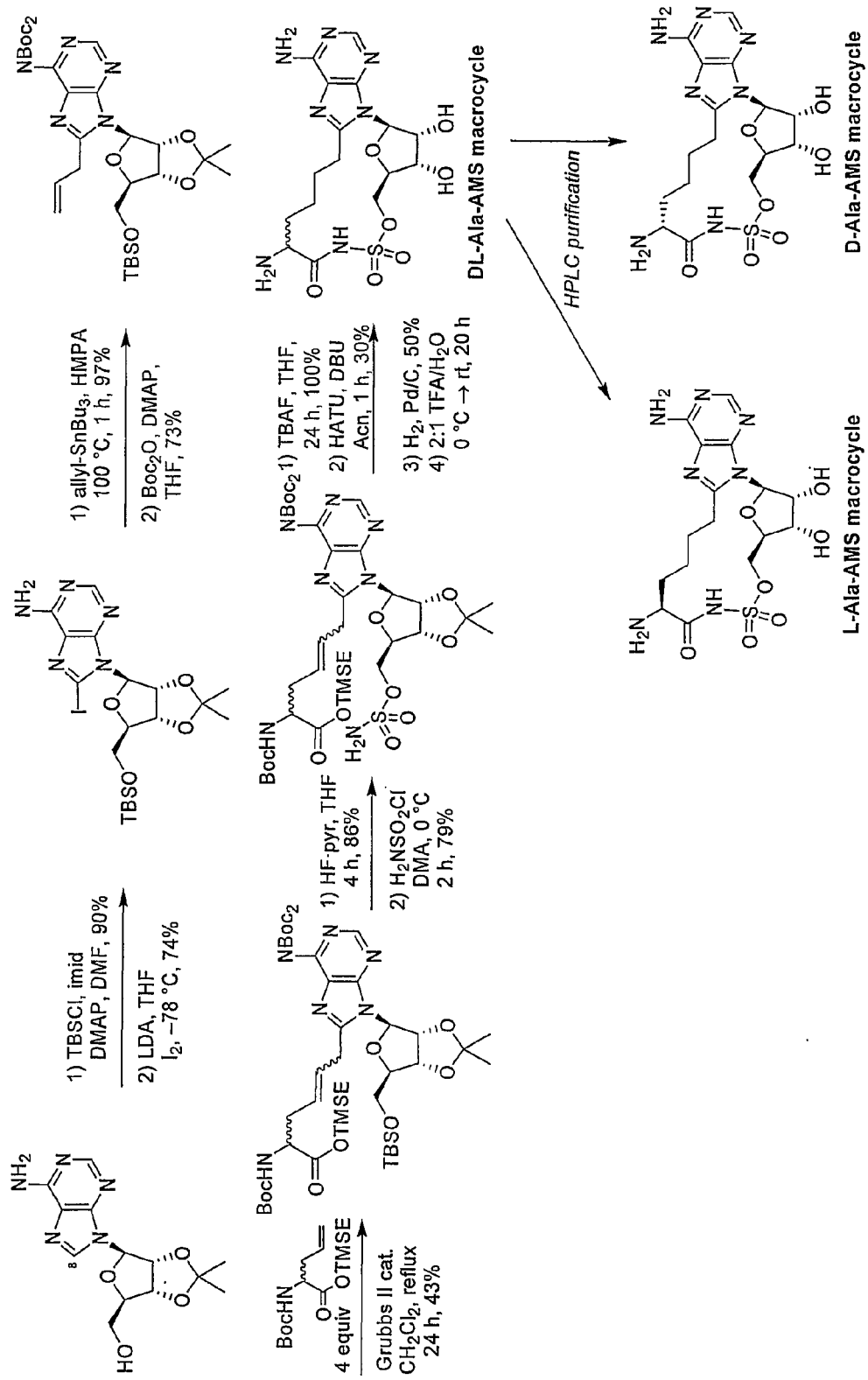
FIG. 23 shows the an exemplary synthesis of macrocyclic analogs. In particular, the synthesis of L-Ala-AMS macrocycle and D-Ala-AMS macrocycle is shown.

We will synthesize the cyclic sulfamidate analogs 33a-g using Mitsunobu alkylations (Posakony et al. "New routes to N-alkylated cyclic sulfamidates." *J. Org. Chem.* 2002, 67, 5164-5169) (FIG. 18) of 2',3'-O-bis-TBS-adenosine 1 (FIG. 5). The requisite cyclic sulfamate 43a will be synthesized from the corresponding benzaldehyde by asymmetric addition of cyanide (Brunel, J.-M.; Holmes, I. P. "Chemically catalyzed asymmetric cyanohydrin syntheses." *Angew. Chem. Intl. Ed.* 2004, 43, 2752-2778; incorporated herein by reference) followed by nitrile reduction and precedented two-step sulfonylation (Melendez, R. E.; Lubell, W. D. "Synthesis and reactivity of cyclic sulfamidites and sulfamidates." *Tetrahedron* 2003, 59, 2581-2616; incorporated herein by reference). Alternatively, regioselective asymmetric aminohydroxylation of the corresponding styrene would also provide the required aminoalcohol intermediate (Nesterenko, V.; Byers, J. T.; Hergenrother, P. J. "The use of pH to influence regio- and chemoselectivity in the asymmetric aminohydroxylation of styrenes." *Org. Lett.* 2003, 5, 281-284; incorporated herein by reference). Additional analogs 33b-g will be synthesized analogously using 43b-g. We will synthesize oxathiazolidinone 43b (Dovlatyan, V. V.; Mirzoyan, R. S. "Synthesis of 2,2-dioxo-4-chloro-1,2,3-oxathiazole-A3 and its 5,5-dimethyl derivative and some of their transformations." *Armyan. Khim. Z.* 1975, 28, 311-316; incorporated herein by reference), thiadiazolidines 43c-d (Nicolaou et al. "A new method for the synthesis of nonsymmetrical sulfamides using Burgess-type reagents." *Angew. Chem. Intl. Ed.* 2002, 41, 3866-3870; incorporated herein by reference), imidazolidinone 43e (Ambroise, L.; Dumez, E.; Szeki, A.; Jackson, R. F. W. "Stereocontrolled synthesis of anti-α-hydroxy-β-amino and anti-α,β-diamino acid derivatives by epoxidation of 1-arylthio-1-nitroalkenes." *Synthesis* 2002, 2296-2308; incorporated herein by reference), and oxazolidinones 43f-g (Schnur, R. C.; Morville, M. "Improved glucose tolerance in rats treated with oxazolidinediones." *J. Med. Chem.* 1986, 29, 770-778; incorporated herein by reference) according to the literature.

Evaluation of Inhibitors in Biochemical and Cellular Assays to Assess Pharmacological Factors Influencing Cellular Activity and to Identify Analogs for Further Study Our results with salicyl-AMS suggest that its cellular activity is restricted by one or more of the following pharmacological factors: (1) permeability, (2) efflux, (3) specificity, (4) stability. Thus, we will test the salicyl-AMS lead compound in a panel of biochemical and cellular assays to assess the influence of these factors directly. The results will help to guide our early efforts to design salicyl-AMS analogs. Subsequently, we will use a multi-tiered approach to evaluate these analogs by first testing for biochemical inhibition of YbtE and MbtA. We will then test active inhibitors (IC$_{50}$≈100 nM or better) in cellular assays against *Y. pestis* and *M. tuberculosis* growth, yersiniabactin and mycobactin siderophore biosynthesis, and [$^{55}$Fe]-iron uptake. Compounds having cellular activity (IC$_{50}$≈50 μM or better) will then be advanced to the additional panel of assays for pharmacological factors to complete the SAR profile for comparison to salicyl-AMS.

Evaluation of Salicyl-AMS Analogs for Biochemical Enzyme Inhibition and Cellular Activity We will first test the analogs for biochemical inhibition of YbtE and MbtA using the ATP-[$^{32}$P]PPi exchange assay that we have used previously to evaluate salicyl-AMS. Except for designed prodrugs, only compounds that inhibit at least one of these enzymes will be advanced to cellular assays. We will test these compounds for inhibition of *Y. pestis* and *M. tuberculosis* growth in iron-deficient and iron-sufficient media, for inhibition of siderophore biosynthesis, and for inhibition of iron uptake. Importantly, even inhibitors with no detectable antibacterial activity will still be tested in the latter two assays, since they may have insufficient penetration or potency to inhibit growth, but still cause a detectable reduction in siderophore biosynthesis and/or iron uptake. Such inhibitors could then be improved by additional structural alternations.

ATP-[$^{32}$P]PPi Exchange Assays.

The first step (adenylation) of salicyl-ArCP formation is classically measured by the salicylate-dependent ATP-[$^{32}$P] PPi exchange assay, which exploits the reversibility of adenylate formation in the presence of excess PPi (Fersht, A. *Enzyme Structure and Mechanism;* 2 nd ed.; W.H. Freeman. New York, 1985; Santi, D. V.; Webster, R. W., Jr.; Cleland, W. W. "Kinetics of aminoacyl-tRNA synthetases catalyzed ATP-PPi exchange." *Methods Enzymol.* 1974, 29, 620-627; Eigner, E. A.; Loftfield, R. B. "Kinetic techniques for the investigation of amino acid: tRNA ligases (aminoacyl-tRNA synthetases, amino acid activating enzymes)." *Methods Enzymol.* 1974, 29, 601-619; Midelfort, C. F.; Mehler, A. H. "Applications of kinetic methods to aminoacyl-tRNA synthetases." *Methods Enzymol.* 1974, 29, 627-642; each of which is incorporated herein by reference). In the assay, ATP, [$^{32}$P]PPi, salicylate, and YbtE or MbtA are incubated, and [$^{32}$P]ATP generation kinetics are measured by liquid scintillation counting (LSC). The assay permits calculation of K$_m$ and k$_{cat}$ values for substrates, derivation of IC$_{50}$ and K$_i$ values for inhibitors, and characterization of inhibitors (e.g. as reversible, irreversible, non/competitive, tight-binding, etc.), and will allow us to conduct quantitative assessment of the ability of each salicyl-AMS analog to inhibit YbtE and MbtA. These exchange assays will be conducted as reported by Dr. Quadri (Quadri, L. E. N.; Keating, T. A.; Patel, H. M.; Walsh, C. T. "Assembly of the *Pseudomonas aeruginosa* nonribosomal peptide siderophore pyochelin: In vitro reconstitution of aryl-4,2-bisthiazoline synthetase activity from PchD, PchE, and PchF." *Biochemistry* 1999, 38, 14941-14954; Weinreb, P. H.; Quadri, L. E. N.; Walsh, C. T.; Zuber, P. "Stoichiometry and specificity of in vitro phosphopantetheinylation and aminoacylation of the valine-activating module of surfactin synthetase." *Biochemistry* 1998, 37, 1575-158; each of which is incorporated herein by reference) and others (Gehring, A. M.; Mori, I.; Perry, R. D.; Walsh, C. T. "The nonribosomal peptide synthetase HMWP2 forms a thiazoline ring during biogenesis of yersiniabactin, an iron-chelating virulence factor of *Yersinia pestis*." *Biochemistry* 1998, 37, 11637-11650; Gehring et al. "Iron acquisition in plague: Modular logic in enzymic biogenesis of yersiniabactin by *Yersinia pestis*." *Chem. Biol.* 1998, 5, 573-586; Suo et al. "Tandem heterocyclization activity of the multidomain 230 kDa HMWP2 subunit of *Yersinia pestis* yersiniabactin synthetase: Interaction of the 1-1382 and 1383-2035 fragments." *Biochemistry* 1999, 38, 14023-14035; each of which is incorporated herein by reference). Inhibitors will be defined as those that reduce activity by a meaningful statistically significant percentage relative to DMSO-containing control. $IC_{50}$ values will be determined.

Bacterial Growth Inhibition Assays.

These assays will investigate the ability of the analogs to inhibit the growth (measured as optical density of the cultures) of *Y. pestis* and *M. tuberculosis* in both iron-limiting and iron-rich liquid culture media. Siderophore production is required for efficient growth in iron-limiting media but not in iron-rich media. Thus, analogs that inhibit bacterial growth in both media may act by mechanisms other than solely siderophore synthesis inhibition. These growth inhibition assays will provide a quantitative measure of the antimicrobial properties of each analog in each of the two media.

*Y. pestis* KIIV16-2082.1+ ($Yfe^-Yfu^-$) (Gong et al. "Characterization of the *Yersinia pestis* Yfu ABC inorganic iron transport system." *Infect. Immun.* 2001, 69, 2829-2837; incorporated herein by reference) will be used in the *Y. pestis* assay. The strain is deficient for two low-affinity iron transport systems and is therefore more sensitive to yersiniabactin synthesis inhibition in iron-deficient medium *Y. pestis* will be grown in extremely deferrated medium [chelex-100 deferrated PMH medium (PMH-D) further deferrated with 0.5 mM $Na_2CO_3$, 0.01 mM $MgCl_2$, and 4 mM $CaCl_2$ (PMH-DS)] for iron-deficient conditions, and in $FeCl_3$ (10 μM) supplemented PMH-DS (PMH-F medium) for iron-sufficient conditions (Fetherston, J. D.; Lillard, J. W., Jr.; Perry, R. D. "Analysis of the pesticin receptor from *Yersinia pestis*: Role in iron-deficient growth and possible regulation by its siderophore." *J. Bacteriol.* 1995, 177, 1824-1833; Bearden, S. W.; Fetherston, J. D.; Perry, R. D. "Genetic organization of the Yersiniabactin biosynthetic region and construction of avirulent mutants in *Yersinia pestis." Infect. Immun.* 1997, 65, 1659-1668; each of which is incorporated herein by reference). Yersiniabactin production is induced in PMH-D and allows KIM6-2082.1+ to grow in all PMH media. Loss of yersiniabactin production produces a very drastic growth reduction only in PMH-DS. Thus, *Y. pestis* will be adapted by growing in PMH-D, harvested, and resuspended ($OD_{620}$ 0.01) in PMH-DS. The suspension will be loaded (100 μL/well) into 96-well plates containing PMH-DS (100 μL/well) with test compounds at various concentrations or DMSO controls. For testing in iron-sufficient medium, *Y. pestis* will be adapted in PMH-F, harvested, resuspended in PMH-F, and loaded into wells containing PMH-F (100 L) and test compounds or DMSO as above. *Y. pestis* KIM6-2082.1 ($Ybt^-Yfe^-Yfu^-$) (Gong, S.; Bearden, S. W.; Geoffroy, V. A.; Fetherston, J. D.; Perry, R. D. "Characterization of the *Yersinia pestis* Yfu ABC inorganic iron transport system." *Infect. Immun.* 2001, 69, 2829-2837; incorporated herein by reference) will also be loaded into DMSO-treated wells as positive controls to provide a reference for yersiniabactin-deficient growth.

Wild-type *M. tuberculosis* H37Rv will be grown in GAST low-iron medium (De Voss et al. "The salicylate-derived mycobactin siderophores of *Mycobacterium tuberculosis* are essential for growth in macrophages." *Proc. Natl. Acad. Sci. U.S.A.* 2000, 97, 1252-1257; incorporated herein by reference) further deferrated with chelex-100 (GAST-D) for iron-deficient conditions, and in $FeCl_3$ (5 μM) supplemented GAST-D (GAST-F) for iron-sufficient conditions. *M. tuberculosis* wt grows well in both media, while an $mbtB^-$ strain displays a significant growth reduction in GAST and a very drastic growth reduction in GAST-D (De Voss et al. "The salicylate-derived mycobactin siderophores of *Mycobacterium tuberculosis* are essential for growth in macrophages." *Proc. Natl. Acad. Sci. U.S.A.* 2000, 97, 1252-1257; incorporated herein by reference). *M. tuberculosis* wt will be adapted in GAST and GAST-F before being used in assays with iron-deficient and iron-sufficient media, respectively. Adapted cells will be harvested, resuspended ($OD_{620}$ 0.05) in assay medium, and loaded (100 μL/well) in wells with the respective media (100 μL/well) and test compounds or DMSO as above. The $mbtB^-$ strain will be loaded into DMSO-treated wells to provide a reference for mycobactin-deficient growth.

The $OD_{620}$ values of the cultures will be measured with a plate reader before and after plate incubation (24 h, 37° C., 220 rpm for *Y. pestis;* 10 days, 37° C. for *M. tuberculosis*). Inhibitors will be defined as those that reduce $OD_{620}$ by a meaningful statistically significant value below that of the DMSO-containing controls. $IC_{50}$ values will be determined.

Siderophore Biosynthesis Inhibition Assays.

This assay will allow us to detect and quantify the ability of the compounds to inhibit production of the siderophores yersiniabactin and mycobactin in *Y. pestis* and *M. tuberculosis*, respectively, growing in iron-deficient media. Detection of the yersiniabactin siderophore in culture supernatant will be conducted using a sensitive bioassay (Fetherston, J. D.; Lillard, J. W., Jr.; Perry, R. D. "Analysis of the pesticin receptor from *Yersinia pestis*: Role in iron-deficient growth and possible regulation by its siderophore." *J. Bacteriol.* 1995, 177, 1824-1833; Gehring et al. "Iron acquisition in plague: Modular logic in enzymic biogenesis of yersiniabactin by *Yersinia pestis." Chem. Biol.* 1998, 5, 573-586; each of which is incorporated herein by referenc). The assay exploits the ability of yersiniabactin-containing supernatants to promote the growth of a yersiniabactin-deficient strain in iron-limiting media. Growth promotion is proportional to the concentration of yersiniabactin in the sample tested. Growth promotion obtained for samples from compound-treated cultures is then compared to that obtained with samples from controls treated with DMSO to permit relative quantification of yersiniabactin concentration in the samples. The results will be confirmed by HPLC analysis as reported (Miller et al. "Yersiniabactin synthetase: A four-protein assembly line producing the nonribosomal peptide/polyketide hybrid siderophore of *Yersinia pestis." Chem. Biol.* 2002, 9, 333-344; incorporated herein by reference). For these assays, *Y. pestis* KIM6+ (Sikkema, D. J.; Brubaker, R. R. "Resistance to pesticin, storage of iron, and invasion of HeLa cells by *Yersiniae." Infect. Immun.* 1987, 55, 572-578; incorporated herein by reference) will be grown in PMH-D in the presence of compounds at various concentrations or DMSO controls. Yersiniabactin production is induced in this medium. However, inhibition of yersiniabactin production does not cause a dramatic growth reduction because of the residual iron in PMH-D. Aliquots of filter-sterilized culture supernatants (taken at $OD_{620}$ 0.4) will be loaded into wells made in PMH-DS agar plates (Fetherston, J. D.; Lillard, J. W., Jr.; Perry, R. D. "Analysis of the pesticin receptor from *Yersinia pestis*: Role in iron-deficient growth and possible regulation by its siderophore." *J. Bacteriol.* 1995, 177, 1824-1833; Gehring et al. "Iron acquisition in plague: Modular logic in enzymic biogenesis of yersiniabactin by *Yersinia pestis*." *Chem. Biol.* 1998, 5, 573-586; each of which is incorporated herein by reference) overlaid with *Y. pestis* KIM6-2082.1 (Ybt⁻Yfe⁻Yfu⁻) grown in PMH-D. *Y. pestis* KIM6-2082.1 is unable to produce yersiniabactin but can utilize exogenous siderophore. The strain will grow around the wells only if the loaded supernatant contains yersiniabactin. The growth halo is proportional to the yersiniabactin concentration in the well. Additional wells will be loaded with aliquots of PMH-D or PMH-D serially-diluted filter-sterilized supernatants of *Y. pestis* KIM6+grown without the compounds or DMSO. These aliquots will be supplemented with the compounds at various concentrations or DMSO before well loading. These wells will provide a reference to allow relative quantitation of yersiniabactin in the tested supernatants. These wells will also reveal potential effects that the test compounds might have on the indicator strain (KIM6-2082.1). Plates will be incubated (37° C., 24 h) before growth assessment.

For *M. tuberculosis*, mycobactin production will be quantified using a radiometric assay. This assays relies of the fact that [$^{14}$C]-salicylate supplemented into the media is incorporated selectively in mycobactins with a 1:1 stoichiometry. The radiolabeled mycobactins are then extracted and quantified by radiometric TLC analysis. Mycobactin production by *M. tuberculosis* H37Rv growing in GAST supplemented with [$^{14}$C]-salicylate in the presence of compounds at various concentrations or DMSO controls will be measured by quantitative radiometric TLC analysis as reported (De Voss, J. J.; Rutter, K.; Schroeder, B. G.; Su, H.; Zhu, Y.; Barry, C. E. "The salicylate-derived mycobactin siderophores of *Mycobacterium tuberculosis* are essential for growth in macrophages." *Proc. Natl. Acad. Sci. U.S.A.* 2000, 97, 1252-1257; incorporated herein by reference). GAST induces mycobactin production, and inability to produce mycobactin results in a moderate growth reduction. Amounts analyzed will be corrected for the $OD_{620}$ of the cultures. Mycobactin and yersiniabactin production inhibitors will be defined as those that reduce production by a meaningful statistically significant percentage relative to DMSO-containing control. $IC_{50}$ values will be determined.

Iron Uptake Inhibition Assay.

This assay will allow us to monitor the capacity of each compound to inhibit uptake of iron in *Y. pestis* and *M. tuberculosis*. The assay measures the accumulation of $^{55}$Fe into bacterial cells over time. Cell-associated $^{55}$Fe is measured by LSC. Iron uptake in *Y. pestis* KIM6-2082.1+(Yfe⁻Yfu⁻) and *M. tuberculosis* H37Rv will be measured as reported (Olakanmi et al. "Gallium disrupts iron metabolism of mycobacteria residing within human macrophages." *Infect. Immun.* 2000, 68, 5619-5627; incorporated herein by reference). *Y. pestis* and *M. tuberculosis* will be grown in PMH-D and GAST, respectively, containing DMSO or test compounds added at various concentrations. Growing cultures ($OD_{620}$ 0.2) will be pulsed with $^{55}FeCl_3$ and samples will be taken at regular intervals during 40 min for *Y. pestis* and 8 h for *M. tuberculosis*. Cell-associated $^{55}$Fe will be measured by LSC for each sample. Counts will be corrected for sample $OD_{620}$. Parallel experiments with *Y. pestis* KIM6-2082.1 (Ybt⁻Yfe⁻Yfu⁻) and *M. tuberculosis* mbtB⁻ will be done to determine uptake without siderophores for reference. Inhibitors will be defined as those that reduce uptake by a meaningful statistically significant percentage relative to DMSO treated controls. $IC_{50}$ values will be determined.

Evaluation of Salicyl-AMS and Analogs for Pharmacological Factors in Biochemical and Cellular Assays We hypothesize that the difference between the biochemical and cellular potencies of salicyl-AMS most likely arises from one or a combination of the following factors: poor cell permeability, high inhibitor efflux, poor inhibitor specificity, poor inhibitor stability. Consequently, we will conduct experiments to assess the kinetics of intracellular accumulation of compound, and the effect of efflux blockers upon it. We will also investigate compound specificity by assessing the binding of the compounds to cellular components. Lastly, we will test compound stability in the culture media and bacterial cells and lysates. We will first carry out these experiments using salicyl-AMS. Subsequently, analogs will be evaluated further with these assays.

Compound Accumulation Experiments.

Although parallel artificial membrane permeation assays (PAMPA) have been developed to predict passive diffusion rates into mammalian cells (Kansy, M.; Senner, F.; Gubernator, K. "Physicochemical high throughput screening: Parallel artificial membrane permeation assay in the description of passive absorption processes." *J. Med. Chem.* 1998, 41, 1007-1010; incorporated herein by reference), these assays are not applicable to bacteria, since the latter have radically different membrane lipid compositions (Hancock, "The bacterial outer membrane as a drug barrier." *Trends Microbiol.* 1997, 5, 37-42; Brennan et al. "The envelope of mycobacteria." *Ann. Rev. Biochem.* 1995, 64, 29-63; each of which is incorporated herein by reference). Thus, we will use cell-based assays to assess compound accumulation, which is influenced by both permeability and efflux. These two effects can then be differentiated by the addition of known efflux inhibitors.

We will measure compound accumulation in *Y. pestis* using methods developed to assay antibiotic accumulation in other Gram-negative bacteria. These include the accumulation of tetracycline, chloramphenicol, and norfloxacin in *Pseudomonas aeruginosa*, accumulation of ciprofloxacin in *Salmonella enterica* serovar typhimurium, and accumulation of norfloxacin in *Escherichia coli* (Giraud, E.; Cloeckaert, A.; Kerboeuf, D.; Chaslus-Dancla, E. "Evidence for active efflux as the primary mechanism of resistance to ciprofloxacin in *Salmonella enterica* serovar typhimurium." *Antimicrob. Agents Chemother.* 2000, 44, 1223-1228; Li, X. Z.; Livermore, D. M.; Nikaido, H. "Role of efflux pump(s) in intrinsic resistance of *Pseudomonas aeruginosa*: Resistance to tetracycline, chloramphenicol, and norfloxacin." *Antimicrob. Agents Chemother.* 1994, 38, 1732-1741; Tavio, M. M.; Vila, J.; Ruiz, J.; Martin-Sanchez, A. M.; Jimenez de Anta, M. T. "Mechanisms involved in the development of resistance to fluoroquinolones in *Escherichia coli* isolates." *J. Antimicrob. Chemother.* 1999, 44, 735-742; each of which is incorporated herein by reference). To measure compound accumulation in *M. tuberculosis* cells, we will use methodologies previously applied to other antibiotics in *Mycobacterium* spp. These include the accumulation of pyrazinamide in *M. tuberculosis* and *M. bovis* BCG, accumulation of rifampicin in *M. tuberculosis*, *M. aurum*, and *M. smegmatis*, and accumulation of isoniazid in *M. smegmatis* (Zhang, Y.; Scorpio, A.; Nikaido, H.; Sun, Z. "Role of acid pH and deficient efflux of pyrazinoic acid in unique susceptibility of *Mycobacterium tuberculosis* to pyrazinamide." *J. Bacteriol.* 1999, 181, 2044-2049; Piddock, L. J.; Williams, K. J.; Ricci, V. "Accumulation of rifampicin by *Mycobacterium aurum*, *Mycobacterium smeg-* matis and *Mycobacterium tuberculosis.*" *J. Antimicrob. Chemother.* 2000, 45, 159-165; Choudhuri, B. S.; Sen, S.; Chakrabarti, P. "Isoniazid accumulation in *Mycobacterium smegmatis* is modulated by proton motive force-driven and ATP-dependent extrusion systems." *Biochem. Biophys. Res. Comm.* 1999, 256, 682-684; each of which is incorporated herein by reference). Briefly, we will use two approaches to determine the kinetics of intracellular accumulation. The first involves traditional detection of radiolabeled compound. [$^3$H]-salicyl-AMS will be synthesized using [$^3$H]-salicylate and our established route. Analogs can be labeled on the salicyl ring or on a 2'-OH substituent (cf. compound 14m, FIG. 9). Exponentially growing cultures will be used to prepare bacterial cell suspensions in sodium phosphate buffer. Various concentrations of radiolabeled compound will be added to the suspensions, and samples of the suspension will be taken at multiple time points after compound addition. The cells in each sample will be centrifuged and washed, then the cell-associated radioactivity will be quantified by LSC. Standards of the radiolabeled compound will be used to convert counts into compound amounts. We also propose to develop a second approach that will not require synthesis of radiolabeled compounds, involving LC-MS-MS analysis. Cells will be incubated with compound, harvested, and washed as above, then lysed and extracted. The amount of compound in the extract will be quantified by LC-MS-MS. Calibration curves will be determined for each compound to permit conversion of LC peak areas to compound amounts based on external reference standards. The tandem MS-MS detector will permit verification of peak identity as well as quantitative assessment of the compounds in the samples.

The effect of efflux on the kinetics of compound accumulation in *Y. pestis* and *M. tuberculosis* will be investigated essentially as described for ciprofloxacin in *Salmonella enterica* serovar typhimurium and isoniazid in *M. smegmatis* (Giraud et al. "Evidence for active efflux as the primary mechanism of resistance to ciprofloxacin in *Salmonella enterica* serovar typhimurium." *Antimicrob. Agents Chemother.* 2000, 44, 1223-1228; Choudhuri, B. S.; Sen, S.; Chakrabarti, P. "Isoniazid accumulation in *Mycobacterium smegmatis* is modulated by proton motive force-driven and ATP-dependent extrusion systems." *Biochem. Biophys. Res. Comm.* 1999, 256, 682-684; each of which is incorporated herein by reference). Briefly, the compound accumulation rate determined above is compared to the rate in the presence of carbonylcyanide m-chlorophenylhydrazone (CCCP), an uncoupler of proton motive force, and ortho-vanadate, an inhibitor of ATP-dependent efflux pumps (Giraud et al. "Evidence for active efflux as the primary mechanism of resistance to ciprofloxacin in *Salmonella enterica* serovar typhimurium." *Antimicrob. Agents Chemother.* 2000, 44, 1223-1228; Choudhuri, B. S.; Sen, S.; Chakrabarti, P. "Isoniazid accumulation in *Mycobacterium smegmatis* is modulated by proton motive force-driven and ATP-dependent extrusion systems." *Biochem. Biophys. Res. Comm.* 1999, 256, 682-684; each of which is incorporated herein by reference). The difference in rates is indicative of the influence of efflux pumps upon compound accumulation.

Compound Specificity Experiments.

To assess the target specificity of salicyl-AMS and its analogs, we will investigate their binding to cellular components using two standard approaches. First, radiolabeled compounds will be incubated with the soluble fractions of *Y. pestis* or *M. tuberculosis* lysates prepared in PBS buffer (phosphate-buffered saline: 0.02 M sodium phosphate, 0.15 M sodium chloride, pH 7.4), supplemented with protease inhibitors. Various ratios of protein-to-compound concentrations and incubation times will be evaluated. The samples will then be analyzed by HPLC (C2 or C4 column) or by size-exclusion HPLC (Cserhati, T.; Forgacs, E.; Deyl, Z.; Miksik, I.; Echardt, A. "Binding of low molecular mass compounds to proteins studied by liquid chromatographic techniques." *Biomed. Chromatog.* 2003, 17, 353-360; Oravcova, J.; Boehs, B.; Lindner, W. "Drug-protein binding studies. New trends in analytical and experimental methodology." *J. Chromatog. B* 1996, 677, 1-28; Markaverich, B. M.; Shoulars, K.; Brown, M. A. T. "Purification and characterization of nuclear type II [$^3$H]estradiol binding sites from the rat uterus: Covalent labeling with [$^3$H]luteolin." *Steroids* 2001, 66, 707-719; Dunaway, H. E.; Hutchens, T. W.; Besch, P. K. "Isolation of unliganded steroid receptor proteins by high-performance size-exclusion chromatography. An investigation of steroid-dependent structural alterations." *Journal of Chromatography* 1985, 327, 221-235; each of which is incorporated herein by reference). Bound (and free) compound will be detected by LSC of the fractions. Overall off-target binding will be estimated by comparison of the compound elution profile to a reference sample prepared by incubation of the compound with purified YbtE or MbtA. LC-MS-MS and capillary electrophoresis methods can also be used with non-labeled compounds. If a significant amount of off-target binding is observed in this preliminary analysis, we will carry out additional affinity chromatography experiments to obtain a more detailed assessment (Burdine, L.; Kodadek, T. "Target identification in chemical genetics: The (often) missing link" *Chem. Biol.* 2004, 11, 593-597; Wissing et al. "Chemical proteomic analysis reveals alternative modes of action for pyrido[2,3-d]pyrimidine kinase inhibitors." *Mol. Cell. Proteomics* 2004, 3, 1181-1193; each of which is incorporated herein by reference). Briefly, biotin-labeled analogs such as 14k,l (FIG. 9) will be incubated with lysates, loaded onto streptavidin beads, and washed. Bound proteins will be eluted and analyzed by 1D or 2D gel electrophoresis. Purified YbtE and MbtA will be used as standards. Gel staining will provide a semiquantitative indication of off-target binding. We will then attempt to identify some of the major binding partners by band excision and MS-MS sequencing. This information would be useful for delineating structural modifications to the inhibitor that might improve specificity. Notably, additional analogs can be analyzed conveniently using the salicyl-AMS affinity matrix in a displacement assay. The parent salicyl-AMS affinity matrix is loaded with lysate, washed, then eluted with the desired analog. The eluted binding proteins are analyzed by gel electrophoresis. This approach has recently been used to identify quinolone-binding proteins by displacement from a γ-phosphate-linked ATP affinity matrix (Graves, P. R.; Kwiek, J. J.; Fadden, P.; Ray, R.; Hardeman, K.; Coley, A. M.; Foley, M.; Haystead, T. A. J. "Discovery of novel targets of quinoline drugs in the human purine binding proteome." *Mol. Pharmacol.* 2002, 62, 1364-1372; incorporated herein by reference).

Compound Stability Experiments.

The kinetics of degradation or modification of salicyl-AMS and its analogs will be investigated by incubating known amounts of compounds with sterile new culture media, sterilized spent culture supernatant, bacterial cell lysates prepared in PBS, and live bacterial cells for defined time intervals at 37° C. After incubation, the samples will be analyzed by LC-MS-MS as described above to quantify the compounds. In the case of live bacterial cell samples, cell lysates will be prepared in PBS before analysis. The concentration of the compounds in these samples will be compared with the concentration of the compounds in freshly prepared samples. If a significant reduction in compound concentration over time is observed (e.g., ≥20%), we will attempt to identify degradation and modification pathways by LC-MS-MS. We will use both a mechanism-based, hypothesis-driven approach, involving mass scans for prospective degradation products, and an empirical approach, involving initial detection of degradation products from radiolabeled analogs, followed by LC-MS-MS identification of the corresponding degradation products from non-labeled compounds. We will particularly consider common nucleoside breakdown pathways, such as depurination or modification of the adenine ring, (Hammer-Jespersen, K. "Nucleoside catabolism." In *Metabolism of nucleotides, nucleosides, and nucleobases in microorganisms*; Munch-Petersen, A., Ed.; Academic Press: London, 1983, p 203-258; incorporated herein by reference) as well as hydrolysis of the salicylimide or sulfamate, and nucleophilic displacement of the sulfamate from the 5'-position. This information will allow us to design analogs that are less susceptible to these degradation pathways.

Example 2

Stability of Salicyl-AMS

A deuterated analog, salicyl-AMS-$d_4$ (as shown below) for use as an LC-MS-MS internal standard in quantitative pharmacological assays was prepared.

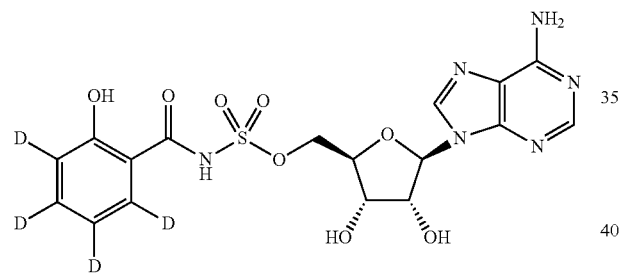

The compound was synthesized using a route starting with adenosine acetonide and using a tin-free sulfamoylation reaction. 3,4,5,6-deuterosalicylic acid (Cambridge Isotope Labs) was used in the second step. The corresponding protonated parent compound (salicyl-AMS) is isotopically stable in $D_2O$ for ≥54 days at room temperature (NMR). The deuterated analog is, hence, expected to exhibit similar isotopic stability in $H_2O$, making it a useful probe for quantitive pharmacological analyses.

LC-MS-MS analysis identified a 467/121 amu parent/fragment ion pair for salicyl-AMS-$h_4$ and a corresponding 471/125 amu ion pair for salicyl-AMS-$d_4$. Detection using these ion pairs provides a linear response from ≥50 mM to ≤50 nM concentration. Increased sensitivity can be achieved using alternative probes having [$^{13}C$]$_5$-labeling of the ribose ring (268 and 347 amu fragments; 15- to 20-fold higher abundance; available from [$^{13}C$]$_6$-glucose[b]), [$^{15}N$]$_5$-labeling of the adenine ring (136 amu fragment; >1000-fold higher abundance; available from [$^{15}N$]$_5$-adenosine, Cambridge Isotope Labs), [$^{15}N$]$_3$-labeling of the adenine ring (136 amu fragment; >1000-fold higher abundance; available from ammonium [$^{15}N$]-nitrate and [$^{15}N$]-ammonium hydroxide[c]), or [$^{13}C$]$_{10}$/[$^{15}N$]$_5$-labeling of the entire adenosine portion (available from [$^{13}C$]$_{10}$/[$^{15}N$]$_5$-adenosine, Cambridge Isotope Labs). Related references for isotopic incorporation: (a) Quant, S.; Wechselberger, R. W.; Wolter, M. A.; Wörner, K.-H.; Schell, P.; Engels, J. W.; Griesinger, C.; Schwalbe, H. *Tetrahedron Lett.* 1994, 35, 6649-6652. (b) Saito, Y.; Zevaco, T. A.; Agrofoglio, L. A. *Tetrahedron* 2002, 58, 9593-9603. (c) Jain, M. L.; Tsao, Y.-P.; Ho, N.-L.; Cheng. J.-W. *J. Org. Chem.* 2001, 66, 6472-6475; each of which is incorporated herein by reference.

Figure 24:
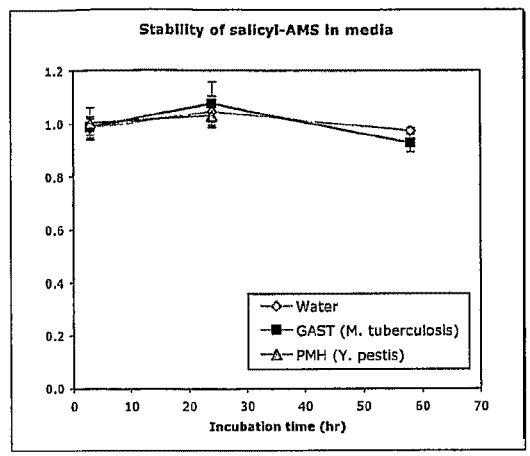
Figure 24:
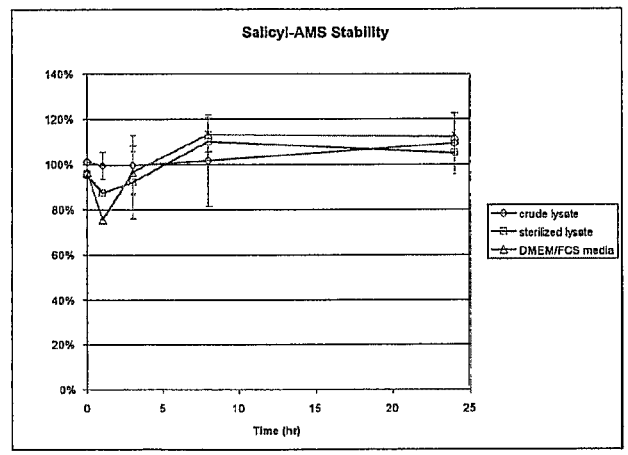

The stability of salicyl-AMS at 50 mM in water, in *Y. pestis* culture media (PMH-D), and in *M. tuberculosis* culture media (GAST-D) for 3, 24, and 58 hours at 37° C. was tested (FIG. 24). The stabiliting of salicyl-AMS was also tested in *Y. pestis* lysates (grown to late log phase $OD_{620}$=0.93, lysed in spent broth via French press and sonication, centrifuged 3000 rpm× 10 min; total protein concentration=110 mg/mL), in *Y. pestis* filter sterilized lysates (as above followed by filtration; total protein concentration=12.4 mg/mL), and in mammalian cell culture media (DMEM, 10% FCS) for 1, 3, 8, and 24 hours at 37° C. (FIG. 24). The salicyl-AMS-$d_4$ internal standard was then added at the appropriate time point, proteins were precipitated with 1.5 vol $CH_3CN$, and the supernatant samples were analyzed by LC-MS-MS.

As shown in FIG. 24, no degradation of salicyl-AMS was observed for any of the conditions tested.

Example 3

Cytotoxicity of Salicyl-AMS

The cytotoxicity of salicyl-AMS was evaluated using an established eukaryotic cell model of cytotoxicity. Salicyl-AMS was tested for cytotoxicity in vitro using Chinese hamster ovary (CHO) cells, a mammalian cell line commonly utilized for cytotoxicity testing. The effect of exposure to salicyl-AMS on cell monolayer density was investigated using a 398-well plate platform. The effect of salicyl-AMS was compared with that produced by the vehicle along (DMSO) and untreated controls. In this assay, a reduction of cell density in the well compare with untreated controls is operationally considered a reduction of cell viability secondary of cytotoxicity. The effect of exposure to the anti-tuberculosis drug PAS (p-aminosalicylate, which has a clinically acceptable low cytotoxicity) and the cytotoxic compound cycloheximide was also tested. These compounds were included in the experiments to provide a relative reference of cytotoxicity in our experimental conditions. Cell density was determined after 20 hours of exposure using a Discovery-1 High Content Screening System (Universal Imaging Corporation.) equipped with a fluorescence microscope for automated high resolutions/magnification image acquisition and MetaMorph Image Processing and Analysis Software (Molecular Devices) for cell counting in the images at the WMC Cell Screening Core Facility.

Figure 2:
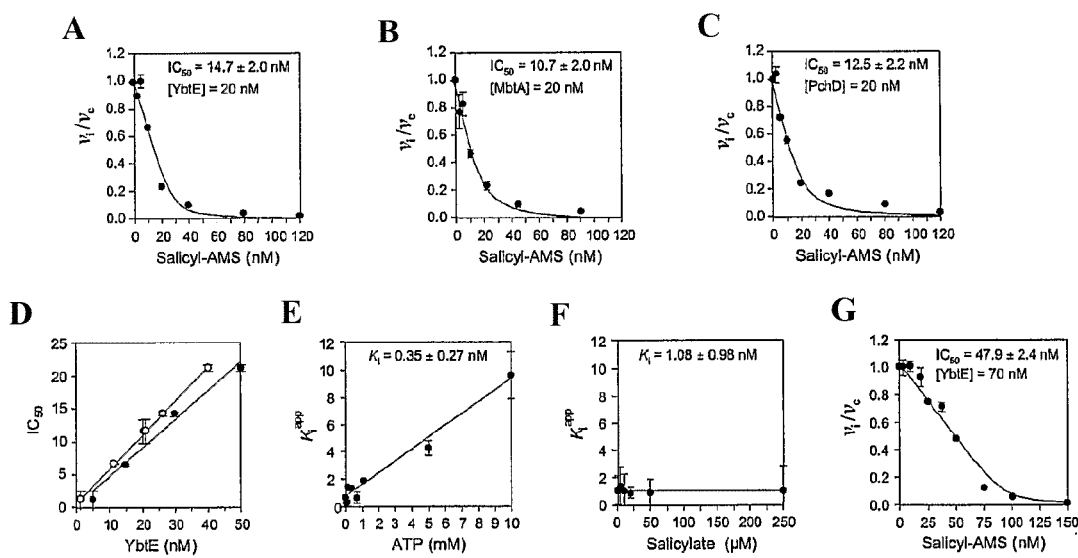
FIG. 2 demonstrates the inhibition of YbtE, MbtA, and PchD by salicyl-AMS. A-C. Dose-response for inhibition of adenylation activity plotted with fractional velocity as a function of salicyl-AMS concentration. The data sets were fitted to the Morrison equation (Eq. (1)) for tight-binding inhibitors. v$_i$ and v$_c$ are the velocities measured in inhibitor- and DMSO-containing reactions, respectively. D. Plot of salicyl-AMS IC$_{50}$ as a function of nominal YbtE concentration in the adenylation assay (filled circles) and as a function of the calculated actual YbtE concentration derived from the Eq. (1) fitted to the dose-response data (open circles). E. Plot of $K_i^{app}$ as a function of ATP concentration. F. Plot of $K_i^{app}$ as a function of salicylate concentration. G. Dose-response for YbtE-catalyzed domain salicylation plotted with fractional velocity (with $v_i$ and $v_c$ as above) of as a function of salicyl-AMS concentration. Plots show means of triplicates with standard errors.

In these experiments, salicyl-AMS exhibited acceptable low cytotoxicity against mammalian cells, similar to that observed with PAS (FIG. 2).

Example 4

Biological Testing of Salicyl-A MS Analogs

Approximately twenty salicyl-AMS analogs have been synthesized, and many have been tested for biochemical inhibition of YbtE and, in some cases, for inhibition of *Y. pestis* and *M. tuberculosis* growth in iron-deficient versus iron-rich media.

New macrocyclic analogs of aminoacyl-AMS compounds have also been synthesized using an olefin cross-metathesis-based route (FIG. 23) and are currently being tested as potential inhibitors of amino acid adenylation domains. As such, these macrocyclic compounds could have potent, broad-spectrum activity against any microorganism that requires production of a non-ribosomal peptide for growth, virulence, or survival.

These biological data are shown in the table below. The table also includes $IC_{50}$ data for isoniazid and p-aminosalicylate. Isoniazid and p-aminosalicylate do not exhibit iron-deficient media selectivity, which would be expected for compounds targeting the siderophore biosynthetic pathway.

Also, the C log P value and tPSA are listed for each compound. The C log P value is a calculated value for log P, the 1-octanol/water coefficient. The higher the number, the more hydrophobic the compound. This number has been used to preduct solubility and cell permeability in the drug discovery setting (Lipinski et al., *Adv. Drug Delivery Rev.* 23:3-25, 1997; incorporated herein by reference). The value for tPSA is the topological polar surface area of the compound. This number has been correlated with oral bioavailability and cell permeability (Veber et al., *J. Med. Chem.* 45:2615-2623, 2002; incorporated herein by reference).

Siderophore Biosynthesis Inhibitor Data

| | salicyl-AMS | Assay | IC50 | MIC90 |
|---|---|---|---|---|
| 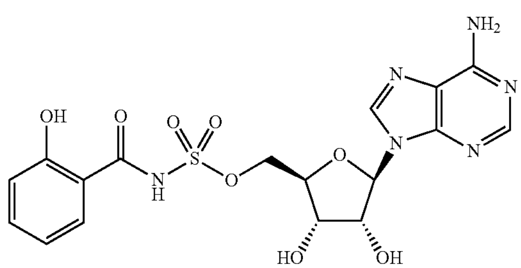 [SMILES: Nc1ncnc2c1ncn2[C@@H]1O[C@H](COS(=O)(=O)NC(=O)c2ccccc2O)[C@@H](O)[C@H]1O]  | short name: Sal-AMS | YbtE, FlashPlate, 30 nM | 14.5 nM | |
| | MW: 466.43 | YbtE, FlashPlate, 70 nM | 47.9 nM | |
| | tPSA: 238.8 | Yp, growth, −Fe | 51.2 uM | |
| | C logP: 0.29 | Yp, growth, +Fe | >400 uM | |
| | | Mtb, growth, −Fe | 2.2 uM | |
| | | Mtb growth, +Fe | 39.9 uM | |
| | | Mtb, growth, −Fe | 15 uM | ~50 uM |
| | | Mtb growth, +Fe | 20 uM | ~50 uM |
| | | Mtb, growth, −Fe | 18 uM | ~100 uM |
| | | Mtb growth, +Fe | 18 uM | ~100 uM |
| | | Yp, growth, −Fe | 92 uM | ~500 uM |
| | | Yp, growth, +Fe | >500 uM | >500 uM |
| | | Yp, growth, −Fe | 132 uM | ~500 uM |
| | | Yp, growth, +Fe | >500 uM | >500 uM |
| | | Yp, growth, −Fe | 9 uM | ~62.5 uM |
| | | Yp, growth, +Fe | 264 uM | >500 uM |
| | | Yp, growth, −Fe | 13 uM | ~62.5 uM |
| | | Yp, growth, +Fe | 245 uM | >500 uM |
| | | Mtb, growth, −Fe | 1.2 uM | ~50 uM |
| | | Mtb growth, +Fe | 21.6 uM | ~100 uM |
| | | Mtb, growth, −Fe | 0.8 uM | >200 uM |
| | | Mtb growth, +Fe | 10.0 uM | >200 uM |
| | | Mtb, growth, −Fe | 0.7 uM | >200 uM |
| | | Mtb growth, +Fe | 12.8 uM | >200 uM |
| | | YbtE, FlashPlate, 30 nM | 9 nM | |
| | | Mtb, growth, −Fe | 1.55 uM | ~18 uM |
| | | Mtb growth, +Fe | ~20 uM | ~200 uM |
| | isoniazid | Assay | IC50 | MIC90 |
| 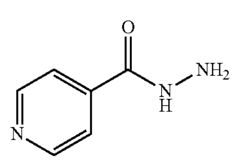  | short name: isoniazid | Mtb, growth, −Fe | 0.12 uM | 0.20 uM |
| | MW: 137.14 | Mtb growth, +Fe | 0.11 uM | 0.20 uM |
| | tPSA: 68.0 | Mtb, growth, −Fe | 0.08 uM | 0.16 uM |
| | C logP: −0.67 | Mtb growth, +Fe | 0.10 uM | 0.31 uM |
| | p-aminosalicylic acid | Assay | IC50 | MIC90 |
| 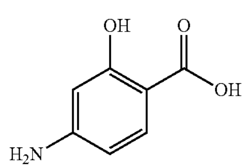 [SMILES: Nc1ccc(C(=O)O)c(O)c1]  | snort name: PAS | Mtb, growth, −Fe | 0.09 uM | 0.78 uM |
| | MW: 153.14 | Mtb growth, +Fe | 0.08 uM | 0.59 uM |
| | tPSA: 83.6 | | | |
| | C logP: 106 | | | |

| Ribose Region Modifications |||||
|---|---|---|---|---|
| | salicyl-dAMS | Assay | IC50 | MIC90 |
| 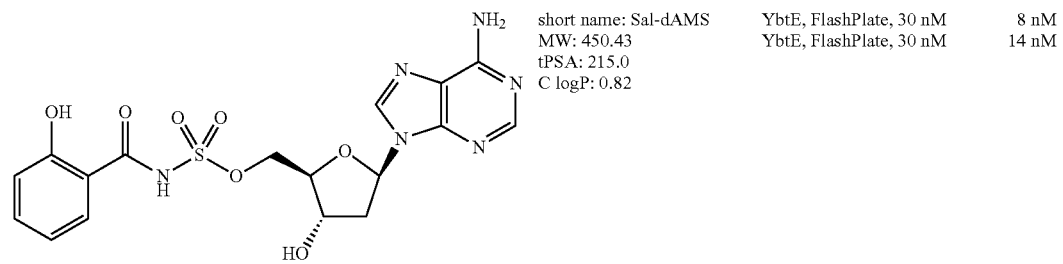 | short name: Sal-dAMS<br>MW: 450.43<br>tPSA: 215.0<br>C logP: 0.82 | YbtE, FlashPlate, 30 nM<br>YbtE, FlashPlate, 30 nM | 8 nM<br>14 nM | |
| | salicyl-ddAMS | Assay | IC50 | MIC90 |
| 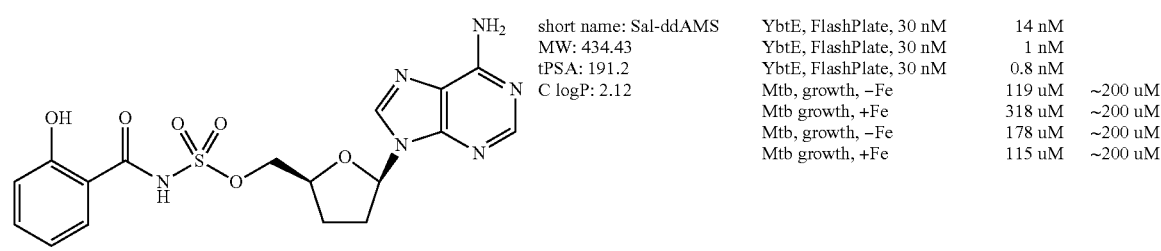 | short name: Sal-ddAMS<br>MW: 434.43<br>tPSA: 191.2<br>C logP: 2.12 | YbtE, FlashPlate, 30 nM<br>YbtE, FlashPlate, 30 nM<br>YbtE, FlashPlate, 30 nM<br>Mtb, growth, −Fe<br>Mtb growth, +Fe<br>Mtb, growth, −Fe<br>Mtb growth, +Fe | 14 nM<br>1 nM<br>0.8 nM<br>119 uM<br>318 uM<br>178 uM<br>115 uM | <br><br><br>~200 uM<br>~200 uM<br>~200 uM<br>~200 uM |
| | (RS)-5'-methyl-salicyl-AMS | Assay | IC50 | MIC90 |
| 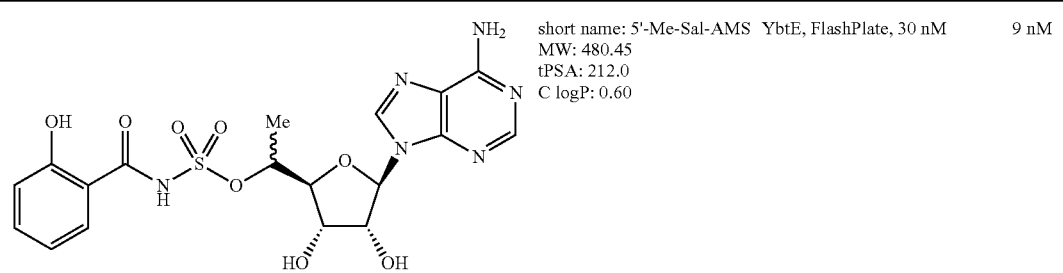 | short name: 5'-Me-Sal-AMS<br>MW: 480.45<br>tPSA: 212.0<br>C logP: 0.60 | YbtE, FlashPlate, 30 nM | 9 nM | |
| | 2',3'-diacetyl-salicyl-AMS | Assay | IC50 | MIC90 |
| 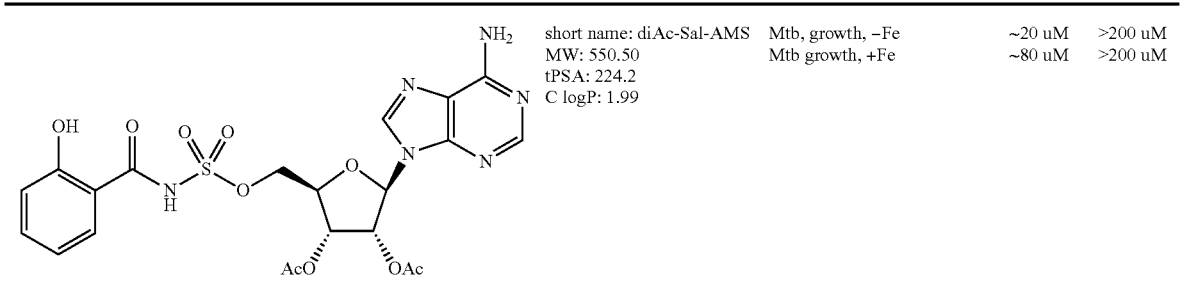 | short name: diAc-Sal-AMS<br>MW: 550.50<br>tPSA: 224.2<br>C logP: 1.99 | Mtb, growth, −Fe<br>Mtb growth, +Fe | ~20 uM<br>~80 uM | >200 uM<br>>200 uM |

| | Salicyl Region Modifications | | | |
|---|---|---|---|---|
| | AMS | Assay | IC50 | MIC90 |
| | short name: AMS<br>MW: 346.32<br>tPSA: 202.8<br>C logP: −3.24 | YbtE, FlashPlate, 70 nM<br>YbtE, FlashPlate, 30 nM<br>Mtb, growth, −Fe<br>Mtb, growth, +Fe<br>Mtb, growth, −Fe<br>Mtb growth, +Fe | >400 uM<br>1.9 uM<br>35 uM<br>39 uM<br>43 uM<br>55 uM | <br><br>~100 uM<br>~100 uM<br>~100 uM<br>~100 uM |
| | acetyl-AMS | Assay | IC50 | MIC90 |
| | Short name: Ac-AMS<br>MW: 388.36<br>tPSA: 215.0<br>C logP: −2.45 | YbtE, FlashPlate, 30 nM | >400 uM | |
| | benzoyl-AMS | Assay | IC50 | MIC90 |
| | short name: Bz-AMS<br>MW: 450.43<br>tPSA: 215.0<br>C logP: −0.53 | YbtE, FlashPlate, 30 nM<br>YbtE, FlashPlate, 30 nM<br>Mtb, growth, −Fe<br>Mtb growth, +Fe<br>Mtb, growth, −Fe<br>Mtb growth, +Fe<br>Mtb, growth, −Fe<br>Mtb growth, +Fe<br>Mtb, growth, −Fe<br>Mtb growth, +Fe<br>Yp, growth, −Fe<br>Yp, growth, +Fe<br>Yp, growth, −Fe<br>Yp, growth, +Fe<br>Yp, growth, −Fe<br>Yp, growth, +Fe<br>Yp, growth, −Fe<br>Yp, growth, +Fe | 4 nM<br>12 nM<br>105 uM<br>166 uM<br>110 uM<br>133 uM<br>75 uM<br>68 uM<br>105 uM<br>133 uM<br>326 uM<br>>500 uM<br>430 uM<br>>500 uM<br>76 uM<br>500 uM<br>47 uM<br>500 uM | <br><br>>200 uM<br>>200 uM<br>~200 uM<br>~200 uM<br>~200 uM<br>~200 uM<br>>200 uM<br>>200 uM<br>>500 uM<br>>500 uM<br>>500 uM<br>>500 uM<br>~500 uM<br>>500 uM<br>~500 uM<br>>500 uM |
| | 2-methoxybenzoyl-AMS | Assay | IC50 | MIC90 |
| | short name: 2-MeOBz-AMS<br>MW: 480.45<br>tPSA: 229.1<br>C logP: −0.38 | YbtE, FlashPlate, 30 nM<br>YbtE, FlashPlate, 30 nM<br>Mtb, growth, −Fe<br>Mtb growth, +Fe<br>Mtb, growth, −Fe<br>Mtb growth, +Fe | >80 nM<br>65 uM<br>>200 uM<br>>200 uM<br>>200 uM<br>>200 uM | <br><br>>200 uM<br>>200 uM<br>>200 uM<br>>200 uM |

Salicyl Region Modifications

1-hydroxy-2-napthyl-AMS

| | Assay | IC50 | MIC90 |
|---|---|---|---|
| short name: HONap-AMS | YbtE, FlashPlate, 30 nM | >80 nM | |
| MW: 516.48 | Mtb, growth, −Fe | 36 uM | ~100 uM |
| tPSA: 238.8 | Mtb growth, +Fe | 33 uM | ~100 uM |
| C logP: 1.46 | Mtb, growth, −Fe | 35 uM | ~100 uM |
| | Mtb growth, +Fe | 36 uM | ~100 uM |

6-methylsalicyl-AMS

| | Assay | IC50 | MIC90 |
|---|---|---|---|
| short name: 6-MeSal-AMS | YbtE, FlashPlate, 30 nM | 23 nM | |
| MW: 480.45 | | | |
| tPSA: 238.8 | | | |
| C logP: 0.45 | | | |

4-hydroxybenzoyl-AMS

| | Assay | IC50 | MIC90 |
|---|---|---|---|
| short name: 4-HOBz-AMS | YbtE, FlashPlate, 30 nM | >80 nM | |
| MW: 466.43 | YbtE, FlashPlate, 30 nM | 6 uM | |
| tPSA: 238.8 | Mtb, growth, −Fe | >200 uM | >200 uM |
| C logP: −0.66 | Mtb growth, +Fe | >200 uM | >200 uM |
| | Mtb, growth, −Fe | >200 uM | >200 uM |
| | Mtb growth, +Fe | 110 uM | >200 uM |

Adenine Region Modifications (and Prodrugs thereof)

salicyl-IRMS

| | Assay | IC50 | MIC90 |
|---|---|---|---|
| short name: sal-IRMS | YbtE, FlashPlate, 30 nM | 21 nM | |
| MW: 448.45 | Mtb, growth, −Fe | >200 uM | >200 uM |
| tPSA: 182.0 | Mtb growth, +Fe | >200 uM | >200 uM |
| C logP: 3.28 | Mtb, growth, −Fe | >200 uM | >200 uM |
| | Mtb growth, +Fe | >200 uM | >200 uM |
| | Mtb, growth, −Fe | >200 uM | >200 uM |
| | Mtb growth, +Fe | >200 uM | >200 uM |
| | Mtb, growth, −Fe | >200 uM | >200 uM |
| | Mtb growth, +Fe | >200 uM | >200 uM |
| | Yp, growth, −Fe | >500 uM | >500 uM |
| | Yp, growth, +Fe | >500 uM | >500 uM |
| | Yp, growth, −Fe | >500 uM | >500 uM |
| | Yp, growth, +Fe | >500 uM | >500 uM |

IRMS

| | Assay | IC50 | MIC90 |
|---|---|---|---|
| short name: IRMS | YbtE, FlashPlate, 30 nM | >20 uM | |
| MW: 328.34 | Mtb, growth, −Fe | >200 uM | >200 uM |
| tPSA: 146.0 | Mtb, growth, −Fe | >200 uM | >200 uM |
| C logP: −0.25 | Mtb, growth, −Fe | >200 uM | >200 uM |
| | Mtb growth, +Fe | >200 uM | >200 uM |

| Adenine Region Modifications (and Prodrugs thereof) | | | | |
|---|---|---|---|---|
| | 2',3'-diacetylsalicyl-IRMS | Assay | IC50 | MIC90 |
| 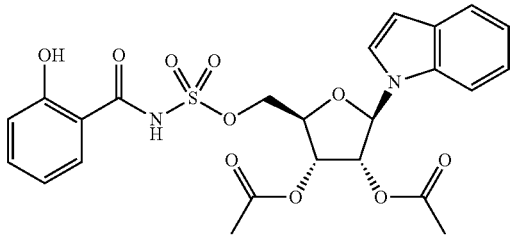 [SMILES: CC(=O)O[C@@H]1[C@H](OC(C)=O)[C@@H](COS(=O)(=O)NC(=O)c2ccccc2O)O[C@H]1n1ccc2ccccc21] | short name: Ac2-Sal-IRMS<br>MW: 532.52<br>tPSA: 207.2<br>C logP: 4.99<br><br><br><br><br><br>up to 200 uM<br><br>up to 200 uM | YbtE, FlashPlate, 30 nM<br>Mtb, growth, −Fe<br>Mtb growth, +Fe<br>Mtb, growth, −Fe<br>Mtb growth, +Fe<br>Mtb, growth, −Fe<br>Mtb growth, +Fe<br>Mtb, growth, −Fe<br>Mtb growth, +Fe<br>Yp, growth, −Fe<br>Yp, growth, +Fe<br>Yp, growth, −Fe<br>Yp, growth, +Fe | 3.9 uM<br>>200 uM<br>>200 uM<br>>200 uM<br>>200 uM<br>>200 uM<br>>200 uM<br>>200 uM<br>>200 uM<br>>200 uM<br>>200 uM<br>>200 uM<br>>200 uM | <br>>200 uM<br>>200 uM<br>>200 uM<br>>200 uM<br>>200 uM<br>>200 uM<br>>200 uM<br>>200 uM<br>>200 uM<br>>200 uM<br>>200 uM<br>>200 uM |
| | 2',2'',3'-triacetylsalicyl-IRMS | Assay | IC50 | MIC90 |
| 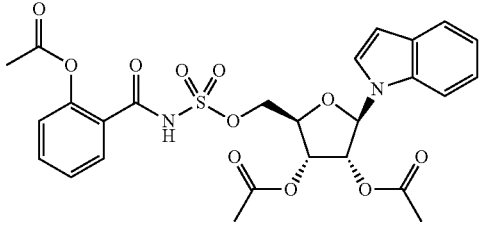 [SMILES: CC(=O)Oc1ccccc1C(=O)NS(=O)(=O)OC[C@H]1O[C@@H](n2ccc3ccccc32)[C@H](OC(C)=O)[C@@H]1OC(C)=O] | short name: Ac3-Sal-IRMS<br>MW: 574.56<br>tPSA: 219.8<br>C logP: 3.76 | YbtE, FlashPlate, 30 nM<br>Mtb, growth, −Fe<br>Mtb growth, +Fe<br>Mtb, growth, −Fe<br>Mtb growth, +Fe<br>Mtb, growth, −Fe<br>Mtb growth, +Fe<br>Mtb, growth, −Fe<br>Mtb growth, +Fe<br>Yp, growth, −Fe<br>Yp, growth, +Fe<br>Yp, growth, −Fe<br>Yp, growth, +Fe<br>Yp, growth, −Fe<br>Yp, growth, +Fe<br>Yp, growth, −Fe<br>Yp, growth, +Fe | 1.8 uM<br>24 uM<br>25 uM<br>22 uM<br>24 uM<br>33 uM<br>31 uM<br>35 uM<br>35 uM<br>302 uM<br>>500 uM<br>407 uM<br>>500 uM<br>97 uM<br>183 uM<br> | <br>~50 uM<br>~50 uM<br>~50 uM<br>~50 uM<br>~100 uM<br>~100 uM<br>~100 uM<br>~100 uM<br>~500 uM<br>>500 uM<br>~500 uM<br>>500 uM<br>~250 uM<br>~500 uM<br>~250 uM<br>~500 uM |

| Macrocycles | | | | |
|---|---|---|---|---|
| | cyclo-hexynoyl-AMS | Assay | IC50 | MIC90 |
| 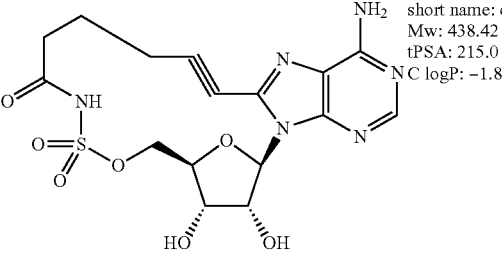 | short name: c-Hxy-AMS<br>Mw: 438.42<br>tPSA: 215.0<br>C logP: −1.83 | YbtE, FlashPlate, 30 nM | >40 uM | |
| | cyclo-hexanoyl-AMS | Assay | IC50 | MIC90 |
| 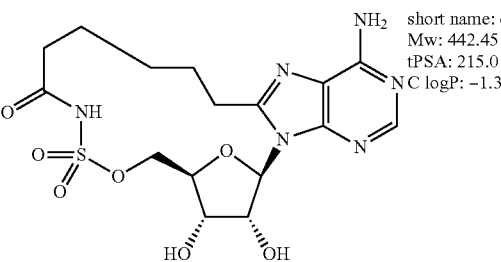 | short name: c-Hex-AMS<br>Mw: 442.45<br>tPSA: 215.0<br>C logP: −1.30 | YbtE, FlashPlate, 30 nM | >40 uM | |

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:
1. A compound of the formula:

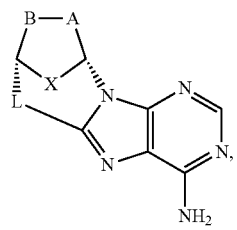

wherein:
X is O, S, —CH$_2$—, NH, or N—Ac;
A-B is —(R$_A$)$_2$C—C(R$_B$)$_2$— or —R$_A$C=CR$_B$—, wherein each occurrence of R$_A$ and R$_B$ is independently hydrogen, halogen, cyano, azido, hydroxyl, sulfhydryl, alkoxy, amino, alkylamino, dialkylamino, cyclic or acyclic, unsubstituted or substituted, branched or unbranched aliphatic, cyclic or acyclic, unsubstituted or substituted, branched or unbranched heteroaliphatic, substituted or unsubstituted, branched or unbranched acyl, substituted or unsubstituted, branched or unbranched aryl, substituted or unsubstituted, branched or unbranched heteroaryl; and
L is substituted or unsubstituted, branched or unbranched acyl, or substituted or unsubstituted, branched or unbranched, cyclic or acyclic heteroaliphatic;
or a pharmaceutically acceptable salt thereof.

2. The compound of claim 1 of the formula:

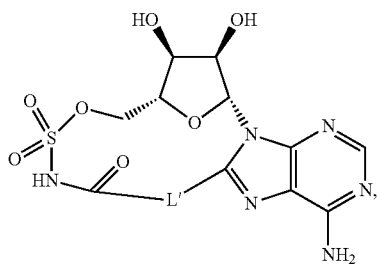

or a pharmaceutically acceptable salt thereof, wherein L' is substituted or unsubstituted, branched or unbranched, cyclic or acyclic aliphatic; substituted or unsubstituted, branched or unbranched acyl;
or substituted or unsubstituted, branched or unbranched, cyclic or acyclic heteroaliphatic.

3. The compound of claim 1 of the formula:

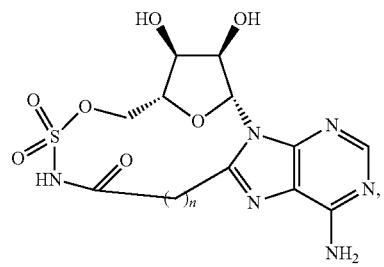

or a pharmaceutically acceptable salt thereof, wherein n is 0, 1, 2, 3, 4, 5, or 6.

4. The compound of claim 1 of the formula:

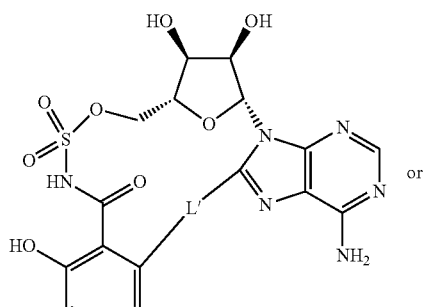

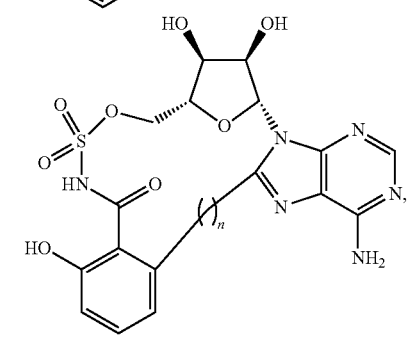

or a pharmaceutically acceptable salt thereof, wherein n is 0, 1, 2, 3, or 4; and L' is substituted or unsubstituted, branched or unbranched, cyclic or acyclic aliphatic; substituted or unsubstituted, branched or unbranched acyl; or substituted or unsubstituted, branched or unbranched, cyclic or acyclic heteroaliphatic.

5. The compound of claim 1 of the formula:

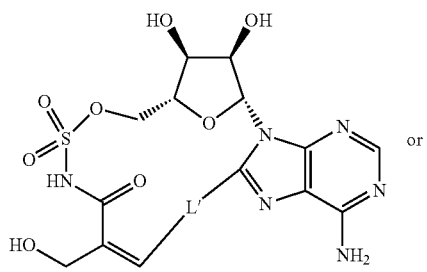

-continued

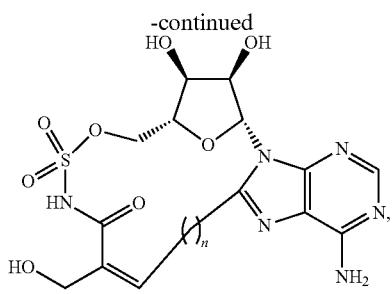

or a pharmaceutically acceptable salt thereof, wherein n is 0, 1, 2, 3, or 4; and L' is substituted or unsubstituted, branched or unbranched, cyclic or acyclic aliphatic; substituted or unsubstituted, branched or unbranched acyl; or substituted or unsubstituted, branched or unbranched, cyclic or acyclic heteroaliphatic.

6. The compound of claim 1 of the formula:

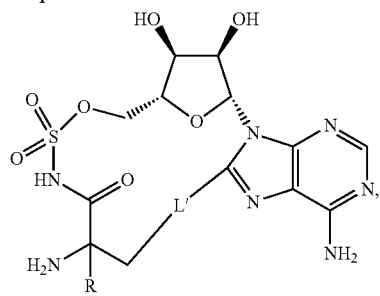

or a pharmaceutically acceptable salt thereof, wherein:
L' is substituted or unsubstituted, branched or unbranched, cyclic or acyclic aliphatic;
substituted or unsubstituted, branched or unbranched acyl; or substituted or unsubstituted, branched or unbranched, cyclic or acyclic heteroaliphatic; and
R is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR'; —C(=O)R'; —CO$_2$R'; —CN; —N$_3$; —SCN; —SR'; —SOR'; —SO$_2$R'; —NO$_2$; —N(R')$_2$; —NHC(O)R'; or —C(R')$_3$; wherein each occurrence of R' is independently hydrogen, a protecting group, an aliphatic moiety, a heteroaliphatic moiety, an acyl moiety, an aryl moiety, a heteroaryl moiety, alkoxy, aryloxy, alkylthio, arylthio, amino, alkylamino, dialkylamino, heteroaryloxy, or heteroarylthio moiety.

7. The compound of claim 6 of the formula:

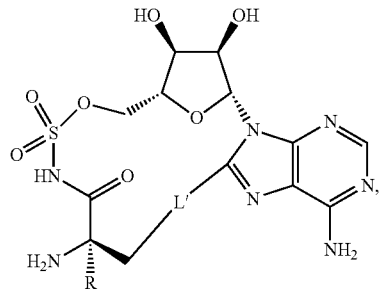

or a pharmaceutically acceptable salt thereof.

8. The compound of claim 6 of the formula:

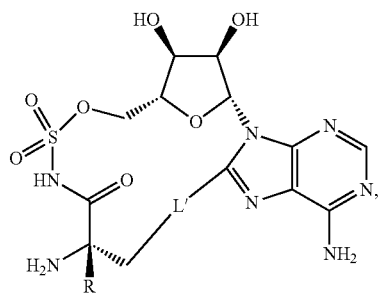

or a pharmaceutically acceptable salt thereof.

9. The compound of claim 6 of formula:

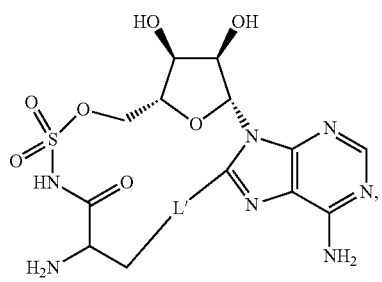

or a pharmaceutically acceptable salt thereof.

10. The compound of claim 9 of formula:

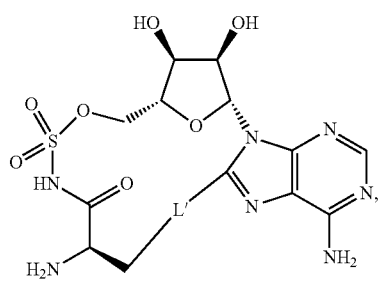

or a pharmaceutically acceptable salt thereof.

11. The compound of claim 9 of formula:

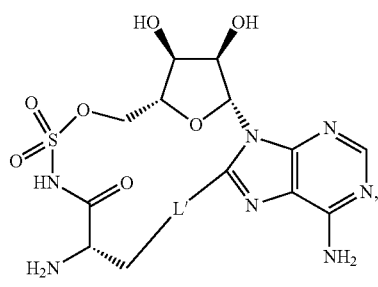

or a pharmaceutically acceptable salt thereof.

12. The compound of claim 1 of formula:

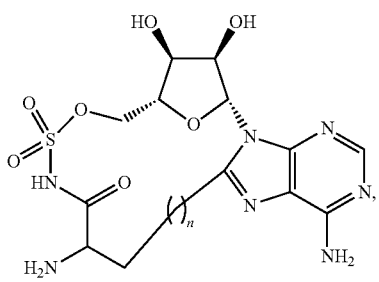

or a pharmaceutically acceptable salt thereof, wherein n is 0, 1, 2, 3, 4, 5, or 6.

13. The compound of claim 1 of formula:

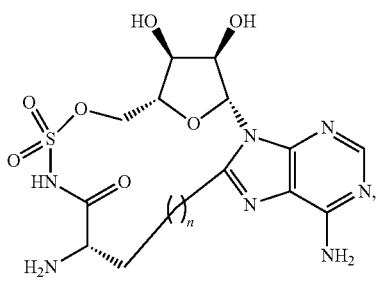

or a pharmaceutically acceptable salt thereof, wherein n is 0, 1, 2, 3, 4, 5, or 6.

14. The compound of claim 1 of formula:

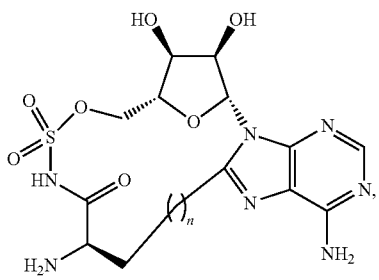

or a pharmaceutically acceptable salt thereof, wherein n is 0, 1, 2, 3, 4, 5, or 6.

15. The compound of claim 1 of the formula:

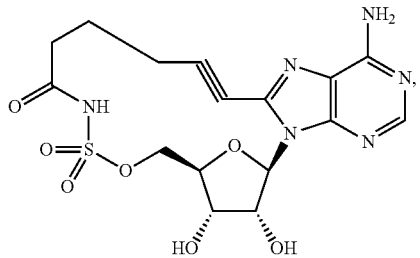

-continued

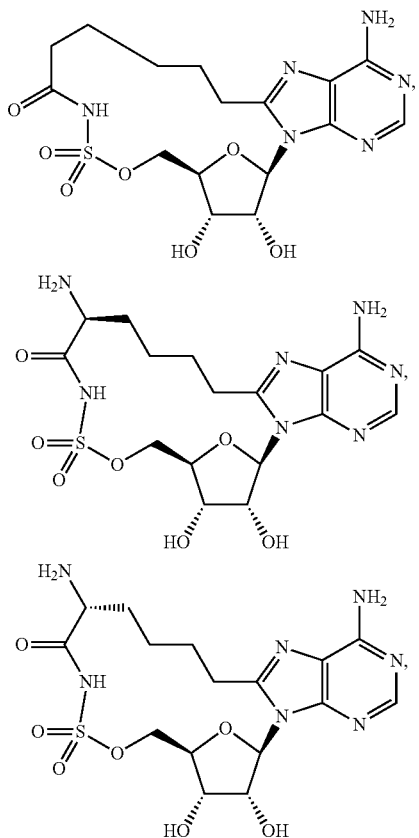

or a pharmaceutically acceptable salt thereof.

16. A pharmaceutical composition comprising a compound of claim 1, or a pharmaceutically acceptable salt thereof, and a pharmaceutically acceptable excipient.

17. The pharmaceutical composition of claim 16 comprising approximately 1 mg to approximately 500 mg of the compound.

18. The pharmaceutical composition of claim 16 suitable for treating an infection.

19. A method of treating a subject infected with a microorganism comprising administering to the subject a therapeutically effective amount of a compound of claim 1, or a pharmaceutically acceptable salt thereof.

20. The compound of claim 1 of the formula:

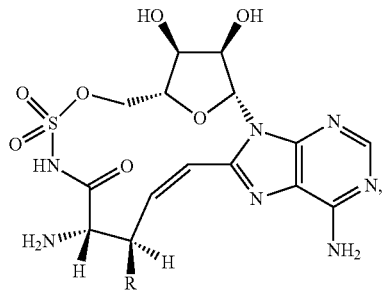

-continued

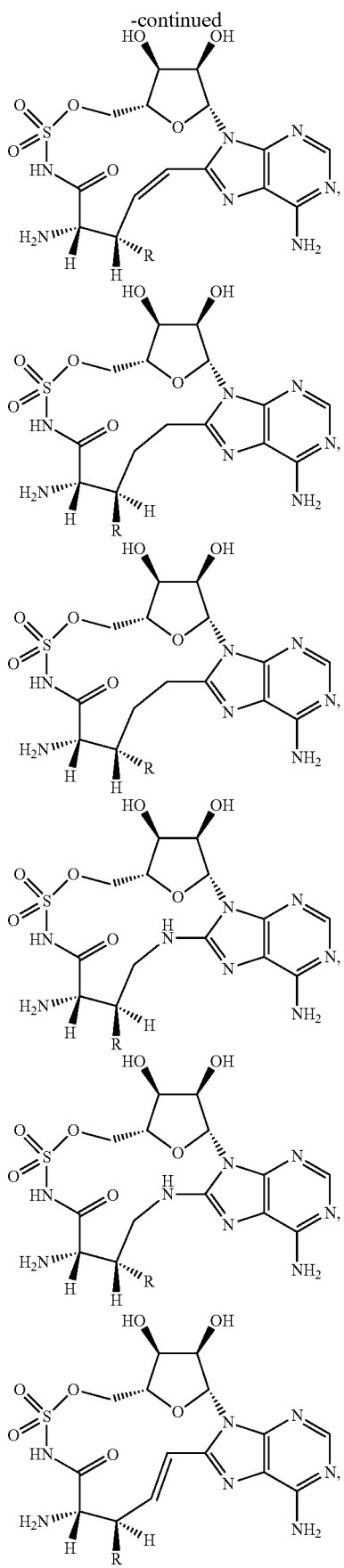

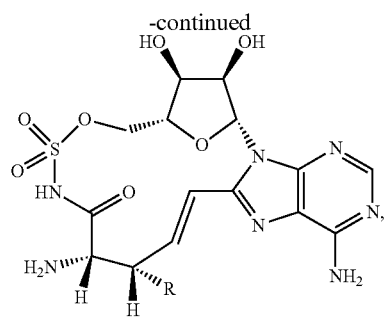

or a pharmaceutically acceptable salt thereof, wherein R is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR'; —C(=O)R'; —CO$_2$R'; —CN; —N$_3$; —SCN; —SR'; —SOR'; —SO$_2$R'; —NO$_2$; —N(R')$_2$; —NHC(O)R'; or —C(R')$_3$; wherein each occurrence of R' is independently hydrogen, a protecting group, an aliphatic moiety, a heteroaliphatic moiety, an acyl moiety, an aryl moiety, a heteroaryl moiety, alkoxy, aryloxy, alkylthio, arylthio, amino, alkylamino, dialkylamino, heteroaryloxy, or heteroarylthio moiety.

21. The compound of claim 1 of the formula:

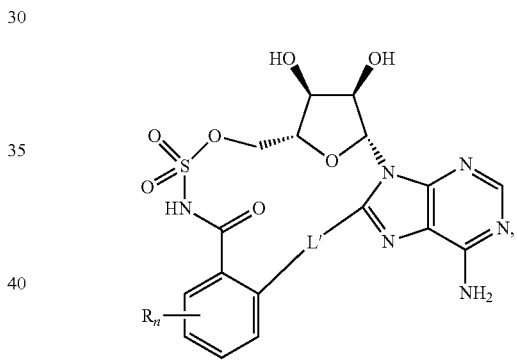

or a pharmaceutically acceptable salt thereof, wherein:
L' is substituted or unsubstituted, branched or unbranched, cyclic or acyclic aliphatic; substituted or unsubstituted, branched or unbranched acyl; or substituted or unsubstituted, branched or unbranched, cyclic or acyclic heteroaliphatic;
each occurrence of R is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR'; —C(=O)R'; —CO$_2$R'; —CN; —N$_3$; —SCN; —SR'; —SOR'; —SO$_2$R'; —NO$_2$; —N(R')$_2$; —NHC(O)R'; or —C(R')$_3$; wherein each occurrence of R' is independently hydrogen, a protecting group, an aliphatic moiety, a heteroaliphatic moiety, an acyl moiety, an aryl moiety, a heteroaryl moiety, alkoxy, aryloxy, alkylthio, arylthio, amino, alkylamino, dialkylamino, heteroaryloxy, or heteroarylthio moiety; and
n is 0, 1, 2, 3, or 4.

22. The compound of claim 1 of the formula:

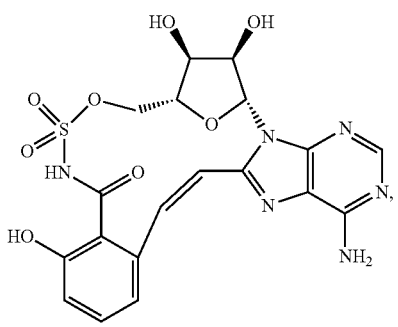

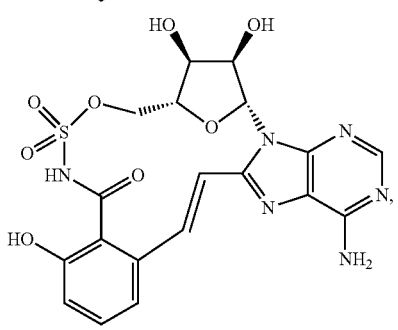

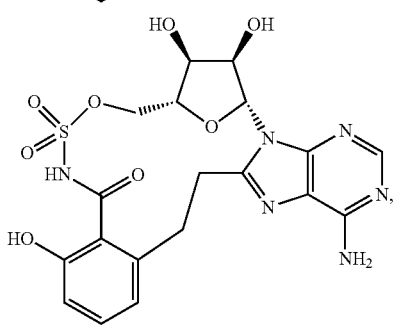

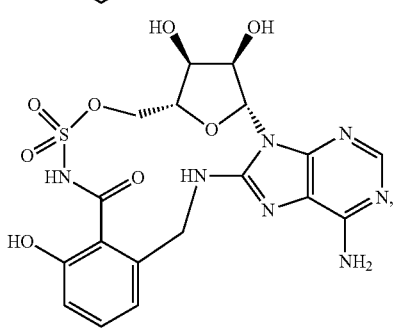

or a pharmaceutically acceptable salt thereof.

23. The compound of claim 1 of the formula:

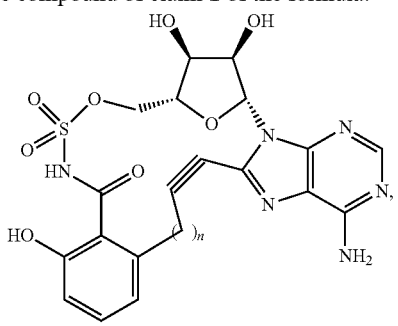

-continued

![structure]

![structure]

![structure]

![structure]

or a pharmaceutically acceptable salt thereof, wherein n is 0 or 1.

24. The compound of any one of claims 2, 4-11, and 22, wherein L' is of the formula:

![linker structures]

wherein n is 0, 1, 2, 3, 4, 5, or, 6.

25. The method of claim 19, wherein the microorganism is *Yersinia pestis* or *Yersinia enterocolitica*.

26. The method of claim 19, wherein the microorganism is *Mycobacterium tuberculosis*.

27. The method of claim 19, wherein the microorganism is selected from the group consisting of *Pseudomonas aeruginosa*, *Acinetobacter calcoaceticus*, *Acinetobacter baumannii*, *Escherichia coli*, *Salmonella enterica*, *Shigella spp.*, *Vibrio anguillarum*, and *Vibrio cholerae*.
28. The compound of any one of claims 2, 4-11, and 22, wherein L' is of the formula:
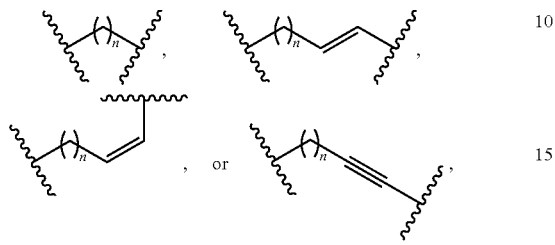
wherein n is 0, 1, 2, 3, 4, 5, or, 6.
* * * * *

UNITED STATES PATENT AND TRADEMARK OFFICE
CERTIFICATE OF CORRECTION

| | | |
|---|---|---|
| PATENT NO. | : 8,946,188 B2 | Page 1 of 1 |
| APPLICATION NO. | : 13/897807 | |
| DATED | : February 3, 2015 | |
| INVENTOR(S) | : Derek Shieh Tan et al. | |

It is certified that error appears in the above-identified patent and that said Letters Patent is hereby corrected as shown below:

*In the Specification*

At column 1, lines 16-21, please amend the GOVERNMENT SUPPORT section as shown below:

This invention was made with Government support under Grant Numbers P01AI056293 and R21 AI063384-01 awarded by the National Institutes of Health. The Government has certain rights in the invention.

*In the Claims*

In claim 24, at column 132, line 53, please replace the claim number "22" with the claim number --21--.

In claim 28, at column 133, line 6, please replace the claim number "22" with the claim number --21--.

Signed and Sealed this
Twenty-eighth Day of July, 2015

Michelle K. Lee
*Director of the United States Patent and Trademark Office*